United States Patent
Acton, III et al.

(10) Patent No.: US 7,345,085 B2
(45) Date of Patent: *Mar. 18, 2008

(54) INDOLES HAVING ANTI-DIABETIC ACTIVITY

(75) Inventors: John J. Acton, III, Cranford, NJ (US); Sheryl D. Debenham, Scotch Plains, NJ (US); Kun Liu, Edison, NJ (US); Peter T. Meinke, Plainfield, NJ (US); Harold B. Wood, Westfield, NJ (US); Regina M. Black, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/714,341

(22) Filed: Mar. 6, 2007

(65) Prior Publication Data

US 2007/0161689 A1 Jul. 12, 2007

Related U.S. Application Data

(62) Division of application No. 10/524,697, filed as application No. PCT/US03/27156 on Aug. 27, 2003, now Pat. No. 7,186,746.

(60) Provisional application No. 60/440,672, filed on Jan. 17, 2003, provisional application No. 60/406,741, filed on Aug. 29, 2002.

(51) Int. Cl.
*A61K 31/40* (2006.01)
*C07D 209/36* (2006.01)
(52) U.S. Cl. ...................................... 514/419; 548/484
(58) Field of Classification Search ................ 514/419; 548/484
See application file for complete search history.

(56) References Cited

U.S. PATENT DOCUMENTS

| 5,482,960 | A | 1/1996 | Berryman et al. |
| 5,686,481 | A | 11/1997 | Elliott et al. |
| 7,186,746 | B2 * | 3/2007 | Acton et al. ............... 514/419 |

FOREIGN PATENT DOCUMENTS

| EP | 1 424 325 | 6/2004 |
| WO | WO 98/08818 | 3/1998 |
| WO | WO 99/43651 | 9/1999 |
| WO | WO 99/43654 | 9/1999 |
| WO | WO 99/43672 | 9/1999 |
| WO | WO 00/35886 | 6/2000 |
| WO | WO 01 30343 | 5/2001 |
| WO | WO 02 08188 | 1/2002 |
| WO | WO 02/30895 | 4/2002 |
| WO | WO 2004/006920 | 1/2004 |

OTHER PUBLICATIONS

Expert Opin. Emerging Drugs, 2006, 11(3), 379-401.*

* cited by examiner

*Primary Examiner*—Rebecca Anderson
*Assistant Examiner*—Susannah Chung
(74) *Attorney, Agent, or Firm*—Richard C. Billups; James L. McGinnis; Catherine D. Fitch

(57) ABSTRACT

Indoles having aryloxyalkanoic acid substituents or arylalkanoic acid substituents are agonists or partial agonists of PPAR gamma and are useful in the treatment and control of hyperglycemia that is symptomatic of type II diabetes, as well as dyslipidemia, hyperlipidemia, hypercholesterolemia, hypertriglyceridemia, and obesity that are often associated with type 2 diabetes.

14 Claims, No Drawings

INDOLES HAVING ANTI-DIABETIC ACTIVITY

CROSS REFERENCE TO RELATED APPLICATIONS

This application is a Divisional of U.S. application Ser. No. 10/524,697, filed Feb. 16, 2005, now U.S. Pat. No. 7,186,746 which is the U.S. National Phase application under 35 U.S.C. § 371 of PCT Application No. PCT/US03/27156, filed Aug. 27, 2003, and claims priority under 35 U.S.C. § 119 (e) from U.S. application No. 60/406,741 filed Aug. 29, 2002, and U.S. application No. 60/440,672 filed Jan. 17, 2003.

FIELD OF THE INVENTION

The instant invention is concerned with indoles having an aryloxyalkanoic acid substituent, and pharmaceutically acceptable salts and prodrugs thereof, which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Insulin resistance is not primarily caused by a diminished number of insulin receptors but by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption, especially of foods containing high amounts of fat. A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. When administration of a sulfonylurea or meglitinide becomes ineffective, the amount of insulin in the body can be supplemented by the injection of insulin so that insulin concentrations are high enough to stimulate even the very insulin-resistant tissues. However, dangerously low levels of plasma glucose can result from administration of insulin and/or insulin secretagogues, and an increased level of insulin resistance due to the even higher plasma insulin levels can occur.

The biguanides are another class of drugs that are widely used to treat type 2 diabetes. The two best known biguanides, phenformin and metformin, cause some correction of hyperglycemia without risk of causing hypoglycemia. The biguanides can be used either with insulin or with an insulin secretagogue without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism.

PPAR agonists, and particularly glitazones, have had shortcomings which have so far detracted from their attractiveness. Some of the compounds, and especially troglitazone, have exhibited liver toxicity. Troglitazone was eventually withdrawn from the marketplace because of hepatotoxicity. Another weakness in the currently marketed PPAR agonists is that monotherapy for type 2 diabetes produces only modest efficacy—a reduction in average plasma glucose of ≈20% and a decline from ≈9.0% to ≈8.0% in HemoglobinA1C. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or partial agonists. WO01/30343 describes a specific compound that is a PPAR partial agonist/antagonist that is useful for the treatment of obesity and Type 2 diabetes. WO02/08188 discloses a class of PPAR agonists and partial agonists that are indole derivatives and that are useful in the treatment of Type 2 diabetes, with reduced side effects relating to body and heart weight gain.

SUMMARY OF THE INVENTION

The class of compounds described herein is a new class of PPAR agonists that do not contain a 1,3-thiazolidinedione moiety. The class of compounds includes many compounds that are PPARγ partial agonists, but also may include PPARγ full agonists and/or PPARγ antagonists. Some compounds may also have PPARα activity in addition to PPARγ activity. Some compounds may be mixed full or partial PPARα/γ agonists. These compounds are useful in the treatment and control of diabetes, hyperglycemia, and insulin resistance.

The compounds may also be useful in the treatment of one or more lipid disorders, including mixed or diabetic dyslipidemia, isolated hypercholesterolemia, which may be manifested by elevations in LDL-C and/or non-HDL-C, hyperapoBliproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The present invention is directed to compounds of formula I:

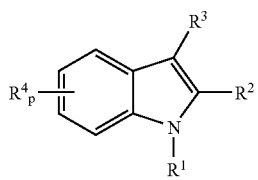

I and pharmaceutically acceptable salts and prodrugs thereof.

In the compounds of formula I,
$R^1$ is selected from
(a) —X-Aryl-Y-Z, and
(b) —X-Heteroaryl-Y-Z,
where Aryl and Heteroaryl are unsubstituted or substituted with 1-3 groups independently selected from A;
Aryl is phenyl or naphthyl;
Heteroaryl is a monocyclic or fused bicyclic aromatic ring structure containing 1-4 heteroatoms independently selected from N, O, and $S(O)_n$; (Note that S(O) and $S(O)_2$ are included in the ring structure through the S atom, and that Heteroaryl may be a benzene ring that is fused to an aromatic heterocycle, such as occurs in indole.);
X is a bond or a divalent group selected from $CH_2$, $CH(CH_3)$, $C(CH_3)_2$, and $C_3$-$C_6$cycloalkylidene;
Y is a divalent group selected from —CH=CH—, —CH(OH)CH(OH)—, —OCR$^7$R$^8$—, —CR$^7$R$^8$—, and —CH$_2$CR$^5$R$^6$—;
Z is selected from the group consisting of —CO$_2$H and tetrazole;
A is selected from the group consisting of $C_{1-4}$ alkyl, $C_{1-4}$ alkenyl, —OC$_{1-4}$ alkyl, and halogen, wherein alkyl, alkenyl, and —Oalkyl are each optionally substituted with 1-5 halogens;
$R^5$, $R^6$, $R^7$, and $R^8$ are each independently selected from the group consisting of H, halogen, $C_1$-$C_5$ alkyl, —OC$_1$-$C_5$ alkyl, $C_2$-$C_5$ alkenyl, —OC$_2$-$C_5$ alkenyl, $C_{3-6}$ cycloalkyl, phenyl, and —CO$_2$H, wherein $C_1$-$C_5$ alkyl, —OC$_1$-$C_5$ alkyl, $C_2$-$C_5$ alkenyl, —OC$_2$-$C_5$ alkenyl, $C_{3-6}$ cycloalkyl, and phenyl are optionally substituted with 1-5 halogens, and $C_{3-6}$ cycloalkyl and phenyl are further optionally substituted with 1-3 groups independently selected from $C_1$-$C_3$ alkyl and —OC$_1$-$C_3$ alkyl, said $C_1$-$C_3$ alkyl and —OC$_1$-$C_3$ alkyl being optionally substituted with 1-3 halogens;
Or alternatively $R^7$ and $R^8$ may be joined to form a $C_3$-$C_6$ cycloalkyl group, said $C_3$-$C_6$ cycloalkyl group being optionally substituted with 1-3 halogens;
Or alternatively, when $R^1$ is —X-Phenyl-Y-Z, Y is —OCR$^7$R$^8$, and $R^7$ is selected from the group consisting of H, halogen, $C_1$-$C_5$ alkyl, —OC$_1$-$C_5$ alkyl, $C_{2-5}$ alkyl, —OC$_{2-5}$ alkyl, $C_{3-6}$ cycloalkyl, and phenyl, then $R^8$ may optionally be a 1-2-carbon bridge connected to the phenyl ring at the position ortho to Y, thereby yielding a 5 or 6-membered heterocyclic ring fused to the phenyl ring;
$R^2$ is $C_1$-$C_4$ alkyl, which is optionally substituted with 1-5 halogens;
$R^3$ is selected from the following substituent groups:
(a) benzisoxazolyl,
(b) benzisothiazolyl,
(c) benzpyrazolyl,
(d) Aryl,
(e) —C(=O)Aryl,
(f) —C(=O)Heteroaryl,
(g) —OAryl,
(h) —OHeteroaryl,
(i) —S(O)$_n$Aryl, and
(j) —S(O)$_n$Heteroaryl,
wherein $R^3$ is optionally substituted with 1-3 substituent groups independently selected from halogen, $C_{1-3}$alkyl, —OC$_{1-3}$alkyl, and —SC$_{1-3}$alkyl, wherein $C_{1-3}$alkyl, —OC$_{1-3}$alkyl, and —SC$_{1-3}$alkyl are optionally substituted with 1-5 halogens;

each $R^4$ is optionally selected from H, halogen, $C_1$-$C_5$ alkyl and —$OC_1$-$C_5$ alkyl, wherein $C_1$-$C_5$ alkyl and —$OC_1$-$C_5$ alkyl are optionally substituted with 1-5 halogens;

n is an integer from 0-2; and p is an integer from 1 to 3.

In the above definitions and subsequent definitions, alkyl groups may be either linear or branched, unless otherwise specified.

The present compounds are effective in lowering glucose, lipids, and insulin in diabetic patients and in non-diabetic patients that have impaired glucose tolerance and/or are in a pre-diabetic condition. The compounds are expected to be efficacious in the treatment of non-insulin dependent diabetes mellitus (NIDDM) in human and other mammalian patients, particularly in the treatment of hyperglycemia and in the treatment of conditions associated with NIDDM, including hyperlipidemia, dyslipidemia, obesity, hypercholesterolemia, hypertriglyceridemia, atherosclerosis, vascular restenosis, inflammatory conditions, and other PPAR mediated diseases, disorders and conditions.

DETAILED DESCRIPTION OF THE INVENTION

The invention has numerous embodiments. It provides compounds of formula I, including pharmaceutically acceptable salts of these compounds, prodrugs of these compounds, and pharmaceutical compositions comprising these compounds and a pharmaceutically acceptable carrier.

In preferred embodiments, $R^3$ is selected from the group consisting of 3-benzisoxazolyl, —O-Phenyl, and —C(=O)Phenyl, wherein $R^3$ is optionally substituted with 1-3 substituents independently selected from halogen, —$OC_1$-$C_3$alkyl, and $C_{1-3}$alkyl, wherein said —$OC_1$-$C_3$alkyl and $C_1$-$C_3$alkyl are optionally substituted with 1-5 halogens.

In preferred embodiments of the invention, $R^1$ is —X-Phenyl-Y-Z, where Phenyl is unsubstituted or substituted with 1-3 groups independently selected from A.

A subset of compounds of Formula I includes compounds in which X is a bond.

A subset of compounds of Formula I includes compounds in which X is $CH_2$.

In a desirable subset of compounds, Y is —$OCR^7R^8$—, $R^7$ is selected from the group consisting of H and $C_1$-$C_3$ alkyl, and $R^8$ is $C_1$-$C_3$ alkyl, where $R^7$ and $R^8$ are optionally substituted with 1-3 halogens.

In another desirable subset of compounds, Y is —$OCR^7R^8$—, $R^7$ is selected from H and $C_1$-$C_3$ alkyl, and $R^8$ is $C_1$-$C_3$ alkyl.

In another useful set of compounds, Y is —$CH_2CHR^6$—, where $R^6$ is selected from $C_{1-3}$alkyl and —$OC_{1-3}$ alkyl, which are optionally substituted with 1-3 halogens.

In another set of compounds, Y is —$CH_2CHR^6$—, where $R^6$ is —$OC_{1-3}$ alkyl, which is optionally substituted with 1-3 halogens.

In preferred embodiments, A is selected from the group consisting of $C_1$-$C_3$alkyl, $CF_3$, —$OCH_3$, —$OCF_3$, and halogen.

A preferred subset of compounds includes compounds in which $R^2$ is $C_{1-3}$ alkyl or $CF_3$.

In many preferred compounds, $R^3$ is —C(=O)Phenyl, where $R^3$ is optionally substituted with 1-3 substituents independently selected from —$OCH_3$, —$OCF_3$, and halogen.

In other useful compounds, $R^3$ is 3-benzisoxazolyl or aryl, which is optionally substituted with 1-3 substituents independently selected from halogen, $OCH_3$, $OCF_3$, $CH_3$, and $CF_3$.

In another subset of compounds, $R^3$ is 3-benzisoxazolyl, aryl, —OPhenyl, or —SPhenyl, where $R^3$ is optionally substituted with 1 substituent selected from halogen, $OCH_3$, $OCF_3$, and $CF_3$.

In another subset of compounds, $R^1$ is —X-Pyridinyl-Y-Z.

A subset of compounds includes compounds in which p is 1.

Preferred compounds generally have a group Z which is —$CO_2H$.

In preferred sets of compound, $R^1$ is generally

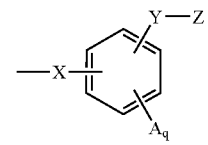

where X is selected from the group consisting of a bond, $CH_2$, $CH(CH_3)$, $C(CH_3)_2$, and $C_3$-$C_6$cycloalkylidene;

Y is selected from the group consisting of —$OCR^7R^8$— and $CH_2CR^5R^6$;

Z is selected from —$CO_2H$ and tetrazole;

A is selected from $C_1$-$C_3$ alkyl, $CF_3$, —$OCH_3$, —$OCF_3$, and halogen;

$R^5$, $R^6$, and $R^7$ are each independently selected from the group consisting of H, halogen, $C_1$-$C_3$ alkyl, and —$OC_1$-$C_3$ alkyl, and $R^8$ is selected from the group consisting of halogen, $C_1$-$C_3$ alkyl, and —$OC_1$-$C_3$ alkyl, wherein $C_1$-$C_3$ alkyl and —$OC_1$-$C_3$ alkyl of $R^5$, $R^6$, $R^7$, and $R^8$ are each optionally substituted with 1-3 halogens;

q is an integer from 0-3;

p is 1;

$R^2$ is selected from $CF_3$ and $C_1$-$C_3$ alkyl;

$R^3$ is selected from the group consisting of
(a) 3-benzisoxazolyl,
(b) 3-benzisothiazolyl,
(c) 3-benzpyrazolyl,
(d) Aryl
(e) —C(=O)Phenyl,
(f) —C(=O)Heteroaryl,
(g) —OPhenyl,
(h) —OHeteroaryl,
(i) —S(O)$_n$Phenyl, and
(j) —S(O)$_n$Heteroaryl,
  wherein Heteroaryl is selected from the group consisting of pyridyl and quinolyl,
  n is an integer from 0-2, and
  $R^3$ is optionally substituted with 1-3 groups independently selected from halogen, —$OC_1$-$C_3$alkyl, and $C_{1-3}$alkyl, wherein said —$OC_1$-$C_3$alkyl and $C_1$-$C_3$alkyl are optionally substituted with 1-5 halogens.

A desirable subset of the compounds described immediately above have the following substituents:

X is a bond or $CH_2$;
Y is —$OCR^7R^8$— or —$CH_2CR^5R^6$—;
Z is —$CO_2H$;
A is selected from $CH_3$, $CF_3$, —$OCH_3$, —$OCF_3$, and halogen;

$R^5$ is H;

$R^6$ is selected from the group consisting of H, $C_1$-$C_3$ alkyl, and —$OC_1$-$C_3$ alkyl, wherein $C_1$-$C_3$ alkyl and —$OC_1$-$C_3$ alkyl are optionally substituted with 1-3 halogens;

$R^7$ is selected from the group consisting of H and $C_1$-$C_3$ alkyl;

$R^8$ is $C_1$-$C_3$ alkyl;

$R^2$ is $CH_3$;

$R^3$ is selected from the group consisting of
(a) 3-benzisoxazolyl,
(b) Aryl,
(c) —C(=O)Phenyl,
(d) —C(=O)Pyridyl, and
(e) —C(=O)Quinolyl,
wherein $R^3$ is optionally substituted with 1-3 groups independently selected from halogen, —$OC_1$-$C_3$alkyl, and $C_{1-3}$alkyl, wherein said —$OC_1$-$C_3$alkyl and $C_1$-$C_3$alkyl are optionally substituted with 1-5 halogens; and q is an integer from 0-3.

In preferred groups of the above compounds, Y is —$OCR^7R^8$—, $R^7$ is H, and $R^8$ is $C_{1-3}$alkyl, which is optionally substituted with 1-3 halogens.

In other preferred groups of the above compounds, Y is —$CH_2CR^5R^6$—, $R^5$ is H, and $R^6$ is $C_{1-3}$alkyl or —$OC_{1-3}$ alkyl, where $C_{1-3}$ alkyl and —$OC_{1-3}$ alkyl are optionally substituted with 1-3 halogen atoms.

In preferred compounds, the X and —YZ substitutents on the phenyl group above are meta or para to one another, and in more preferred compounds, X and —YZ are meta with respect to one another, as shown below as Formula IA.

Compounds having Formula IA as shown below, and pharmaceutically acceptable salts thereof, have especially useful properties in treating insulin resistance, type 2 diabetes, and dyslipidemia that is associated with type 2 diabetes and insulin resistance:

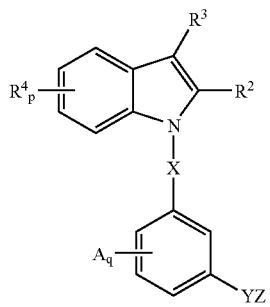

1A

In the compounds of Formula IA, X is a bond or $CH_2$;

Y is —$OC^*R^7R^8$— or —$CH_2C^*R^5R^6$—;

Z is —$CO_2H$;

A is selected from $CH_3$, $CF_3$, —$OCH_3$, —$OCF_3$, and halogen;

q is 0 or 1;

$R^4$ is $C_{1-3}$alkyl, $CF_3$, —$OCH_3$, or —$OCF_3$;

p is 0 or 1;

$R^5$ is selected from H and $C_1$-$C_3$ alkyl, wherein $C_1$-$C_3$ alkyl is optionally substituted with 1-3 halogens;

$R^6$ is $C_1$-$C_3$ alkyl or —$OC_1$-$C_3$ alkyl, wherein $C_1$-$C_3$ alkyl, and —$OC_1$-$C_3$ alkyl are optionally substituted with 1-3 halogens;

$R^7$ is selected from the group consisting of H and $C_1$-$C_3$ alkyl, which is optionally substituted with 1-3 halogens;

$R^8$ is $C_1$-$C_3$ alkyl, which is optionally substituted with 1-3 halogens;

$R^2$ is $CH_3$; and $R^3$ is selected from the group consisting of
(a) 3-benzisoxazolyl,
(b) —O-Phenyl, and
(c) —C(=O)Phenyl,
where $R^3$ is optionally substituted with 1-3 groups independently selected from halogen, —$OC_1$-$C_3$alkyl, and $C_{1-3}$alkyl, wherein said —$OC_1$-$C_3$alkyl and $C_1$-$C_3$alkyl are optionally substituted with 1-5 halogens.

In a subset of the compounds described immediately above, p is 1.

The carbon atom which is indicated with an asterisk (C*) in the structures above, when Y is —$OC^*H(R^8)$— or —$CH_2C^*H(R^6)$—, is an asymmetric carbon. Generally, both the R and S stereochemical configurations at the carbon C* are active, though they have somewhat different activities in terms of the amount of PPARα and PPARγ activity.

Preferred sets of compounds of Formula IA in which X is a bond have the following substituents:

Y is —$OC^*R^7R^8$—;

$R^4$ is $CH_3$, $CF_3$, —$OCH_3$, or —$OCF_3$;

p is 0 or 1;

$R^7$ is H; and $R^8$ is $C_1$-$C_3$ alkyl, which is optionally substituted with 1-3 halogens.

These compounds have an asymmetric center on the carbon of Y. Compounds having the R and S stereochemical configuration at C* are active PPAR agonists, though they have somewhat different activities in terms of the relative amounts of PPARα and PPARγ activity.

In another preferred subset of compounds of formula IA, X is $CH_2$;

Y is —$OC^*R^7R^8$—;

$R^4$ is $CH_3$, $CF_3$, —$OCH_3$, or —$OCF_3$;

p is 0 or 1;

$R^7$ is H; and $R^8$ is $C_1$-$C_3$ alkyl, which is optionally substituted with 1-3 halogens.

These compounds also have an asymmetric center on the carbon of Y. Compounds having the R and S stereochemical configuration at C* are active PPAR agonists, though they have somewhat different activities in terms of the relative amounts of PPARα and PPARγ activity.

In other preferred subsets of compounds of Formula IA, where X is either $CH_2$ or a bond, $R^3$ is —C(=O)Phenyl, which is optionally substituted with 1-2 groups independently selected from the group consisting of Cl, $CH_3$, $CF_3$, —$OCH_3$, and —$OCF_3$.

In a subset of the compounds above, p is 1.

Structures of specific compounds are disclosed in Tables 1-4. The names are provided for the compounds in separate Tables 1A-4A. Each compound is given the same number in the two sets of tables. Each compound is a specific embodiment of the current invention. The syntheses of some of these compounds are also provided in the Examples.

The compounds of this invention can be used in pharmaceutical compositions comprising the compound or a pharmaceutically acceptable salt thereof and a pharmaceutically acceptable carrier. The compounds of this invention can also be used in pharmaceutical compositions in which a compound of Formula I or a pharmaceutically acceptable salt thereof is the only active ingredient.

The compounds of the invention and pharmaceutically acceptable salts thereof can be used in the manufacture of medicaments for the treatment of type 2 diabetes mellitus in a human or other mammalian patient.

Some of the compounds of this invention were disclosed in a provisional application which was filed after the filing dates of the two U.S. Provisional Applications from which priority is claimed in this application, to illustrate the use of these compounds in the invention disclosed in the later application. The seven compounds are listed below according to where they are disclosed herein:

1. Tables 1 and 1A, Compound 1
2. Tables 1 and 1A, Compound 10
3. Tables 2 and 2A, Compound 8; also Example 31
4. Tables 2 and 2A, Compound 25
5. Tables 3 and 3A, Compound 29
6. Tables 3 and 3A, Compound 60; also Example 29
7. Tables 3 and 3A, Compound 78

It is to be understood that the invention herein includes the generic claims as written, and furthermore includes each of the generic claims with a disclaimer of one or more of the seven compounds listed above. Such a disclaimer may be made during examination. The compounds themselves are also claimed.

The compounds as defined above may be used in the following methods to treat diseases, as well as other diseases not listed below:

(1) a method for treating non-insulin dependent diabetes mellitus (type 2 diabetes) in a human or other mammalian patient in need of such treatment which comprises administering to the patient a therapeutically effective amount of a compound of Formula I;

(2) a method for treating or controlling hyperglycemia in a human or other mammalian patient in need of such treatment which comprises administering to the patient a therapeutically effective amount of a compound of Formula I;

(3) a method for treating or controlling the metabolic syndrome in a human or other mammalian patient in need of such treatment which comprises administering to the patient a therapeutically effective amount of a compound of Formula I;

(4) a method for treating or controlling obesity in a human or other mammalian patient in need of such treatment which comprises administering to the patient a therapeutically effective amount of a compound of Formula I;

(5) a method for treating or controlling hypercholesterolemia in a human or other mammalian patient in need of such treatment which comprises administering to the patient a therapeutically effective amount of a compound of Formula I;

(6) a method for treating or controlling hypertriglyceridemia in a human or other mammalian patient in need of such treatment which comprises administering to the patient a therapeutically effective amount of a compound of Formula I;

(7) a method for treating or controlling one or more lipid disorders, including mixed or diabetic dyslipidemia, low HDL cholesterol, high LDL cholesterol, hyperlipidemia, hypercholesterolemia, and hypertriglyceridemia in a human or other mammalian patient in need of such treatment which comprises administering to the patient a therapeutically effective amount of a compound of Formula I;

(8) a method for reducing the risks of adverse sequelae associated with metabolic syndrome in a human or other mammalian patient in need of such treatment which comprises administering to the patient a therapeutically effective amount of a compound of Formula I; and (9) a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount to a patient in need of treatment:

(1) type 2 diabetes, and especially hyperglycemia;
(2) metabolic syndrome;
(3) obesity; and
(4) hypercholesterolemia;

Definitions

"Ac" is acetyl, which is $CH_3C(O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms, unless otherwise stated. The term also includes a monocyclic ring fused to an aryl group. Examples of cycloalkyl include cyclopropyl, cyclopentyl, cyclohexyl, cycloheptyl, and the like.

A cycloalkylidene group is a divalent cycloalkane radical in which both attachments are at the same carbon. For example, the cyclopropyl group of 1,1-dimethylcyclopropane is a cyclopropylidene group.

"Aryl" (and "arylene") when used to describe a substituent or group in a structure means a monocyclic, bicyclic or tricyclic compound in which all the rings are aromatic and which contains only carbon ring atoms. The term "aryl" can also refer to an aryl group that is fused to a cycloalkyl or heterocycle. "Heterocyclyl," "heterocycle," and "heterocyclic" means a fully or partially saturated monocyclic, bicyclic or tricyclic ring system containing at least one heteroatom selected from N, S and O, each of said rings having from 3 to 10 atoms. Examples of aryl substituents include phenyl and naphthyl. Aryl rings fused to cycloalkyls are found in indanyl, indenyl, and tetrahydronaphthyl. Examples of aryl fused to heterocyclic groups are found in 2,3-dihydrobenzofuranyl, benzopyranyl, 1,4-benzodioxanyl, and the like. Examples of heterocycles include tetrahydrofuran, piperazine, and morpholine. Preferred aryl groups are phenyl or naphthyl. Phenyl is generally the most preferred.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites of other compounds, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention. A non-limiting example of a prodrug of the carboxylic acids of this invention would be an ester of the carboxylic acid group, for example a $C_1$ to $C_6$ ester, which may be linear or branched, which metabolizes to a carboxylic acid of this invention. An ester which has functionality that makes it more easily hydrolyzed after administration to a patient may also be a prodrug.

Prodrugs of the class of compounds of this invention may be described as compounds having the Formula I, wherein Z is a group that is easily metabolized under physiological conditions during or after administration to a mammalian or human patient to yield a compound where Z is a carboxylic acid group, or a salt thereof (in solution).

Examples of prodrugs of Formula I include compounds in which Z is —$CO_2R^a$, where the $OR^a$ group can be —$OR^b$, —$OCH_2OR^b$, —$OCH(CH_3)OR^b$, —$OCH_2OC(O)R^b$, —$OCH(CH_3)OC(O)R^b$, —$OCH_2OC(O)OR^b$, and —$OCH(CH_3)OC(O)OR^b$, where $OR^b$ is selected from $C_{1-6}$ alkyl optionally substituted with one or two groups selected from —$CO_2H$, —$CONH_2$, —$NH_2$, —OH, —OAc, —NHAc, and phenyl.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ subtype, resulting in mixed PPARα/γ agonism or in agonism of mainly the PPARα subtype. Some compounds (generally less preferred) may also be PPARδ ligands and have PPARδ activity in addition to their other PPAR activity. The compounds of this invention are useful in treating or controlling diseases, disorders or conditions which are mediated by one or more ligands of the individual PPAR subtypes (e.g. γ or α) or a combination of PPAR subtypes (e.g. α/γ). One aspect of the present invention provides a method for the treatment and control of diseases that can be mediated by administration of a PPAR agonist or partial agonist, such as type 2 diabetes. One aspect of the present invention provides a method for the treatment and control of such diseases, disorders, or conditions in a mammal which comprises administering to such mammal a therapeutically effective amount of a compound of Formula I. Compounds of the present invention may be useful in treating or controlling many PPAR mediated diseases and conditions, including, but not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, and Alzheimer's disease.

The compounds may also have utility in treating osteoporosis. The compounds of this invention may treat osteoporosis or reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors, niacin, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, and 250 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure;

(b) biguanides such as metformin and phenformin;

(c) protein tyrosine phosphatase-1B (PTP-1B) inhibitors, (d) dipeptidyl peptidase IV (DP-IV) inhibitors;

(e) insulin or insulin mimetics;

(f) sulfonylureas such as tolbutamide and glipizide, or related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, and (viii) phenolic anti-oxidants, such as probucol;

(i) PPARα/γ dual agonists, such as KRP-297;

(j) PPARδ agonists such as those disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, and (q) GLP-1 analogs, such as exendins.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C. For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptorγ (PPARγ) and PPARδ ligands produce distinct biological effects. 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ±test compound. (L-797733 is (3-(4-(3-phenyl-7-propyl-6-benz-[4,5]-isoxazoloxy)butyloxy))phenylacetic acid, Ex. 62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention have EC50 values in the range of 1 nM to 3000 nM.

C) In Vivo Studies

Male db/db mice (10-11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3-5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

EXAMPLES

The following Examples are provided to illustrate the invention and are not to be construed as limiting the invention in any manner. The scope of the invention is defined by the appended claims.

Specific compounds that were made are presented in Tables 1-4. The names are provided in Tables 1A-4A. The tables are provided immediately after the examples below. The compounds in the tables are grouped according to similar structural features, as follows. Representative syntheses of some of the compounds are presented below. The remaining compounds were made using similar synthetic strategies and methods and readily available reagents and starting materials. Such syntheses are readily apparent to practitioners in the field of synthetic organic chemistry.

Table 1: $R^3$ is Phenoxy or Thiophenoxy;
Table 2: $R^3$ is Benzisoxazole;
Table 3: $R^3$ is Benzoyl; and
Table 4: $R^3$ is Phenyl.

All compounds in Tables 1-4 were analyzed by tandem high pressure liquid chromatography—mass spectrometry (LC-MS) and/or proton NMR. LC-MS samples were analyzed using an Agilent 1100 Series high pressure liquid chromatograph coupled to a Waters Micromass ZQ mass spectrometer. The column used was a Waters XTerra and compounds were eluted using a gradient elution program (10% B to 100% B in 4.5 min) with a flow rate of 2.5 ml/min. Solvent A: water containing 0.06% trifluoroacetic acid. Solvent B: acetonitrile containing 0.05% trifluoroacetic acid. Retention times are given in minutes.

Syntheses of Compounds in which $R^3$ is Benzoyl (Table 3)

Example 1

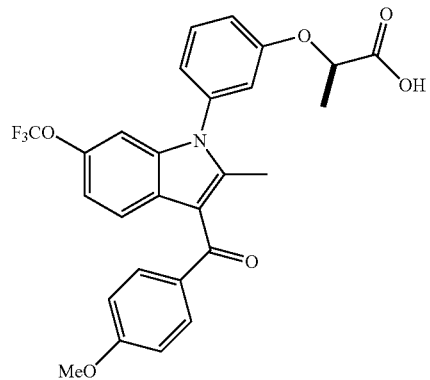

(2R)-2-{3-[3-(4-methoxy)benzoyl-2-methyl-6-(trifluoromethoxy)-1H-indol-1-yl]phenoxy}propanoic acid Step 1: 1-(3-methoxy)phenyl-2-methyl-6-trifluoromethoxyindole (1): 2-Methyl-6-trifluoromethoxyindole (645 mg, 3.0 mmole), 3-bromoanisole (0.456 ml, 3.6 mmole), sodium t-butoxide (404 mg, 4.2 mmole), trisdibenzylidine dipalladium (206 mg, 0.225 mmole) and 2-di-t-butylphosphinobiphenyl (201 mg, 0.675 mmole) were stirred in toluene at 80° C. and monitored by TLC (3/1 hexanes/methylene chloride) or reversed phase HPLC until complete. The reaction mixture was then cooled, filtered over celite, and the filtrate evaporated to give a crude isolate, which was purified by silica gel chromatography to give the title compound.

$^1$H NMR (500 MHz, CDCl$_3$): δ 7.53 (d, Ph, 1H), 7.48 (t, Ph, 1H), 7.05 (dd, Ph, 1H), 7.02 (m, Ph, 2H), 6.95 (dd, ph, 1H), 6.89 (t, Ph, 1H), 6.42 (s, Ph, 1H), 3.88 (s, OCH$_3$, 3H), 2.33 (s, 2-CH$_3$, 3H).

Step 2: 1-(3-hydroxy)phenyl-2-methyl-6-trifluoromethoxyindole (2): 460 mg (1.43 mmole) of (1) was dissolved in 7 mL of dichloromethane at 0° C. Boron tribromide (1.0 N, 2.86 mL) in dichloromethane was added, the cooling bath was removed and the reaction was stirred at room temperature overnight. The reaction was then quenched with ice for 30 minutes and partitioned. The organic was washed with water and dried over sodium sulfate. After filtering the drying agent, the filtrate was evaporated and the residue chromatographed over silica gel to give the title compound.

$^1$H NMR (500 MHz, CDCl$_3$): δ 7.51 (d, Ph, 1H), 7.42 (t, Ph, 1H), 7.00 (d, Ph, 1H), 6.98 (s, Ph, 1H), 6.95 (dd, ph, 1H), 6.92 (dd, Ph, 1H), 6.82 (t, Ph, 1H), 6.39 (s, Ph, 1H), 5.03 (s, OH, 1H), 2.31 (s, 2-CH$_3$, 3H).

Step 3: 1-(3-hydroxy)phenyl-2-methyl-3-(4-methoxy)benzoyl-6-trifluoromethoxyindole (3): 242 mg (0.788 mmole) of (2) was dissolved in methylene chloride (4 ml) and cooled to −20° C. A solution of diethylaluminum chloride in toluene (1.8M, 1.23 ml) was added slowly (over 1-2 minutes) and stirred for 5-15 minutes. Then added a solution of 4-methoxybenzoyl chloride (377 mg, 2.21 mmole) in methylene chloride (1 mL) and allowed to stir overnight while slowly reaching room temperature. Added pH 7.0 buffer dropwise until gas evolution ceased, then partitioned. The aqueous layer was extracted twice more with methylene chloride, and then the combined organic layers were washed twice with saturated NaCl solution, dried over sodium sulfate, filtered and evaporated. The crude isolate was then dissolved in methanol (5 mL) and sodium hydroxide solution (1.0 M, 1.6 mL) was added. Monitored by TLC for disappearance of di-acyl indole, then neutralized with HCl (1.0 M, 1.6 mL). The reaction mixture was then diluted with water and extracted with ethyl acetate. The ethyl acetate layer was dried over sodium sulfate, filtered, evaporated and the residue chromatographed by silica gel chromatography to give the title compound.

$^1$H NMR (500 MHz, CDCl$_3$): δ 7.84 (d, Ph, 2H), 7.46 (d, Ph, 1H), 7.42 (t, Ph, 1H), 7.06 (dd, Ph, 1H), 6.98 (m, Ph, 3H), 6.95 (s, ph, 1H), 6.92 (dd, Ph, 1H), 6.86 (t, Ph, 1H), 6.38 (s, OH, 1H), 3.91 (s, OCH3, 3H), 2.35 (s, 2-CH$_3$, 3H).

Step 4: (2R)-2-{3-[3-(4-methoxy)benzoyl-2-methyl-6-(trifluoromethoxy)-1H-indol-1-yl]phenoxy}propanoic acid ethyl ester (4): 45.9 mg (0.100 mmole) of (3) was dissolved in tetrahydrofuran (0.5 mL) and cooled to 0° C. Triphenylphosphine (34 mg, 0.130 mmole) and (S)-ethyl lactate (14.7 μL, 0.130 mmole) were then added, followed by diethylazodicarboxylate (20.5 μL, 0.13 mmole). The reaction was stirred overnight and then directly chromatographed on silica gel to give the title compound.

$^1$H NMR (500 MHz, CDCl$_3$): δ 7.88 (d, Ph, 2H), 7.53 (t, Ph, 1H), 7.47 (d, Ph, 1H), 7.090 (d, Ph, 1H), 7.01 (m, Ph, 4H), 6.95 (m, Ph, 1H), 6.89 (s, Ph, 1H), 4.83 (br m, OC<u>H</u>(CH$_3$)CO$_2$Et, 1H), 3.93 (s, OCH$_3$, 3H), 4.25 (q, OCH(CH$_3$)CO$_2$C<u>H</u>$_2$CH$_3$, 2H), 2.40 (s, 2-CH$_3$, 3H), 1.70 (d, OCH(C<u>H</u>$_3$)CO$_2$Et, 3H), 1.28 (q, OCH(CH$_3$)CO$_2$CH$_2$C<u>H</u>$_3$, 3H).

Step 5: (2R)-2-{3-[3-(4-methoxy)benzoyl-2-methyl-6-(trifluoromethoxy)-1H-indol-1-yl]phenoxy}propanoic acid (5): 56 mg of (4) was dissolved in ethanol (1 mL) and aqueous sodium hydroxide (1.0 M, 0.200 mL) and stirred until hydrolysis was complete. The reaction was diluted with water, acidified with dilute aqueous HCl and extracted with ethyl acetate. The organic was dried over sodium sulfate, filtered and evaporated to give the title compound.

$^1$H NMR (500 MHz, CDCl$_3$): δ 7.87 (d, Ph, 2H), 7.54 (t, Ph, 1H), 7.45 (br s, Ph, 1H), 7.11 (br s, Ph, 1H), 7.02 (m, Ph, 4H), 6.95 (m, Ph, 2H), 4.88 (br m, OC<u>H</u>(CH$_3$)CO$_2$H, 1H), 3.93 (s, OCH$_3$, 3H), 2.41 (s, 2-CH$_3$, 3H), 1.74 (d, OCH(C<u>H</u>$_3$)CO$_2$H, 3H).

RP LC/MS: $t_R$=3.88 min, m/e 514 (M+1)

Example 2

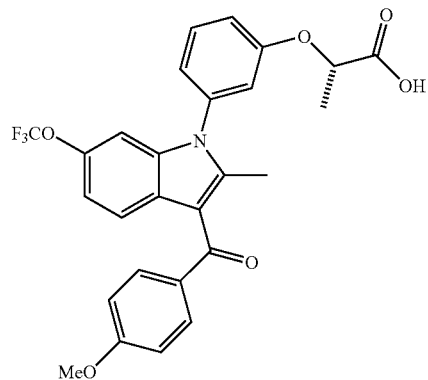

(2S)-2-{3-[3-(4-methoxy)benzoyl-2-methyl-6-(trifluoromethoxy)-1H-indol-1-yl]phenoxy}propanoic acid This compound was made using a synthetic method analogous to Example 1 and using readily available reagents and starting materials. Such a synthesis can be readily carried out by a practitioner in the field of synthetic organic chemistry.

$^1$H NMR (500 MHz, CDCl$_3$): δ 7.87 (d, Ph, 2H), 7.54 (t, Ph, 1H), 7.45 (br s, Ph, 1H), 7.11 (br s, Ph, 1H), 7.02 (m, Ph, 4H), 6.95 (m, Ph, 2H), 4.88 (br m, OC<u>H</u>(CH$_3$)CO$_2$H, 1H), 3.93 (s, OCH$_3$, 3H), 2.41 (s, 2-CH$_3$, 3H), 1.74 (d, OCH(C<u>H</u>$_3$)CO$_2$H, 3H).

RP LC/MS: $t_R$=3.88 min, m/e 514 (M+1)

Example 3

Scheme for Example 3:

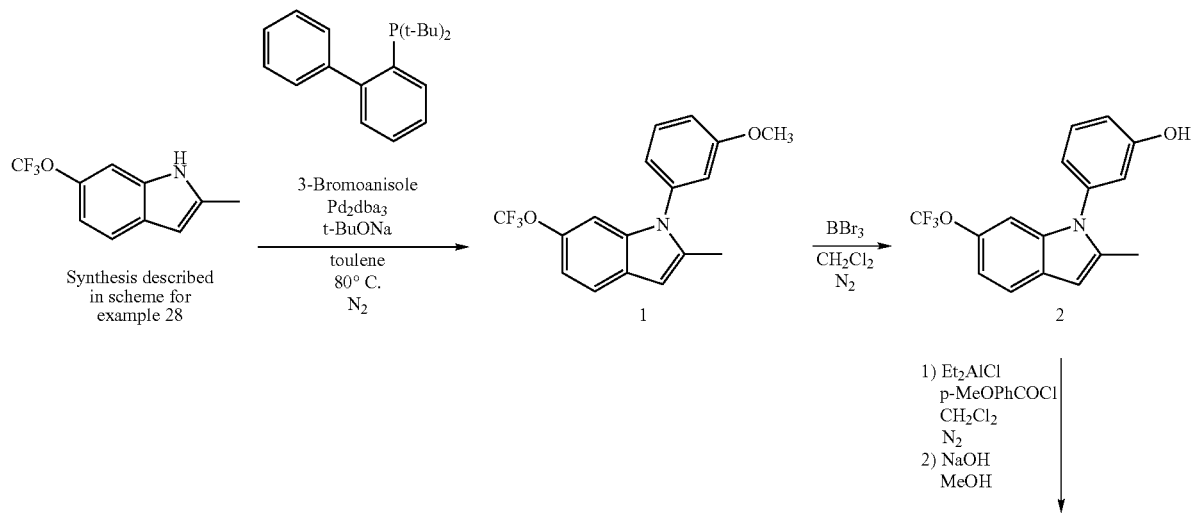

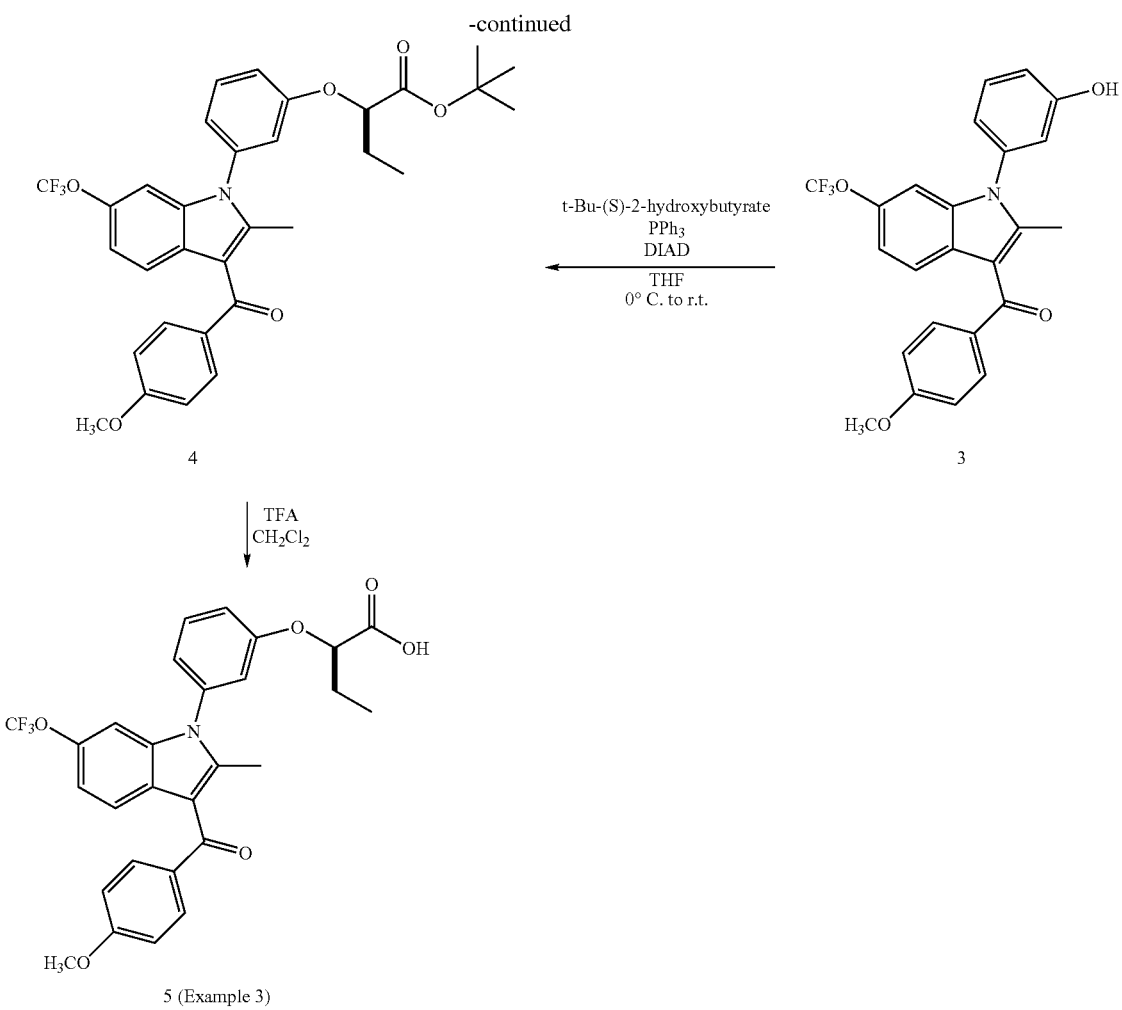

Example 3

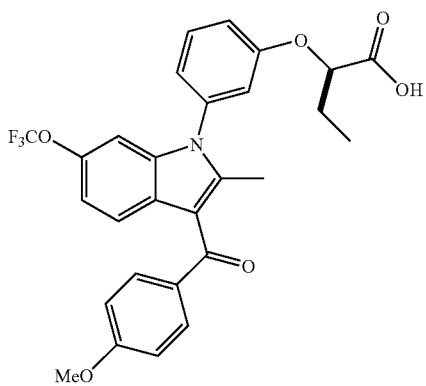

(2R)-2-{3-[3-(4-methoxy)benzoyl-2-methyl-6-(trifluoromethoxy)-1H-indol-1-yl]phenoxy}butanoic acid Step 1: 1-(3-methoxy)phenyl-2-methyl-6-trifluoromethoxyindole (1): 2-Methyl-6-trifluoromethoxyindole (645 mg, 3.0 mmole), 3-bromoanisole (0.456 ml, 3.6 mmole), sodium t-butoxide (404 mg, 4.2 mmole), trisdibenzylidine dipalladium (206 mg, 0.225 mmole) and 2-di-t-butylphosphinobiphenyl (201 mg, 0.675 mmole) were stirred in toluene at 80° C. and monitored by TLC (3/1 hexanes/methylene chloride) or reversed phase HPLC until complete. The reaction mixture was then cooled, filtered over celite, and the filtrate evaporated to give a crude isolate, which was purified by silica gel chromatography to give the title compound.

$^1$H NMR (500 MHz, CDCl$_3$): δ 7.53 (d, Ph, 1H), 7.48 (t, Ph, 1H), 7.05 (dd, Ph, 1H), 7.02 (m, Ph, 2H), 6.95 (dd, ph, 1H), 6.89 (t, Ph, 1H), 6.42 (s, Ph, 1H), 3.88 (s, OCH$_3$, 3H), 2.33 (s, 2-CH$_3$, 3H).

Step 2: 1-(3-hydroxy)phenyl-2-methyl-6-trifluoromethoxyindole (2): 460 mg (1.43 mmole) of (1) was dissolved in 7 mL of dichloromethane at 0° C. Boron tribromide (1.0 N, 2.86 mL) in dichloromethane was added, the cooling bath was removed and the reaction was stirred at room temperature overnight. The reaction was then quenched with ice for 30 minutes and partitioned. The organic was washed with water and dried over sodium sulfate. After filtering the drying agent, the filtrate was evaporated and the residue chromatographed over silica gel to give the title compound.

¹H NMR (500 MHz, CDCl₃): δ 7.51 (d, Ph, 1H), 7.42 (t, Ph, 1H), 7.00 (d, Ph, 1H), 6.98 (s, Ph, 1H), 6.95 (dd, ph, 1H), 6.92 (dd, Ph, 1H), 6.82 (t, Ph, 1H), 6.39 (s, Ph, 1H), 5.03 (s, OH, 1H), 2.31 (s, 2-CH₃, 3H).

Step 3: 1-(3-hydroxy)phenyl-2-methyl-3-(4-methoxy) benzoyl-6-trifluoromethoxyindole (3): 242 mg (0.788 mmole) of (2) was dissolved in methylene chloride (4 ml) and cooled to −20° C. A solution of diethylaluminum chloride in toluene (1.8M, 1.23 ml) was added slowly (over 1-2 minutes) and stirred for 5-15 minutes. Then added a solution of 4-methoxybenzoyl chloride (377 mg, 2.21 mmole) in methylene chloride (1 mL) and allowed to stir overnight while slowly reaching room temperature. Added pH 7.0 buffer dropwise until gas evolution ceased, then partitioned. The aqueous layer was extracted twice more with methylene chloride, and then the combined organic layers were washed twice with saturated NaCl solution, dried over sodium sulfate, filtered and evaporated. The crude isolate was then dissolved in methanol (5 mL) and sodium hydroxide solution (1.0 M, 1.6 mL) was added. Monitored by TLC for disappearance of di-acyl indole, then neutralized with HCl (1.0 M, 1.6 mL). The reaction mixture was then diluted with water and extracted with ethyl acetate. The ethyl acetate layer was dried over sodium sulfate, filtered, evaporated and the residue chromatographed by silica gel chromatography to give the title compound.

¹H NMR (500 MHz, CDCl₃): δ 7.84 (d, Ph, 2H), 7.46 (d, Ph, 1H), 7.42 (t, Ph, 1H), 7.06 (dd, Ph, 1H), 6.98 (m, Ph, 3H), 6.95 (s, ph, 1H), 6.92 (dd, Ph, 1H), 6.86 (t, Ph, 1H), 6.38 (s, OH, 1H), 3.91 (s, OCH3, 3H), 2.35 (s, 2-CH₃, 3H).

Step 4: (2R)-2-{3-[3-(4-methoxy)benzoyl-2-methyl-6-(trifluoromethoxy)-1H-indol-1-yl]phenoxy}butanoic acid t-butyl ester (4): 110 mg (0.25 mmole) of (3) was dissolved in tetrahydrofuran (1.25 mL) and cooled to 0° C. Triphenylphosphine (78.5 mg, 0.30 mmole) and t-butyl-(S)-2-hydroxybutyrate (Sigma-Aldrich, 48 mg, 0.30 mmole) were then added, followed by diisopropylazodicarboxylate (59 μL, 0.30 mmole). The reaction was stirred overnight and then directly chromatographed on silica gel to give 100 mg of the title compound. Chiral purity was assessed by chromatographic comparison on a Chiralcel AD column (heptane/isopropanol as eluents) with the opposite enantiomer (prepared as above using t-butyl-(R)-2-hydroxybutyrate in place of t-butyl-(S)-2-hydroxybutyrate).

Chiral LC: 10% isopropanol/heptane, 0.5 ml/min, λ=220 nm, Chiralcel AD column (4.6×250 mm, 10 μ):

$t_R$ (4): 12.68 min (99.7%), 14.16 (0.3%). $t_R$ of (S) enantiomer (t-butyl ester of example 2): 12.68 min (2.2%), 14.18 min (97.8%).

¹H NMR (500 MHz, CDCl₃): δ 7.87 (d, Ph, 2H), 7.51 (t, Ph, 1H), 7.47 (d, Ph, 1H), 7.08 (d, Ph, 1H), 7.00 (m, Ph, 4H), 6.93 (m, Ph, 1H), 6.89 (br t, Ph, 1H), 4.52 (t, OCH(CH₂CH₃)CO₂t-Bu, 1H), 3.93 (s, OCH₃, 3H), 2.39 (s, 2-CH₃, 3H), 2.03 (m, OCH(CH₂CH₃)CO₂t-Bu, 2H), 1.45 (s, OCH(CH₂CH₃)CO₂t-Bu, 9H), 1.13 (t, OCH(CH₂CH₃)CO₂t-Bu, 3H),

Step 5: (2R)-2-{3-[3-(4-methoxy)benzoyl-2-methyl-6-(trifluoromethoxy)-1H-indol-1-yl]phenoxy}butanoic acid (5): 17 mg (0.03 mole) of (4) was dissolved in dichloromethane (1 mL) and trifluoroacetic acid (0.5 mL, large excess) was added. The reaction was stirred until complete (monitored by TLC). Evaporated solvent and trifluoroacetic acid, reconstituted in dichloromethane, washed successively with pH 7.0 phosphate buffer (Fisher Scientific) and sodium chloride solution. The dichloromethane was dried over sodium sulfate, filtered and evaporated. The compound can then be purified by either ODS or silica gel column (0.5% to 1% acetic acid/ethyl acetate/hexanes needed for silica gel purification).

¹H NMR (500 MHz, CDCl₃): δ 7.84 (d, Ph, 2H), 7.62 (t, Ph, 1H), 7.61 (br m, Ph, 1H), 7.22 (dd, Ph, 1H), 7.17 (br m, Ph, 2H), 7.11 (m, Ph, 1H), 7.08 (m, Ph, 2H), 7.04-6.96 (br d, pH, 1H), 4.90 (m, OCH(CH₂CH₃)CO₂H, 1H), 3.93 (s, OCH₃, 3H), 2.33 (br s, 2-CH₃, 3H), 2.06 (m, OCH(CH₂CH₃)CO₂H, 2H), 1.11 (t, OCH(CH₂CH₃)CO₂H, 3H).

RP LC/MS: $t_R$=3.74 min, m/e 528 (M+1)

Examples 4-27

The following compounds were prepared in a similar manner to the examples above using analogous synthetic methods and strategies and readily available starting materials and reagents. Such methods and starting materials are readily apparent to a practitioner in the field of synthetic organic chemistry.

Example 4

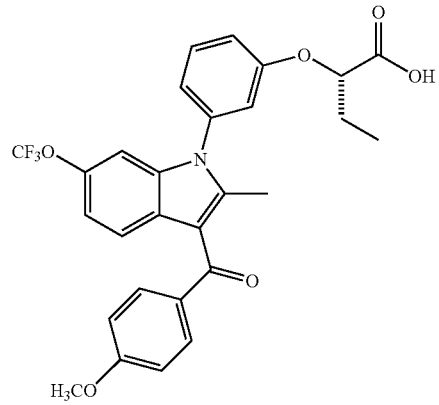

(2S)-2-{3-[3-(4-methoxy)benzoyl-2-methyl-6-(trifluoromethoxy)-1H-indol-1-yl]phenoxy}butanoic acid ¹H NMR (500 MHz, CDCl₃): δ 7.84 (d, Ph, 2H), 7.62 (t, Ph, 1H), 7.61 (br m, Ph, 1H), 7.22 (dd, Ph, 1H), 7.17 (br m, Ph, 2H), 7.11 (m, Ph, 1H), 7.08 (m, Ph, 2H), 7.04-6.96 (br d, pH, 1H), 4.90 (m, OCH(CH₂CH₃)CO₂H, 1H), 3.93 (s, OCH₃, 3H), 2.33 (br s, 2-CH₃, 3H), 2.06 (m, OCH(CH₂CH₃)CO₂H, 2H), 1.11 (t, OCH(CH₂CH₃)CO₂H, 3H).

RP LC/MS: $t_R$=3.74 min, m/e 528 (M+1).

Example 5

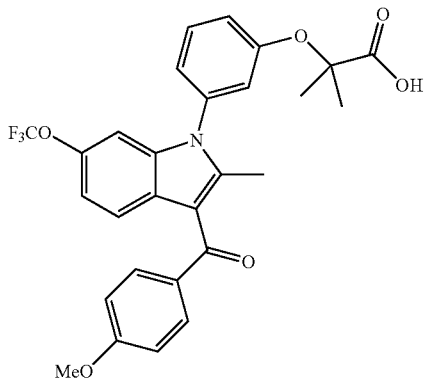

2-{3-[3-(4-methoxy)benzoyl-2-methyl-6-(trifluoromethoxy)-1H-indol-1-yl]phenoxy}-2-methylpropanoic acid $^1$H NMR (500 MHz, CDCl$_3$): δ 7.88 (br, Ph, 2H), 7.53 (t, Ph, 1H), 7.44 (d, Ph, 1H), 7.14 (d, Ph, 1H), 7.08 (d, Ph, 1H), 7.01 (m, Ph, 3H), 6.95 (d, Ph, 2H), 3.93 (s, OCH$_3$, 3H), 2.43 (br s, 2-CH$_3$, 3H), 1.70 (s, OC(CH$_3$)$_2$CO$_2$H, 6H).

RP LC/MS: t$_R$=3.96 min, m/e 528 (M+1)

Example 6

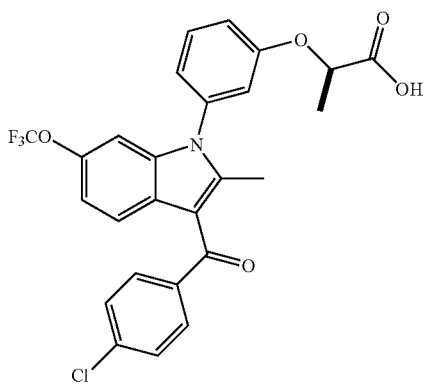

(2R)-2-{3-[3-(4-chloro)benzoyl-2-methyl-6-(trifluoromethoxy)-1H-indol-1-yl]phenoxy}propanoic acid $^1$H NMR (500 MHz, CDCl$_3$): δ 7.79 (d, Ph, 2H), 7.55 (t, Ph, 1H), 7.49 (d, Ph, 2H), 7.37 (br m, Ph, 1H), 7.12 (br m, Ph, 1H), 7.03 (br m, Ph, 2H), 6.93 (br m, Ph, 2H), 4.88 (br m, OCH(CH$_3$)CO$_2$H, 1H), 3.93 (s, OCH$_3$, 3H), 2.41 (s, 2-CH$_3$, 3H), 1.74 (d, OCH(CH$_3$H)CO$_2$H, 3H).

RP LC/MS: t$_R$=4.18 min, m/e 518 (M+1)

Example 7

(2S)-2-{3-[3-(4-chloro)benzoyl-2-methyl-6-(trifluoromethoxy)-1H-indol-1-yl]phenoxy}propanoic acid $^1$H NMR (500 MHz, CDCl$_3$): δ 7.79 (d, Ph, 2H), 7.55 (t, Ph, 1H), 7.49 (d, Ph, 2H), 7.37 (br m, Ph, 1H), 7.12 (br m, Ph, 1H), 7.03 (br m, Ph, 2H), 6.93 (br m, Ph, 2H), 4.88 (br m, OCH(CH$_3$)CO$_2$H, 1H), 3.93 (s, OCH$_3$, 3H), 2.41 (s, 2-CH$_3$, 3H), 1.74 (d, OCH(CH$_3$)CO$_2$H, 3H).

RP LC/MS: t$_R$=4.18 min, m/e 518 (M+1)

Example 8

(2R)-2-{3-[3-(4-chloro)benzoyl-2-methyl-6-(trifluoromethoxy)-1H-indol-1-yl]phenoxy}butanoic acid $^1$H NMR (500 MHz, CDCl$_3$): δ 7.79 (d, Ph, 2H), 7.55 (t, Ph, 1H), 7.50 (d, Ph, 2H), 7.37 (br m, Ph, 1H), 7.13 (br m, Ph, 1H), 7.03 (br m, Ph, 2H), 6.95 (br m, Ph, 2H), 4.72 (br m, OCH(CH$_2$CH$_3$)CO$_2$H, 1H), 2.42 (s, 2-CH$_3$, 3H), 2.11 (m, OCH(CH$_2$CH$_3$)CO$_2$H, 2H), 1.17 (t, OCH(CH$_2$CH$_3$)CO$_2$H, 3H).

RP LC/MS: t$_R$=4.01 min, m/e 532 (M+1)

Example 9

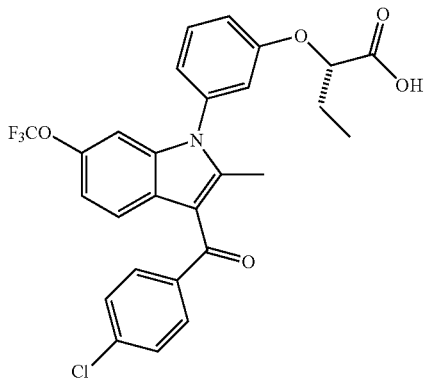

(2S)-2-{3-[3-(4-chloro)benzoyl-2-methyl-6-(trifluoromethoxy)-1H-indol-1-yl]phenoxy}butanoic acid $^1$H NMR (500 MHz, CDCl$_3$): δ 7.79 (d, Ph, 2H), 7.55 (t, Ph, 1H), 7.50 (d, Ph, 2H), 7.37 (br m, Ph, 1H), 7.13 (br m, Ph, 1H), 7.03 (br m, Ph, 2H), 6.95 (br m, Ph, 2H), 4.72 (br m, OC_H(CH$_2$CH$_3$)CO$_2$H, 1H), 2.42 (s, 2-CH$_3$, 3H), 2.11 (m, OCH(C_H$_2$CH$_3$)CO$_2$H, 2H), 1.17 (t, OCH(CH$_2$C_H$_3$)CO$_2$H, 3H).

RP LC/MS: t$_R$=4.01 min, m/e 532 (M+1)

Example 10

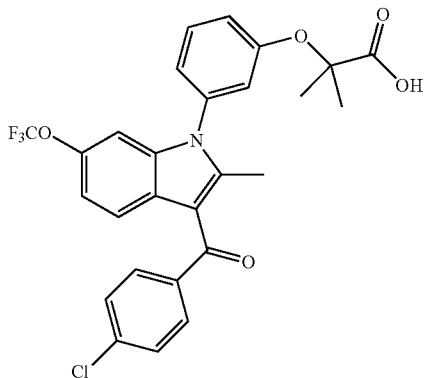

2-{3-[3-(4-chloro)benzoyl-2-methyl-6-(trifluoromethoxy)-1H-indol-1-yl]phenoxy}-2-methylpropanoic acid $^1$H NMR (500 MHz, CDCl$_3$): δ 7.79 (br, Ph, 2H), 7.53 (t, Ph, 1H), 7.44 (d, Ph, 2H), 7.37 (d, Ph, 1H), 7.15 (dd, Ph, 1H), 7.07 (dd, Ph, 1H), 7.03 (d, Ph, 1H), 6.95 (t, Ph, 1H), 6.93 (s, Ph, 1H), 2.42 (br s, 2-CH$_3$, 3H), 1.71 (s, OC(CH$_3$)$_2$CO$_2$H, 6H).

RP LC/MS: t$_R$=4.30 min, m/e 532 (M+1)

Example 11

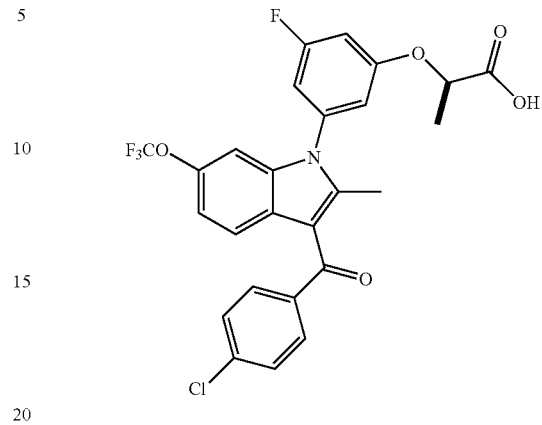

(2R)-2-{3-[3-(4-chlorobenzoyl)-2-methyl-6-(trifluoromethoxy)-1H-indol-1-yl]-5-fluorophenoxy}propanoic acid $^1$H NMR (500 MHz, CDCl$_3$): δ 7.79 (d, Ph, 2H), 7.49 (d, Ph, 2H), 7.36 (br m, Ph, 1H), 7.04 (d, Ph, 1H), 6.97 (br m, Ph, 1H), 6.86 (d, Ph, 1H), 6.78 (d, Ph, 1H), 6.72 (m, Ph, 1H), 4.85 (q, OC_H(CH$_3$)CO$_2$H, 1H), 2.43 (s, 2-CH$_3$, 3H), 1.75 (d, OCH(C_H$_3$)CO$_2$H, 3H).

RP LC/MS: t$_R$=4.21 min, m/e 536 (M+1)

Example 12

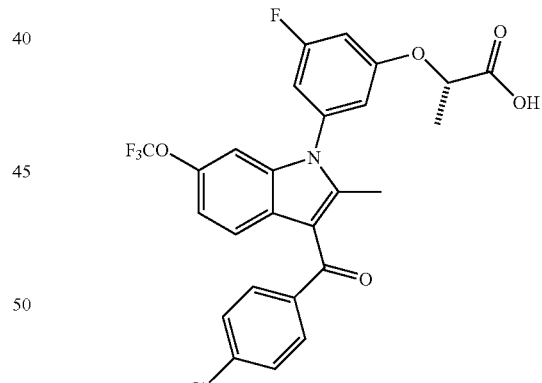

(2S)-2-{3-[3-(4-chlorobenzoyl)-2-methyl-6-(trifluoromethoxy)-1H-indol-1-yl]-5-fluorophenoxy}propanoic acid $^1$H NMR (500 MHz, CDCl$_3$): δ 7.79 (d, Ph, 2H), 7.49 (d, Ph, 2H), 7.36 (br m, Ph, 1H), 7.04 (d, Ph, 1H), 6.97 (br m, Ph, 1H), 6.86 (d, Ph, 1H), 6.78 (d, Ph, 1H), 6.72 (m, Ph, 1H), 4.85 (q, OC_H(CH$_3$)CO$_2$H, 1H), 2.43 (s, 2-CH$_3$, 3H), 1.75 (d, OCH(C_H$_3$)CO$_2$H, 3H).

RP LC/MS: t$_R$=4.21 min, m/e 536 (M+1)

Example 13

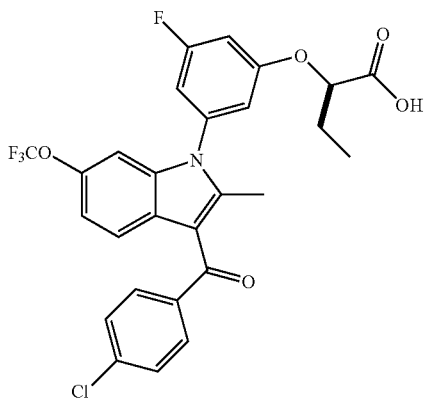

(2R)-2-{3-[3-(4-chlorobenzoyl)-2-methyl-6-(trifluoromethoxy)-1H-indol-1-yl]-5-fluorophenoxy}butanoic acid $^1$H NMR (500 MHz, CDCl$_3$): δ 7.79 (d, Ph, 2H), 7.49 (d, Ph, 2H), 7.36 (br m, Ph, 1H), 7.04 (d, Ph, 1H), 6.97 (br m, Ph, 1H), 6.86 (d, Ph, 1H), 6.78 (d, Ph, 1H), 6.73 (m, Ph, 1H), 4.68 (q, OC$\underline{H}$(CH$_2$CH$_3$)CO$_2$H, 1H), 2.43 (s, 2-CH$_3$, 3H), 2.11 (m, OCH(C$\underline{H}_2$CH$_3$)CO$_2$H, 2H), 1.16 (t, OCH(CH$_2$C$\underline{H}_3$)CO$_2$H, 3H).

RP LC/MS: t$_R$=4.05 min, m/e 550 (M+1)

Example 14

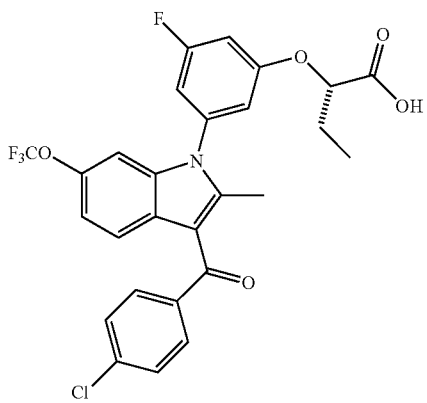

(2S)-2-{3-[3-(4-chlorobenzoyl)-2-methyl-6-(trifluoromethoxy)-1H-indol-1-yl]-5-fluorophenoxy}butanoic acid $^1$H NMR (500 MHz, CDCl$_3$): δ 7.79 (d, Ph, 2H), 7.49 (d, Ph, 2H), 7.36 (br m, Ph, 1H), 7.04 (d, Ph, 1H), 6.97 (br m, Ph, 1H), 6.86 (d, Ph, 1H), 6.78 (d, Ph, 1H), 6.73 (m, Ph, 1H), 4.68 (q, OC$\underline{H}$(CH$_2$CH$_3$)CO$_2$H, 1H), 2.43 (s, 2-CH$_3$, 3H), 2.11 (m, OCH(C$\underline{H}_2$CH$_3$)CO$_2$H, 2H), 1.16 (t, OCH(CH$_2$C$\underline{H}_3$)CO$_2$H, 3H).

RP LC/MS: t$_R$=4.05 min, m/e 550 (M+1)

Example 15

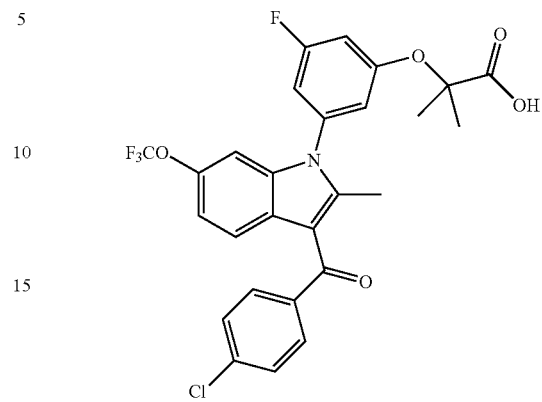

2-{3-[3-(4-chlorobenzoyl)-2-methyl-6-(trifluoromethoxy)-1H-indol-1-yl]-5-fluorophenoxy}-2-methylpropanoic acid $^1$H NMR (500 MHz, CDCl$_3$): δ 7.79 (d, Ph, 2H), 7.49 (d, Ph, 2H), 7.35 (d, Ph, 1H), 7.03 (d, Ph, 1H), 6.94 (s, Ph, 1H), 6.87 (dt, Ph, 1H), 6.80 (dt, Ph, 1H), 6.71 (m, Ph, 1H), 2.42 (s, 2-CH$_3$, 3H), 1.71 (s, OC(C$\underline{H}_3$)$_2$CO$_2$H, 6H).

RP LC/MS: t$_R$=4.41 min, m/e 550 (M+1)

Example 16

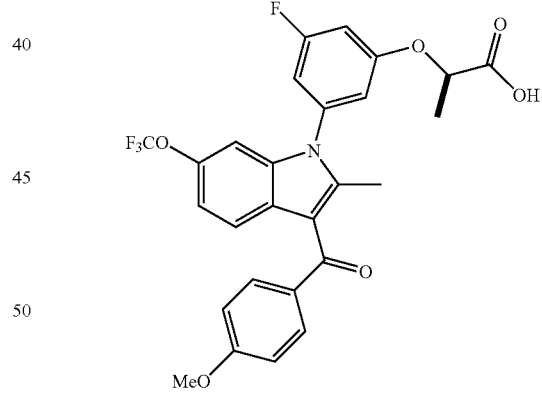

(2R)-2-{3-[3-(4-methoxybenzoyl)-2-methyl-6-(trifluoromethoxy)-1H-indol-1-yl]-5-fluorophenoxy}propanoic acid $^1$H NMR (500 MHz, CDCl$_3$): δ 7.86 (d, Ph, 2H), 7.44 (br m, Ph, 1H), 7.03 (d, Ph, 1H), 7.00 (d, Ph, 2H), 6.97 (br m, Ph, 1H), 6.85 (d, Ph, 1H), 6.79 (d, Ph, 1H), 6.73 (m, Ph, 1H), 4.86 (q, OC$\underline{H}$(CH$_3$)CO$_2$H, 1H), 3.93 (s, OCH$_3$, 3H), 2.42 (s, 2-CH$_3$, 3H), 1.75 (d, OCH(C$\underline{H}_3$)CO$_2$H, 3H).

RP LC/MS: t$_R$=3.64 min, m/e 532 (M+1)

Example 17

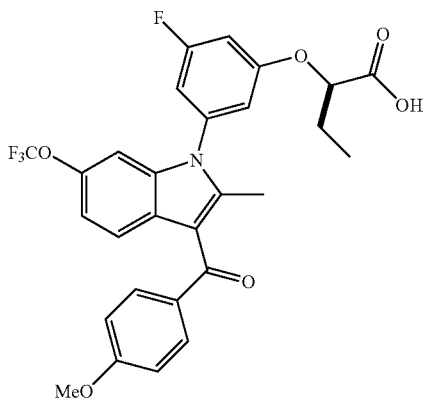

(2R)-2-{3-[3-(4-methoxybenzoyl)-2-methyl-6-(trifluoromethoxy)-1H-indol-1-yl]-5-fluorophenoxy}butanoic acid $^1$H NMR (500 MHz, CDCl$_3$): δ 7.86 (d, Ph, 2H), 7.44 (br m, Ph, 1H), 7.03 (d, Ph, 1H), 7.00 (d, Ph, 2H), 6.97 (br m, Ph, 1H), 6.86 (d, Ph, 1H), 6.78 (d, Ph, 1H), 6.73 (m, Ph, 1H), 4.67 (q, OC<u>H</u>(CH$_2$CH$_3$)CO$_2$H, 1H), 2.42 (s, 2-CH$_3$, 3H), 2.11 (m, OCH(C<u>H</u>$_2$CH$_3$)CO$_2$H, 2H), 1.16 (t, OCH(CH$_2$C<u>H</u>$_3$)CO$_2$H, 3H).

RP LC/MS: t$_R$=4.13 min, m/e 546 (M+1)

Example 18

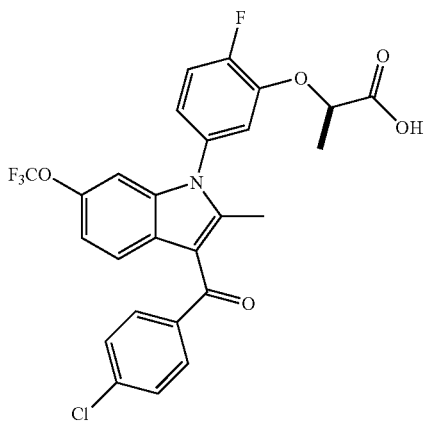

(2R)-2-{3-[3-(4-chlorobenzoyl)-2-methyl-6-(trifluoromethoxy)-1H-indol-1-yl]-4-fluorophenoxy}propanoic acid $^1$H NMR (500 MHz, CDCl$_3$): δ 7.78 (d, Ph, 2H), 7.49 (d, Ph, 2H), 7.36 (dd, Ph, 1H), 7.31 (m, Ph, 1H), 7.02 (br m, Ph, 2H), 6.96 (br d, Ph, 1H), 6.89 (d, Ph, 1H), 4.88 (m, OC<u>H</u>(CH$_3$)CO$_2$H, 1H), 2.40 (s, 2-CH$_3$, 3H), 1.76 (d, OCH(C<u>H</u>$_3$)CO$_2$H, 3H).

RP LC/MS: t$_R$=4.15 min, m/e 536 (M+1)

Example 19

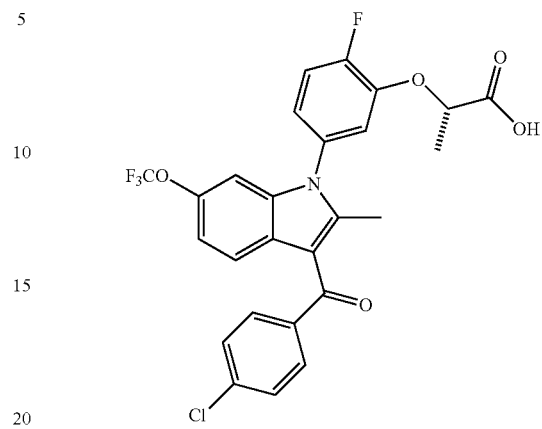

(2S)-2-{3-[3-(4-chlorobenzoyl)-2-methyl-6-(trifluoromethoxy)-1H-indol-1-yl]-4-fluorophenoxy}propanoic acid $^1$H NMR (500 MHz, CDCl$_3$): δ 7.78 (d, Ph, 2H), 7.49 (d, Ph, 2H), 7.36 (dd, Ph, 1H), 7.31 (m, Ph, 1H), 7.02 (br m, Ph, 2H), 6.96 (br d, Ph, 1H), 6.89 (d, Ph, 1H), 4.88 (m, OC<u>H</u>(CH$_3$)CO$_2$H, 1H), 2.40 (s, 2-CH$_3$, 3H), 1.76 (d, OCH(C<u>H</u>$_3$)CO$_2$H, 3H).

RP LC/MS: t$_R$=4.15 min, m/e 536 (M+1)

Example 20

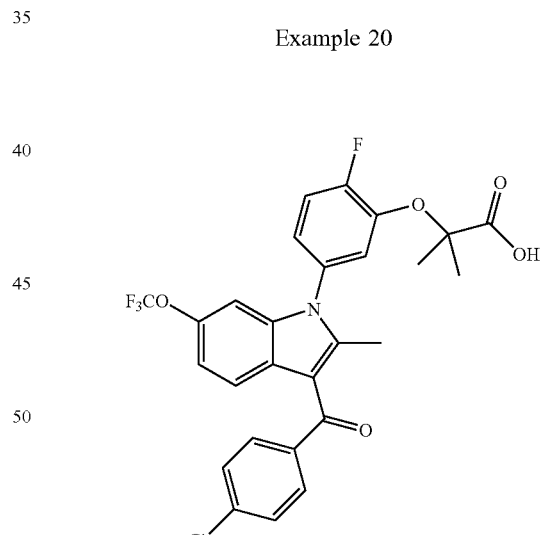

(2S)-2-{3-[3-(4-chlorobenzoyl)-2-methyl-6-(trifluoromethoxy)-1H-indol-1-yl]-4-fluorophenoxy}-2-methyl propanoic acid $^1$H NMR (500 MHz, CDCl$_3$): δ 7.79 (d, Ph, 2H), 7.49 (d, Ph, 2H), 7.36 (dd, Ph, 1H), 7.34 (m, Ph, 1H), 7.12 (m, Ph, 2H), 7.03 (br d, Ph, 1H), 6.89 (d, Ph, 1H), 2.42 (s, 2-CH$_3$, 3H), 1.70 (s, OC(C<u>H</u>$_3$)$_2$CO$_2$H, 6H).

RP LC/MS: t$_R$=4.33 min, m/e 550 (M+1)

Example 21

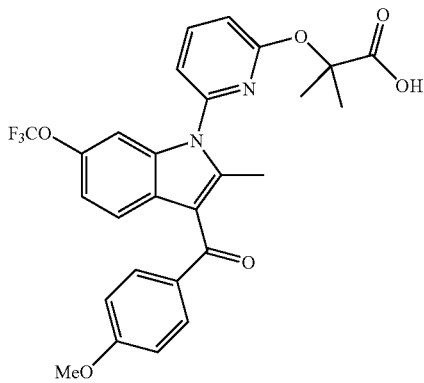

2-({6-[3-(4-methoxybenzoyl)-2-methyl-6-(trifluoromethoxy)-1H-indol-1-yl]pyridin-2-yl}oxy)-2-methylpropanoic acid $^1$H NMR (500 MHz, CDCl$_3$): δ 7.67 (d, Ph, 2H), 7.51 (m, Ph, 1H), 7.11 (d, Ph, 1H), 7.00 (s, Ph, 1H), 6.82 (m, Ph, 5H), 3.83 (s, OCH$_3$, 3H), 2.42 (s, 2-CH$_3$, 3H), 1.70 (s, OC(CH$_3$)$_2$CO$_2$H, 6H).
RP LC/MS: t$_R$=3.91 min, m/e 529 (M+1)

Example 22

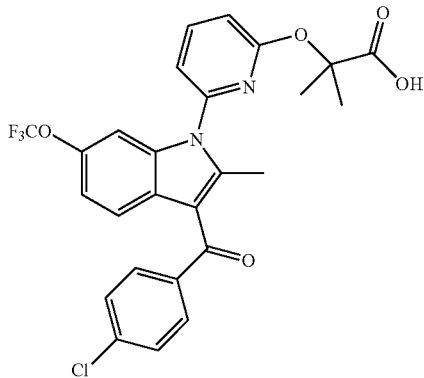

2-({6-[3-(4-chlorobenzoyl)-2-methyl-6-(trifluoromethoxy)-1H-indol-1-yl]pyridin-2-yl}oxy)-2-methylpropanoic acid $^1$H NMR (500 MHz, CDCl$_3$): δ 7.90 (t, Ph, 1H), 7.79 (d, Ph, 2H), 7.49 (d, Ph, 2H), 7.41 (d, Ph, 1H), 7.05 (m, Ph, 3H), 6.98 (d, Ph, 1H), 2.44 (s, 2-CH$_3$, 3H), 1.65 (s, OC(CH$_3$)$_2$CO$_2$H, 6H).
RP LC/MS: t$_R$=4.17 min, m/e 533 (M+1)

Example 23

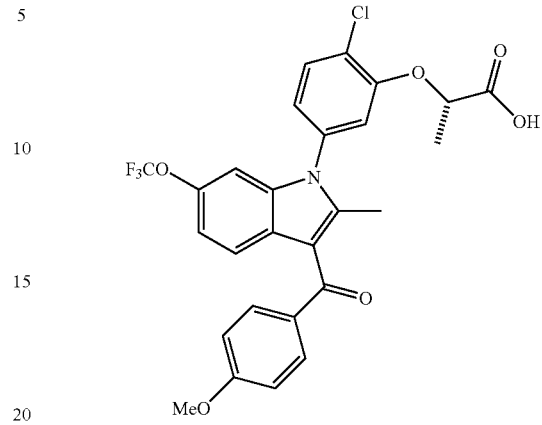

(2S)-2-{3-[3-(4-methoxybenzoyl)-2-methyl-6-(trifluoromethoxy)-1H-indol-1-yl]-4-chlorophenoxy}propanoic acid $^1$H NMR (500 MHz, CDCl$_3$): δ 7.85 (d, Ph, 2H), 7.65 (d, Ph, 1H), 7.31 (m, Ph, 1H), 7.03-6.90 (br m, Ph, 6H), 4.85 (m, OCH(CH$_3$)CO$_2$H, 1H), 3.93 (s, OCH$_3$, 3H), 2.41 (s, 2-CH$_3$, 3H), 1.78 (d, OCH(CH$_3$)CO$_2$H, 3H).

Example 24

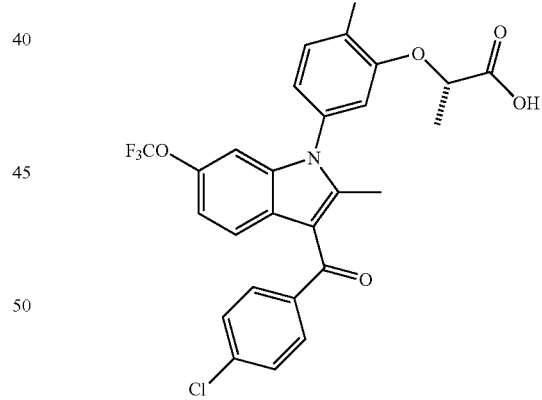

(2S)-2-{3-[3-(4-chlorobenzoyl)-2-methyl-6-(trifluoromethoxy)-1H-indol-1-yl]-4-chlorophenoxy}propanoic acid $^1$H NMR (500 MHz, CDCl$_3$): δ 7.78 (d, Ph, 2H), 7.65 (d, Ph, 1H), 7.49 (d, Ph, 2H), 7.34 (m, Ph, 1H), 7.02-6.86 (br m, Ph, 4H), 4.86 (br m, OCH(CH$_3$)CO$_2$H, 1H), 2.41 (s, 2-CH$_3$, 3H), 1.79 (d, OCH(CH$_3$)CO$_2$H, 3H).
RP LC/MS: t$_R$=4.37 min, m/e 551 (M+1)

Example 25

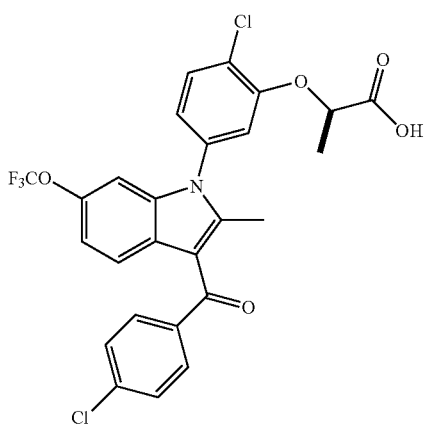

(2R)-2-{3-[3-(4-chlorobenzoyl)-2-methyl-6-(trifluoromethoxy)-1H-indol-1-yl]-4-chlorophenoxy}propanoic acid $^1$H NMR (500 MHz, CDCl$_3$): δ 7.78 (d, Ph, 2H), 7.65 (d, Ph, 1H), 7.49 (d, Ph, 2H), 7.34 (m, Ph, 1H), 7.02-6.86 (br m, Ph, 4H), 4.86 (br m, OCH(CH$_3$)CO$_2$H, 1H), 2.41 (s, 2-CH$_3$, 3H), 1.79 (d, OCH(CH$_3$)CO$_2$H, 3H).

Example 26

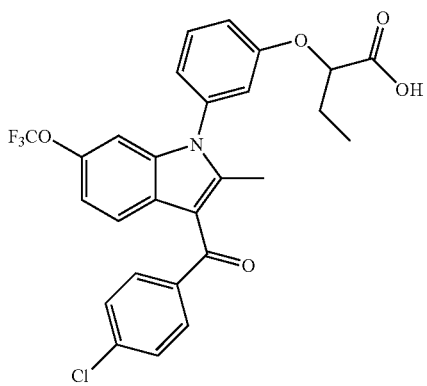

2-{3-[3-(4-chlorobenzoyl)-2-methyl-6-(trifluoromethoxy)-1H-indol-1-yl]phenoxy}butanoic acid $^1$H NMR (500 MHz, CDCl$_3$): δ 7.80 (d, Ph, 2H), 7.55 (t, Ph, 1H), 7.50 (d, Ph, 2H), 7.37 (m, Ph, 1H), 7.16-6.85 (br m, Ph, 5H), 4.60 (br s, OCH(CH$_2$CH$_3$)CO$_2$H, 1H), 2.41 (s, 2-CH$_3$, 3H), 2.11 (m, OCH(CH$_2$CH$_3$)CO$_2$H, 2H), 1.16 (t, OCH(CH$_2$CH$_3$)CO$_2$H, 3H).

Example 27

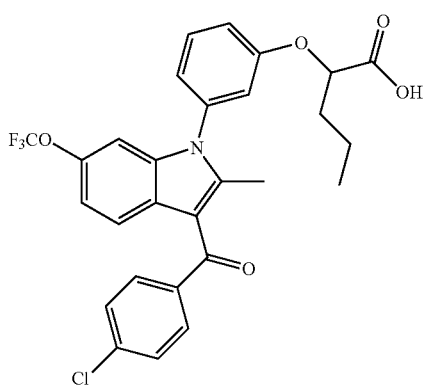

2-{3-[3-(4-chlorobenzoyl)-2-methyl-6-(trifluoromethoxy)-1H-indol-1-yl]phenoxy}pentanoic acid $^1$H NMR (500 MHz, CDCl$_3$): δ 7.79 (d, Ph, 2H), 7.54 (t, Ph, 1H), 7.49 (d, Ph, 2H), 7.38-7.34 (m, Ph, 1H), 7.12-6.89 (br m, Ph, 5H), 4.74 (br s, OCH(CH$_2$CH$_2$CH$_3$)CO$_2$H, 1H), 2.41 (s, 2-CH$_3$, 3H), 2.04 (m, OCH(CH$_2$CH$_2$CH$_3$)CO$_2$H, 2H), 1.63 (m, OCH(CH$_2$CH$_2$CH$_3$)CO$_2$H, 2H), 1.03 (t, OCH(CH$_2$CH$_2$CH$_3$)CO$_2$H, 3H).

Scheme for the Synthesis of Example 28

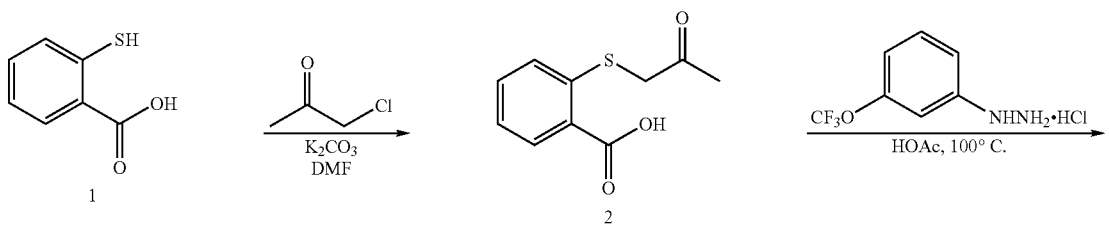

-continued
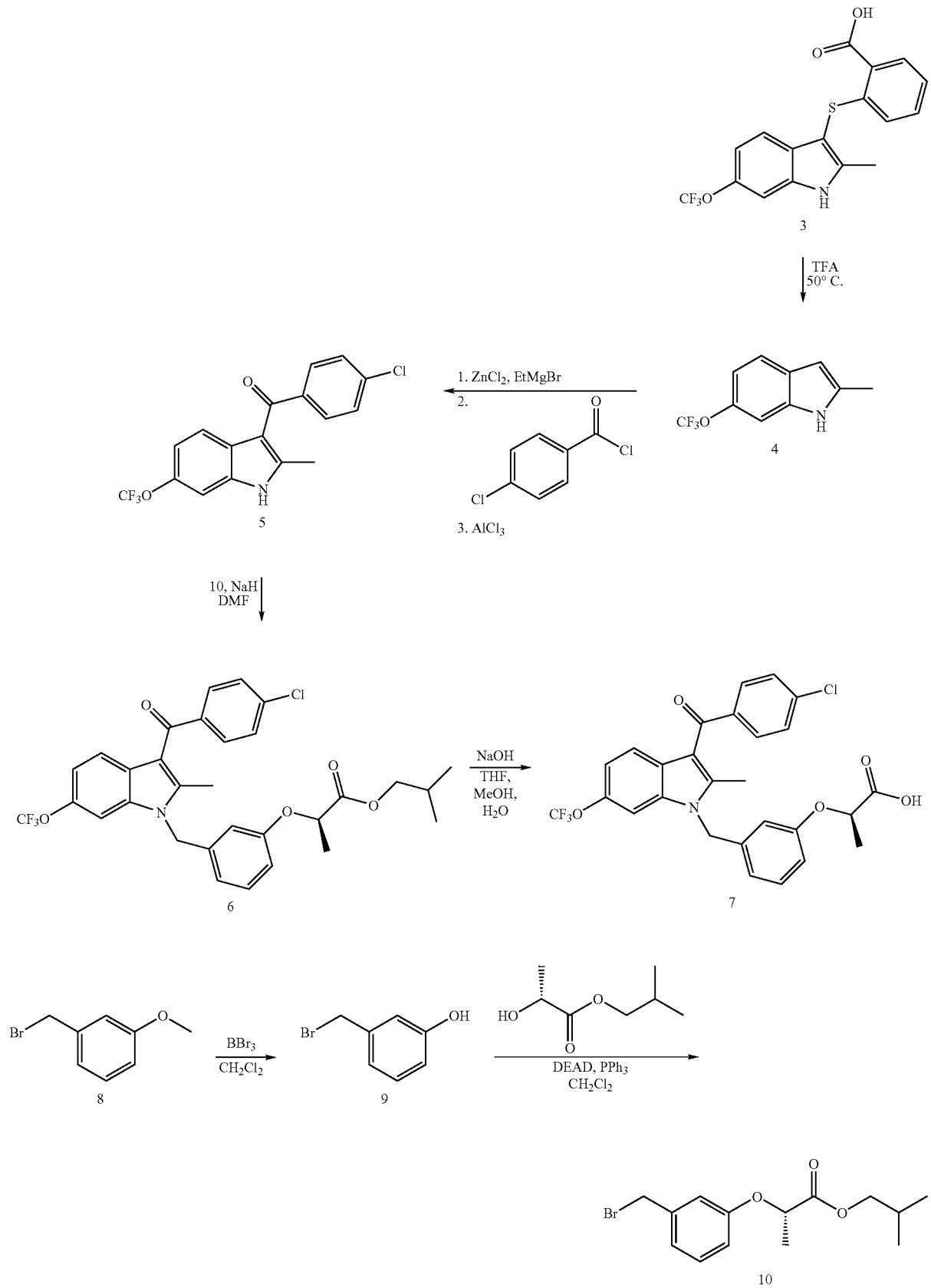

Example 28

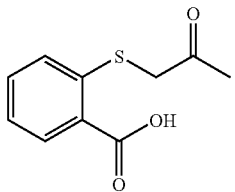

2

Ketone 2: A suspension of chloroacetone (6.00 gr, 65 mmol, the chloroacetone was filtered through basic alumina prior to use), phenol 1 (10.00 gr, 65 mmole) and potassium carbonate (8.96 gr, 65 mmol) was stirred in DMF at room temperature under nitrogen atmosphere for 1 h. After this time the reaction was diluted with ethyl acetate/H2O and the layers were separated. The aqueous layer was acidified with 1N HCl and extracted with ethyl acetate (3x). The organic layer was then washed with water (2x), and brine (1x), dried with sodium sulfate, filtered and evaporated to give a pink solid: $^1$H-NMR (CDCl$_3$, 500 MHz) δ 8.14 (t, 1H), 7.53 (t, 1H), 7.35 (d, 1H), 7.27 (d, 1H), 3.78 (s, 2H), 2.35 (s, 3H).

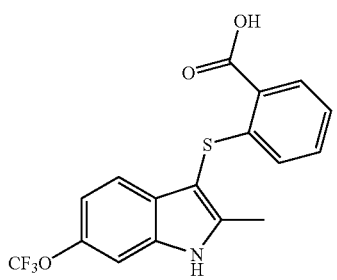

3

Indole 3: Ketone 2 (1.84 gr, 8.75 mmol) and 4-trifluoromethoxy phenylhydrazine hydrochloride (2.00 gr, 4.76 mmol) were stirred at 100° C. in acetic acid (40 ml, 0.22M) for 1 hour under nitrogen atmosphere to give a 1:2 mixture of 4- and 6-trifluoromethoxy indoles (desired 6-substituted indole is slightly less polar by TLC). The reaction was cooled to room temperature, the acetic acid was removed under reduced pressure and the residue was diluted with ethyl acetate and washed with water (1x) and brine (1x). The organic layer was dried with sodium sulfate, filtered and evaporated to afford 3 as a yellow oil after column chromatography (hexanes/ethyl acetate/1% acetic acid, 6:1); $^1$H-NMR (CDCl$_3$, 500 MHz) δ 8.43 (br s, 1H), 8.16 (dd, 1H), 7.46 (d, 1H), 7.23 (t, 1H), 7.14 (t, 1H), 7.03 (d, 1H), 6.74 (d, 1H), 2.54 (s, 3H).

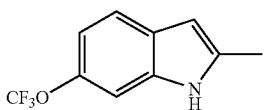

4

3-H Indole 4: A solution of indole 3 (0.29 gr, 0.78 mmol) and thiosalicylic acid (0.12 gr, 0.78 mmol) in trifluoroacetic acid (3 mL, 0.26M) was heated to 50° C. under nitrogen atmosphere for 2 hr. After this time the reaction was cooled to room temperature, diluted with ethyl acetate and washed with 1N NaOH (2x), and brine (1x). The organic layer was dried with sodium sulfate, filtered and evaporated to afford a brown solid: $^1$H-NMR (CDCl$_3$, 500 MHz) δ 8.01 (br s, 1H), 7.49 (d, 1H), 7.17 (s, 1H), 6.99 (d, 1H), 6.26 (s, 1H), 2.46 (s, 3H).

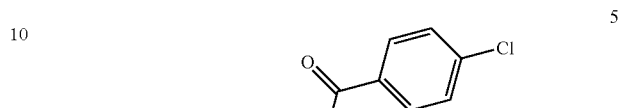

5

3-Acylindole 5: Zinc chloride (0.23 gr, 1.66 mmol) and ethyl magnesium bromide (0.29 ml of a 3M solution in ether, 0.87 mmol) were added to a solution of indole 4 (0.16 gr, 0.74 mmol) in CH$_2$Cl$_2$. The resulting mixture was stirred at room temperature under a nitrogen atmosphere for 1 hr. 4-Chlorobenzoyl chloride (0.21 gr, 1.18 mmol) was then added and stirring was continued for 1 hr. Finally, aluminum chloride (0.053 gr, 0.39 mmol) was added and the reaction mixture was stirred for 3 hr. After this time, the reaction was quenched with NH$_4$Cl(aq), diluted with CH$_2$Cl$_2$, washed with 1N NaOH (1x) and brine (3x). The organic layer was dried with sodium sulfate, filtered and evaporated to afford a light yellow oil after column chromatography (hexanes/ethyl acetate, 4:1); $^1$H-NMR (CDCl$_3$, 500 MHz) δ 8.54 (br s, 1H), 7.73 (d, 2H), 7.48 (d, 2H), 7.40 (d, 1H), 7.24 (s, 1H), 7.02 (d, 1H), 2.60 (s, 3H).

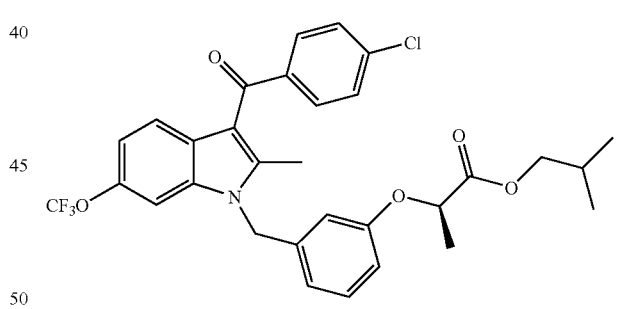

6

N-benzyl Indole 6: Sodium hydride (14 mg, 0.35 mmol, 60% dispersion in mineral oil) was added to a solution of indole 5 (111 mg, 0.32 mmol) in DMT (3.0 ml, 0.1M). The resulting mixture was stirred at room temperature under nitrogen for 10 min, then bromide 10 (110 mg, 0.35 mmol) was added. Stirring was continued at room temperature for 2 hr. The reaction mixture was then diluted with ethyl acetate, washed with water (2x) and brine (1x), dried with sodium sulfate, filtered, and evaporated to give a yellow oil after column chromatography (4:1 hexanes/ethyl acetate). $^1$H-NMR (CDCl$_3$, 500 MHz) δ 7.76 (d, 2H), 7.48 (d, 2H), 7.37 (d, 1H), 7.26 (dd, 1H), 7.14 (s, 1H), 7.02 (d, 1H), 6.79 (dd, 1H), 6.65 (d, 1H), 6.60 (s, 1H), 5.34 (s, 2H), 4.72 (q, 1H), 3.89 (m, 2H), 2.55 (s, 3H), 1.88 (m, 1H), 1.62 (d, 3H), 0.85 (d, 6H).

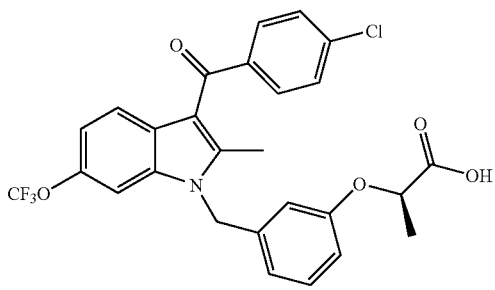

7

Acid 7: N-Benzyl indole 6 (121 mg, 0.206 mmol) and aqueous sodium hydroxide (0.50 mL, 5.0M) were stirred in tetrahydrofuran, methanol, and water (2.5 ml, 3:1:1) at room temperature for 7 hr. After this time, the reaction concentrated by rotary evaporation and purified by reverse phase HPLC to give acid 7 as a white solid. $^1$H-NMR (CDCl$_3$, 500 MHz) δ 7.76 (d, 2H), 7.48 (d, 2H), 7.34 (d, 1H), 7.26 (d, 1H), 7.16 (s, 1H), 7.02 (d, 1H), 6.82 (dd, 1H), 6.72 (d, 1H), 6.44 (s, 1H), 5.36 (dd, 2H), 4.64 (q, 1H), 2.51 (s, 3H), 1.62 (d, 3H).

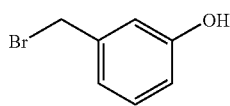

9

Phenol 9: 3-Methoxybenzyl bromide (3.0 gr, 15 mmol) was dissolved in CH$_2$Cl$_2$ and cooled to 0° C. A 1M solution of boron tribromide in CH$_2$Cl$_2$ (17.9 ml, 17.9 mmol) was then added dropwise. After 30 min, the ice bath was removed and stirring was continued for an additional 30 min. The rxn was then quenched with ice and diluted with CH$_2$Cl$_2$, H2O. The layers were separated and the organic layer was washed with H2O (2×) and brine (1×), dried with sodium sulfate, filtered, and evaporated to give phenol 9 as a white solid. $^1$H-NMR (CDCl$_3$, 500 MHz) δ 7.25 (t, 1H), 6.99 (d, 1H), 6.90 (s, 1H), 6.80 (d, 1H), 4.81 (br s, 1H), 4.45 (s, 2H).

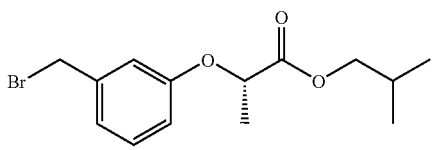

10

Bromide 10: R-Isobutyl lactate (1.02 gr, 6.95 mmol) was dissolved in CH$_2$Cl$_2$ and cooled to 0° C. Triphenylphosphine (1.83 gr, 6.95 mmol) was then added followed by dropwise addition of diethylazodicarboxylate (1.21 gr, 6.95 mmol). Finally, phenol 9 was added. After addition, the ice bath was removed and stirring was continued for 30 min. The reaction was diluted with CH$_2$Cl$_2$, washed with H$_2$O (2×) and brine (1×), dried with sodium sulfate, filtered and evaporated to give a colorless oil (1.02 gr, 60%) after chromatography (hexanes/ethyl acetate, 8:1). $^1$H-NMR (CDCl$_3$, 500 MHz) δ 7.26 (dd, 1H), 7.01 (d, 1H), 6.94 (dd, 1H), 6.83 (dd, 1H), 4.81 (q, 1H), 4.46 (s, 2H), 3.23-4.01 (m, 2H), 1.95 (m, 1H), 1.65 (d, 3H), 0.90 (dd, 6H).

Scheme for the Synthesis of Example 29

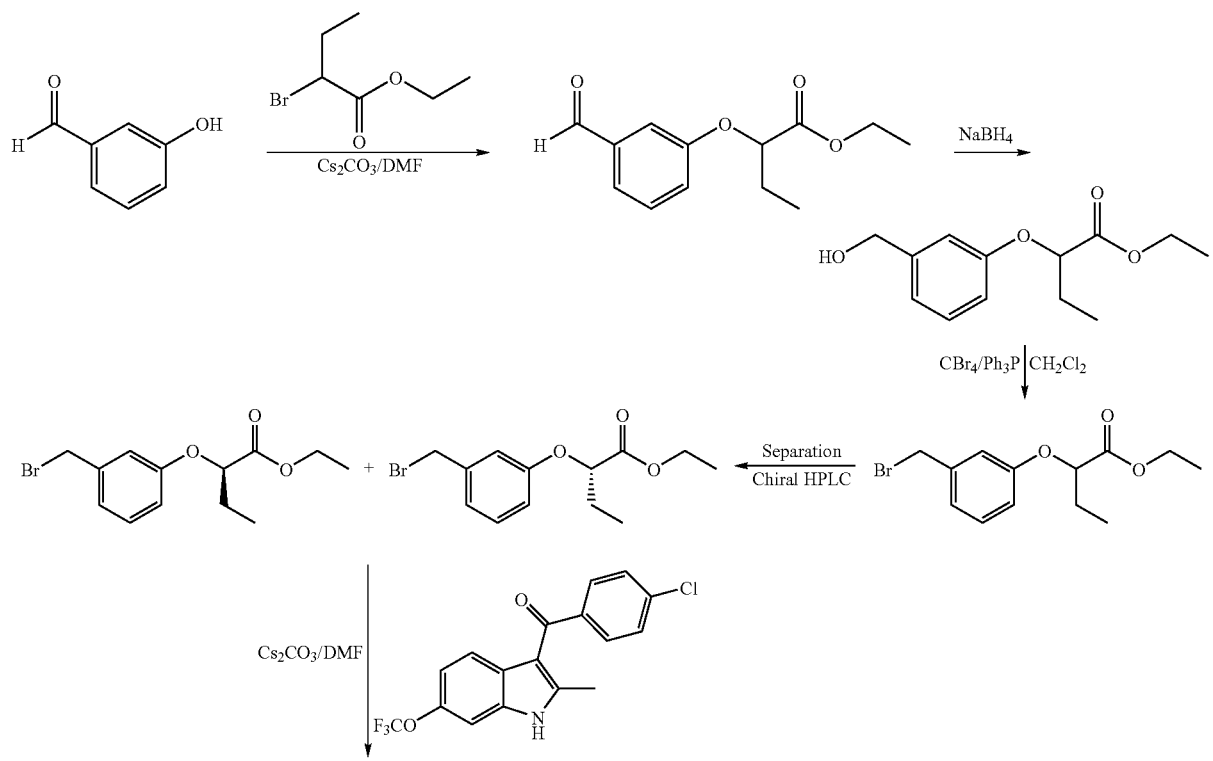

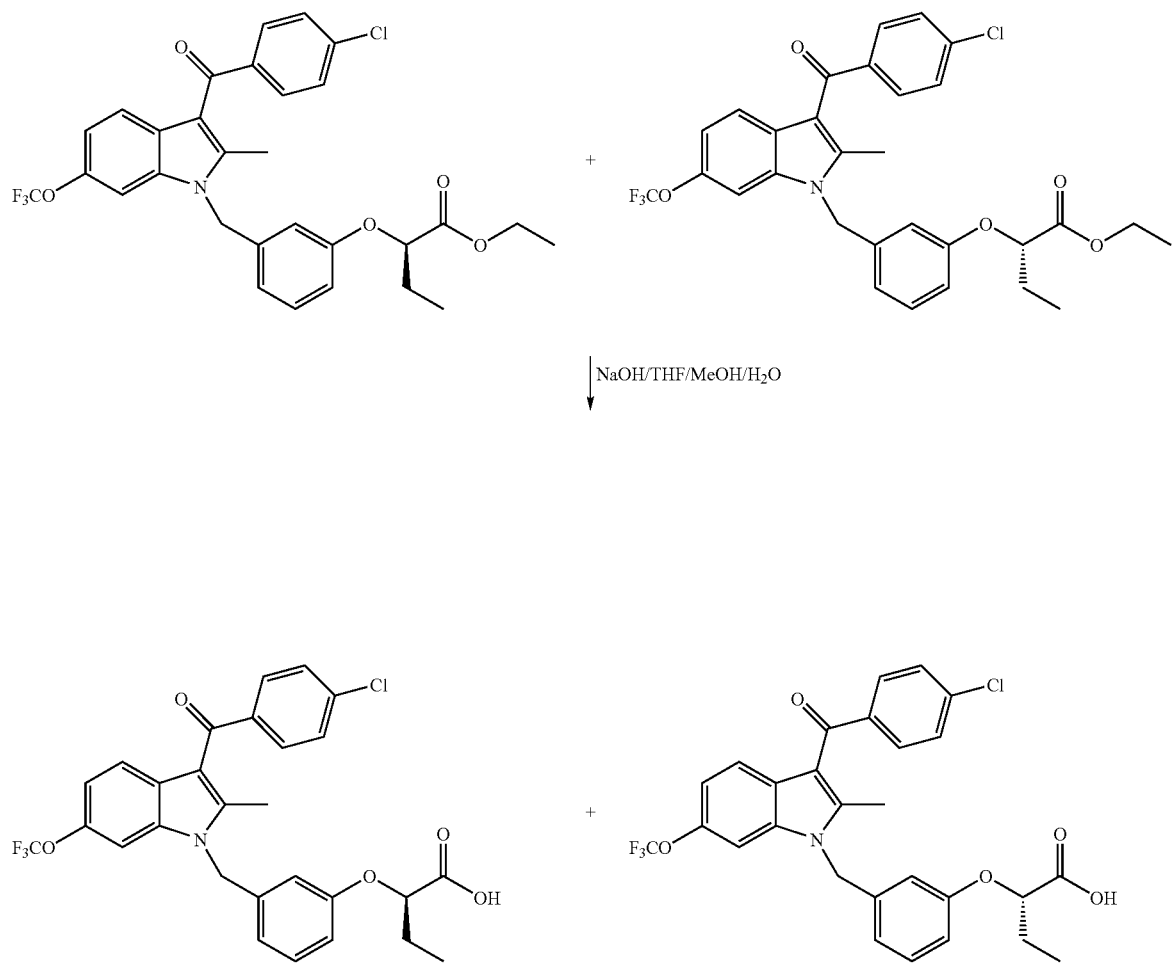

Example 29

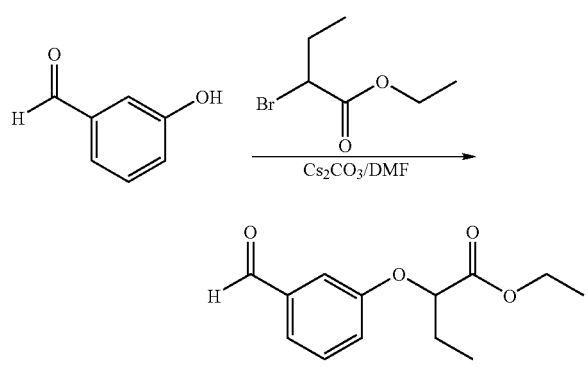

Ethyl 2-(3-formyl)phenoxybutyrate

To a solution of 3-hydroxybenzaldehyde (26.8 g, 219.6 mmol) in DMF (250 ml) at 0 to 10° C., was added $Cs_2CO_3$ (142 g, 439 mmol) and ethyl 2-bromobutyrate (32.4 ml, 219.6 mmol). The reaction mixture was first stirred for at 0 to 10° C. for 2 hours, then at room temperature overnight. The mixture was diluted with water (400 ml), and extracted with diethyl ether (2×150 ml). The ether extract was washed with water (2×100 ml) and brine (100 ml), and dried over anhydrous $MgSO_4$, and concentrated under vacuum to dryness to obtain the product as a clear oil. $^1H$ NMR ($CDCl_3$, 500 MHz) δ 9.97 (s, 1H), 7.51 (m, 2H), 7.36 (s, 1H), 7.21 (dd, 1H), 4.66 (t, 1H), 4.21 (q, 2H), 2.06 (m, 2H), 1.28 (t, 3H), 1.12 (t, 3H).

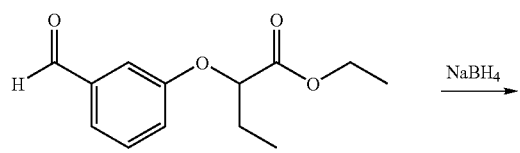

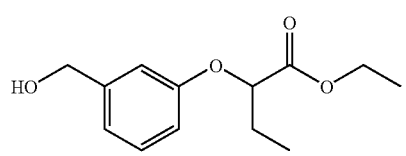

Ethyl 2-(3-hydroxymethyl)phenoxybutyrate

Sodium borohydride (NaBH$_4$, 7.4 g, 194 mmol) was added in proportions to a solution of ethyl 2-(3-formyl)phenoxybutyrate (46 g, 194 mmol) in ethanol (500 ml) at 0° C. The reaction mixture was stirred in an ice bath for 1 hour. Water was added slowly to destroy excess NaBH. The mixture was then diluted with 300 ml of water and extracted with diethyl ether (2×200 ml). The ether extract was washed with water (2×100 ml) and brine (100 ml), and dried over anhydrous MgSO$_4$, and concentrated under vacuum to dryness to obtain the product as a clear oil. $^1$H NMR (CDCl$_3$, 500 MHz) 7.27 (dd, 1H), 6.97 (d, 1H), 6.93 (s, 1H), 6.81 (d, 1H), 4.65 (s, 2H), 4.58 (t, 1H), 4.22 (q, 2H), 2.01 (m, 2H), 1.28 (t, 3H), 1.11 (t, 3H).

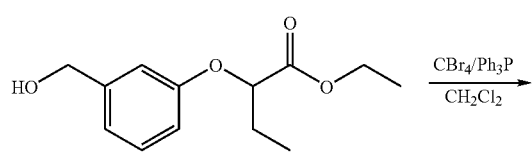

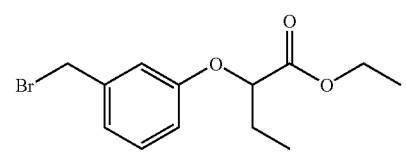

Ethyl 2-(3-bromomethyl)phenoxybutyrate

To a solution of ethyl 2-(3-hydroxymethyl)phenoxybutyrate (41 g, 172.2 mmol) in dichloromethane (400 ml) at 0° C., was added carbon tetrabromide (CBr$_4$, 86 g, 260 mmol) and triphenylphosphine (Ph$_3$P, 68 g, 260 mmol). The reaction mixture was stirred at 0° C. for 2 hours, then washed with saturated sodium bicarbonate (NaHCO$_3$, 200 ml) and brine (200 ml) and concentrated under vacuum to a small volume. The residue was chromatographed on silica gel with hexane/ethyl acetate (9:1) as the solvent system to obtain the product as a colorless oil. $^1$H NMR (CDCl$_3$, 500 MHz) 7.26 (t, 1H), 7.01 (d, 1H), 6.95 (s, 1H), 6.82 (d, 1H), 4.58 (m, 1H), 4.46 (s, 2H), 4.25 (q, 2H), 2.01 (m, 2H), 1.28 (t, 3H), 1.11 (t, 3H).

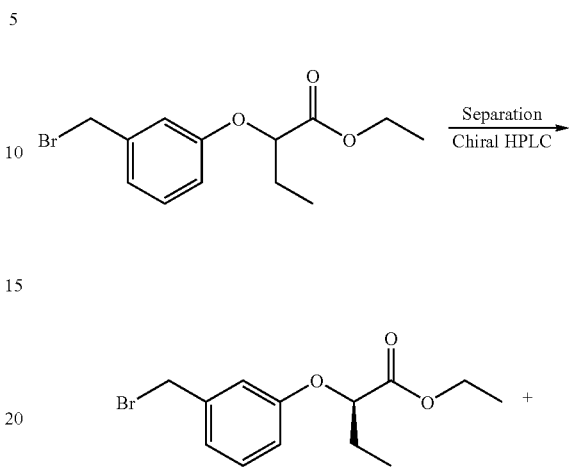

Preparation of Optically Active Ethyl 2-(3-bromomethyl)phenoxybutyrate

For analysis of enantiomeric purities of the product: a 10 µl sample solution of approximately 1.0 mg/ml in concentration was injected onto a Chiracel OD analytical column (4.6×250 mm, 10 micron). The column was then eluted with an isocratic solvent system consisting of 5% isopropanol in heptane at a flow rate of 0.5 ml/min. Peaks were recorded at the wavelength of 254 µm with an UV detector. Under these conditions, the retention time of the S enantiomer is approximately 10 minutes while the retention time of the R enantiomer is about 20 minutes. Enantiomeric excess (ee %) are calculated as area under curve of the S enantiomer subtract area under curve of the R enantiomer and divided by the sum of the two areas.

For preparative purpose, the Chiracel OD Semi-Prep column (20×250 mm, 10 micron) was used. A 1.8 ml sample solution of approximately 40 mg/ml in concentration was injected. The column was then eluted with an isocratic solvent system consisting of 5% isopropanol in heptane at a flow rate of 9.0 ml/min. Peaks detected above 0.5 mV threshold at the wavelength of 254 µm were collected with a Gilson fraction collector. Fractions containing the S enantiomer were collected between 20-25 minutes after injection, while those containing the R enantiomer were collected at about 40-45 minutes. Repeated injections resulted in continuous separation of the two enantiomers. Fractions containing the separated enantiomers were then combined, and concentrated to obtain the optically active product as a clear oil. The enantiomeric purities of the material ranges from 96-99% ee

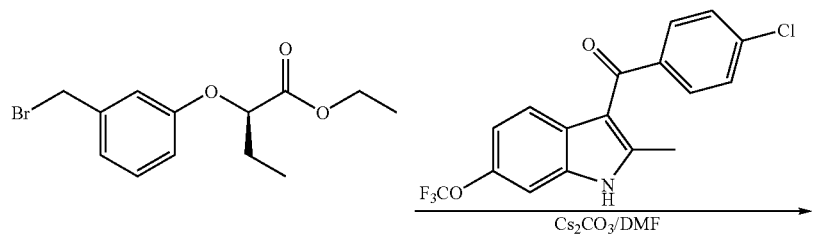

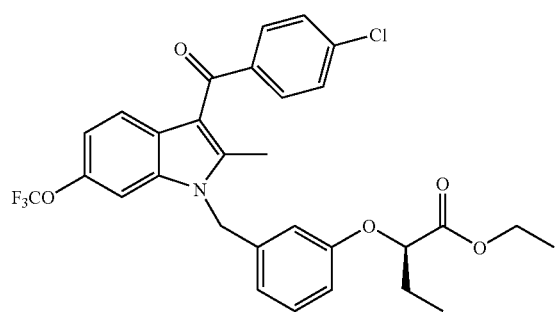

Ethyl (2R)-2-{3-[[3-(4-chlorobenzoyl)-2-methyl-6-(trifluoromethoxy)-1H-indol-1-yl]methyl]phenoxy}butyrate To a solution of 3-(4-chlorobenzoyl)-2-methyl-6-(trifluoromethoxy)-1H-indole (15 g, 50 mmol) in DMF (300 mL) at 0 to 10° C., was added Cs$_2$CO$_3$ (45 g, 124 mmol) and ethyl (2R)-2-(3-bromomethyl)phenoxy butyrate (18 g, 50 mmol). The reaction mixture was first stirred at 0 to 10° C. for 2 hours, then at room temperature overnight. The mixture was diluted with water (400 ml), and extracted with ethyl acetate (2×150 ml). The organic extract was washed with water (2×100 ml) and brine (100 ml), and dried over anhydrous MgSO$_4$, and concentrated under vacuum. The residue was chromatographed on silica gel with hexane/ethyl acetate (4:1) as the solvent system to obtain the product as a white solid. $^1$H NMR (CDCl$_3$, 500 MHz) δ 7.76 (d, 2H), 7.48 (d, 2H), 7.36 (d, 1H), 7.25 (t, 1H), 7.15 (s, 1H), 7.02 (d, 1H), 6.79 (d, 1H), 6.67 (d, 1H), 6.56 (s, 1H), 5.35 (s, 2H), 4.49 (t, 1H), 4.21 (q, 2H), 2.55 (s, 3H), 1.97 (m, 2H), 1.28 (t, 3H), 1.07 (t, 3H). Enantiomeric purity of the product ranges from 98-99% ee based on analytical chiral HPLC analysis (Chiracel OD, 10% ethanol in heptane).

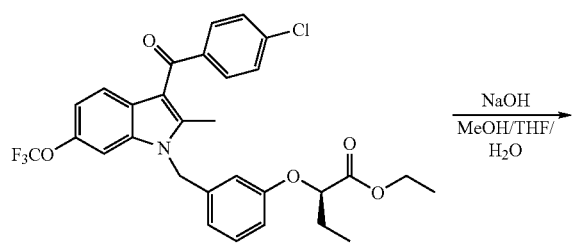

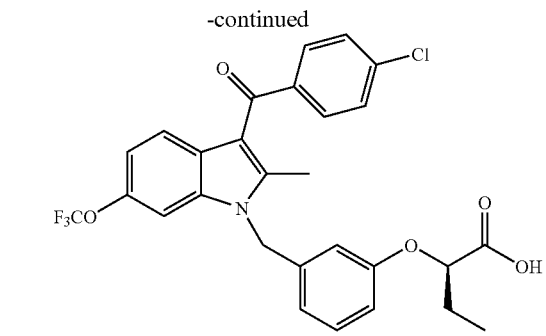

(2R)-2-{3-[[3-(4-chlorobenzoyl)-2-methyl-6-(trifluoromethoxy)-1H-indol-1-yl]methyl]phenoxy}butyric acid To a solution of Ethyl (2R)-2-{3-[[3-(4-chlorobenzoyl)-2-methyl-6-(trifluoromethoxy)-1H-indol-1-yl]methyl]phenoxy}butyrate (23 g, 40 mmol) in tetrahydrofuran (THF, 200 ml) was added 200 ml of methanol and 160 ml of an 1N NaOH solution (160 mmol). The clear solution was stirred at room temperature overnight, and neutralized (to pH=4) with 2N HCl solution. The mixture was concentrated under reduced pressure to remove most of the organic solvent, and then stirred at room temperature for crystallization. The suspension was then filtered and the solid washed with water and dried under vacuum to obtain the product as a white solid. $^1$H NMR (CDCl$_3$, 500 MHz) δ 7.77 (d, 2H), 7.48 (d, 2H), 7.35 (d, 1H), 7.27 (t, 1H), 7.17 (s, 1H), 7.02 (d, 1H), 6.84 (d, 1H), 6.73 (d, 1H), 6.38 (s, 1H), 5.36 (q, 2H), 4.44 (t, 1H), 2.49 (s, 3H), 1.98 (m, 2H), 1.07 (t, 3H). MS: (M+1)=546. Enantiomeric purity of the product ranges from 98-99% ee. (Chiralcel OD-RH, acetonitrile/water gradient).

Synthesis of a Compound where R³ is Phenoxy (Table 1)

Compounds in which R³ is phenoxy or thiophenoxy are shown in Table 1. The synthesis of a representative compound (Example 30) from Table 1 is shown in the scheme below, which is followed by a detailed description of the synthesis. The other compounds in Table 1 can be synthesized by one of ordinary skill in the art by using similar synthetic strategies and readily available materials.

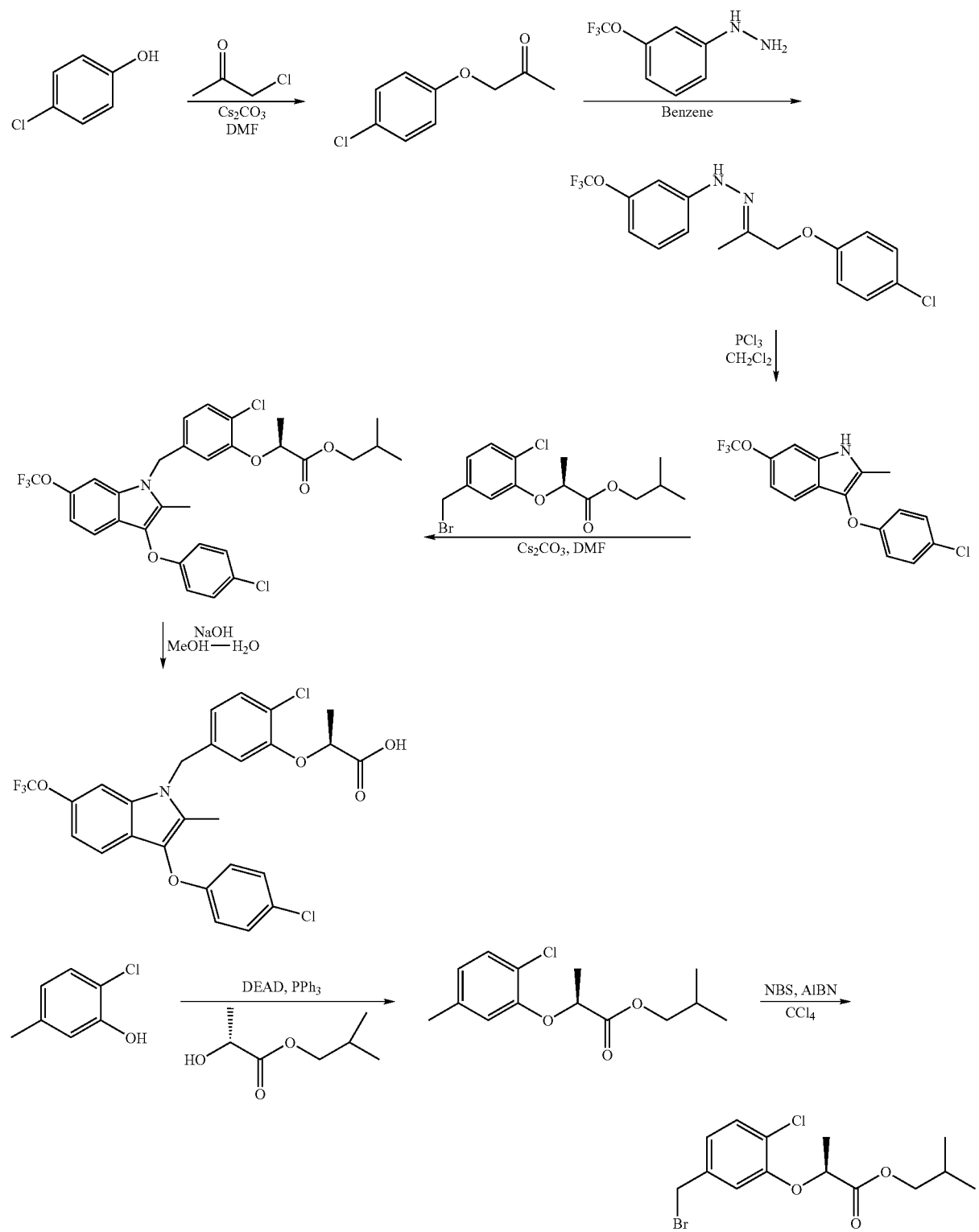

Example 30

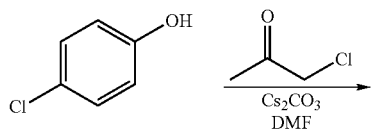

To a solution of 4-chlorophenol (15.36 g) in DMF (150 mL) at room temperature was added Cs$_2$CO$_3$ (64.4 g). After 15 min, chloroacetone (14.8 mL) was introduced via syringe. The reaction mixture was stirred for 3 hours, then partitioned between ether and water. The organic layer was washed sequentially with water, 1N aqueous NaOH solution (2×), and brine, dried over anhydrous MgSO$_4$, filtered, and concentrated in vacuo. Distillation under high vacuum gave 14 g of the product as slightly yellow oil. $^1$H NMR (CDCl$_3$, 500 MHz) δ 7.28 (d, 2H), 6.83 (d, 2H), 4.54 (s, 2H), 2.29 (s, 3H).

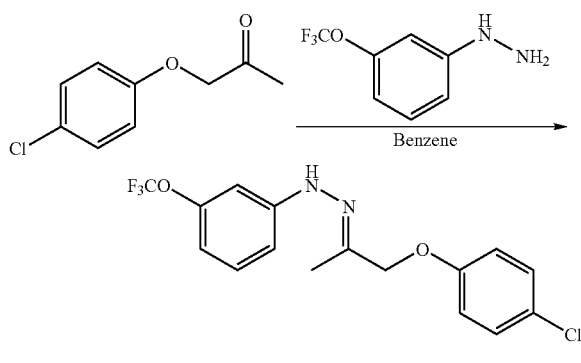

The above obtained ketone (12.89 g) and 3-trifluoromethoxyphenyl hydrazine (12.22 g) were dissolved in benzene (50 mL). The reaction mixture was heated at 60° C. for 45 min, cooled to room temperature, dried over anhydrous Na$_2$SO$_4$, filtered, and concentrated in vacuo to give the phenylhydrazone (23 g), which was used immediately without further purification.

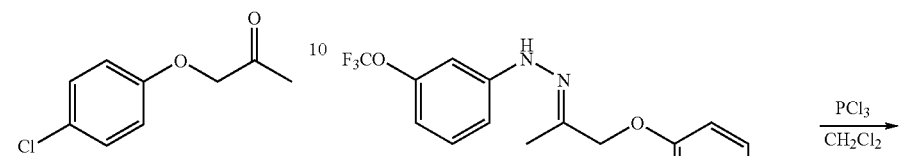

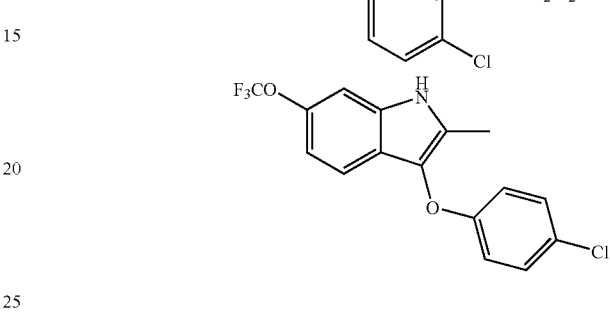

To a solution of the above obtained hydrazone (23 g) in CH$_2$Cl$_2$ (200 mL) at room temperature was added PCl$_3$ (11 mL). The reaction was stirred at room temperature for 24 h before water (3 mL) was introduced and the reaction was vigorously stirred for another 15 min. After cooling to 0° C. by an ice-water bath, the reaction was neutralized to pH 7 by adding 5N aqueous NaOH solution. Most of the solvent was removed in vacuo. The residue was partitioned between ether and water. The organic layer was washed with water and brine, dried over anhydrous MgSO$_4$, filtered, and concentrated in vacuo. Purification by flash chromatography (SiO$_2$, EtOAc/hex 25/1) gave the desired product (7.3 g) along with the corresponding 4-trifluoromethoxyindole isomer (2.4 g). $^1$H NMR (CDCl$_3$, 500 MHz) δ 7.80 (s, broad, 1H), 7.24 (d, J=8.7 Hz, 2H), 7.22 (d, J=8.4 Hz, 1H), 7.19 (s, 1H), 6.95 (d, J=8.4 Hz, 1H), 6.91 (d, J=8.7 Hz, 2H), 2.35 (s, 3H).

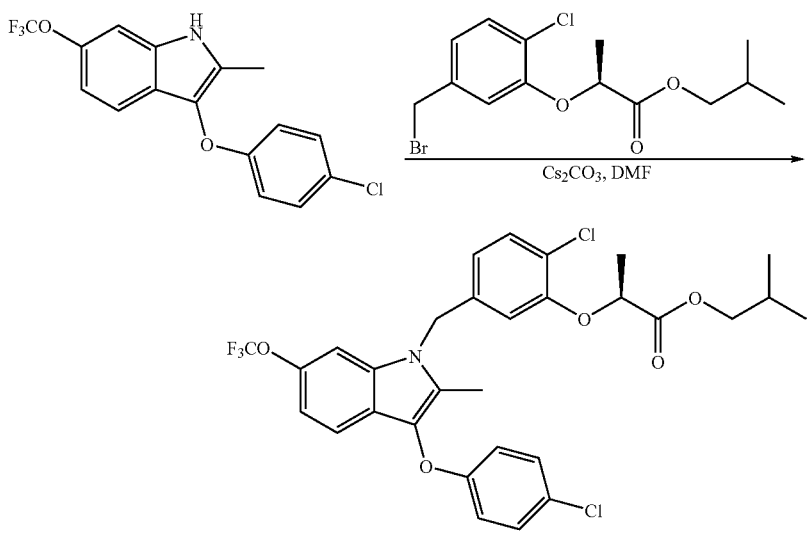

To a solution of the above obtained indole (3.16 g) and benzyl bromide (3.55 g) in DMF (40 mL) at room temperature was added Cs$_2$CO$_3$ (6.03 g). The reaction mixture was stirred for 15 h, poured into water, extracted with EtOAc (2×). The combined organic layers were washed with water and brine, dried over anhydrous MgSO$_4$, filtered, and concentrated in vacuo. Purification by flash chromatography gave the desired product. $^1$H NMR (CDCl$_3$, 500 MHz) δ 7.34 (d, J=8.2 Hz, 1H), 7.28 (d, J=7.6 Hz, 1H), 7.25 (d, J=9.0 Hz, 2H), 7.08 (s, 1H), 6.96 (d, J=8.0 Hz, 1H), 6.92 (d, J=9.0 Hz, 2H), 6.60 (dd, J=8.0, 1.7 Hz, 1H), 6.46 (d, J=1.7 Hz, 1H), 5.23 (s, 2H), 4.62 (q, J=6.8 Hz, 1H), 3.85 (dd, J=6.8, 10.5 Hz, 1H), 3.70 (dd, J=6.8, 10.5 Hz, 1H), 2.24 (s, 3H), 1.81 (m, 1H), 1.64 (d, J=6.9 Hz, 3H), 0.84 (d, J=6.6 Hz, 6H).

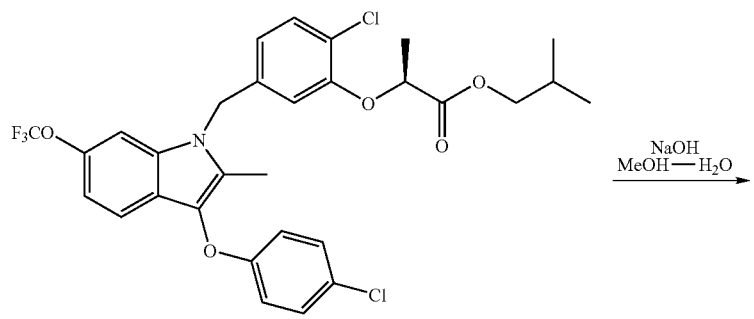

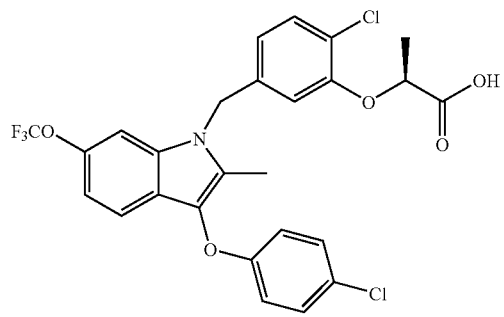

To a solution of the ester (5.0 g) in MeOH (200 mL) was added aqueous NaOH (1.0 N, 20 mL). The mixture was stirred at room temperature for 5 h, cooled to 0° C., acidified with 1.0 N HCl, diluted with water (200 mL), extracted with EtOAc (2×). The combined organic layers were washed with water and brine, dried over anhydrous MgSO$_4$, filtered, and concentrated in vacuo. The residue was purified by crystallization from ether/hexanes to give the product. $^1$H NMR (CDCl$_3$, 500 MHz) δ 7.36 (d, J=8.2Hz, 1H), 7.28 (d, J=7.6 Hz, 1H), 7.25 (d, J=9.2 Hz, 2H), 7.09 (s, 1H), 6.96 (d, J=8.7 Hz, 1H), 6.90 (d, J=9.0 Hz, 2H), 6.65 (d, J=8.0 Hz, 1H), 6.45 (s, 1H), 5.26 (s, 2H), 4.63 (q, J=6.9 Hz, 1H), 2.24 (s, 3H), 1.64 (d, J=6.9 Hz, 3H).

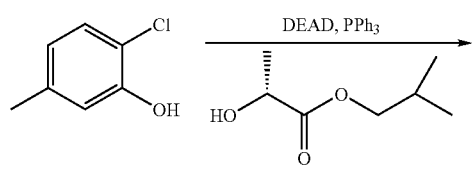

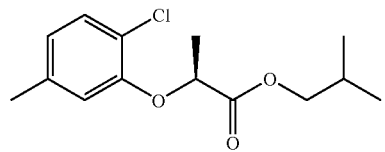

To a solution of phenol (10.23 g) in methylene chloride (200 mL) at room temperature were added alcohol (14.1 mL), PPh$_3$ (24.4 g), and DEAD (14.6 mL). The reaction mixture was stirred overnight. The solvent was removed in vacuo. Purification by flash chromatography gave the desired product. $^1$H NMR (CDCl$_3$, 500 MHz) δ 7.25 (d, J=8.0 Hz, 1H), 6.75 (d, J=8.0 Hz, 1H), 6.70 (s, 1H), 4.79 (q, J=6.7 Hz, 1H), 3.99 (m, 1H), 2.30 (s 3H), 1.97 (m, 1H), 1.70 (d, J=6.9 Hz, 3H), 0.90 (d, J=6.8 Hz, 6H).

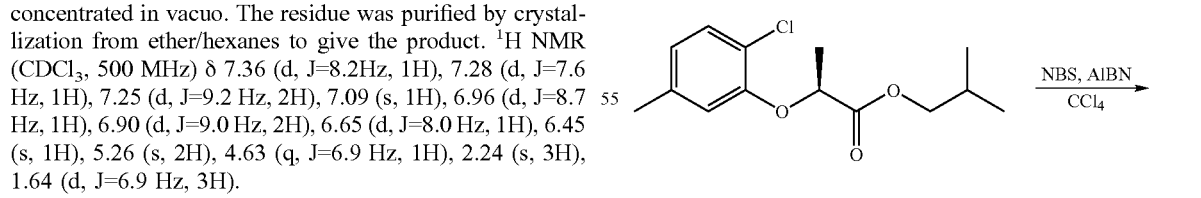

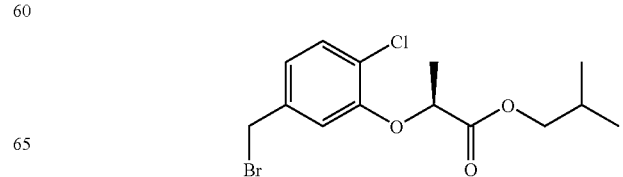

To a solution of starting ester (15.3 g) in CCl$_4$ were added NBS (9.58 g) and catalytic AIBN (200 mg). The mixture was stirred at 80° C. overnight, cooled to room temperature, filtered, and concentrated in vacuo. Purification by chromatography gave the desired benzyl bromide. $^1$H NMR (CDCl$_3$, 500 MHz) δ 7.35 (d, J=8.0 Hz, 1H), 6.98 (dd, J=8.0, 2.0 Hz, 1H), 6.89 (d, J=2.0 Hz, 1H), 4.84 (q, J=6.7 Hz, 1H), 4.43 (d, J=10.5 Hz, 1H), 4.41 (d, J=10.5 Hz, 1H), 3.98 (m, 1H), 1.97 (m, 1H), 1.72 (d, J=6.9 Hz, 3H), 0.90 (d, J=6.7 Hz, 3H), 0.90 (d, J=6.7 Hz, 3H).

Compounds in which R$^3$ is Benzisoxazole (Table 2)

The synthesis of a compound in which R$^3$ is benzisoxazole is shown in the scheme below, which is followed by a description of the procedure in Example 31. Other compounds in which R$^3$ is benzisoxazole are show in Table 2. These can all be made by a skilled practitioner in synthetic organic chemistry using the methods and strategies disclosed herein.

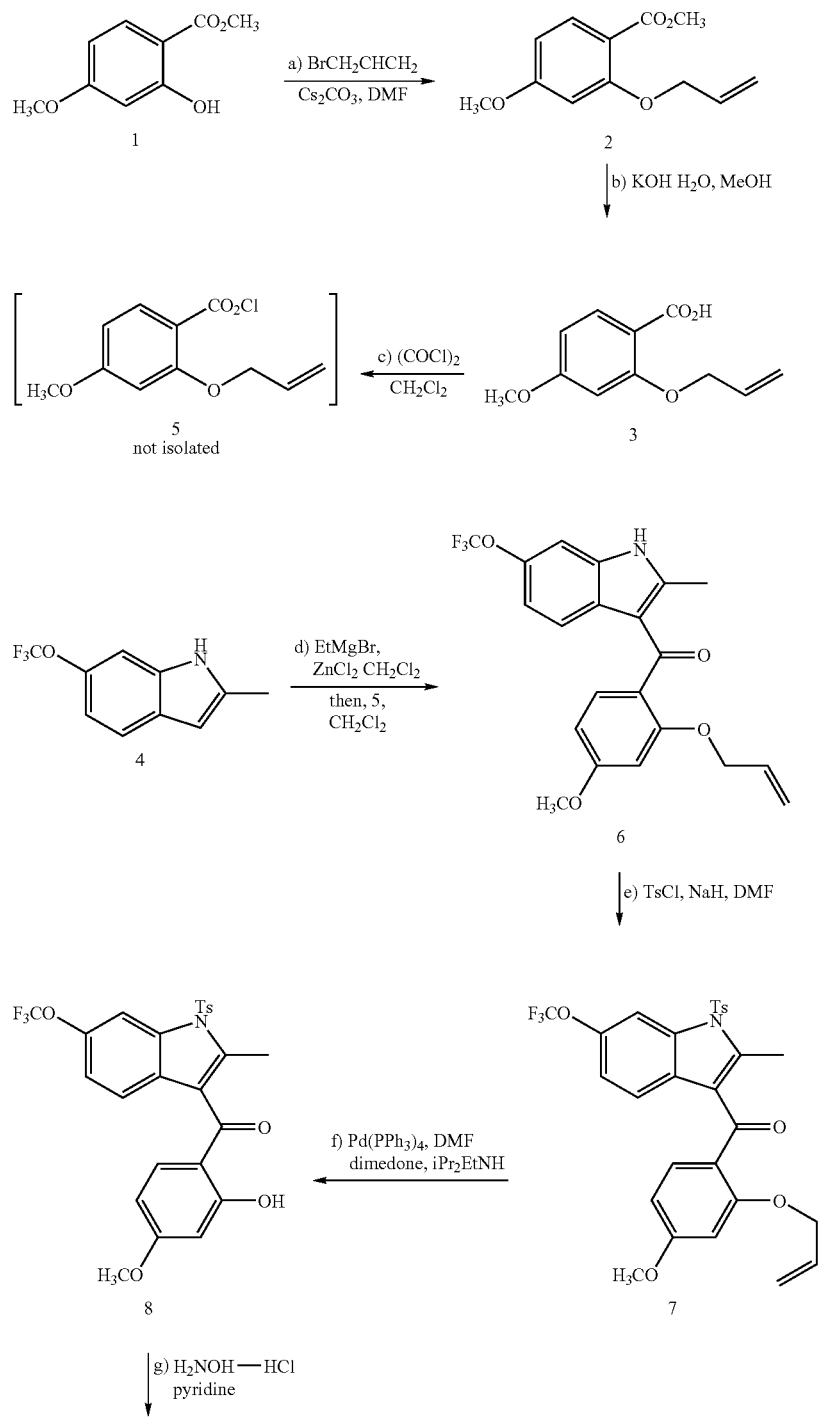

-continued
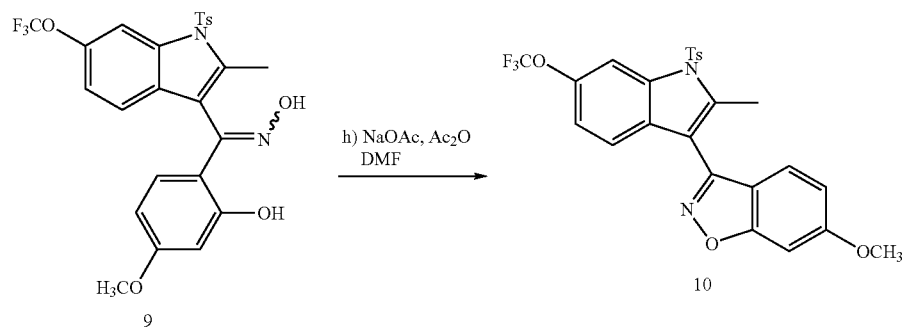
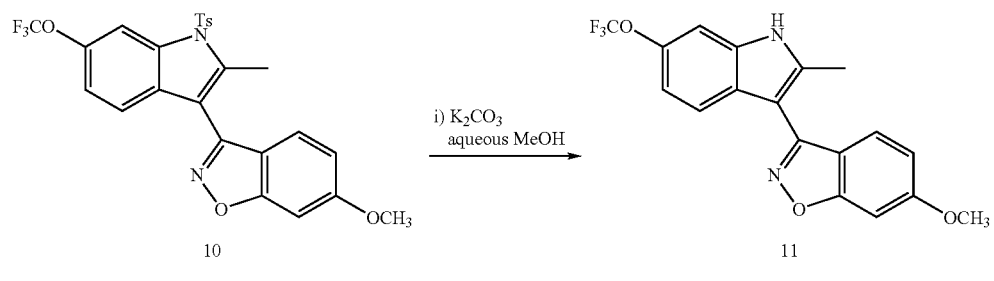
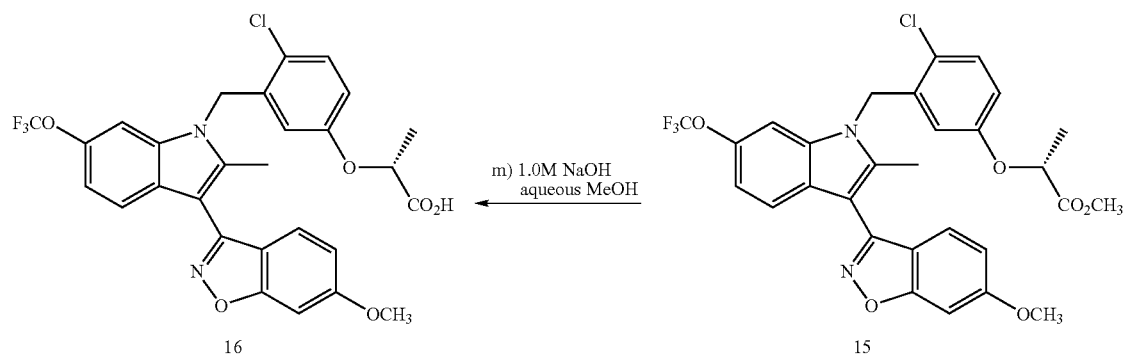
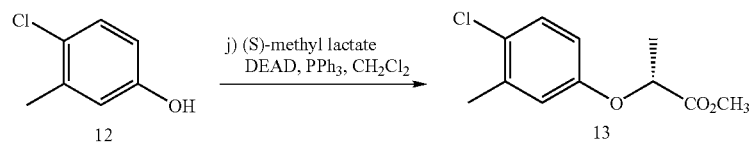
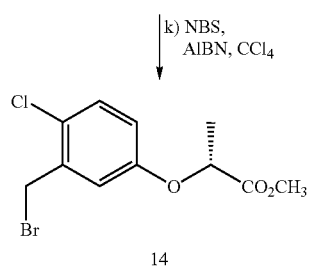

Example 31

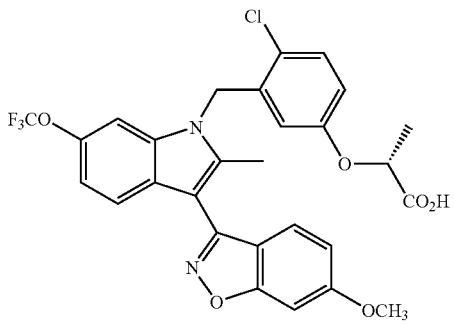

(2R)-2-(4-chloro-3-{[3-(6-methoxy-1,2-benzisoxazol-3-yl)-2-methyl-6-(trifluoromethoxy)-1H-indol-1-yl]methyl}phenoxy)propanoic acid Step 1. Methyl 2-(allyloxy)-4-methoxybenzoate (2)

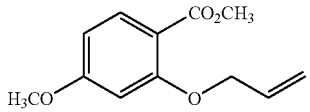

To a solution of methyl 4-methoxysalicylate (2.0 g, 11 mmol) in DMF (20 mL) at room temperature was added $Cs_2CO_3$ (1.3 eq, 4.7 g) and allyl bromide (1.3 eq, 1.23 mL). After 2 hr, reaction mixture was diluted with EtOAc and washed with water (3×), brine (1×). The organic layer was dried over $Na_2SO_4$ and concentrated to provide the product as a pale yellow oil. Product was used without further purification.

$^1$H NMR (500 MHz, $CDCl_3$): δ 7.89 (d, 1H), 6.53 (dd, 1H), 6.49 (d, 1H), 6.08 (m, 1H), 5.55 (d, 1H), 5.33 (d, 1H), 4.63 (d, 2H), 3.89 (s, 3H), 3.86 (s, 3H).

Step 2. 2-(allyloxy)-4-methoxybenzoic acid (3)

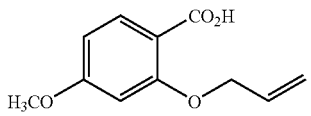

To a solution of 2 (2.5 g, 11 mmol) in aqueous methanol (30 mL) was added KOH (1 eq, 630 mg). Reaction was heated to 50° C. for 12 hours before the addition of more KOH (630 mg). After 12 hours, the mixture was cooled, diluted with EtOAc and washed with 1M HCl. Aqueous layer was extracted with EtOAc (3×). Combined organic layers, dried over $Na_2SO_4$, and concentrated. Product was isolated as an off white solid and used without further purification.

$^1$H NMR (500 MHz, $CD_3OD$): δ 7.85 (d, 1H), 6.60 (m, 2H), 6.08 (m, 1H), 5.49 (d, 1H), 5.30 (d, 1H), 4.68 (d, 2H), 3.84 (s, 3H).

Step 3. [2-(allyloxy)-4-methoxyphenyl][2-methyl-6-(trifluoromethoxy)-1H-indol-3-yl]methanone (6)

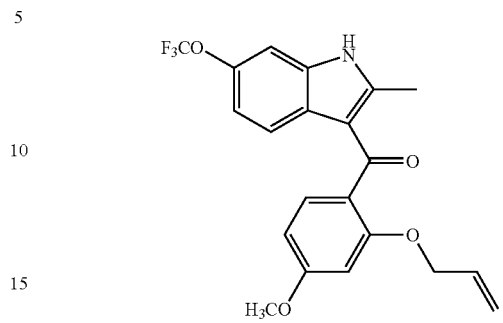

To a slurry of 4 (6.34 g, 29 mmol) and $ZnCl_2$ (2.1 eq, 8.3 g) in $CH_2Cl_2$ (220 mL) at ambient temperature was added EtMgBr (3.0M in ether). In a separate flask, oxallyl chloride (1.3 eq, 3.3 mL) was added to a solution of 3 (1.1 eq, 6.8 g) in $CH_2Cl_2$ (200 mL). After 1 hour, the newly formed acid chloride (5) solution was added via cannula to the indole. The reaction stirred for 1 hour before being quenched by pouring into a solution of satd $NH_4Cl$. Layers were allowed to separate and then the organic layer was washed with $NH_4Cl$ (2×) and $NaHCO_3$ (2×). The organic layer was dried over $Na_2SO_4$ before being filtered through a pad of silica gel, eluting with 2:1 $CH_2Cl_2$/EtOAc. The filtrate was concentrated to provide a red solid which was triturated with MeOH (50-100 mL). The mother liquor was concentrated and the process repeated. Product was isolated as a colored solid.

$^1$H NMR (500 MHz, $CDCl_3$): δ 8.48 (bs, 1H), 7.45 (d, 1H), 7.40 (d, 1H), 7.16 (s, 1H), 6.97 (d, 1H), 6.60 (d, 1H), 6.52 (d, 1H), 5.67 (m, 1H), 5.03 (d, 1H), 5.00 (s, 1H), 4.40 (d, 2H), 3.89 (s, 3H), 2.54 (s, 3H).

Step 4. [2-(Allyloxy)-4-methoxyphenyl][2-methyl-1-[(4-methylphenyl)sulfonyl]-6-(trifluoromethoxy)-1H-indol-3-yl]methanone (7)

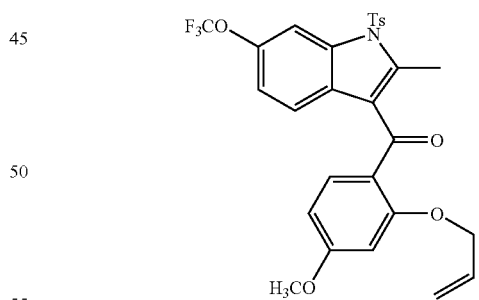

To a solution of 6 (8.0 g, 20 mmol) in DMF (200 mL) was added NaH (1.5 eq). Mixture stirred for 15 min before addition of TsCl (1.5 eq, 5.6 g). After 1 hour, the reaction mixture was poured into ice water and extracted with $CH_2Cl_2$. The organic layer was washed with $NH_4Cl$ (2×), $NaHCO_3$ and brine, then dried with $Na_2SO_4$ and concentrated. Purification via flash chromatography eluding with 20% EtOAc/hexanes afforded the product as a viscous yellow oil.

$^1$H NMR (500 MHz, $CDCl_3$): δ 8.17 (s, 1H), 7.75 (d, 2H), 7.58 (d, 1H), 7.29 (d, 2H), 7.24 (d, 1H), 7.05 (d, 1H), 6.60

(dd, 1H), 6.42 (d, 1H), 5.41 (m, 1H), 4.91 (m, 2H), 4.20 (d, 2H), 3.89 (s, 3H), 2.70 (s, 3H), 2.41 (s, 3H).

Step 5. (2-Hydroxy-4-methoxyphenyl)[2-methyl-1-[(4-methylphenyl)sulfonyl]-6-(trifluoromethoxy)-1H-indol-3-yl]methanone (8)

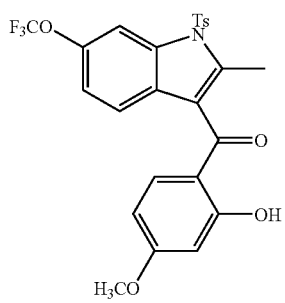

To a solution of 7 (9.0 g, 16 mmol), dimedone (1.5 eq, 3.4 g), and Pd(PPh₃)₄ (5 mol %, 930 mg) in DMF (160 mL) was added diisopropylethylamine (1.5 eq, 4.2 mL). After 30 min, the reaction mixture was diluted with DCM and washed with 0.05M HCl (3×), NaHCO₃, and brine. The organic layer was dried with Na₂SO₄ then filtered through a pad of silica gel to remove remaining palladium. Product was purified via flash chromatography eluding with 14% EtOAc/hexanes to provide the product as an amorphous yellow solid contaminated with ~10% allylated dimedone. Product was used without further purification.

¹H NMR (500 MHz, CDCl₃): δ 12.66 (s, 1H), 8.20 (s, 1H), 7.77 (d, 2H), 7.32 (d, 1H), 7.30 (m, 3H), 7.14 (d, 1H), 6.52 (d, 1H), 6.37 (dd, 1H), 3.89 (s, 3H), 2.63 (s, 3H), 2.42 (s, 3H).

Step 6. (2-Hydroxy-4-methoxyphenyl)[2-methyl-1-[(4-methylphenyl)sulfonyl]-6-(trifluoromethoxy)-1H-indol-3-yl]methanone oxime (9)

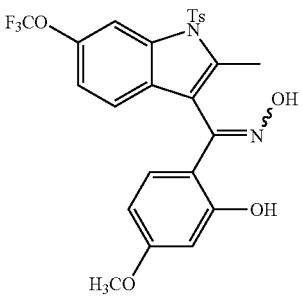

A solution of 8 (16 mmol), hydroxylamine hydrochloride (10 eq, 11.2 g) and pyridine (270 mL) was heated to 80° C. for 24 hours. Additional hydroxylamine (3 g) was added and the temperature increased to 90° C. After LC analysis confirmed the consumption of starting material, the reaction was cooled and the pyridine removed by rotary evaporation. The residue was dissolved in DCM and washed with water and 1M HCl. The organic layer was dried over Na₂SO₄ and concentrated. The reaction mixture was purified by flash chromatography eluding with 20% EtOAc/hexanes, Rf=0.4. The product was isolated as a white foam.

¹H NMR (500 MHz, CDCl₃): δ 8.15 (s, 1H), 7.71 (d, 2H), 7.45 (bs, 1H), 7.27 (d, 2H), 7.09 (m, 2H), 6.56 (m, 2H), 6.23 (dd, 1H), 3.79 (s, 3H), 2.47 (s, 3H), 2.40 (s, 3H).

Step 7. 6-Methoxy-3-[2-methyl-1-[(4-methylphenyl)sulfonyl]-6-(trifluoromethoxy)-1H-indol-3-yl]-1,2-benzisoxazole (10)

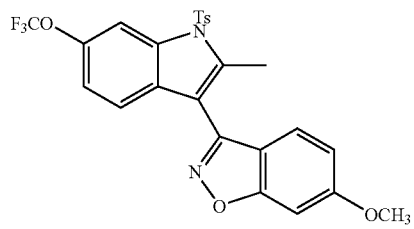

To a solution of 9 (3.8 g, 7.1 mmol) and NaOAc (3 eq, 1.8 g) in DMF (120 mL) was added Ac₂O (3 eq, 2 mL). The reaction was heated to 110° C. for 4 hours at which time no starting material was detected by LC analysis. The reaction was cooled and diluted with DCM. The solution was washed with NH₄Cl, brine and NaHCO₃, then dried over Na₂SO₄ and concentrated. The residue was purified via flash chromatography eluding with 20% EtOAc/hexanes. Product was isolated as white foam.

¹H NMR (500 MHz, CDCl₃): δ 8.23 (s, 1H), 7.77 (d, 2H), 7.48 (d, 1H), 7.36 (d, 1H), 7.28 (d, 2H), 7.15 (d, 1H), 7.09 (d, 1H), 6.94 (dd, 1H), 3.92 (s, 3H), 2.74 (s, 3H), 2.39 (s, 3H).

Step 8. 6-Methoxy-3-[2-methyl-6-(trifluoromethoxy)-1H-indol-3-yl]-1,2-benzisoxazole (11)

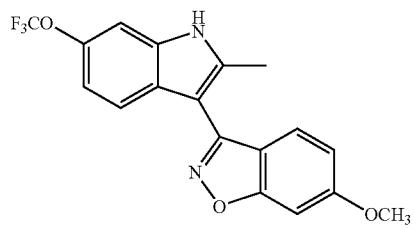

K₂CO₃ (3 eq) and 10 (2.5 g, 4.8 mmol) were heated to reflux in aqueous methanol for 2 hours at which time starting material had been consumed. The reaction mixture was concentrated, diluted with EtOAc and washed with brine. The organic layer was dried over Na₂SO₄ and concentrated. The residue was purified via flash chromatography eluding with 20% EtOAc/hexanes to provide the product as a pale green solid.

¹H NMR (500 MHz, CDCl₃): δ 8.45 (bs, 1H), 7.62 (d, 1H), 7.56 (d, 1H), 7.25 (s, 1H), 7.09 (d, 1H), 7.05 (d, 1H), 6.94 (dd, 1H), 3.93 (s, 3H), 2.63 (s, 3H).

Step 9. Methyl (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoate (15)

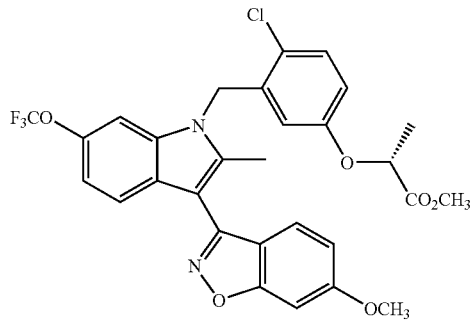

A mixture of 11 (208 mg, 0.57 mmol), Cs$_2$CO$_3$ (3 eq, 500 mg), 14 (1.1 eq, 202 mg) and DMF (4 mL) were combined at rt and stirred for 15 hours. The reaction mixture was diluted with EtOAc and washed with 1M HCl (2×). The organic layer was dried over Na$_2$SO$_4$ and concentrated. The residue was purified via flash chromatography eluding with 5-15% EtOAc/hexanes. Isolated product was a white foam.

$^1$H NMR (500 MHz, CDCl$_3$): δ 7.71 (d, 1H), 7.60 (d, 1H), 7.34 (d, 1H), 7.11 (m, 3H), 6.96 (dd, 1H), 6.72 (dd, 1H), 5.94 (d, 1H), 5.40 (s, 2H), 4.41 (q, 1H), 3.93 (s, 3H), 3.49 (s, 3H), 2.54 (s, 3H), 1.44 (d, 3H).

Step 10. (2R)-2-(4-Chloro-3-{[3-(6-methoxy-1,2-benzisoxazol-3-yl)-2-methyl-6-(trifluoromethoxy)-1H-indol-1-yl]methyl}phenoxy)propanoic acid (16)

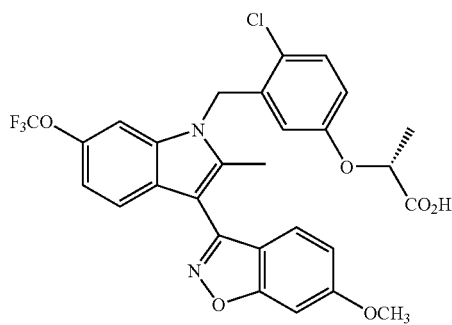

To a solution of 15 (312 mg, 0.46 mmol) in aqueous methanol was added a solution of 1.0M NaOH (1.5 eq). After 2 hours, reaction was complete by TLC. The solution was concentrated and purified by preparatory LC (C18, 100×20 mm I.D., 5 um). Product was isolated as a white amorphous solid.

$^1$H NMR (600 MHz, CDCl$_3$): δ 7.60 (d, 1H), 7.56 (d, 1H), 7.34 (d, 1H), 7.17 (s, 1H), 7.09 (m, 2H), 6.99 (dd, 1H), 6.80 (dd, 1H), 5.61 (d, 1H), 5.41 (dd, 2H), 4.22 (q, 1H), 3.94 (s, 3H), 2.41 (s, 3H), 1.46 (d, 3H). t$_R$=4.34 min, 575.1 (M+H).

Step 11. Methyl (2R)-2-(4-chloro-3-methylphenoxy)propanoate (13)

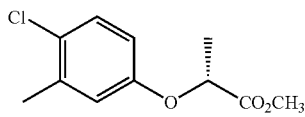

To a solution of 3-methyl-4-chlorophenol (10.0 g, 69 mmol), triphenylphosphine (1.3 eq, 22 g), (S)-methyl lactate (1.3 eq, 9.4 mL) in DCM (230 mL) at 0° C. was added DEAD (1.2 eq, 13 mL) over 1 min. Reaction warmed to rt overnight. The mixture was then filtered through a pad of silica gel and concentrated. The residue was purified via flash chromatography eluting with 10% EtOAc/hexanes to provide the product as a colorless oil.

$^1$H NMR (500 MHz, CDCl$_3$): δ 7.19 (d, 1H), 6.76 (d, 1H), 6.63 (dd, 1H), 4.71 (q, 1H), 3.75 (s, 3H), 2.31 (s, 3H), 1.60 (d, 3H).

Step 12. Methyl (2R)-2-[3-(bromomethyl)-4-chlorophenoxy]propanoate (14)

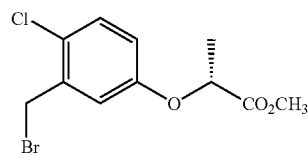

To a solution of lactate (15.8 g, 69 mmol) in CCl$_4$ (150 mL) was added NBS (1.1 eq, 13.5 g) and AIBN (100 mg). The reaction mixture was heated to reflux for 24 hours. The solution was filtered through a pad of silica gel and concentrated. The residue was purified via flash chromatography eluding with 5% EtOAc/hexanes to provide the product as a white solid.

$^1$H NMR (500 MHz, CDCl$_3$): δ 7.27 (d, 1H), 6.96 (d, 1H), 6.76 (dd, 1H), 4.74 (q, 1H), 4.52 (s, 2H), 3.77 (s, 3H), 1.62 (d, 3H).

Synthesis of Compounds in which R$^3$ is Phenyl

A synthetic method is shown below in Example 32 for a compound in which R$^3$ is phenyl. This and other compounds in which R$^3$ is phenyl are shown in Table 4. The other compounds in Table 4 were synthesized using the methods and strategies described herein and readily available materials. Such synthetic methods and materials are readily apparent to a practitioner in the field of synthetic chemistry.

Example 32

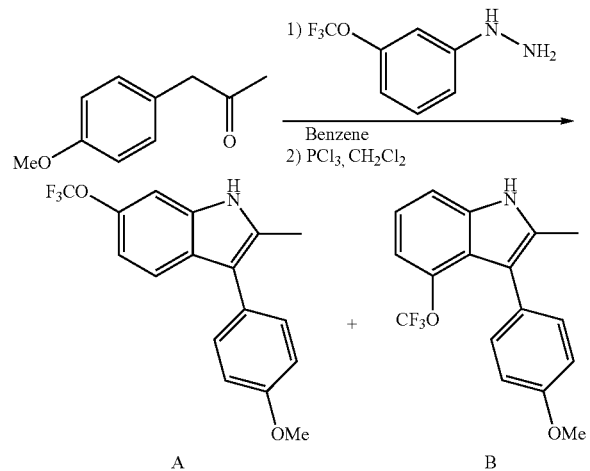

4-Methoxyphenylacetone (1.12 g) and 3-trifluoromethoxyphenyl hydrazine (0.96 g) were dissolved in benzene (20 mL). The reaction mixture was heated at 60° C. for 45 min, cooled to room temperature, dried over anhydrous $Na_2SO_4$, filtered, and concentrated in vacuo to give the phenylhydrazone, which was used immediately without further purification.

To a solution of the above obtained hydrazone (2.0 g) in $CH_2Cl_2$ (100 mL) at room temperature was added $PCd_3$ (0.76 mL). The reaction was stirred at room temperature for 24 h. After cooling to 0° C. by an ice-water bath, the reaction was neutralized to pH 7 by adding 5N aqueous NaOH solution. Most of the solvent was removed in vacuo. The residue was partitioned between ether and water. The organic layer was washed with water and brine, dried over anhydrous $MgSO_4$, filtered, and concentrated in vacuo. Purification by flash chromatography ($SiO_2$, EtOAc/hex 25/1) gave 6-trifluoromethoxy product A (1.0 g) along with the corresponding 4-trifluoromethoxyindole isomer B (0.5 g).

Isomer A: $^1$H NMR ($CDCl_3$, 500 MHz) δ 8.01 (s, broad, 1H), 7.56 (d, J=8.7 Hz, 1H), 7.40 (d, J=8.6 Hz, 2H), 7.20 (s, 1H), 7.02 (d, J=8.7 Hz, 2H), 6.99 (d, J=8.7 Hz, 1H), 3.88 (s, 3H), 2.49 (s, 3H).

Isomer B: $^1$H NMR ($CDCl_3$, 500 MHz) δ 8.09 (s, broad, 1H), 7.31 (d, J=8.7 Hz, 2H), 7.26 (d, J=8.6 Hz, 1H), 7.1 (t, J=8.0 Hz, 1H), 6.96 (overlapping signals, 3H), 3.87 (s, 3H), 2.39 (s, 3H).

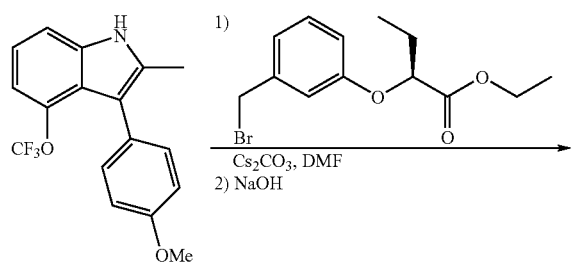

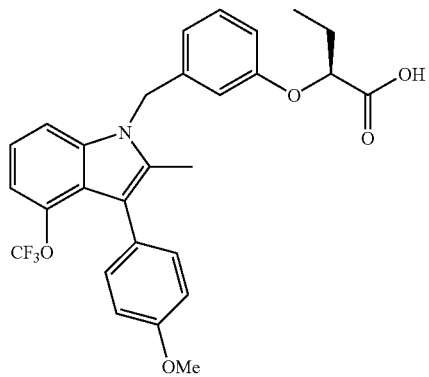

To a solution of indole B (1.0 g) and benzyl bromide (1.0 g) in DMF (40 mL) at room temperature was added $Cs_2CO_3$ (2.0 g). The reaction mixture was stirred for 15 h, poured into water, extracted with EtOAc (2×). The combined organic layers were washed with water and brine, dried over anhydrous $MgSO_4$, filtered, and concentrated in vacuo. Purification by flash chromatography gave the coupling product.

To a solution of the above obtained ester (1.5 g) in MeOH (100 mL) was added aqueous NaOH (1.0 N, 10 mL). The mixture was stirred at room temperature for 5 h, cooled to 0° C., acidified with 1.0 N HCl, diluted with water (200 mL), extracted with EtOAc (2×). The combined organic layers were washed with water and brine, dried over anhydrous $MgSO_4$, filtered, and concentrated in vacuo. The residue was purified by crystallization from ether/hexanes to give the product.

$^1$H NMR ($CDCl_3$, 500 MHz) δ 7.32 (d, J=8.5 Hz, 2H), 7.23 (t, J=8.0 Hz, 1H), 7.17 (d, J=8.2 Hz, 1H), 7.08 (t, J=8.0 Hz, 1H), 6.96 (d+d, overlapping signals, 3H), 6.78 (d, J=8.2 Hz, 1H), 6.66 (d, J=7.6Hz, 1H), 6.58 (s, 1H), 5.34 (s, 2H), 4.53 (t, J=6.0 Hz, 1H), 3.87 (s, 3H), 2.29 (s, 3H), 1.99 (m, 2H), 1.06 (t, J=7.4 Hz, 3H).

TABLE 1

Compounds Where $R^3$ is Phenoxy or Thiophenoxy

| | MOLSTRUCTURE | PARENT WEIGHT | Mass Spec | Retention Time |
|---|---|---|---|---|
| 1 | (structure) | 533.936 | M + H | 4.45 |

TABLE 1-continued

Compounds Where R³ is Phenoxy or Thiophenoxy

| MOLSTRUCTURE | PARENT WEIGHT | Mass Spec | Retention Time |
|---|---|---|---|
| 2 | 431.558 | 432 | 4.15 |
| 3 | 451.976 | 452 | 4.14 |
| 4 | 451.976 | 452 | 4.21 |
| 5 | 547.963 | M + H | 4.51 |

TABLE 1-continued

Compounds Where R³ is Phenoxy or Thiophenoxy

| MOLSTRUCTURE | PARENT WEIGHT | Mass Spec | Retention Time |
| --- | --- | --- | --- |
| 6 | 533.936 | M + H | 4.45 |
| 7 | 535.974 | 536 | 4.7 |
| 8 | 529.518 | M + H | 4.18 |
| 9 | 529.518 | M + H | 4.21 |

TABLE 1-continued
Compounds Where R³ is Phenoxy or Thiophenoxy
| MOLSTRUCTURE | PARENT WEIGHT | Mass Spec | Retention Time |
|---|---|---|---|
| 10 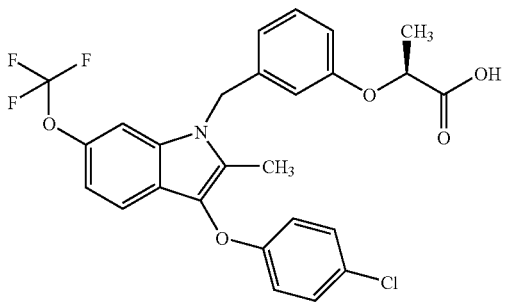 | 519.909 | M + H | 4.49 |
| 11 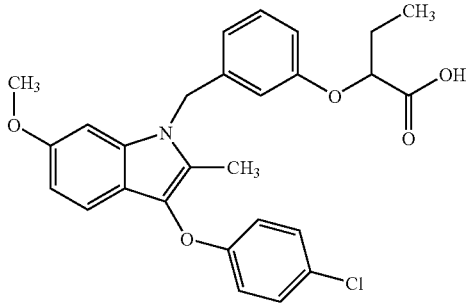 | 479.965 | M + H | 4.18 |
| 12 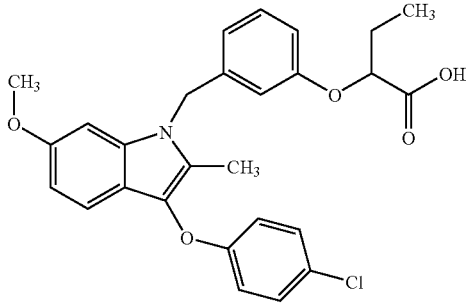 | 479.965 | M + H | 4.21 |
| 13 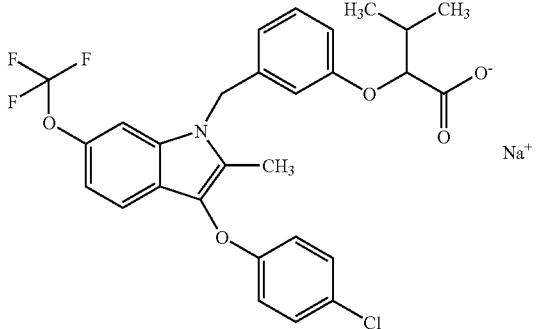 | 547.963 | 4.51 | 548 (M + 1) |

TABLE 1-continued
Compounds Where R³ is Phenoxy or Thiophenoxy
| MOLSTRUCTURE | PARENT WEIGHT | Mass Spec | Retention Time |
|---|---|---|---|
| 14  | 492.02 | | |
| 15  | 492.02 | | |
| 16 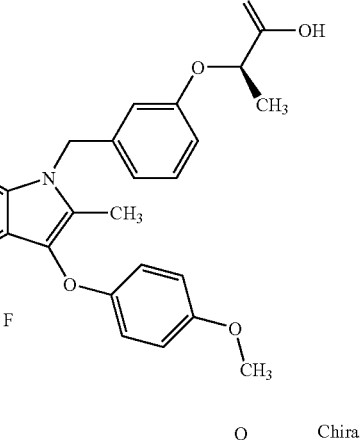 | 499.491 | 500 (M + 1) | 3.8 min |
| 17 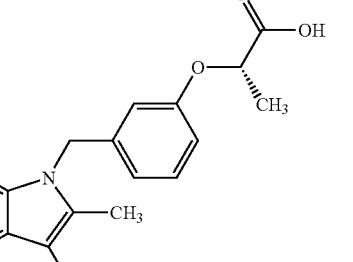 | 499.491 | 500 (M + 1) | 3.8 min |

TABLE 1-continued
Compounds Where R³ is Phenoxy or Thiophenoxy
| MOLSTRUCTURE | PARENT WEIGHT | Mass Spec | Retention Time |
|---|---|---|---|
| 18 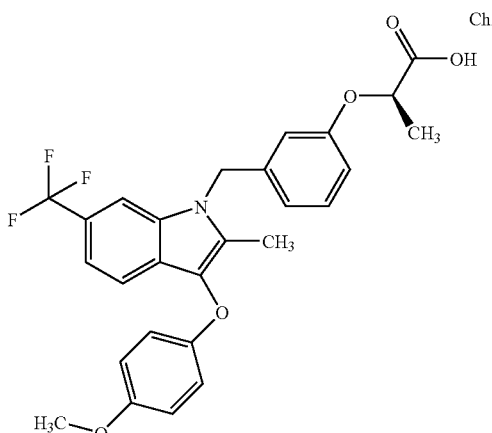 Chiral | 499.491 | 500 (M + 1) | 3.99 min |
| 19 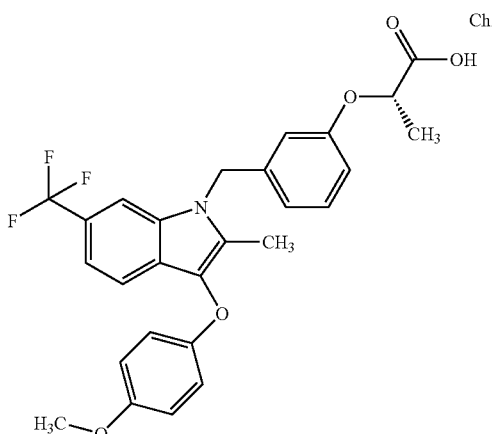 Chiral | 499.491 | 500 (M + 1) | 4.06 min |
| 20 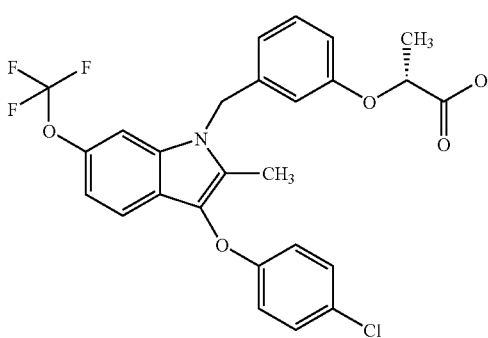 Chiral | 519.909 | M + H | 4.49 |

TABLE 1-continued
| | Compounds Where R³ is Phenoxy or Thiophenoxy | | | |
|---|---|---|---|---|
| MOLSTRUCTURE | | PARENT WEIGHT | Mass Spec | Retention Time |
| 21 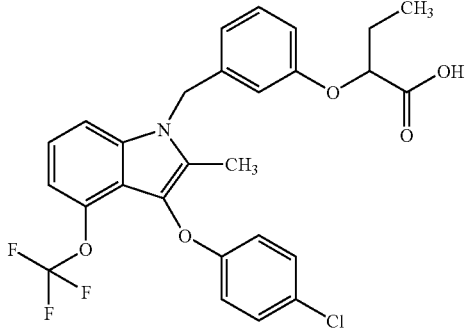 | | 533.936 | M + H | 4.32 |
| 22 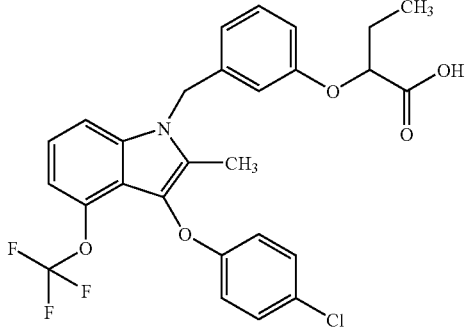 | | 533.936 | M + H | 4.32 |
| 23 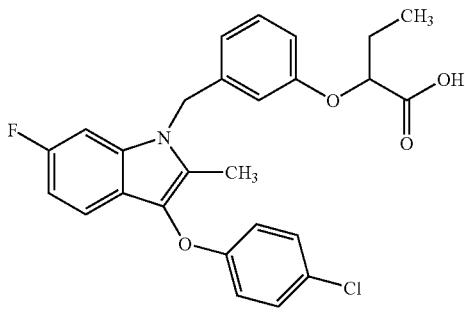 | | 467.929 | M + H | 4.26 |
| 24 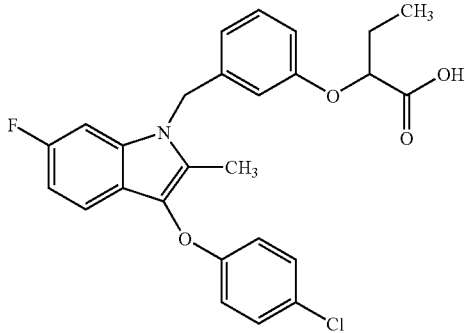 | | 467.929 | M + H | 4.26 |

TABLE 1-continued
Compounds Where R[3] is Phenoxy or Thiophenoxy
| MOLSTRUCTURE | | PARENT WEIGHT | Mass Spec | Retention Time |
|---|---|---|---|---|
| 25 | 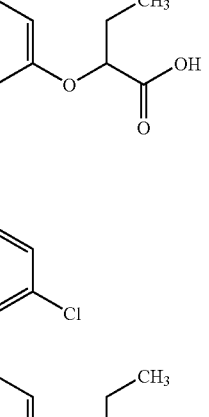 | 467.929 | M + H | 4.16 |
| 26 | 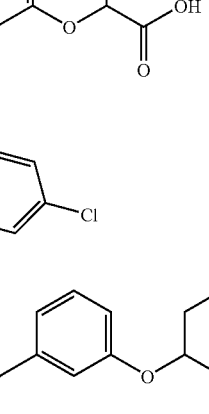 | 467.929 | M + H | 4.13 |
| 27 | 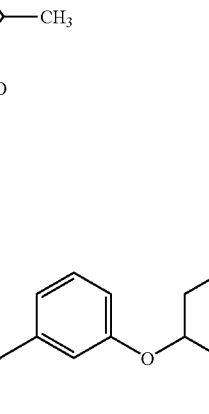 | 513.518 | 514.4 (M + 1) | 3.87 |
| 28 |  | 513.518 | 514.4 (M + 1) | 3.87 |

TABLE 1-continued
Compounds Where R³ is Phenoxy or Thiophenoxy
| MOLSTRUCTURE | PARENT WEIGHT | Mass Spec | Retention Time |
|---|---|---|---|
| 29 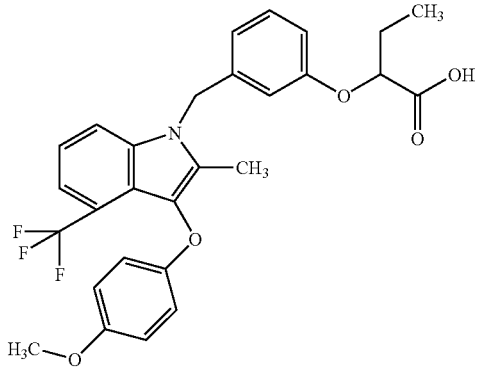 | 513.518 | 514.3 (M + 1) | 3.65 |
| 30 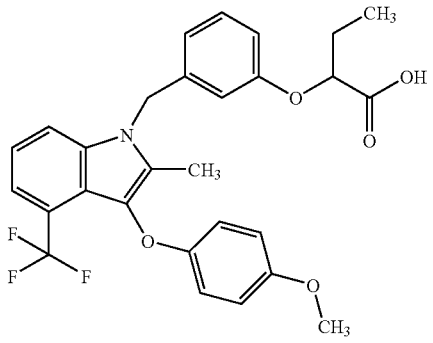 | 513.518 | 514.4 (M + 1) | 3.65 |
| 31 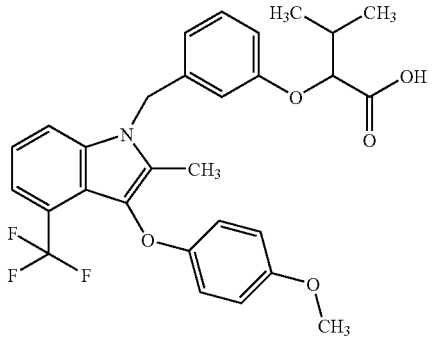 | 527.545 | 528.4 (M + 1) | 3.95 |
| 32 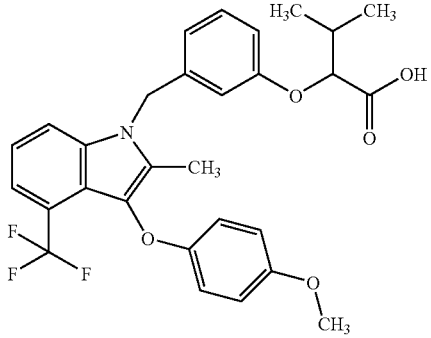 | 527.545 | 528.4 (M + 1) | 3.95 |

TABLE 1-continued
Compounds Where R³ is Phenoxy or Thiophenoxy
| MOLSTRUCTURE | PARENT WEIGHT | Mass Spec | Retention Time |
|---|---|---|---|
| 33 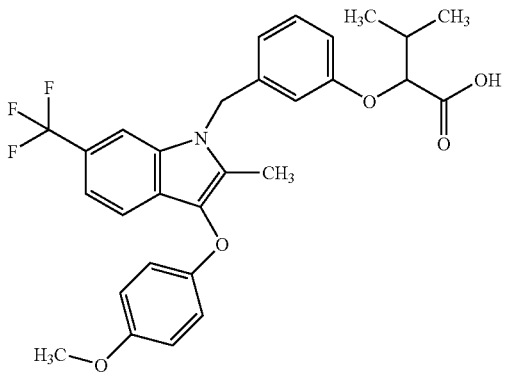 | 527.545 | 528.4 (M + 1) | 4.56 |
| 34 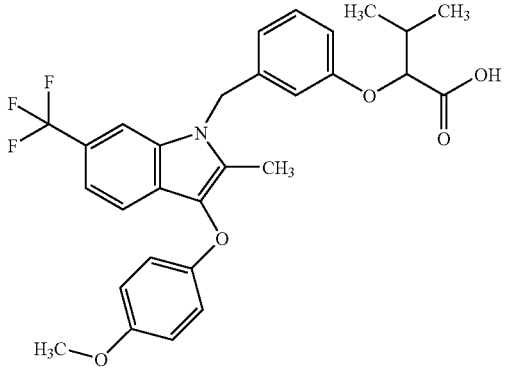 | 527.545 | 528.4 (M + 1) | 4.56 |
| 35 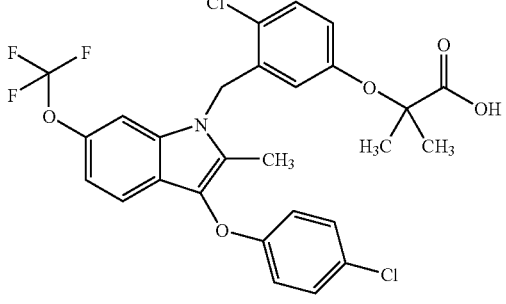 | 568.381 | M + H | 4.79 |
| 36 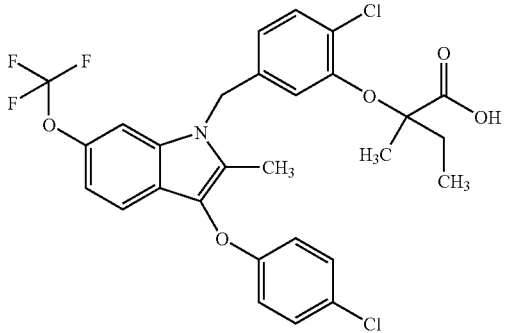 | 582.408 | M + H | 4.89 |

TABLE 1-continued
Compounds Where R³ is Phenoxy or Thiophenoxy
| MOLSTRUCTURE | | PARENT WEIGHT | Mass Spec | Retention Time |
|---|---|---|---|---|
| 37 | 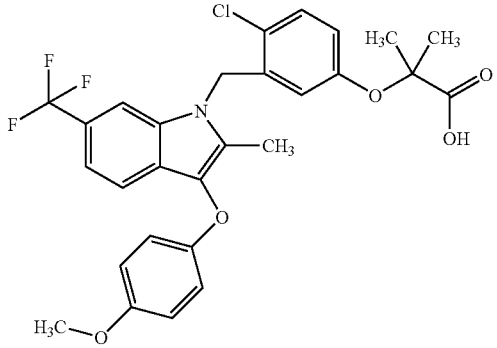 | 547.963 | 548 (M + 1) | 4.19 min |
| 38 | 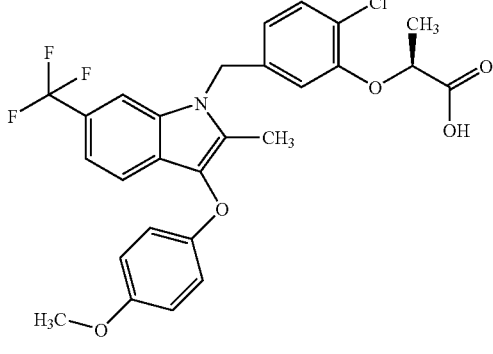 Chiral | 533.936 | 534 (M + 1) | 4.06 min |
| 39 | 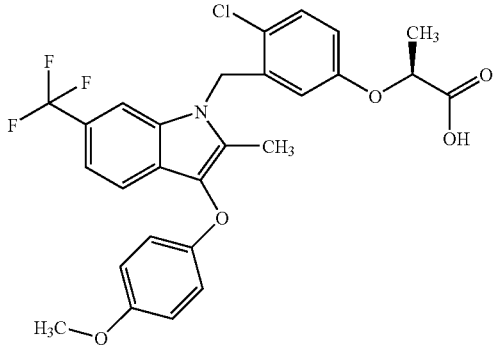 Chiral | 533.936 | 534 (M + 1) | 3.93 min |
| 40 | 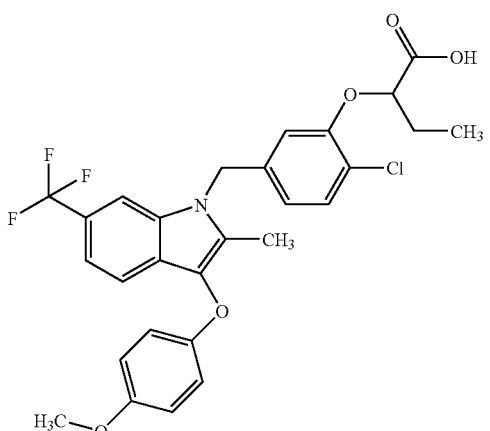 | 547.963 | 548 (M + 1) | 4.18 min |

TABLE 1-continued
Compounds Where R³ is Phenoxy or Thiophenoxy
| MOLSTRUCTURE | PARENT WEIGHT | Mass Spec | Retention Time |
|---|---|---|---|
| 41 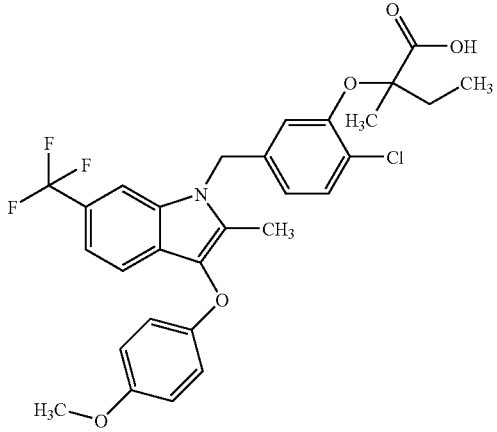 | 561.99 | 562 (M + 1) | 4.26 min |
| 42 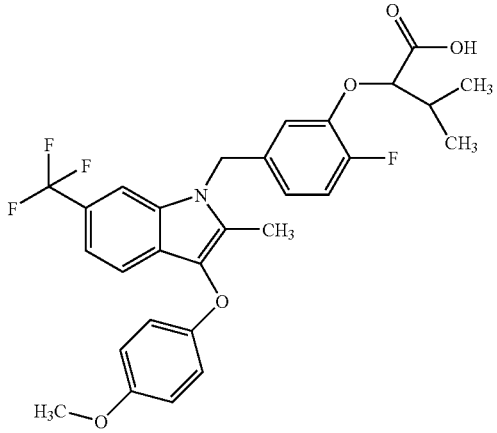 | 545.536 | 546 (M + 1) | 4.14 min |
| 43 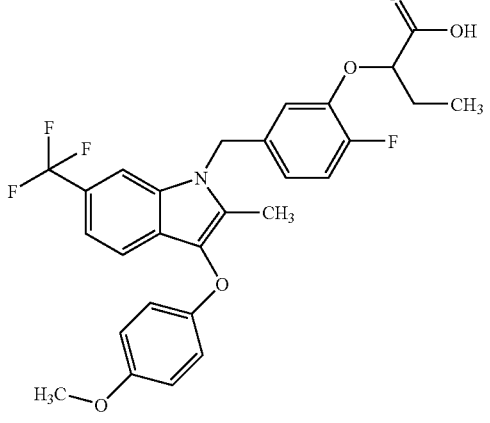 | 531.509 | 532 (M + 1) | 4.08 min |

TABLE 1-continued
Compounds Where R³ is Phenoxy or Thiophenoxy
| MOLSTRUCTURE | | PARENT WEIGHT | Mass Spec | Retention Time |
|---|---|---|---|---|
| 44 | 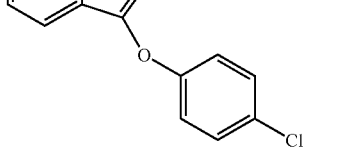 Chiral | 554.354 | M + H | 4.64 |
| 45 | 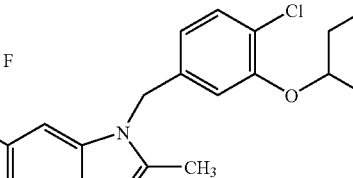 | 568.381 | | |
| 46 | 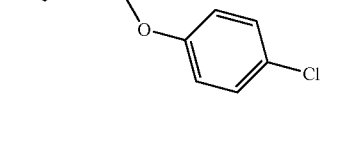 Chiral | 517.482 | 518 (M + 1) | 3.78 min |
| 47 | 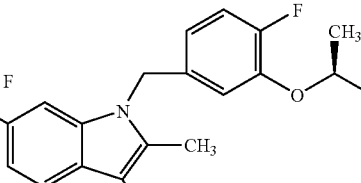 Chiral | 533.936 | 534 (M + 1) | 3.96 min |

TABLE 1-continued

Compounds Where R³ is Phenoxy or Thiophenoxy

| MOLSTRUCTURE | | PARENT WEIGHT | Mass Spec | Retention Time |
|---|---|---|---|---|
| 48 | | 517.482 | 518 (M + 1) | 3.85 min |
| 49 | Chiral | 517.482 | 518 (M + 1) | 3.91 min |
| 50 | Chiral | 517.482 | 518 (M + 1) | 3.91 min |
| 51 | | 554.354 | M + H | 4.5 |

TABLE 1-continued

Compounds Where R³ is Phenoxy or Thiophenoxy

| MOLSTRUCTURE | PARENT WEIGHT | Mass Spec | Retention Time |
|---|---|---|---|
| 52 | 568.381 | M + H | 4.78 |
| 53 | 551.927 | M + H | 4.63 |
| 54 (Chiral) | 515.491 | M + H | 4.13 |
| 55 | 533.936 | M + H | 4.59 |

US 7,345,085 B2
TABLE 1-continued
Compounds Where R³ is Phenoxy or Thiophenoxy
| MOLSTRUCTURE | | PARENT WEIGHT | Mass Spec | Retention Time |
|---|---|---|---|---|
| 56 | 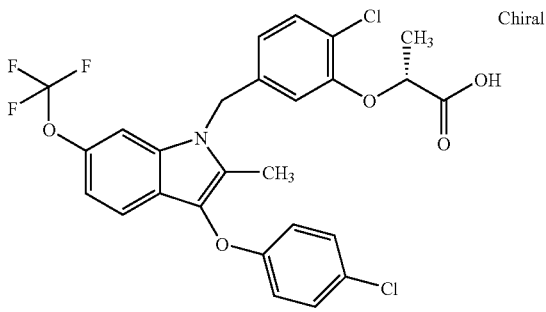 Chiral | 554.354 | M + H | 4.65 |
| 57 | 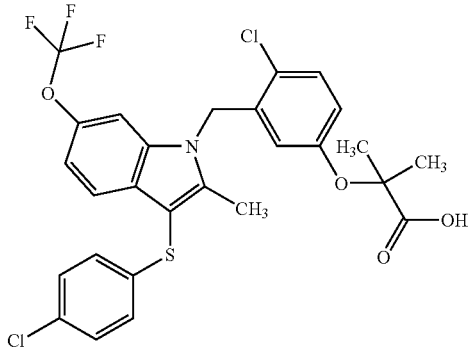 | 584.446 | 584 | 4.74 |
| 58 | 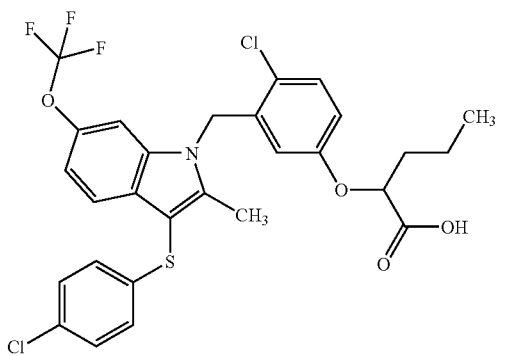 | 598.473 | 598 | 5.05 |
| 59 | 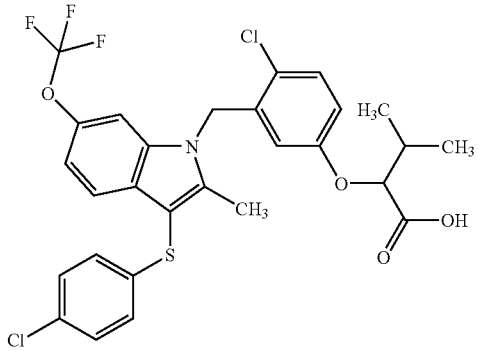 | 598.473 | 598 | 5.02 |

TABLE 1-continued
Compounds Where R³ is Phenoxy or Thiophenoxy
| MOLSTRUCTURE | PARENT WEIGHT | Mass Spec | Retention Time |
|---|---|---|---|
| 60 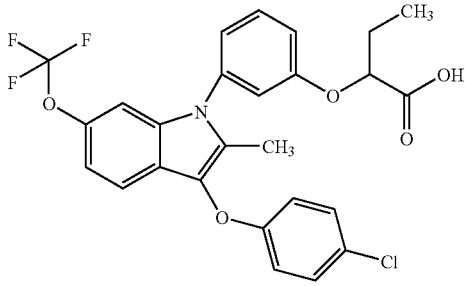 | 519.909 | | |
| 61 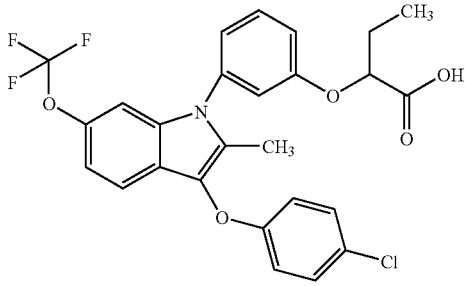 | 519.909 | | |
| 62 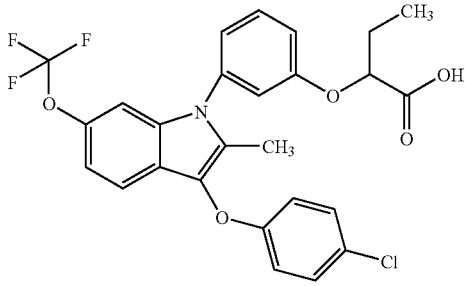 Chiral | 550.001 | 550.3 (M + H) | 4.35 min |
| 63 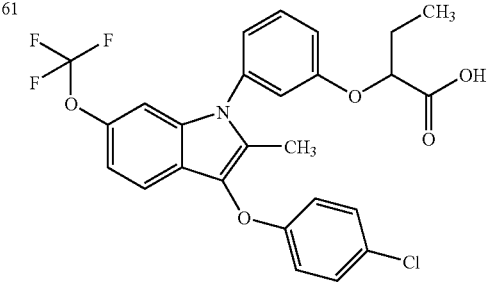 | 517.937 | 518.4 (M + 1) | 4.17 |

TABLE 1-continued
Compounds Where R³ is Phenoxy or Thiophenoxy
| MOLSTRUCTURE | PARENT WEIGHT | Mass Spec | Retention Time |
|---|---|---|---|
| 64 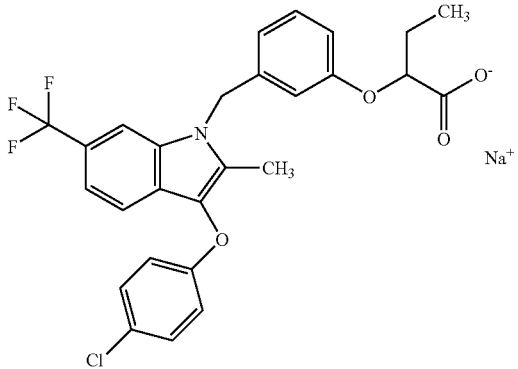 | 517.937 | 518.4 (M + 1) | 4.17 |
| 65 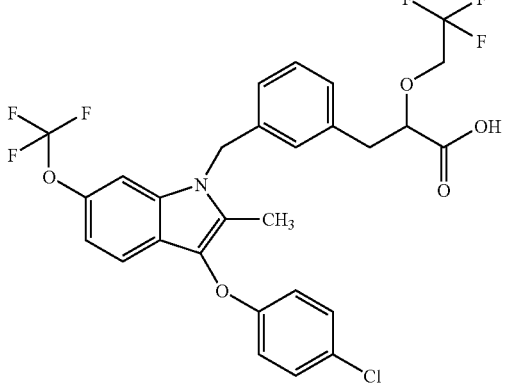 | 601.935 | | |
| 66 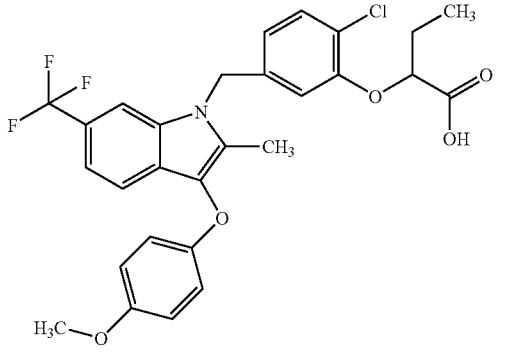 | 547.963 | 548 (M + 1) | 4.18 min |
| 67 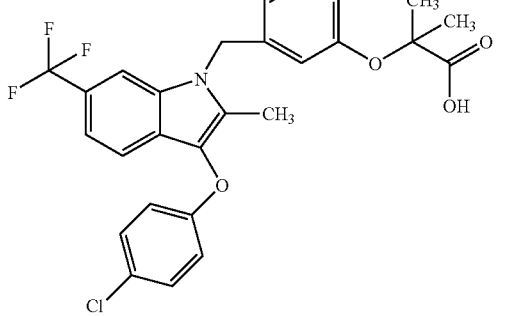 | 517.937 | 518 (M + 1) | 4.12 min |

TABLE 1-continued
Compounds Where R³ is Phenoxy or Thiophenoxy
| MOLSTRUCTURE | | PARENT WEIGHT | Mass Spec | Retention Time |
|---|---|---|---|---|
| 68 | 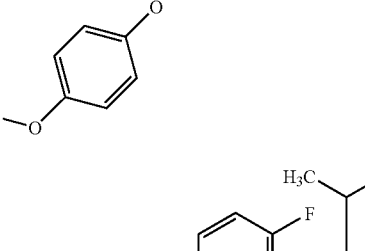 | 547.963 | 548 (M + 1) | 4.18 min |
| 69 | 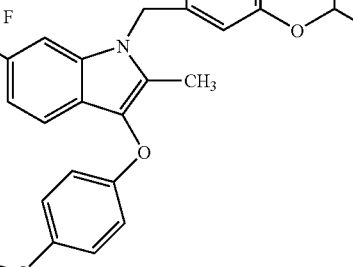 | 545.536 | 546 (M + 1) | 4.34 min |
| 70 | 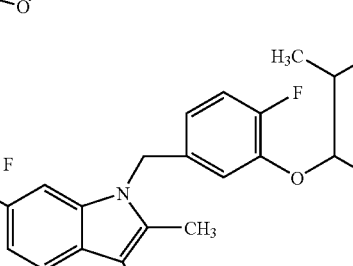 | 545.536 | 546 (M + 1) | 4.34 min |
| 71 | 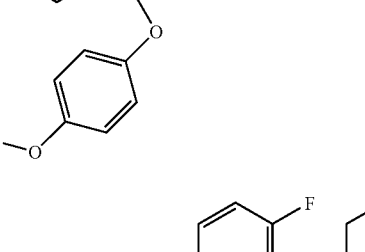 | 531.509 | 532 (M + 1) | 4.19 min |

TABLE 1-continued
Compounds Where R³ is Phenoxy or Thiophenoxy
| MOLSTRUCTURE | PARENT WEIGHT | Mass Spec | Retention Time |
|---|---|---|---|
| 72 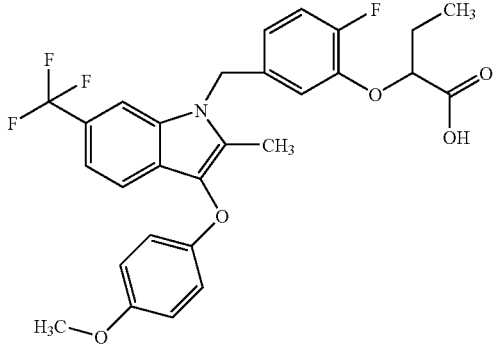 | 531.509 | 532 (M + 1) | 4.21 min |
| 73 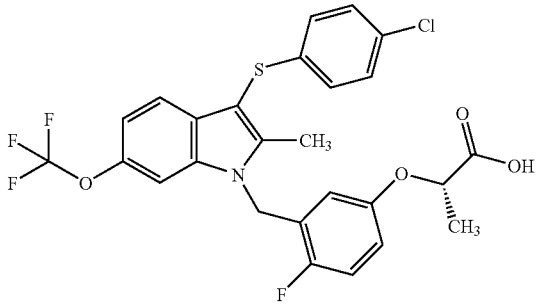 | 553.964 | 554.3 | 4.23 |
| 74 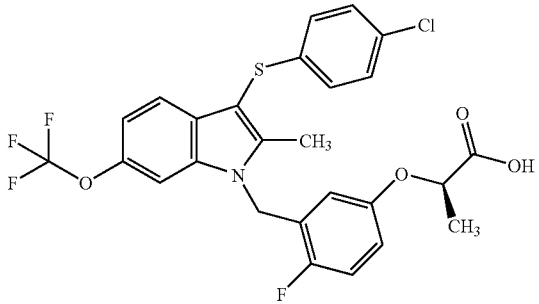 | 553.964 | 554.3 | 4.23 |
| 75 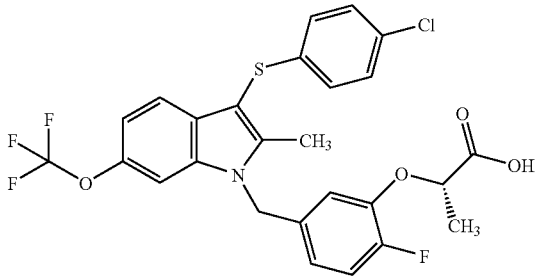 | 553.964 | 554.3 (M + H) | 4.22 |

TABLE 1-continued

Compounds Where R³ is Phenoxy or Thiophenoxy

| MOLSTRUCTURE | PARENT WEIGHT | Mass Spec | Retention Time |
|---|---|---|---|
| 76 | 553.964 | 554.3 (M + H) | 4.23 |
| 77 | 570.419 | 570.3 (M + H) | 4.35 |
| 78 | 570.419 | 570.3 (M + H) | 4.36 |
| 79 | 531.964 | 532 (M + 1) | 4.65 min |

TABLE 1-continued
Compounds Where R[3] is Phenoxy or Thiophenoxy
| MOLSTRUCTURE | PARENT WEIGHT | Mass Spec | Retention Time |
|---|---|---|---|
| 80 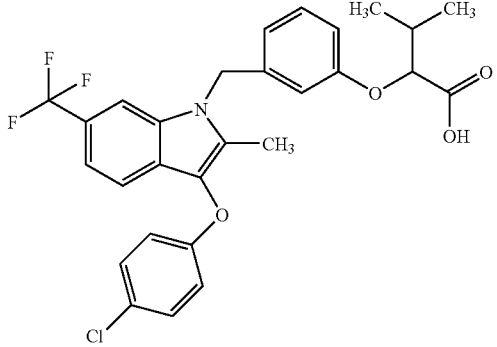 | 531.964 | 532 (M + 1) | 4.65 min |
| 81 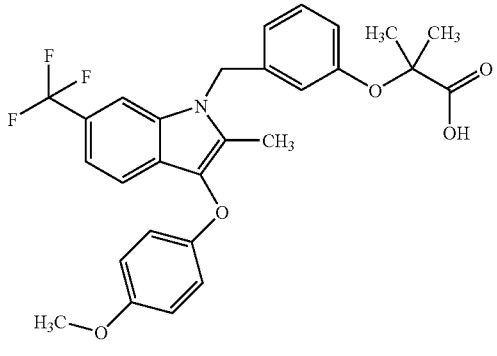 | 513.518 | 514 (M + 1) | 4.14 min |
| 82 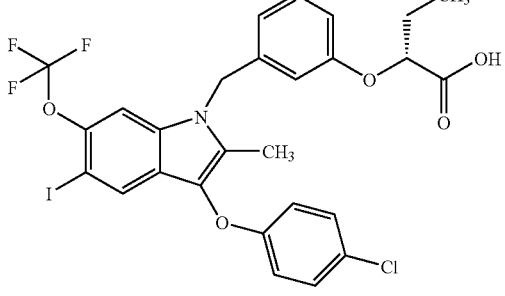 | 659.833 | M + H | 4.43 |
| 83 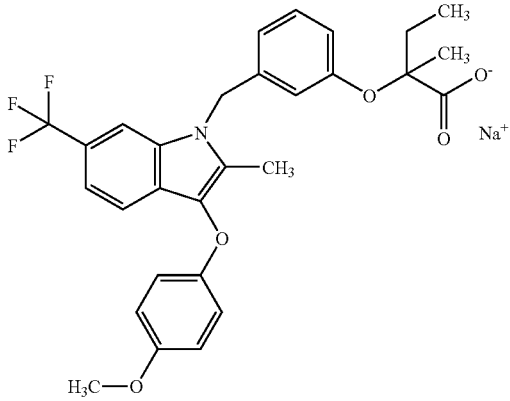 | 527.545 | 528.4 (M + 1) | 4.02 |

TABLE 1-continued

Compounds Where R³ is Phenoxy or Thiophenoxy

| MOLSTRUCTURE | PARENT WEIGHT | Mass Spec | Retention Time |
|---|---|---|---|
| 84 | 527.545 | 528.4 (M + 1) | 4.02 |
| 85 | 566 | 566.3 (M + H) | 3.52 |
| 86 | 519.909 | M + H | 4.33 |
| 87 | 521.9 | 522.4 (M + 1) | 4.08 |

TABLE 1-continued

Compounds Where R³ is Phenoxy or Thiophenoxy

| | MOLSTRUCTURE | PARENT WEIGHT | Mass Spec | Retention Time |
|---|---|---|---|---|
| 88 | 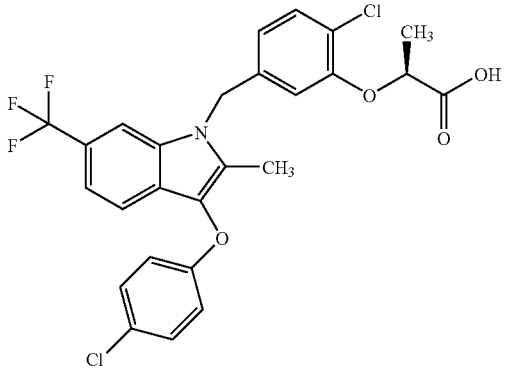 | 538.355 | 538.4 (M + 1) | 4.13 |

TABLE 1A

Compounds Where R³ is Phenoxy or Thiophenoxy 1. (2R)-2-(3-{[3-(4-chlorophenoxy)-2-methyl-6-(trifluoromethoxy)-1H-indol-1-yl]methyl}phenoxy)butanoic acid
2. (2R)-2-(3-{[2-methyl-3-(phenylthio)-1H-indol-1-yl]methyl}phenoxy)butanoic acid
3. (2S)-2-(2-chloro-5-{[2-methyl-3-(phenylthio)-1H-indol-1-yl]methyl}phenoxy)propanoic acid
4. (2R)-2-(4-chloro-3-{[2-methyl-3-(phenylthio)-1H-indol-1-yl]methyl}phenoxy)propanoic acid
5. 2-(3-{[3-(4-chlorophenoxy)-2-methyl-6-(trifluoromethoxy)-1H-indol-1-yl]methyl}phenoxy)-3-methylbutanoic acid
6. 2-(3-{[3-(4-chlorophenoxy)-2-methyl-6-(trifluoromethoxy)-1H-indol-1-yl]methyl}phenoxy)butanoic acid
7. (2S)-2-(3-{[3-[(4-chlorophenyl)thio]-2-methyl-6-(trifluoromethoxy)-1H-indol-1-yl]methyl}phenoxy)propanoic acid
8. 2-(3-{[3-(4-methoxyphenoxy)-2-methyl-6-(trifluoromethoxy)-1H-indol-1-yl]methyl}phenoxy)butanoic acid
9. 2-(3-{[3-(4-methoxyphenoxy)-2-methyl-6-(trifluoromethoxy)-1H-indol-1-yl]methyl}phenoxy)butanoic acid
10. (2S)-2-(3-{[3-(4-chlorophenoxy)-2-methyl-6-(trifluoromethoxy)-1H-indol-1-yl]methyl}phenoxy)propanoic acid
11. 2-(3-{[3-(4-chlorophenoxy)-6-methoxy-2-methyl-1H-indol-1-yl]methyl}phenoxy)butanoic acid
12. 2-(3-{[3-(4-chlorophenoxy)-6-methoxy-2-methyl-1H-indol-1-yl]methyl}phenoxy)butanoic acid
13. 2-(3-{[3-(4-chlorophenoxy)-2-methyl-6-(trifluoromethoxy)-1H-indol-1-yl]methyl}phenoxy)-3-methylbutanoic acid
14. 2-(3-{[3-(4-chlorophenoxy)-6-isopropyl-2-methyl-1H-indol-1-yl]methyl}phenoxy)butanoic acid
15. 2-(3-{[3-(4-chlorophenoxy)-6-isopropyl-2-methyl-1H-indol-1-yl]methyl}phenoxy)butanoic acid
16. (2R)-2-(3-{[3-(4-methoxyphenoxy)-2-methyl-4-(trifluoromethyl)-1H-indol-1-yl]methyl}phenoxy)propanoic acid
17. (2S)-2-(3-{[3-(4-methoxyphenoxy)-2-methyl-4-(trifluoromethyl)-1H-indol-1-yl]methyl}phenoxy)propanoic acid
18. (2R)-2-(3-{[3-(4-methoxyphenoxy)-2-methyl-6-(trifluoromethyl)-1H-indol-1-yl]methyl}phenoxy)propanoic acid
19. (2S)-2-(3-{[3-(4-methoxyphenoxy)-2-methyl-6-(trifluoromethyl)-1H-indol-1-yl]methyl}phenoxy)propanoic acid
20. (2R)-2-(3-{[3-(4-chlorophenoxy)-2-methyl-6-(trifluoromethoxy)-1H-indol-1-yl]methyl}phenoxy)propanoic acid
21. 2-(3-{[3-(4-chlorophenoxy)-2-methyl-4-(trifluoromethoxy)-1H-indol-1-yl]methyl}phenoxy)butanoic acid
22. 2-(3-{[3-(4-chlorophenoxy)-2-methyl-4-(trifluoromethoxy)-1H-indol-1-yl]methyl}phenoxy)butanoic acid
23. 2-(3-{[3-(4-chlorophenoxy)-6-fluoro-2-methyl-1H-indol-1-yl]methyl}phenoxy)butanoic acid
24. 2-(3-{[3-(4-chlorophenoxy)-6-fluoro-2-methyl-1H-indol-1-yl]methyl}phenoxy)butanoic acid
25. 2-(3-{[3-(4-chlorophenoxy)-4-fluoro-2-methyl-1H-indol-1-yl]methyl}phenoxy)butanoic acid TABLE 1A-continued Compounds Where R³ is Phenoxy or Thiophenoxy 26  2-(3-{[3-(4-chlorophenoxy)-4-fluoro-2-methyl-1H-indol-1-yl]methyl}phenoxy)butanoic acid
27  2-(3-{[3-(4-methoxyphenoxy)-2-methyl-6-(trifluoromethyl)-1H-indol-1-yl]methyl}phenoxy)butanoic acid
28  2-(3-{[3-(4-methoxyphenoxy)-2-methyl-6-(trifluoromethyl)-1H-indol-1-yl]methyl}phenoxy)butanoic acid
29  2-(3-{[3-(4-methoxyphenoxy)-2-methyl-4-(trifluoromethyl)-1H-indol-1-yl]methyl}phenoxy)butanoic acid
30  2-(3-{[3-(4-methoxyphenoxy)-2-methyl-4-(trifluoromethyl)-1H-indol-1-yl]methyl}phenoxy)butanoic acid
31  2-(3-{[3-(4-methoxyphenoxy)-2-methyl-4-(trifluoromethyl)-1H-indol-1-yl]methyl}phenoxy)-3-methylbutanoic acid
32  2-(3-{[3-(4-methoxyphenoxy)-2-methyl-4-(trifluoromethyl)-1H-indol-1-yl]methyl}phenoxy)-3-methylbutanoic acid
33  2-(3-{[3-(4-methoxyphenoxy)-2-methyl-6-(trifluoromethyl)-1H-indol-1-yl]methyl}phenoxy)-3-methylbutanoic acid
34  2-(3-{[3-(4-methoxyphenoxy)-2-methyl-6-(trifluoromethyl)-1H-indol-1-yl]methyl}phenoxy)-3-methylbutanoic acid
35  2-(4-chloro-3-{[3-(4-chlorophenoxy)-2-methyl-6-(trifluoromethoxy)-1H-indol-1-yl]methyl}phenoxy)-2-methylpropanoic acid
36  2-(2-chloro-5-{[3-(4-chlorophenoxy)-2-methyl-6-(trifluoromethoxy)-1H-indol-1-yl]methyl}phenoxy)-2-methylbutanoic acid
37  2-(4-chloro-3-{[3-(4-methoxyphenoxy)-2-methyl-6-(trifluoromethyl)-1H-indol-1-yl]methyl}phenoxy)-2-methylpropanoic acid
38  (2S)-2-(2-chloro-5-{[3-(4-methoxyphenoxy)-2-methyl-6-(trifluoromethyl)-1H-indol-1-yl]methyl}phenoxy)propanoic acid
39  (2S)-2-(4-chloro-3-{[3-(4-methoxyphenoxy)-2-methyl-6-(trifluoromethyl)-1H-indol-1-yl]methyl}phenoxy)propanoic acid
40  2-(2-chloro-5-{[3-(4-methoxyphenoxy)-2-methyl-6-(trifluoromethyl)-1H-indol-1-yl]methyl}phenoxy)butanoic acid
41  2-(2-chloro-5-{[3-(4-methoxyphenoxy)-2-methyl-6-(trifluoromethyl)-1H-indol-1-yl]methyl}phenoxy)-2-methylbutanoic acid
42  2-(2-fluoro-5-{[3-(4-methoxyphenoxy)-2-methyl-6-(trifluoromethyl)-1H-indol-1-yl]methyl}phenoxy)-3-methylbutanoic acid
43  2-(2-fluoro-5-{[3-(4-methoxyphenoxy)-2-methyl-6-(trifluoromethyl)-1H-indol-1-yl]methyl}phenoxy)butanoic acid
44  2-(2-chloro-5-{[3-(4-chlorophenoxy)-2-methyl-6-(trifluoromethoxy)-1H-indol-1-yl]methyl}phenoxy)propanoic acid
45  2-(2-chloro-5-{[3-(4-chlorophenoxy)-2-methyl-6-(trifluoromethoxy)-1H-indol-1-yl]methyl}phenoxy)butanoic acid
46  (2S)-2-(2-fluoro-5-{[3-(4-methoxyphenoxy)-2-methyl-6-(trifluoromethyl)-1H-indol-1-yl]methyl}phenoxy)propanoic acid
47  (2R)-2-(2-chloro-5-{[3-(4-methoxyphenoxy)-2-methyl-6-(trifluoromethyl)-1H-indol-1-yl]methyl}phenoxy)propanoic acid
48  (2R)-2-(4-fluoro-3-{[3-(4-methoxyphenoxy)-2-methyl-6-(trifluoromethyl)-1H-indol-1-yl]methyl}phenoxy)propanoic acid
49  (2S)-2-(4-fluoro-3-{[3-(4-methoxyphenoxy)-2-methyl-6-(trifluoromethyl)-1H-indol-1-yl]methyl}phenoxy)propanoic acid
50  (2R)-2-(2-fluoro-5-{[3-(4-methoxyphenoxy)-2-methyl-6-(trifluoromethyl)-1H-indol-1-yl]methyl}phenoxy)propanoic acid
51  (2S)-2-(4-chloro-3-{[3-(4-chlorophenoxy)-2-methyl-6-(trifluoromethoxy)-1H-indol-1-yl]methyl}phenoxy)propanoic acid
52  2-(4-chloro-3-{[3-(4-chlorophenoxy)-2-methyl-6-(trifluoromethoxy)-1H-indol-1-yl]methyl}phenoxy)butanoic acid
53  2-(5-{[3-(4-chlorophenoxy)-2-methyl-6-(trifluoromethoxy)-1H-indol-1-yl]methyl}-2-fluorophenoxy)butanoic acid
54  (2S)-2-(3-{[3-(4-methoxyphenoxy)-2-methyl-6-(trifluoromethoxy)-1H-indol-1-yl]methyl}phenoxy)propanoic acid
55  2-(3-{[3-(4-chlorophenoxy)-2-methyl-6-(trifluoromethoxy)-1H-indol-1-yl]methyl}phenoxy)-2-methylpropanoic acid
56  (2R)-2-(2-chloro-5-{[3-(4-chlorophenoxy)-2-methyl-6-(trifluoromethoxy)-1H-indol-1-yl]methyl}phenoxy)propanoic acid TABLE 1A-continued Compounds Where R³ is Phenoxy or Thiophenoxy 57  2-(4-chloro-3-{[3-[(4-chlorophenyl)thio]-2-methyl-6-(trifluoromethoxy)-1H-indol-1-yl]methyl}phenoxy)-2-methylpropanoic acid
58  2-(4-chloro-3-{[3-[(4-chlorophenyl)thio]-2-methyl-6-(trifluoromethoxy)-1H-indol-1-yl]methyl}phenoxy)pentanoic acid
59  2-(4-chloro-3-{[3-[(4-chlorophenyl)thio]-2-methyl-6-(trifluoromethoxy)-1H-indol-1-yl]methyl}phenoxy)-3-methylbutanoic acid
60  2-{3-[3-(4-chlorophenoxy)-2-methyl-6-(trifluoromethoxy)-1H-indol-1-yl]phenoxy}butanoic acid
61  2-{3-[3-(4-chlorophenoxy)-2-methyl-6-(trifluoromethoxy)-1H-indol-1-yl]phenoxy}butanoic acid
62  (2R)-2-(3-{[3-[(4-chlorophenyl)thio]-2-methyl-6-(trifluoromethoxy)-1H-indol-1-yl]methyl}phenoxy)butanoic acid
63  2-(3-{[3-(4-chlorophenoxy)-2-methyl-6-(trifluoromethyl)-1H-indol-1-yl]methyl}phenoxy)butanoic acid
64  2-(3-{[3-(4-chlorophenoxy)-2-methyl-6-(trifluoromethyl)-1H-indol-1-yl]methyl}phenoxy)butanoic acid
65  3-(3-{[3-(4-chlorophenoxy)-2-methyl-6-(trifluoromethoxy)-1H-indol-1-yl]methyl}phenyl)-2-(2,2,2-trifluoroethoxy)propanoic acid
66  2-(2-chloro-5-{[3-(4-methoxyphenoxy)-2-methyl-6-(trifluoromethyl)-1H-indol-1-yl]methyl}phenoxy)butanoic acid
67  2-(3-{[3-(4-chlorophenoxy)-2-methyl-6-(trifluoromethyl)-1H-indol-1-yl]methyl}phenoxy)-2-methylpropanoic acid
68  2-(2-chloro-5-{[3-(4-methoxyphenoxy)-2-methyl-6-(trifluoromethyl)-1H-indol-1-yl]methyl}phenoxy)butanoic acid
69  2-(2-fluoro-5-{[3-(4-methoxyphenoxy)-2-methyl-6-(trifluoromethyl)-1H-indol-1-yl]methyl}phenoxy)-3-methylbutanoic acid
70  2-(2-fluoro-5-{[3-(4-methoxyphenoxy)-2-methyl-6-(trifluoromethyl)-1H-indol-1-yl]methyl}phenoxy)-3-methylbutanoic acid
71  2-(2-fluoro-5-{[3-(4-methoxyphenoxy)-2-methyl-6-(trifluoromethyl)-1H-indol-1-yl]methyl}phenoxy)butanoic acid
72  2-(2-fluoro-5-{[3-(4-methoxyphenoxy)-2-methyl-6-(trifluoromethyl)-1H-indol-1-yl]methyl}phenoxy)butanoic acid
73  (2S)-2-(3-{[3-[(4-chlorophenyl)thio]-2-methyl-6-(trifluoromethoxy)-1H-indol-1-yl]methyl}-4-fluorophenoxy)propanoic acid
74  (2R)-2-(3-{[3-[(4-chlorophenyl)thio]-2-methyl-6-(trifluoromethoxy)-1H-indol-1-yl]methyl}-4-fluorophenoxy)propanoic acid
75  (2S)-2-(5-{[3-[(4-chlorophenyl)thio]-2-methyl-6-(trifluoromethoxy)-1H-indol-1-yl]methyl}-2-fluorophenoxy)propanoic acid
76  (2R)-2-(5-{[3-[(4-chlorophenyl)thio]-2-methyl-6-(trifluoromethoxy)-1H-indol-1-yl]methyl}-2-fluorophenoxy)propanoic acid
77  (2S)-2-(2-chloro-5-{[3-[(4-chlorophenyl)thio]-2-methyl-6-(trifluoromethoxy)-1H-indol-1-yl]methyl}phenoxy)propanoic acid
78  (2R)-2-(2-chloro-5-{[3-[(4-chlorophenyl)thio]-2-methyl-6-(trifluoromethoxy)-1H-indol-1-yl]methyl}phenoxy)propanoic acid
79  2-(3-{[3-(4-chlorophenoxy)-2-methyl-6-(trifluoromethyl)-1H-indol-1-yl]methyl}phenoxy)-3-methylbutanoic acid
80  2-(3-{[3-(4-chlorophenoxy)-2-methyl-6-(trifluoromethyl)-1H-indol-1-yl]methyl}phenoxy)-3-methylbutanoic acid
81  2-(3-{[3-(4-methoxyphenoxy)-2-methyl-6-(trifluoromethyl)-1H-indol-1-yl]methyl}phenoxy)-2-methylpropanoic acid
82  (2R)-2-(3-{[3-(4-chlorophenoxy)-5-iodo-2-methyl-6-(trifluoromethoxy)-1H-indol-1-yl]methyl}phenoxy)butanoic acid
83  2-(3-{[3-(4-methoxyphenoxy)-2-methyl-6-(trifluoromethyl)-1H-indol-1-yl]methyl}phenoxy)-2-methylbutanoic acid
84  2-(3-{[3-(4-methoxyphenoxy)-2-methyl-6-(trifluoromethyl)-1H-indol-1-yl]methyl}phenoxy)-2-methylbutanoic acid
85  (2R)-2-(3-{[3-[(4-chlorophenyl)sulfinyl]-2-methyl-5-(trifluoromethoxy)-1H-indol-1-yl]methyl}phenoxy)butanoic acid
86  2-{3-[3-(4-chlorophenoxy)-2-methyl-6-(trifluoromethoxy)-1H-indol-1-yl]phenoxy}-2-methylpropanoic acid
87  (2S)-2-(3-{[3-(4-chlorophenoxy)-2-methyl-6-(trifluoromethyl)-1H-indol-1-yl]methyl}-4-fluorophenoxy)propanoic acid
88  (2S)-2-(2-chloro-5-{[3-(4-chlorophenoxy)-2-methyl-6-(trifluoromethyl)-1H-indol-1-yl]methyl}phenoxy)propanoic acid TABLE 2
Compounds Where R³ is Benzisoxazole
| MOLSTRUCTURE | | PARENT WEIGHT | Mass Spec | Retention Time |
|---|---|---|---|---|
| 1 | 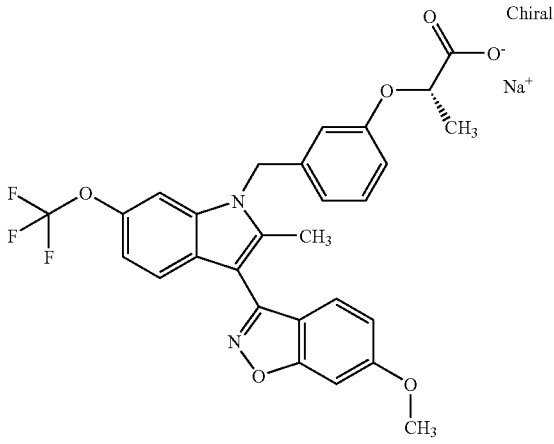 Chiral | 540.501 | 541.1 (M + H) | 3.91 |
| 2 | 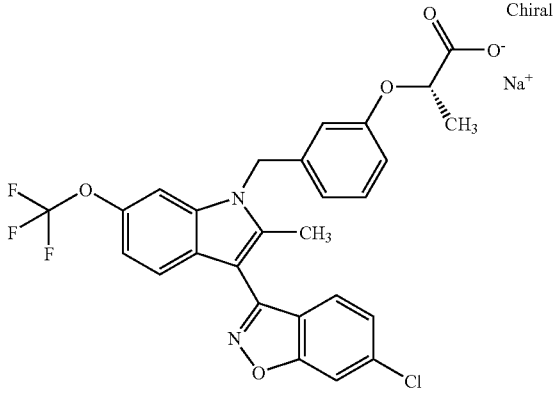 Chiral | 544.919 | 545.3 (M + H) | 4.41 |
| 3 | 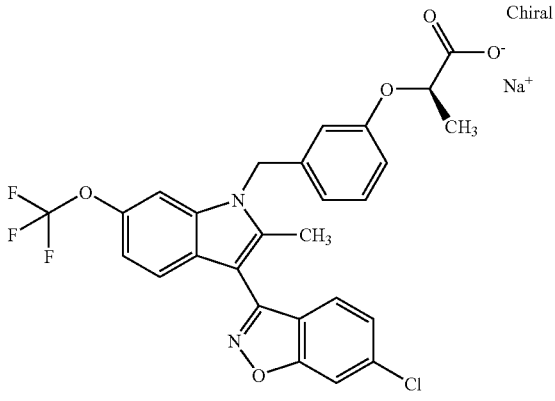 Chiral | 544.919 | 545.3 (M + H) | 4.41 |

TABLE 2-continued
Compounds Where R³ is Benzisoxazole
| MOLSTRUCTURE | PARENT WEIGHT | Mass Spec | Retention Time |
|---|---|---|---|
| 4 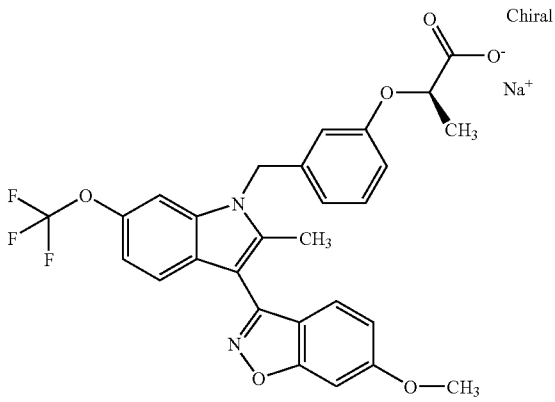 Chiral | 540.501 | 541.1 (M + H) | 4.09 |
| 5 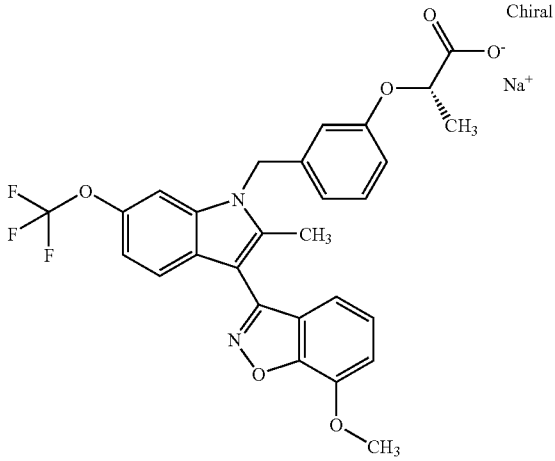 Chiral | 540.501 | 541.1 (M + H) | 4.06 |
| 6 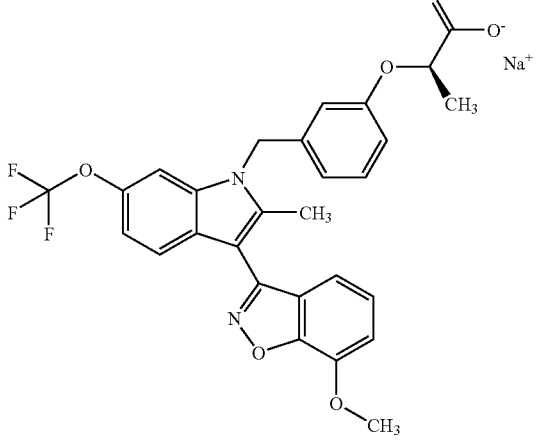 Chiral | 540.501 | 541.1 (M + H) | 4.11 |

TABLE 2-continued
Compounds Where R³ is Benzisoxazole
| MOLSTRUCTURE | PARENT WEIGHT | Mass Spec | Retention Time |
|---|---|---|---|
| 7 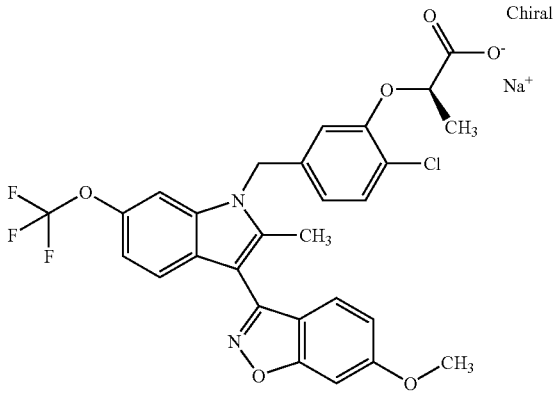 | 574.946 | 575.4 (M + H) | 4.28 |
| 8 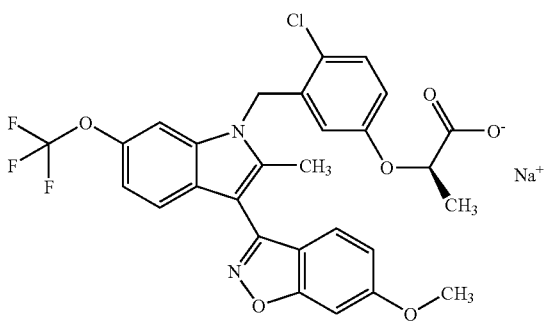 | 574.946 | 575.1 (M + H) | 4.34 |
| 9 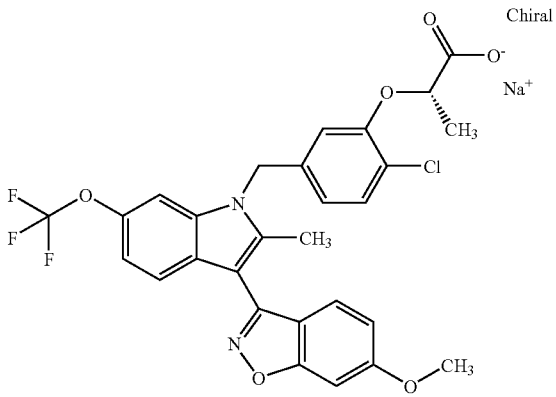 | 574.946 | 575.4 (M + H) | 4.27 |
| 10 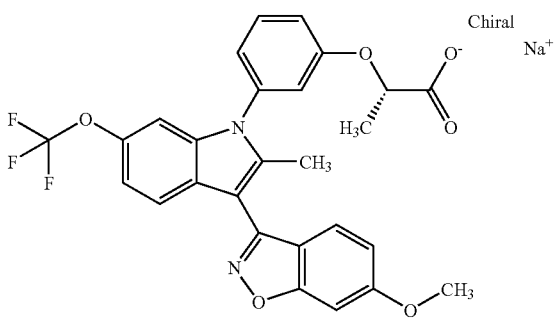 | 526.473 | | |

TABLE 2-continued

Compounds Where R³ is Benzisoxazole

| MOLSTRUCTURE | | PARENT WEIGHT | Mass Spec | Retention Time |
|---|---|---|---|---|
| 11 | Chiral | 540.501 | | |
| 12 | Chiral | 526.473 | | |
| 13 | Chiral | 540.501 | | |
| 14 | Chiral | 554.528 | 555.2 (M + H) | 3.79 |

TABLE 2-continued
Compounds Where R³ is Benzisoxazole
| MOLSTRUCTURE | | PARENT WEIGHT | Mass Spec | Retention Time |
|---|---|---|---|---|
| 15 | 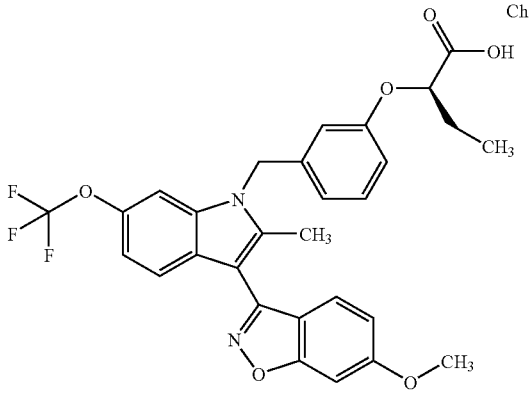 Chiral | 554.528 | 555.2 (M + H) | 3.96 |
| 16 | 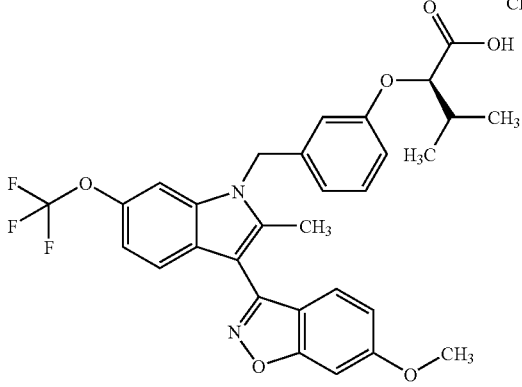 Chiral | 568.555 | 569.4 (M + H) | 4.36 |
| 17 | 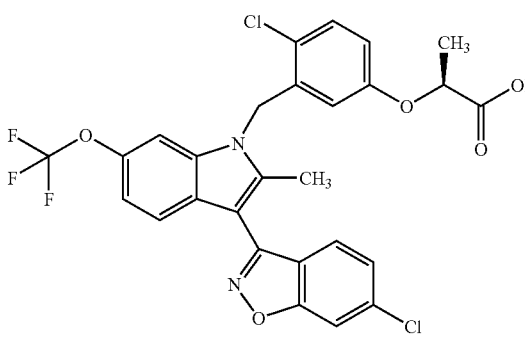 Chiral | 579.364 | 579.1 (M + H) | 4.49 |
| 18 | 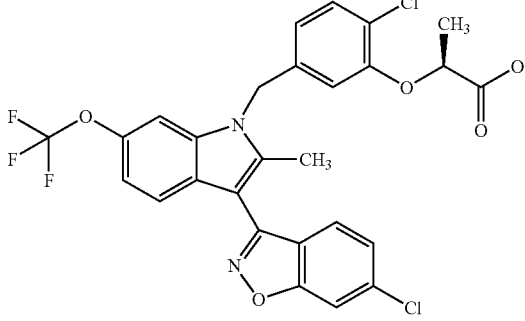 | 579.364 | 579.1 (M + H) | 4.48 |

TABLE 2-continued

| | Compounds Where R³ is Benzisoxazole | | | |
|---|---|---|---|---|
| MOLSTRUCTURE | | PARENT WEIGHT | Mass Spec | Retention Time |
| 19 | Chiral | 579.364 | 579.3 | 4.6 |
| 20 | | 558.946 | 559.1 (M + H) | 4.44 |
| 21 | | 558.946 | 559.3 (M + H) | 4.54 |
| 22 | | 574.946 | 575.3 (M + H) | 4.31 |

TABLE 2-continued
Compounds Where R³ is Benzisoxazole
| MOLSTRUCTURE | PARENT WEIGHT | Mass Spec | Retention Time |
|---|---|---|---|
| 23 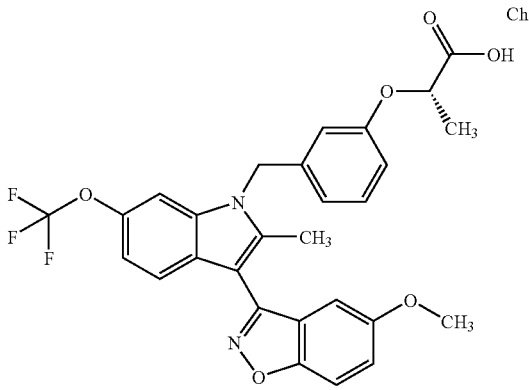 Chiral | 540.501 | | |
| 24 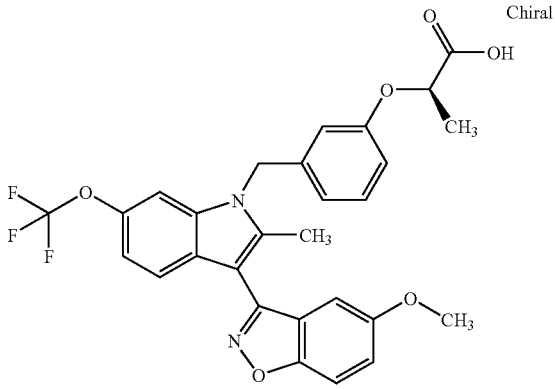 Chiral | 540.501 | | |
| 25 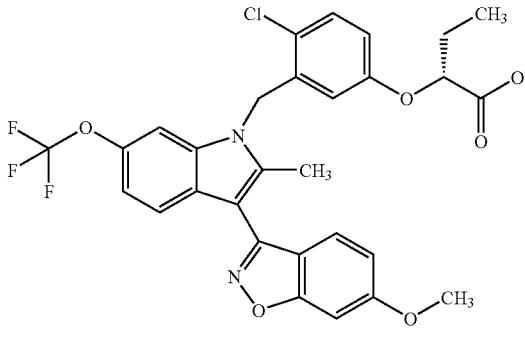 Chiral | 588.973 | 589.1 (M + H) | 4.35 |
| 26 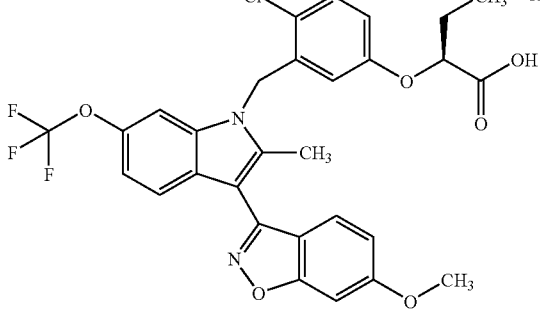 Chiral | 588.973 | 589.1 (M + H) | 4.35 |

TABLE 2-continued

Compounds Where R³ is Benzisoxazole

| MOLSTRUCTURE | PARENT WEIGHT | Mass Spec | Retention Time |
|---|---|---|---|
| 27 | 568.555 | 569.2 (M + H) | 4.30 min |
| 28 | 568.555 | 569.2 (M + H) | 4.30 min |
| 29 (Chiral) | 568.555 | 569.2 (M + H) | 4.29 min |
| 30 (Chiral) | 579.364 | 579.1 | 4.49 min |

TABLE 2-continued

Compounds Where R³ is Benzisoxazole

| MOLSTRUCTURE | PARENT WEIGHT | Mass Spec | Retention Time |
|---|---|---|---|
| 31 | 593.391 | 593.1 | 4.61 min |
| 32 | 593.391 | 593.1 | 4.62 min |
| 33 | 562.909 | 563.1 | 4.34 min |
| 34 | 562.909 | 563.1 | 4.33 min |

TABLE 2-continued

Compounds Where R³ is Benzisoxazole

| MOLSTRUCTURE | | PARENT WEIGHT | Mass Spec | Retention Time |
|---|---|---|---|---|
| 35 | Chiral | 562.909 | 563.1 | 4.34 min |
| 36 | Chiral | 562.909 | 563.1 | 4.33 min |
| 37 | Chiral | 558.491 | 559.0 | 4.05 min |
| 38 | Chiral | 558.491 | 559.1 | 4.05 min |

TABLE 2-continued
Compounds Where R³ is Benzisoxazole
| MOLSTRUCTURE | | PARENT WEIGHT | Mass Spec | Retention Time |
|---|---|---|---|---|
| 39 | 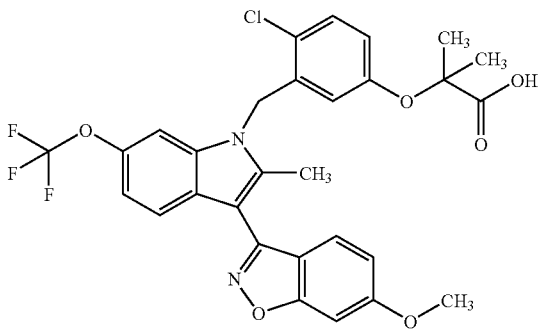 | 588.973 | 589.3 | 4.51 min |
| 40 | 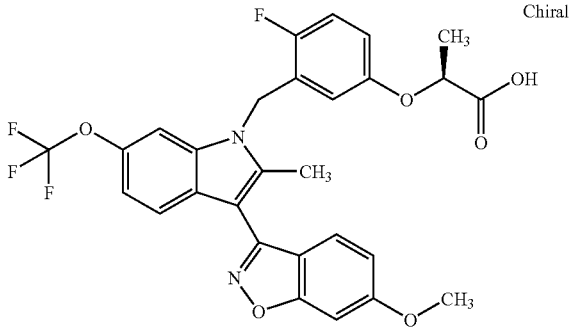 Chiral | 558.491 | 559.3 | 4.11 min |
| 41 | 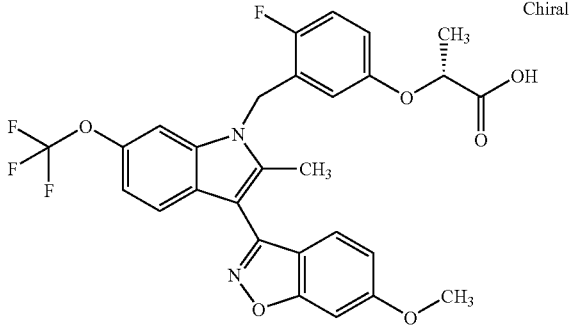 Chiral | 558.491 | 559.3 | 4.11 min |
| 42 | 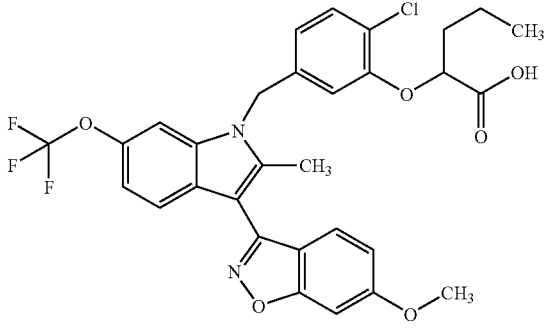 | 603 | 603.4 | 4.58 min |

TABLE 2-continued

Compounds Where R³ is Benzisoxazole

| MOLSTRUCTURE | PARENT WEIGHT | Mass Spec | Retention Time |
|---|---|---|---|
| 43 | 603 | 603.0 | 4.58 min |
| 44 | 603 | 603.4 | 4.58 min |
| 45 | 603 | 603.4 | 4.59 min |
| 46 | 603 | 603.4 | 4.57 min |

TABLE 2-continued

Compounds Where R³ is Benzisoxazole

| | MOLSTRUCTURE | PARENT WEIGHT | Mass Spec | Retention Time |
|---|---|---|---|---|
| 47 | 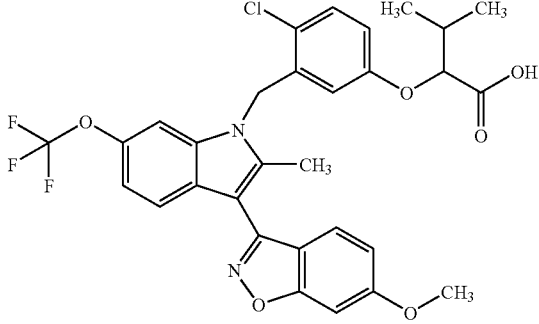 | 603 | 603.4 | 4.56 min |

TABLE 2A

Compounds Where R³ is Benzisoxazole 1. (2S)-2-(3-{[3-(6-methoxy-1,2-benzisoxazol-3-yl)-2-methyl-6-(trifluoromethoxy)-1H-indol-1-yl]methyl}phenoxy)propanoic acid
2. (2S)-2-(3-{[3-(6-chloro-1,2-benzisoxazol-3-yl)-2-methyl-6-(trifluoromethoxy)-1H-indol-1-yl]methyl}phenoxy)propanoic acid
3. (2R)-2-(3-{[3-(6-chloro-1,2-benzisoxazol-3-yl)-2-methyl-6-(trifluoromethoxy)-1H-indol-1-yl]methyl}phenoxy)propanoic acid
4. (2R)-2-(3-{[3-(6-methoxy-1,2-benzisoxazol-3-yl)-2-methyl-6-(trifluoromethoxy)-1H-indol-1-yl]methyl}phenoxy)propanoic acid
5. (2S)-2-(3-{[3-(7-methoxy-1,2-benzisoxazol-3-yl)-2-methyl-6-(trifluoromethoxy)-1H-indol-1-yl]methyl}phenoxy)propanoic acid
6. (2R)-2-(3-{[3-(7-methoxy-1,2-benzisoxazol-3-yl)-2-methyl-6-(trifluoromethoxy)-1H-indol-1-yl]methyl}phenoxy)propanoic acid
7. (2R)-2-(2-chloro-5-{[3-(6-methoxy-1,2-benzisoxazol-3-yl)-2-methyl-6-(trifluoromethoxy)-1H-indol-1-yl]methyl}phenoxy)propanoic acid
8. (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoic acid
9. (2S)-2-(2-chloro-5-{[3-(6-methoxy-1,2-benzisoxazol-3-yl)-2-methyl-6-(trifluoromethoxy)-1H-indol-1-yl]methyl}phenoxy)propanoic acid
10. (2S)-2-{3-[3-(6-methoxy-1,2-benzisoxazol-3-yl)-2-methyl-6-(trifluoromethoxy)-1H-indol-1-yl]phenoxy}propanoic acid
11. (2R)-2-{3-[3-(6-methoxy-1,2-benzisoxazol-3-yl)-2-methyl-6-(trifluoromethoxy)-1H-indol-1-yl]phenoxy}butanoic acid
12. (2R)-2-{3-[3-(6-methoxy-1,2-benzisoxazol-3-yl)-2-methyl-6-(trifluoromethoxy)-1H-indol-1-yl]phenoxy}propanoic acid
13. (2S)-2-{3-[3-(6-methoxy-1,2-benzisoxazol-3-yl)-2-methyl-6-(trifluoromethoxy)-1H-indol-1-yl]phenoxy}butanoic acid
14. (2S)-2-(3-{[3-(6-methoxy-1,2-benzisoxazol-3-yl)-2-methyl-6-(trifluoromethoxy)-1H-indol-1-yl]methyl}phenoxy)butanoic acid
15. (2R)-2-(3-{[3-(6-methoxy-1,2-benzisoxazol-3-yl)-2-methyl-6-(trifluoromethoxy)-1H-indol-1-yl]methyl}phenoxy)butanoic acid
16. (2R)-2-(3-{[3-(6-methoxy-1,2-benzisoxazol-3-yl)-2-methyl-6-(trifluoromethoxy)-1H-indol-1-yl]methyl}phenoxy)-3-methylbutanoic acid
17. (2S)-2-(4-chloro-3-{[3-(6-chloro-1,2-benzisoxazol-3-yl)-2-methyl-6-(trifluoromethoxy)-1H-indol-1-yl]methyl}phenoxy)propanoic acid
18. (2S)-2-(2-chloro-5-{[3-(6-chloro-1,2-benzisoxazol-3-yl)-2-methyl-6-(trifluoromethoxy)-1H-indol-1-yl]methyl}phenoxy)propanoic acid
19. (2R)-2-(4-chloro-3-{[3-(6-chloro-1,2-benzisoxazol-3-yl)-2-methyl-6-(trifluoromethoxy)-1H-indol-1-yl]methyl}phenoxy)propanoic acid
20. (2S)-2-(3-{[3-(6-chloro-1,2-benzisoxazol-3-yl)-2-methyl-6-(trifluoromethoxy)-1H-indol-1-yl]methyl}phenoxy)butanoic acid
21. (2R)-2-(3-{[3-(6-chloro-1,2-benzisoxazol-3-yl)-2-methyl-6-(trifluoromethoxy)-1H-indol-1-yl]methyl}phenoxy)butanoic acid
22. (2S)-2-(4-chloro-3-{[3-(6-methoxy-1,2-benzisoxazol-3-yl)-2-methyl-6-(trifluoromethoxy)-1H-indol-1-yl]methyl}phenoxy)propanoic acid
23. (2S)-2-(3-{[3-(5-methoxy-1,2-benzisoxazol-3-yl)-2-methyl-6-(trifluoromethoxy)-1H-indol-1-yl]methyl}phenoxy)propanoic acid
24. (2R)-2-(3-{[3-(5-methoxy-1,2-benzisoxazol-3-yl)-2-methyl-6-(trifluoromethoxy)-1H-indol-1-yl]methyl}phenoxy)propanoic acid
25. (2R)-2-(4-chloro-3-{[3-(6-methoxy-1,2-benzisoxazol-3-yl)-2-methyl-6-(trifluoromethoxy)-1H-indol-1-yl]methyl}phenoxy)butanoic acid
26. (2S)-2-(4-chloro-3-{[3-(6-methoxy-1,2-benzisoxazol-3-yl)-2-methyl-6-(trifluoromethoxy)-1H-indol-1-yl]methyl}phenoxy)butanoic acid

TABLE 2A-continued

Compounds Where R³ is Benzisoxazole 27. 2-(3-{[3-(6-methoxy-1,2-benzisoxazol-3-yl)-2-methyl-6-(trifluoromethoxy)-1H-indol-1-yl]methyl}phenoxy)pentanoic acid
28. 2-(3-{[3-(6-methoxy-1,2-benzisoxazol-3-yl)-2-methyl-6-(trifluoromethoxy)-1H-indol-1-yl]methyl}phenoxy)pentanoic acid
29. (2S)-2-(3-{[3-(6-methoxy-1,2-benzisoxazol-3-yl)-2-methyl-6-(trifluoromethoxy)-1H-indol-1-yl]methyl}phenoxy)-3-methylbutanoic acid
30. (2R)-2-(2-chloro-5-{[3-(6-chloro-1,2-benzisoxazol-3-yl)-2-methyl-6-(trifluoromethoxy)-1H-indol-1-yl]methyl}phenoxy)propanoic acid
31. (2S)-2-(4-chloro-3-{[3-(6-chloro-1,2-benzisoxazol-3-yl)-2-methyl-6-(trifluoromethoxy)-1H-indol-1-yl]methyl}phenoxy)butanoic acid
32. (2R)-2-(4-chloro-3-{[3-(6-chloro-1,2-benzisoxazol-3-yl)-2-methyl-6-(trifluoromethoxy)-1H-indol-1-yl]methyl}phenoxy)butanoic acid
33. (2S)-2-(5-{[3-(6-chloro-1,2-benzisoxazol-3-yl)-2-methyl-6-(trifluoromethoxy)-1H-indol-1-yl]methyl}-2-fluorophenoxy)propanoic acid
34. (2R)-2-(5-{[3-(6-chloro-1,2-benzisoxazol-3-yl)-2-methyl-6-(trifluoromethoxy)-1H-indol-1-yl]methyl}-2-fluorophenoxy)propanoic acid
35. (2S)-2-(3-{[3-(6-chloro-1,2-benzisoxazol-3-yl)-2-methyl-6-(trifluoromethoxy)-1H-indol-1-yl]methyl}-4-fluorophenoxy)propanoic acid
36. (2R)-2-(3-{[3-(6-chloro-1,2-benzisoxazol-3-yl)-2-methyl-6-(trifluoromethoxy)-1H-indol-1-yl]methyl}-4-fluorophenoxy)propanoic acid
37. (2S)-2-(2-fluoro-5-{[3-(6-methoxy-1,2-benzisoxazol-3-yl)-2-methyl-6-(trifluoromethoxy)-1H-indol-1-yl]methyl}phenoxy)propanoic acid
38. (2R)-2-(2-fluoro-5-{[3-(6-methoxy-1,2-benzisoxazol-3-yl)-2-methyl-6-(trifluoromethoxy)-1H-indol-1-yl]methyl}phenoxy)propanoic acid
39. 2-(4-chloro-3-{[3-(6-methoxy-1,2-benzisoxazol-3-yl)-2-methyl-6-(trifluoromethoxy)-1H-indol-1-yl]methyl}phenoxy)-2-methylpropanoic acid
40. (2S)-2-(4-fluoro-3-{[3-(6-methoxy-1,2-benzisoxazol-3-yl)-2-methyl-6-(trifluoromethoxy)-1H-indol-1-yl]methyl}phenoxy)propanoic acid
41. (2R)-2-(4-fluoro-3-{[3-(6-methoxy-1,2-benzisoxazol-3-yl)-2-methyl-6-(trifluoromethoxy)-1H-indol-1-yl]methyl}phenoxy)propanoic acid
42. 2-(2-chloro-5-{[3-(6-methoxy-1,2-benzisoxazol-3-yl)-2-methyl-6-(trifluoromethoxy)-1H-indol-1-yl]methyl}phenoxy)pentanoic acid
43. 2-(2-chloro-5-{[3-(6-methoxy-1,2-benzisoxazol-3-yl)-2-methyl-6-(trifluoromethoxy)-1H-indol-1-yl]methyl}phenoxy)pentanoic acid
44. 2-(4-chloro-3-{[3-(6-methoxy-1,2-benzisoxazol-3-yl)-2-methyl-6-(trifluoromethoxy)-1H-indol-1-yl]methyl}phenoxy)pentanoic acid
45. 2-(4-chloro-3-{[3-(6-methoxy-1,2-benzisoxazol-3-yl)-2-methyl-6-(trifluoromethoxy)-1H-indol-1-yl]methyl}phenoxy)pentanoic acid
46. 2-(4-chloro-3-{[3-(6-methoxy-1,2-benzisoxazol-3-yl)-2-methyl-6-(trifluoromethoxy)-1H-indol-1-yl]methyl}phenoxy)-3-methylbutanoic acid
47. 2-(4-chloro-3-{[3-(6-methoxy-1,2-benzisoxazol-3-yl)-2-methyl-6-(trifluoromethoxy)-1H-indol-1-yl]methyl}phenoxy)-3-methylbutanoic acid

TABLE 3

Compounds Where R³ is Benzoyl

| | MOLSTRUCTURE | PARENT WEIGHT | Mass Spec | Retention Time |
|---|---|---|---|---|
| 1 | Chiral | 443.504 | 444.1 (M + H) | 3.44 min |

TABLE 3-continued
Compounds Where R³ is Benzoyl
| | MOLSTRUCTURE | PARENT WEIGHT | Mass Spec | Retention Time |
|---|---|---|---|---|
| 2 | 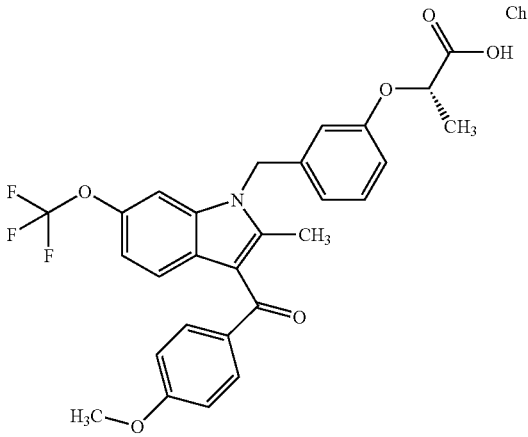 | 527.502 | 528.1 (M + H) | 3.87 min |
| 3 | 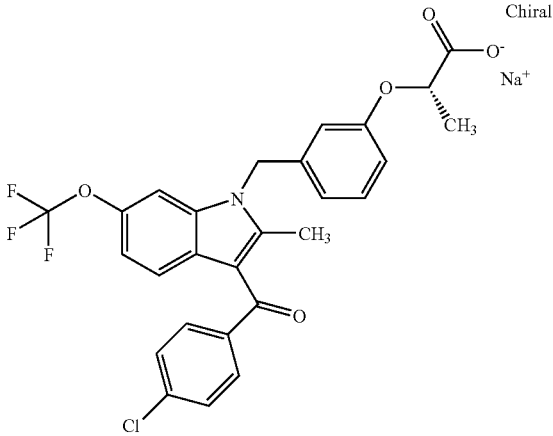 | 531.92 | 532.0 (M + H) | 4.11 min |
| 4 | 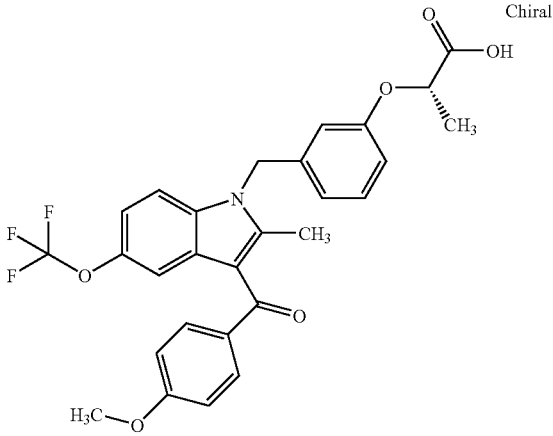 | 527.502 | 528.1 | 3.75 min |

TABLE 3-continued

Compounds Where R³ is Benzoyl

| | MOLSTRUCTURE | PARENT WEIGHT | Mass Spec | Retention Time |
|---|---|---|---|---|
| 5 | (Chiral structure) | 527.502 | 528.1 (M + H) | 3.77 min |
| 6 | (Chiral structure) | 513.475 | 514.0 (M + 1) | 3.88 min |
| 7 | (structure) | 541.529 | 542.0 (M + H) | 3.91 min |

TABLE 3-continued
Compounds Where R³ is Benzoyl
| MOLSTRUCTURE | PARENT WEIGHT | Mass Spec | Retention Time |
|---|---|---|---|
| 8 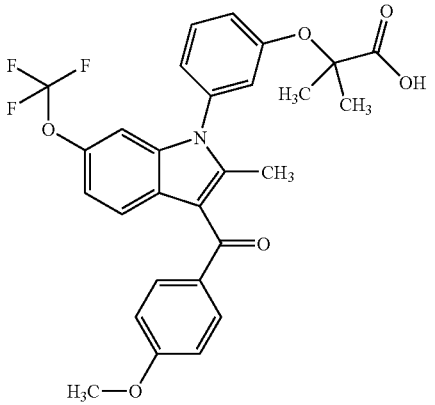 | 527.502 | 528.2 (M + 1) | 3.96 min |
| 9 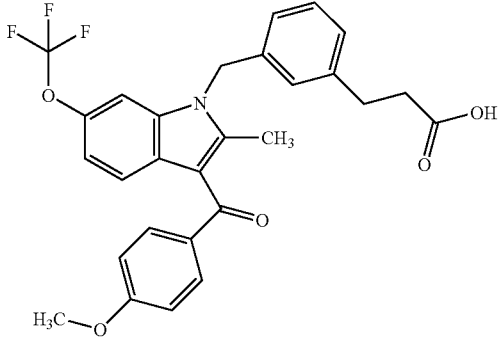 | 511.502 | 512 (M + 1) | 3.95 |
| 10 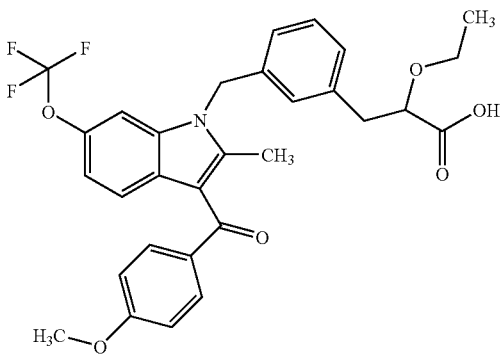 | 555.556 | | |
| 11 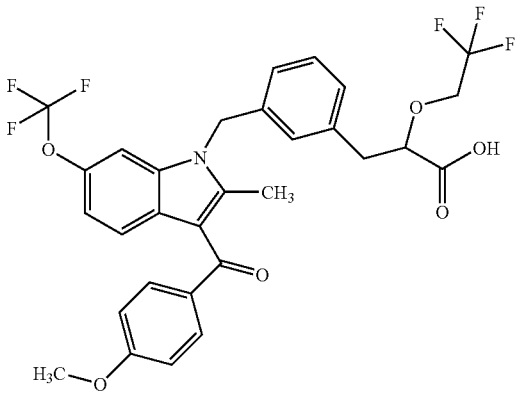 | 609.527 | | |

TABLE 3-continued

Compounds Where R³ is Benzoyl

| | MOLSTRUCTURE | PARENT WEIGHT | Mass Spec | Retention Time |
|---|---|---|---|---|
| 12 | | 531.92 | 532.0 (M + 1) | 4.33 min |
| 13 | | 532.908 | 533.1 (M + 1) | 3.95 min |
| 14 | | 542.516 | 543.1 (M + 1) | 4.12 min |

TABLE 3-continued
Compounds Where R³ is Benzoyl
| MOLSTRUCTURE | PARENT WEIGHT | Mass Spec | Retention Time |
|---|---|---|---|
| 15 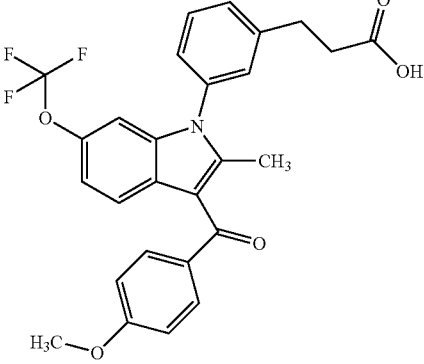 | 497.475 | | |
| 16 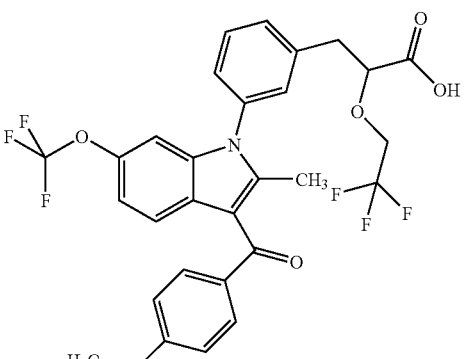 | 595.5 | | |
| 17 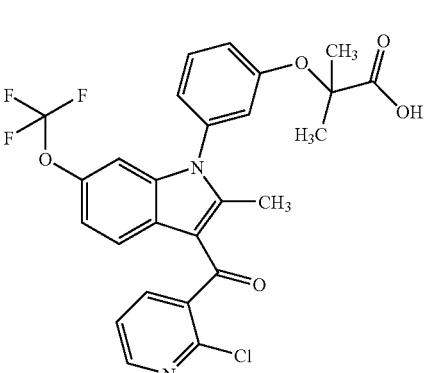 | 532.908 | 533.1 (M + 1) | 3.70 min |
| 18 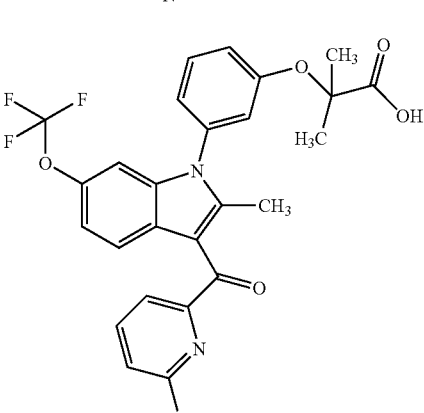 | 512.49 | 513.2 (M + 1) | 3.23 min |

TABLE 3-continued
Compounds Where R³ is Benzoyl
| | MOLSTRUCTURE | PARENT WEIGHT | Mass Spec | Retention Time |
|---|---|---|---|---|
| 19 | 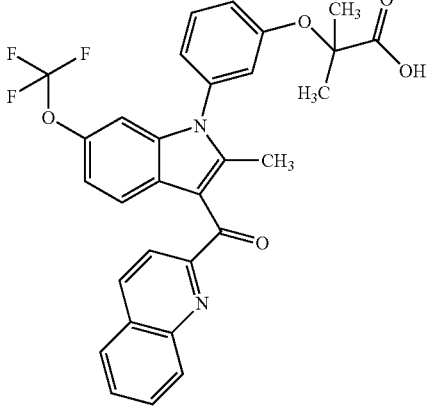 | 548.523 | 549.2 (M + 1) | 4.02 min |
| 20 | 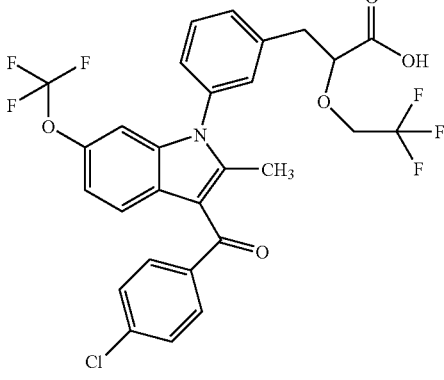 | 599.919 | M + H | 4.43 |
| 21 | 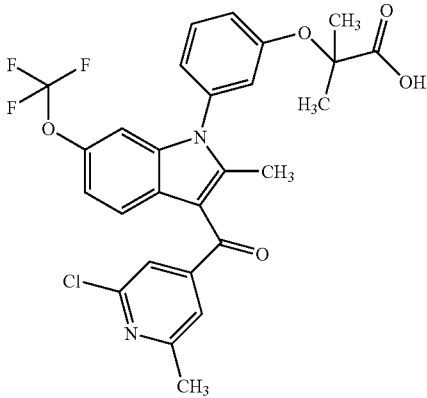 | 546.935 | | |

TABLE 3-continued
Compounds Where R³ is Benzoyl
| MOLSTRUCTURE | PARENT WEIGHT | Mass Spec | Retention Time |
|---|---|---|---|
| 22 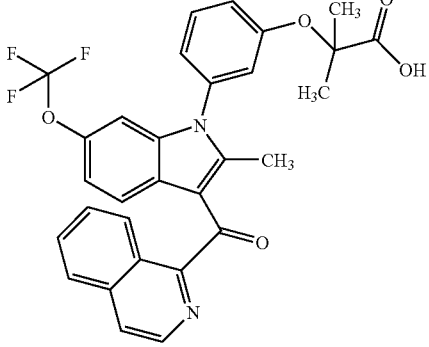 | 548.523 | 549.2 (M + 1) | 3.76 min |
| 23 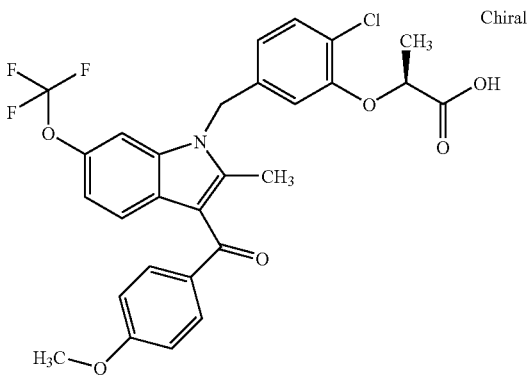 Chiral | 561.947 | M + H | 3.99 |
| 24 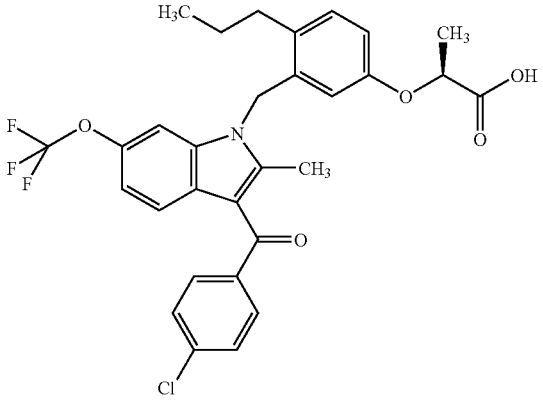 | 574.002 | 574 (M + 1) | 4.28 |
| 25 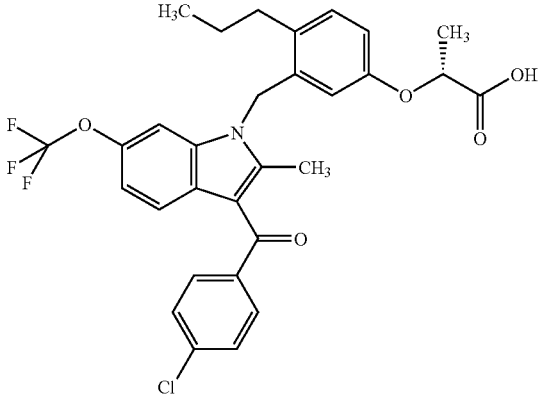 | 574.002 | 574 (M + 1) | 4.28 |

TABLE 3-continued
Compounds Where R³ is Benzoyl
| MOLSTRUCTURE | PARENT WEIGHT | Mass Spec | Retention Time |
|---|---|---|---|
| 26 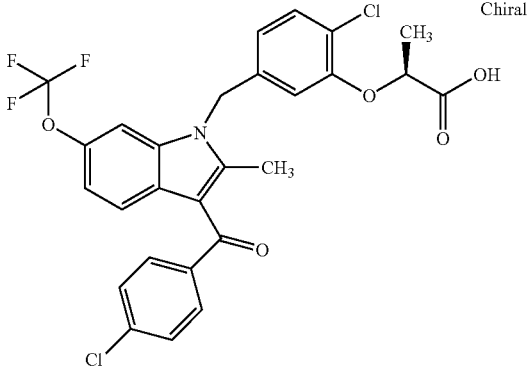 Chiral | 566.365 | M + H | 4.3 |
| 27 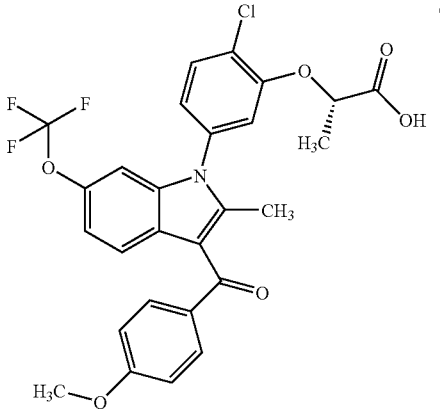 Chiral | 547.92 | M + H | 4.08 |
| 28 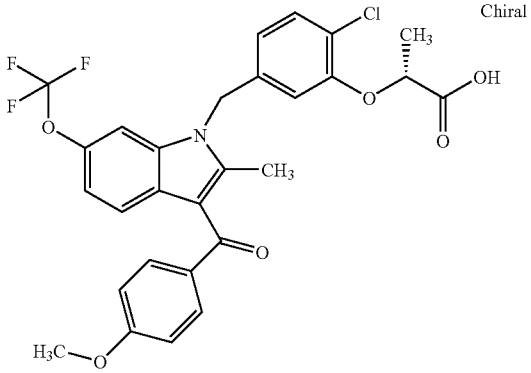 Chiral | 561.947 | M + H | 3.99 |

TABLE 3-continued
Compounds Where R³ is Benzoyl
| MOLSTRUCTURE | PARENT WEIGHT | Mass Spec | Retention Time |
|---|---|---|---|
| 29 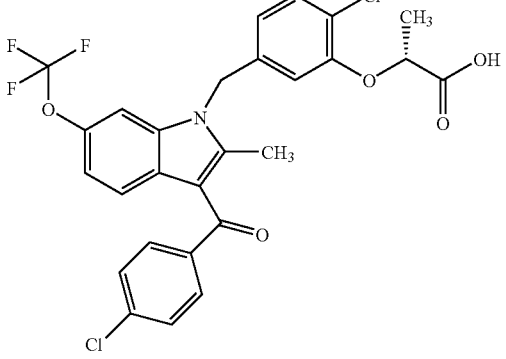 Chiral | 566.365 | M + H | 4.3 |
| 30 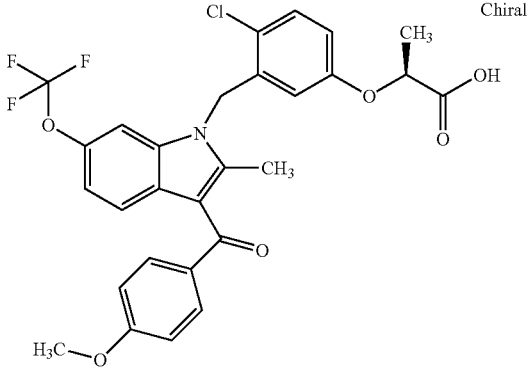 Chiral | 561.947 | M + H | 4.04 |
| 31 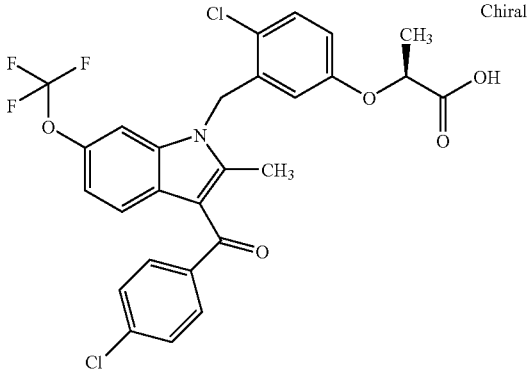 Chiral | 566.365 | M + H | 4.32 |

TABLE 3-continued
Compounds Where R³ is Benzoyl
| MOLSTRUCTURE | | PARENT WEIGHT | Mass Spec | Retention Time |
|---|---|---|---|---|
| 32 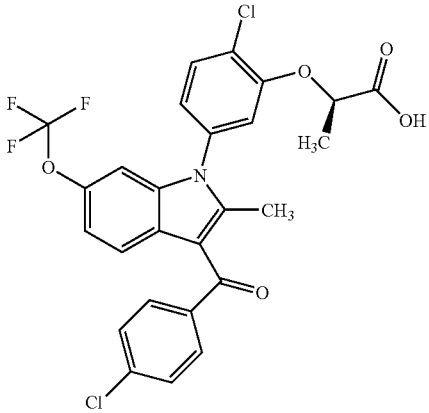 | Chiral | 552.338 | | |
| 33 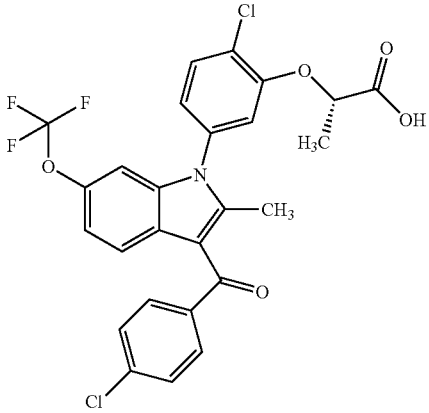 | Chiral | 552.338 | | |
| 34 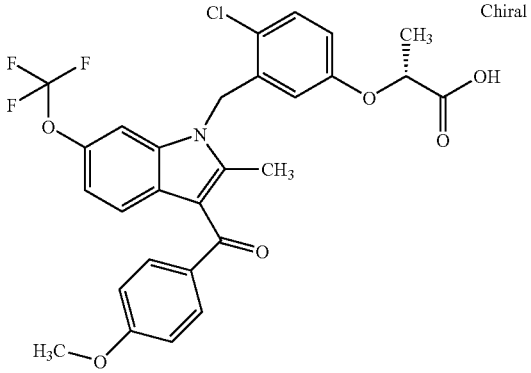 | Chiral | 561.947 | M + H | 4.04 |

TABLE 3-continued

Compounds Where R³ is Benzoyl

| | MOLSTRUCTURE | PARENT WEIGHT | Mass Spec | Retention Time |
|---|---|---|---|---|
| 35 | (structure, Chiral) | 566.365 | M + H | 4.32 |
| 36 | (structure) | 545.947 | 545 | 4.19 |
| 37 | (structure, Chiral) | 566.365 | 566 (M + 1) | 4.09 |
| 38 | (structure, Chiral) | 566.365 | 566 (M + 1) | 4.09 |

TABLE 3-continued

Compounds Where R³ is Benzoyl

| MOLSTRUCTURE | PARENT WEIGHT | Mass Spec | Retention Time |
|---|---|---|---|
| 39 | 553.54 | 554 (M + 1) | 3.96 |
| 40 | 557.959 | 558 (M + 1) | 4.01 |
| 41 | 553.54 | 554 (M + 1) | 3.95 |
| 42 (Chiral) | 517.893 | 518.2 (M + 1) | 4.17 min |

TABLE 3-continued
Compounds Where R³ is Benzoyl
| | MOLSTRUCTURE | PARENT WEIGHT | Mass Spec | Retention Time |
|---|---|---|---|---|
| 43 | 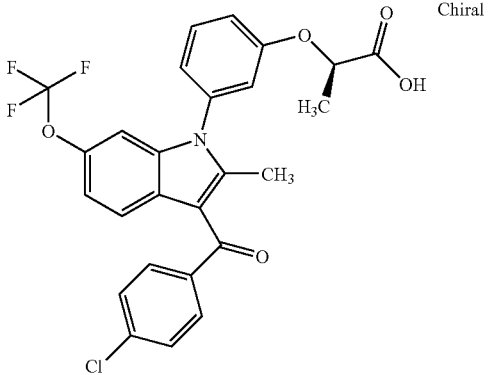 Chiral | 517.893 | 518.2 (M + 1) | 4.18 min |
| 44 | 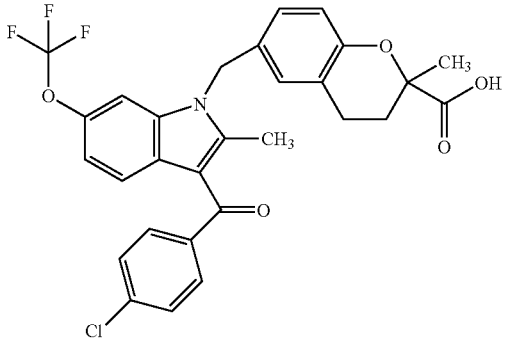 | 557.959 | 558 (M + 1) | 3.89 |
| 45 | 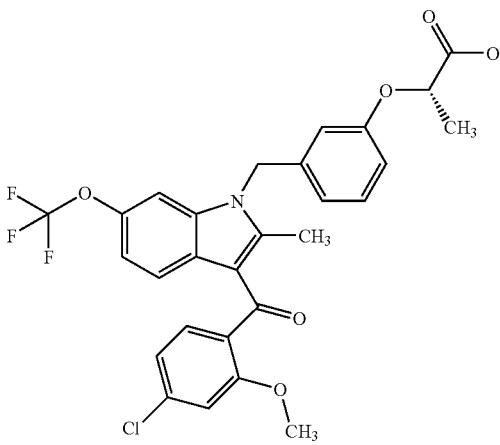 Chiral | 561.947 | 562 (M + 1) | 3.87 |

TABLE 3-continued

Compounds Where R³ is Benzoyl

| MOLSTRUCTURE | PARENT WEIGHT | Mass Spec | Retention Time |
|---|---|---|---|
| 46 | 561.947 | 562 (M + 1) | 3.88 |
| 47 | 545.947 | 546 (M + 1) | 4.13 |
| 48 | 545.947 | 546 (M + 1) | 4.13 |

TABLE 3-continued

Compounds Where R³ is Benzoyl

| MOLSTRUCTURE | PARENT WEIGHT | Mass Spec | Retention Time |
|---|---|---|---|
| 49 | 600.04 | M + 1 = 600 | 4.68 |
| 50 | 545.947 | M + 1 = 546 | 4.21 |
| 51 | 574.002 | M + 1 = 574 | 4.49 |

TABLE 3-continued
Compounds Where R[3] is Benzoyl
| MOLSTRUCTURE | PARENT WEIGHT | Mass Spec | Retention Time |
|---|---|---|---|
| 52 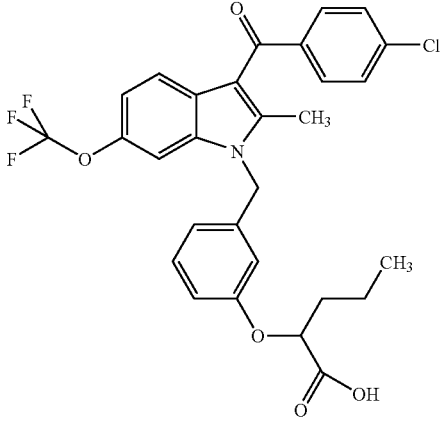 | 559.975 | M + 1 = 560 | 4.4 |
| 53 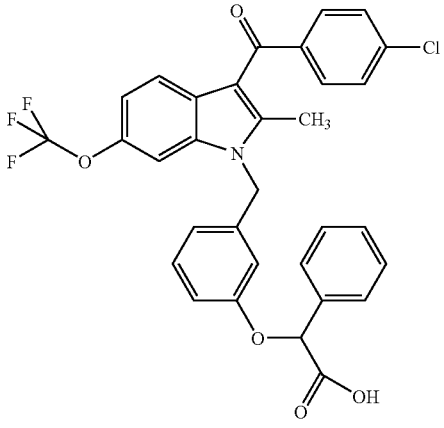 | 593.992 | M + 1 = 594 | 4.26 |
| 54 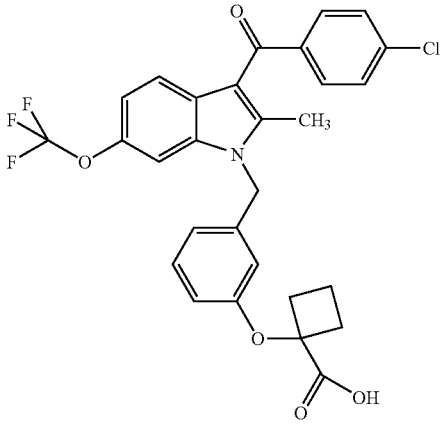 | 557.959 | M + 1 = 558 | 4.28 |

TABLE 3-continued
Compounds Where R³ is Benzoyl
| MOLSTRUCTURE | | PARENT WEIGHT | Mass Spec | Retention Time |
|---|---|---|---|---|
| 55 | 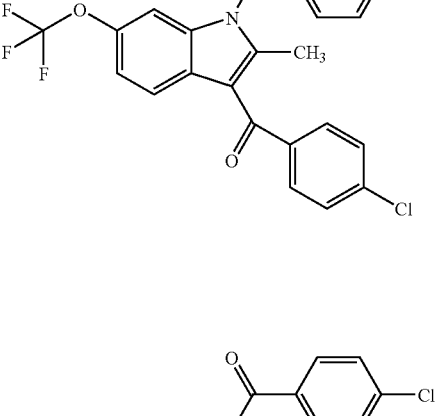 Chiral | 531.92 | 532.3 (M + H) | 4.09 min |
| 56 | 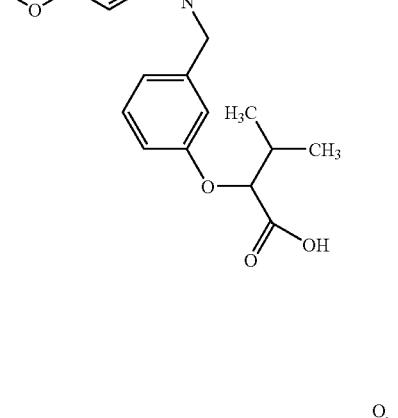 | 559.975 | M + 1 = 560 | 4.35 |
| 57 | 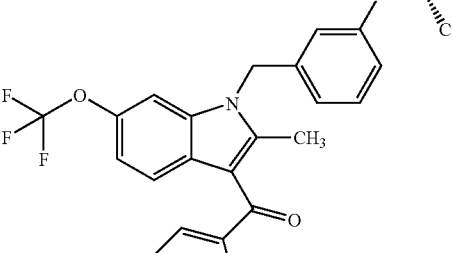 Chiral | 541.529 | 542 (M + 1) | 3.87 |

TABLE 3-continued

Compounds Where R³ is Benzoyl

| MOLSTRUCTURE | PARENT WEIGHT | Mass Spec | Retention Time |
|---|---|---|---|
| 58 (Chiral) | 541.529 | 542 (M + 1) | 3.82 |
| 59 (Chiral) | 545.947 | M + 1 = 546 | 4.2 |
| 60 (Chiral) | 545.947 | M + 1 = 546 | 4.2 |

TABLE 3-continued
Compounds Where R³ is Benzoyl
| MOLSTRUCTURE | PARENT WEIGHT | Mass Spec | Retention Time |
|---|---|---|---|
| 61 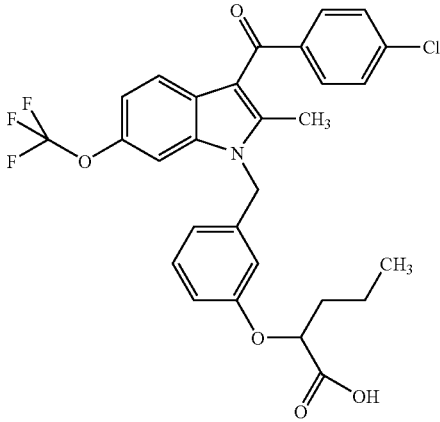 | 559.975 | M + 1 = 560 | 4.36 |
| 62 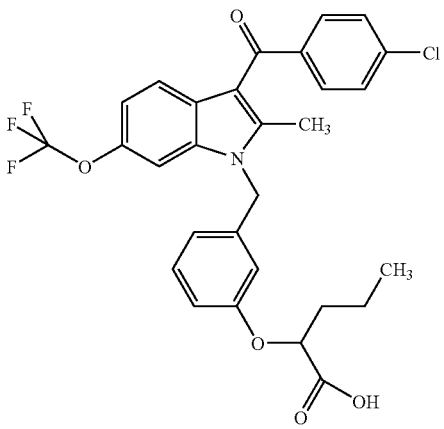 | 559.975 | M + 1 = 560 | 4.36 |
| 63 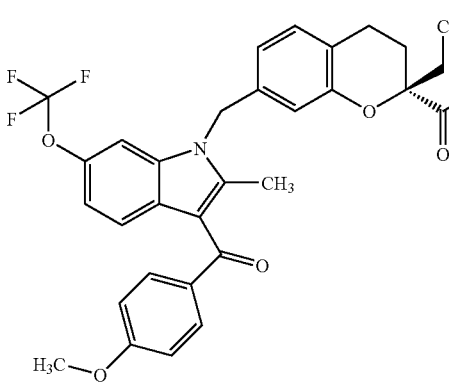  Chiral | 567.567 | M + H | 4.05 |

TABLE 3-continued

Compounds Where R³ is Benzoyl

| MOLSTRUCTURE | | PARENT WEIGHT | Mass Spec | Retention Time |
|---|---|---|---|---|
| 64 | Chiral | 571.986 | M + H | 4.29 |
| 65 | Chiral | 606.431 | M + H | 4.39 |
| 66 | | 567.567 | 568 (M + 1) | 3.92 |
| 67 | | 571.986 | 571 (M + 1) | 3.88 |

TABLE 3-continued

Compounds Where R³ is Benzoyl

| MOLSTRUCTURE | | PARENT WEIGHT | Mass Spec | Retention Time |
|---|---|---|---|---|
| 68 | Chiral | 600.81 | 602 (M + 1) | 4.18 |
| 69 | Chiral | 600.81 | 602 (M + 1) | 4.18 |
| 70 | Chiral | 534.496 | 535.2 (M + 1) | 3.83 min |

TABLE 3-continued
| | Compounds Where R³ is Benzoyl | | | |
|---|---|---|---|---|
| | MOLSTRUCTURE | PARENT WEIGHT | Mass Spec | Retention Time |
| 71 | 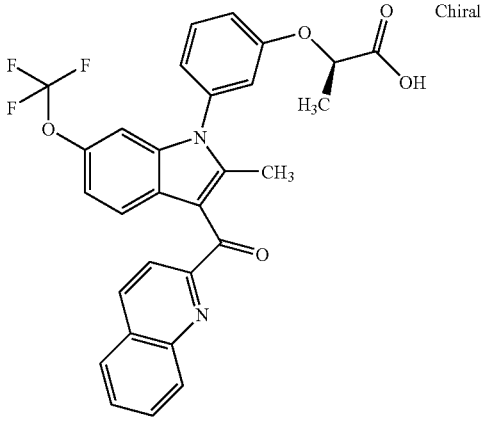 Chiral | 534.496 | 535.2 (M + 1) | 3.84 min |
| 72 | 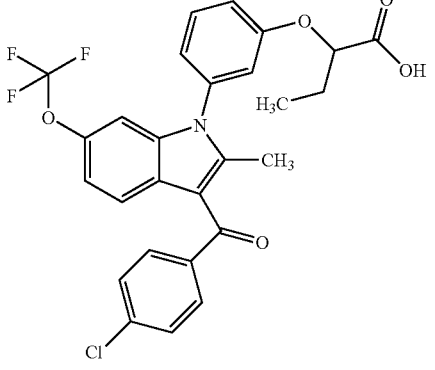 | 531.92 | | |
| 73 | 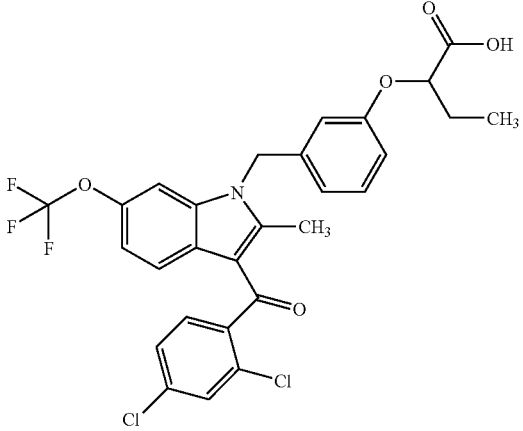 | 580.392 | 580 (M + 1) | 4.22 |

TABLE 3-continued
Compounds Where R³ is Benzoyl
| | MOLSTRUCTURE | PARENT WEIGHT | Mass Spec | Retention Time |
|---|---|---|---|---|
| 74 | 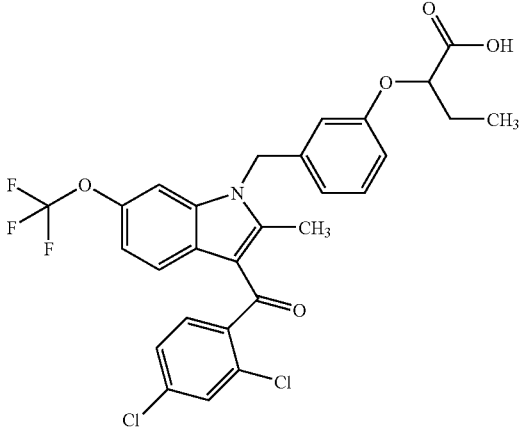 | 580.392 | 580 (M + 1) | 4.22 |
| 75 | 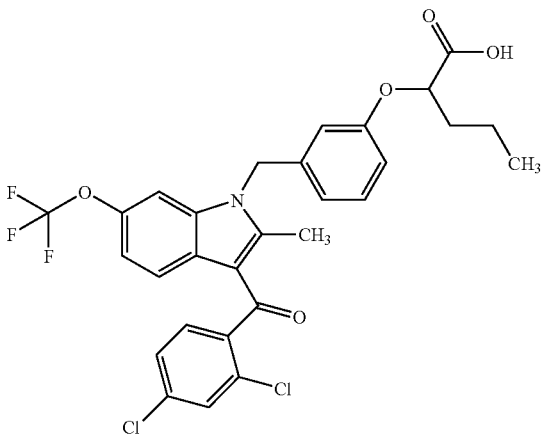 | 594.42 | 594 (M + 1) | 4.36 |
| 76 | 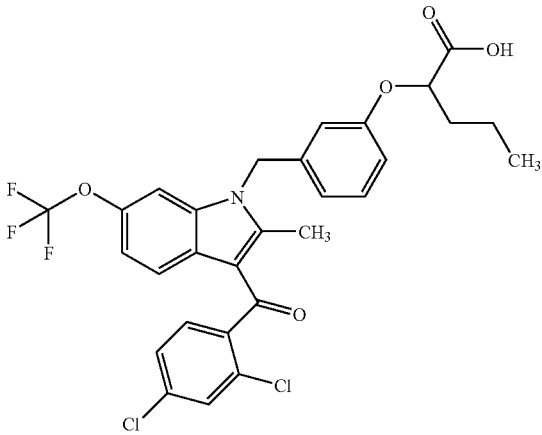 | 594.42 | 594 (M + 1) | 4.36 |

TABLE 3-continued
Compounds Where R³ is Benzoyl
| | MOLSTRUCTURE | PARENT WEIGHT | Mass Spec | Retention Time |
|---|---|---|---|---|
| 77 | 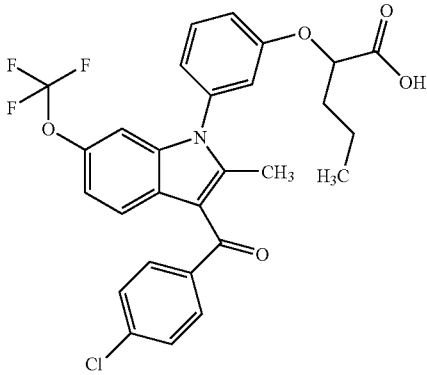 | 545.947 | | |
| 78 | 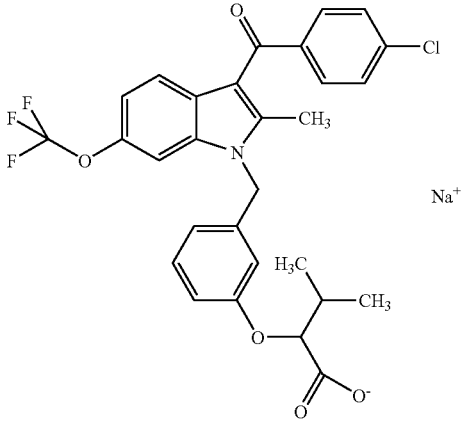 | 559.975 | M + 1 = 560 | 4.36 |
| 79 | 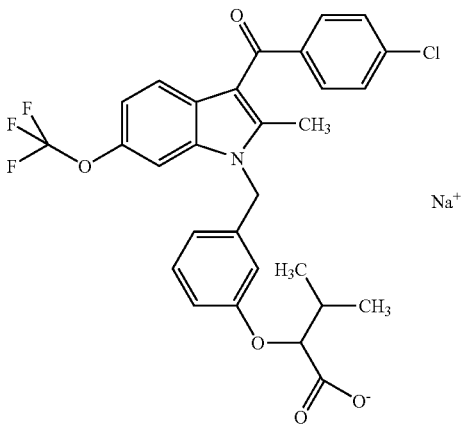 | 559.975 | M + 1 = 560 | 4.36 |

TABLE 3-continued

Compounds Where R³ is Benzoyl

| MOLSTRUCTURE | PARENT WEIGHT | Mass Spec | Retention Time |
|---|---|---|---|
| 80 | 580.392 | 580 (M + 1) | 3.78 |
| 81 | 575.974 | M + H | 4.13 |
| 82 | 580.392 | M + H | 4.34 |

TABLE 3-continued

Compounds Where R³ is Benzoyl

| MOLSTRUCTURE | PARENT WEIGHT | Mass Spec | Retention Time |
|---|---|---|---|
| 83 | 594.42 | 594 (M + 1) | 3.96 |
| 84 | 594.42 | M + H | 4.6 |
| 85 | 575.974 | 580 (M + 1) | 3.88 |

TABLE 3-continued
Compounds Where R³ is Benzoyl
| | MOLSTRUCTURE | PARENT WEIGHT | Mass Spec | Retention Time |
|---|---|---|---|---|
| 86 | 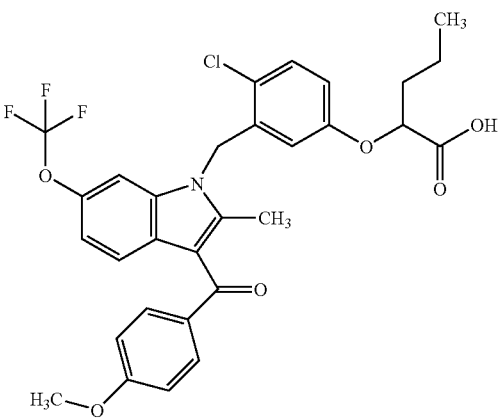 | 590.001 | 590 (M + 1) | 3.96 |
| 87 | 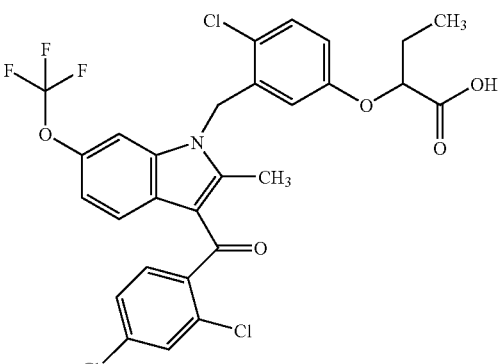 | 614.837 | 614 (M + 1) | 3.77 |
| 88 | 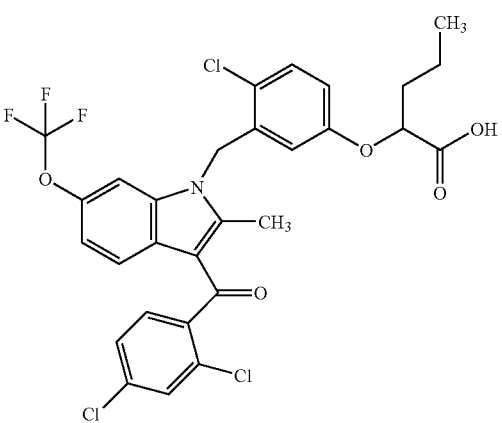 | 628.865 | 628 (M + 1) | 3.82 |

TABLE 3-continued

Compounds Where R³ is Benzoyl

| MOLSTRUCTURE | | PARENT WEIGHT | Mass Spec | Retention Time |
|---|---|---|---|---|
| 89 | Chiral | 561.947 | 562 (M + 1) | 2.26 |
| 90 | Chiral | 561.947 | 562 (M + 1) | 2.26 |
| 91 | | 559.975 | M + 1 = 560 | 4.31 |

TABLE 3-continued
Compounds Where R³ is Benzoyl
| MOLSTRUCTURE | PARENT WEIGHT | Mass Spec | Retention Time |
|---|---|---|---|
| 92 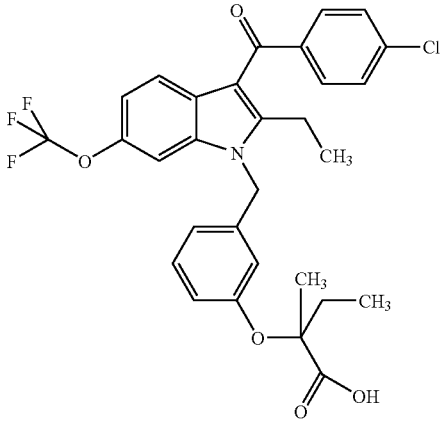 | 574.002 | M + 1 = 574 | 4.48 |
| 93 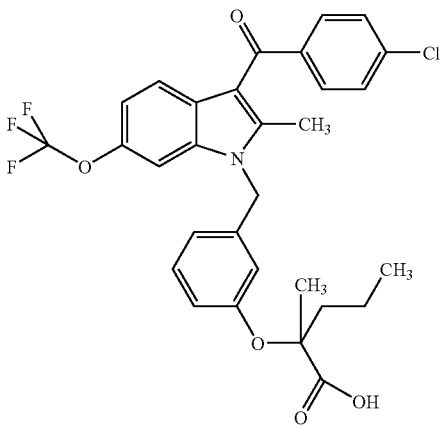 | 574.002 | M + 1 = 574 | 4.46 |
| 94 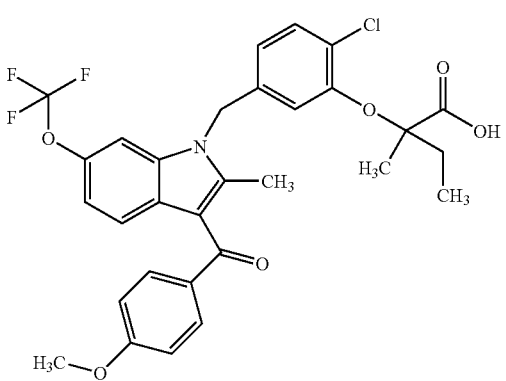 | 590.001 | M + H | 4.26 |

TABLE 3-continued

Compounds Where R³ is Benzoyl

| MOLSTRUCTURE | PARENT WEIGHT | Mass Spec | Retention Time |
|---|---|---|---|
| 95 | 594.42 | M + H | 4.61 |
| 96 | 604.028 | M + H | 4.37 |
| 97 | 608.447 | M + H | 4.56 |
| 98 | 604.028 | M + H | 4.34 |

TABLE 3-continued

Compounds Where R³ is Benzoyl

| MOLSTRUCTURE | PARENT WEIGHT | Mass Spec | Retention Time |
|---|---|---|---|
| 99 | 618.055 | M + H | 4.45 |
| 100 | 608.447 | M + H | 4.72 |
| 101 | 622.474 | M + H | 4.86 |

TABLE 3-continued

Compounds Where R³ is Benzoyl

| MOLSTRUCTURE | PARENT WEIGHT | Mass Spec | Retention Time |
|---|---|---|---|
| 102 | 620.337 | 620 (M + 1) | 4.19 |
| 103 | 575.974 | 576 (M + 1) | 3.93 |
| 104 | 559.975 | M + 1 = 560 | 4.31 |

TABLE 3-continued

Compounds Where R³ is Benzoyl

| MOLSTRUCTURE | PARENT WEIGHT | Mass Spec | Retention Time |
|---|---|---|---|
| 105 | 559.975 | M + 1 = 560 | 4.31 |
| 106 | 575.974 | M + H | 4.17 |
| 107 | 575.974 | M + H | 4.17 |

TABLE 3-continued
| | Compounds Where R³ is Benzoyl | | |
|---|---|---|---|
| MOLSTRUCTURE | PARENT WEIGHT | Mass Spec | Retention Time |
| 108 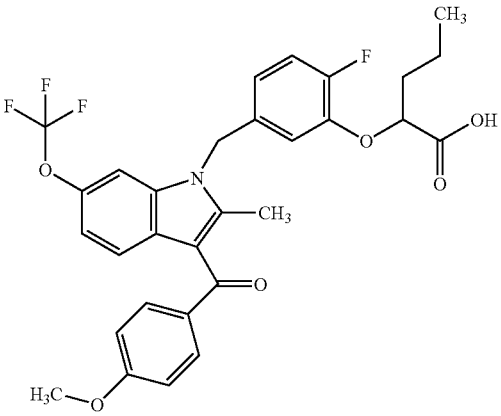 | 573.546 | 574 (M + 1) | 3.91 |
| 109 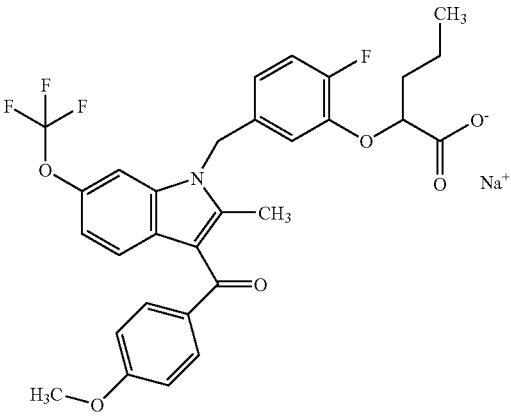 | 573.546 | 574 (M + 1) | 3.92 |
| 110 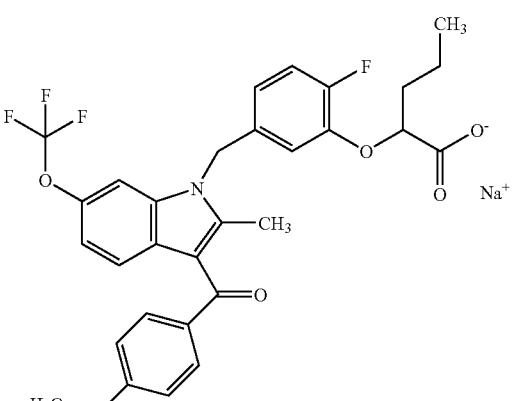 | 573.546 | 574 (M + 1) | 3.92 |

TABLE 3-continued
Compounds Where R³ is Benzoyl
| MOLSTRUCTURE | PARENT WEIGHT | Mass Spec | Retention Time |
|---|---|---|---|
| 111 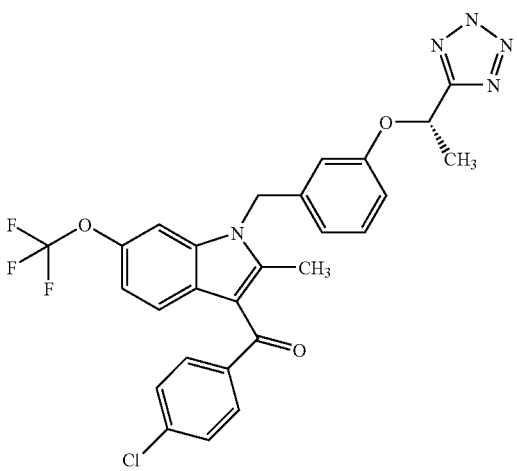 | 555.948 | 556.2 (M + H) | 3.96 min |
| 112 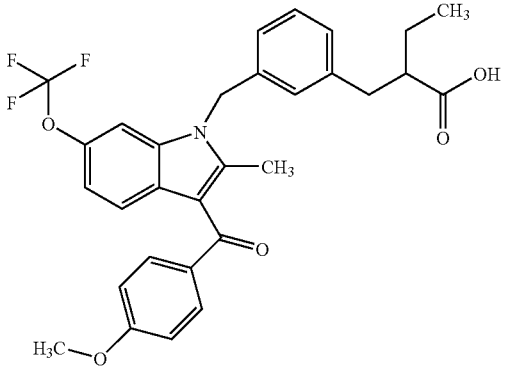 | 539.557 | M + H | 4.04 |
| 113 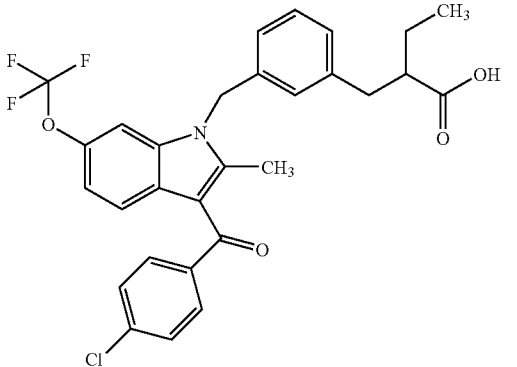 | 543.975 | M + H | 4.36 |

TABLE 3-continued
Compounds Where R³ is Benzoyl
| MOLSTRUCTURE | PARENT WEIGHT | Mass Spec | Retention Time |
|---|---|---|---|
| 114 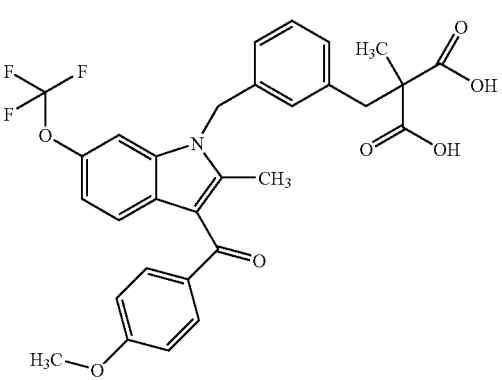 | 569.539 | | |
| 115 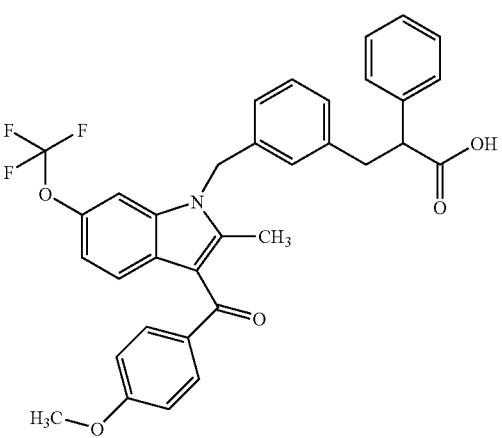 | 587.601 | M + H | 4.12 |
| 116 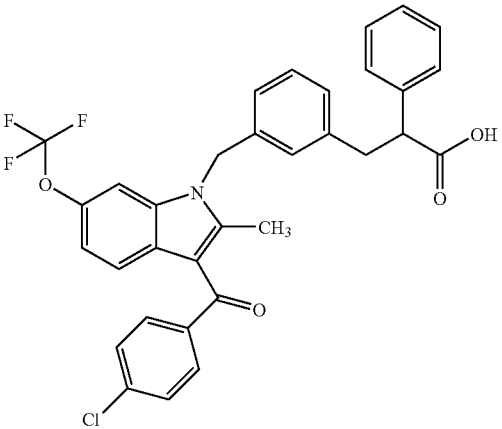 | 592.02 | M + H | 4.43 |

TABLE 3-continued
Compounds Where R³ is Benzoyl
| MOLSTRUCTURE | PARENT WEIGHT | Mass Spec | Retention Time |
|---|---|---|---|
| 117 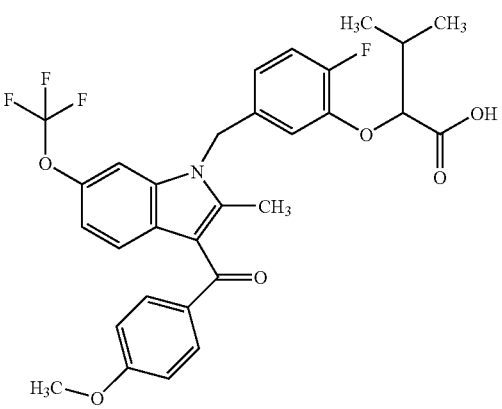 | 573.546 | 574 (M + 1) | 3.96 |
| 118 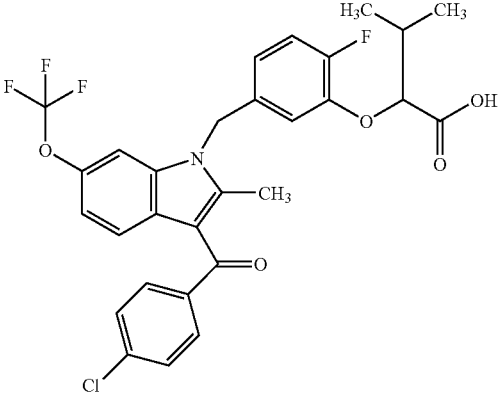 | 577.965 | 578 (M + 1) | 4.12 |
| 119 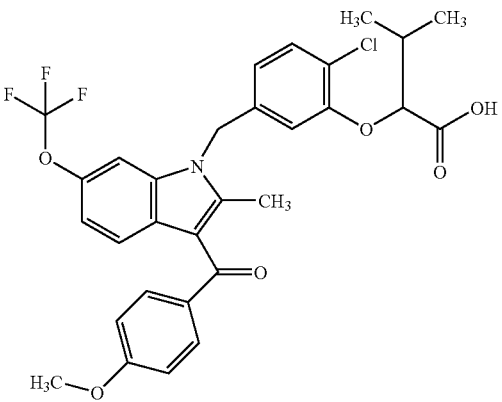 | 590.001 | 590 (M + 1) | 4.01 |

TABLE 3-continued

Compounds Where R³ is Benzoyl

| MOLSTRUCTURE | PARENT WEIGHT | Mass Spec | Retention Time |
|---|---|---|---|
| 120 | 594.42 | 594 (M + 1) | 3.89 |
| 121 | 525.529 | M + H | 3.88 |
| 122 | 529.948 | M + H | 4.23 |

TABLE 3-continued
Compounds Where R³ is Benzoyl
| MOLSTRUCTURE | PARENT WEIGHT | Mass Spec | Retention Time |
|---|---|---|---|
| 123 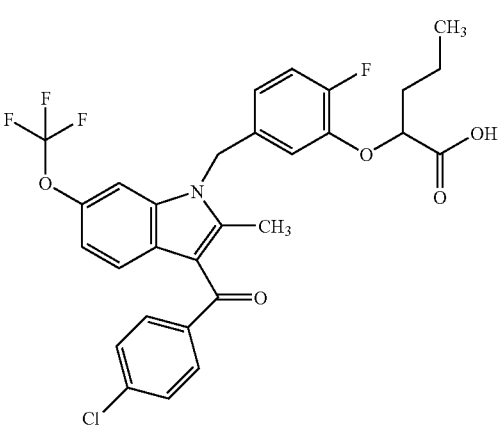 | 577.965 | 578 (M + 1) | 4.02 |
| 124 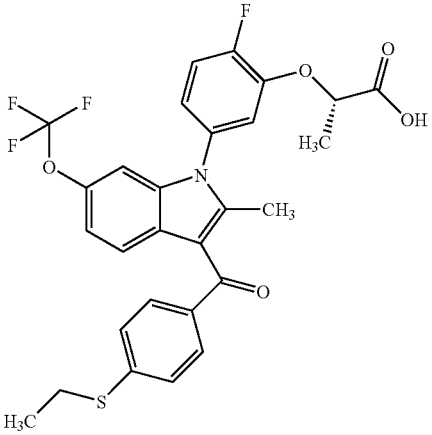 Chiral | 561.557 | 562.0 (M + 1) | 4.37 min |
| 125 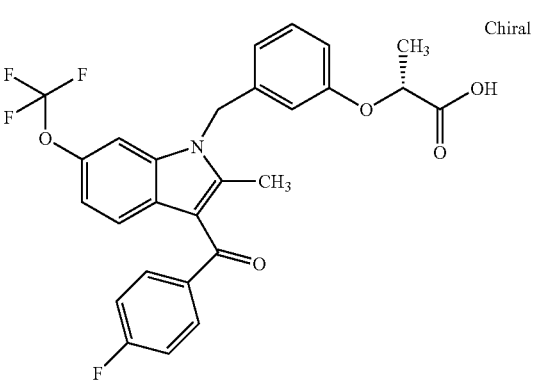 Chiral | 515.466 | M + H | 3.87 |

TABLE 3-continued

Compounds Where R³ is Benzoyl

| MOLSTRUCTURE | PARENT WEIGHT | Mass Spec | Retention Time |
|---|---|---|---|
| 126 (Chiral) | 581.473 | M + H | 4.2 |
| 127 | 513.905 | 514.2 (M + H) | 4.03 min |
| 128 | 547.92 | 548.2 (M + H) | 3.52 min |
| 129 | 569.975 | 570.0 (M + H) | 4.14 min |

TABLE 3-continued

| | Compounds Where R³ is Benzoyl | | |
|---|---|---|---|
| MOLSTRUCTURE | PARENT WEIGHT | Mass Spec | Retention Time |
| 130 | 541.529 | M + 1 = 542 | 3.92 |
| 131 | 559.519 | 560 (M + 1) | 3.82 |
| 132 | 559.519 | 560 (M + 1) | 3.82 |

TABLE 3-continued
Compounds Where R³ is Benzoyl
| MOLSTRUCTURE | PARENT WEIGHT | Mass Spec | Retention Time |
|---|---|---|---|
| 133 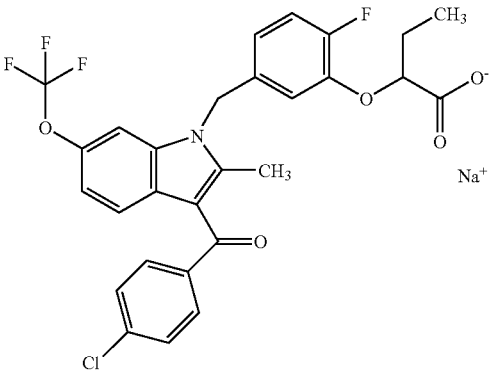 | 563.938 | 564 (M + 1) | 3.85 |
| 134 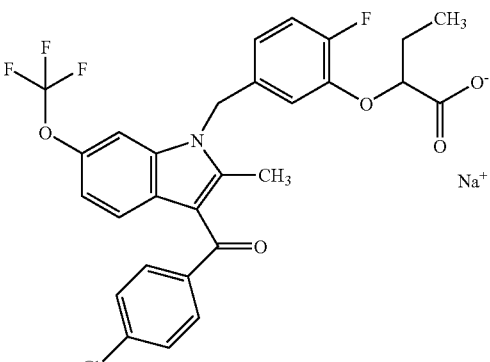 | 563.938 | 564 (M + 1) | 3.85 |
| 135 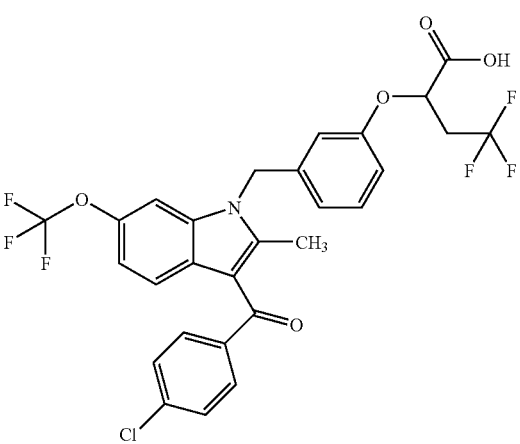 | 599.919 | 600 (M + 1) | 4.21 |

TABLE 3-continued

Compounds Where R³ is Benzoyl

| MOLSTRUCTURE | PARENT WEIGHT | Mass Spec | Retention Time |
|---|---|---|---|
| 136 | 559.975 | M + H | 4.42 |
| 137 | 559.975 | M + H | 4.42 |
| 138 | 549.911 | 550.0 (M + 1) | 4.33 min |

TABLE 3-continued

Compounds Where R³ is Benzoyl

| MOLSTRUCTURE | | PARENT WEIGHT | Mass Spec | Retention Time |
|---|---|---|---|---|
| 139 | Chiral | 535.884 | 536.1 (M + 1) | 4.16 min |
| 140 | Chiral | 535.884 | 536.1 (M + 1) | 4.15 min |
| 141 | Na⁺ | 555.556 | M + 1 = 556 | 4.01 |

TABLE 3-continued
| | Compounds Where R³ is Benzoyl | | | |
|---|---|---|---|---|
| MOLSTRUCTURE | | PARENT WEIGHT | Mass Spec | Retention Time |
| 142 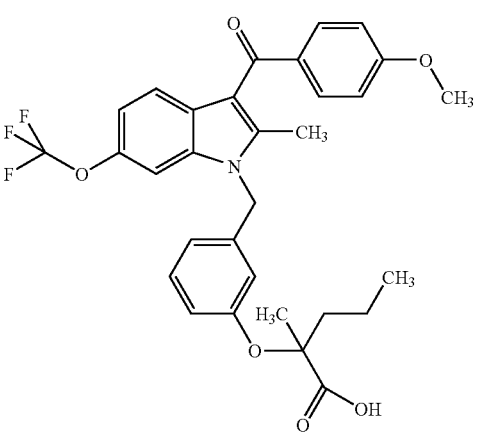 | | 569.583 | M + 1 = 570 | 4.22 |
| 143 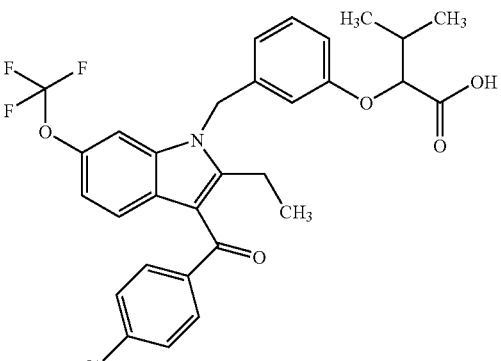 | | 574.002 | | |
| 144 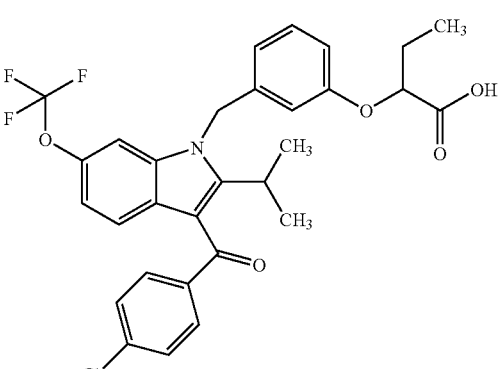 | | 574.002 | M + Na | 4.43 |

TABLE 3-continued
Compounds Where R³ is Benzoyl
| MOLSTRUCTURE | PARENT WEIGHT | Mass Spec | Retention Time |
|---|---|---|---|
| 145 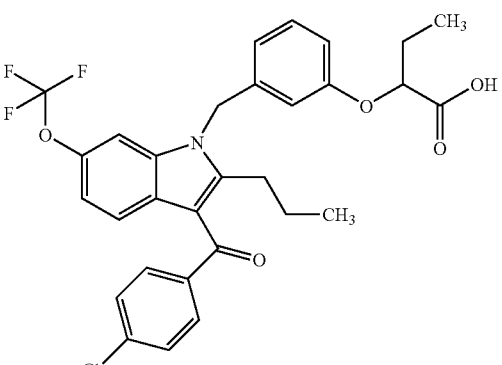 | 574.002 | M + H | 4.4 |
| 146 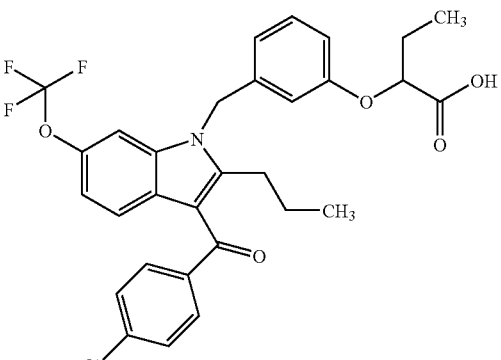 | 574.002 | M + H | 4.4 |
| 147 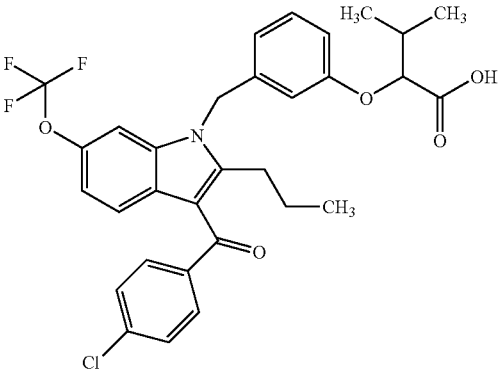 | 588.029 | M + H | 4.51 |
| 148 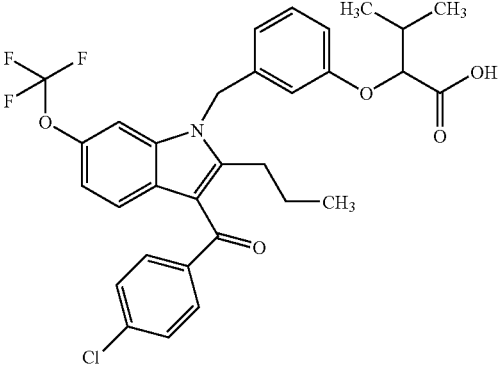 | 588.029 | M + H | 4.51 |

TABLE 3-continued
Compounds Where R³ is Benzoyl
| MOLSTRUCTURE | PARENT WEIGHT | Mass Spec | Retention Time |
|---|---|---|---|
| 149 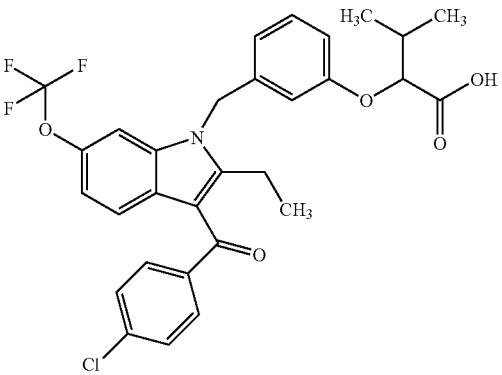 | 574.002 | M + H | 4.43 |
| 150 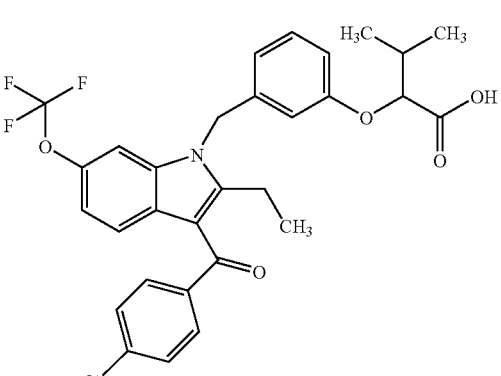 | 574.002 | M + H | 4.43 |
| 151 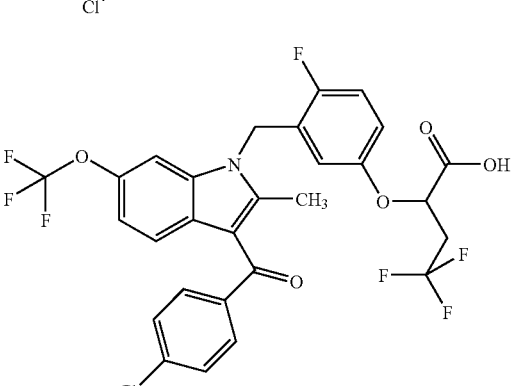 | 617.909 | 618 (M + 1) | 4.28 |
| 152 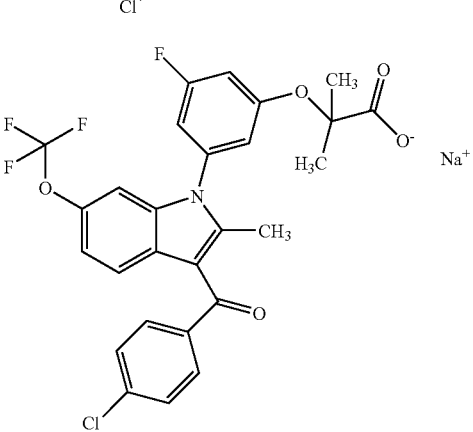 | 549.911 | 550.2 (M + 1) | 4.36 min |

TABLE 3-continued
Compounds Where R³ is Benzoyl
| MOLSTRUCTURE | | PARENT WEIGHT | Mass Spec | Retention Time |
|---|---|---|---|---|
| 153 | 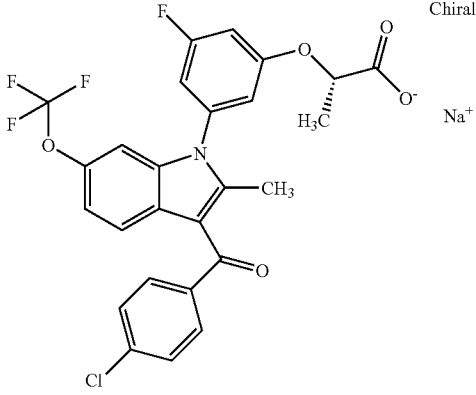 Chiral | 535.884 | 535.9 (M + 1) | 4.27 min |
| 154 | 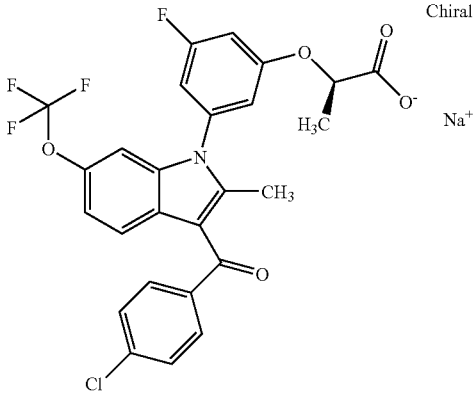 Chiral | 535.884 | 536.1 (M + 1) | 4.21 min |
| 155 | 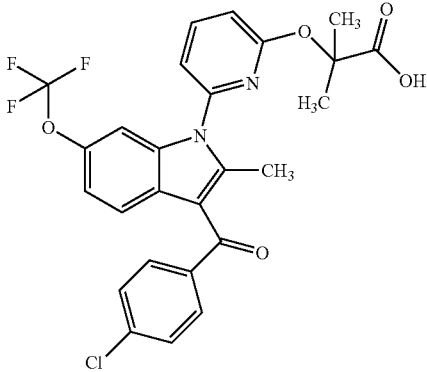 | 532.908 | 533.1 (M + 1) | 4.24 min |

TABLE 3-continued

Compounds Where R³ is Benzoyl

| MOLSTRUCTURE | PARENT WEIGHT | Mass Spec | Retention Time |
|---|---|---|---|
| 156 | 575.974 | M + 1 + Na = 598 | 4.25 |
| 157 | 580.392 | M + 1 = 580 | 4.34 |
| 158 | 561.947 | M + 1 + Na = 584 | 3.96 |

TABLE 3-continued
Compounds Where R³ is Benzoyl
| MOLSTRUCTURE | PARENT WEIGHT | Mass Spec | Retention Time |
|---|---|---|---|
| 159 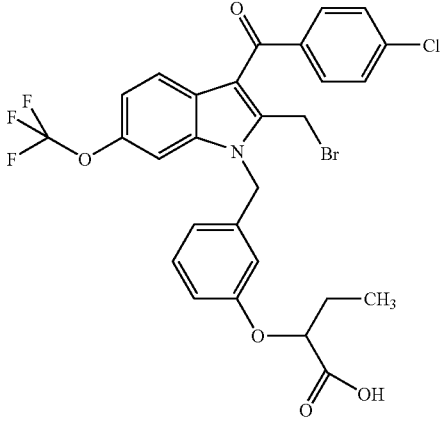 | 624.843 | M − Br = 544 | 4.86 |
| 160 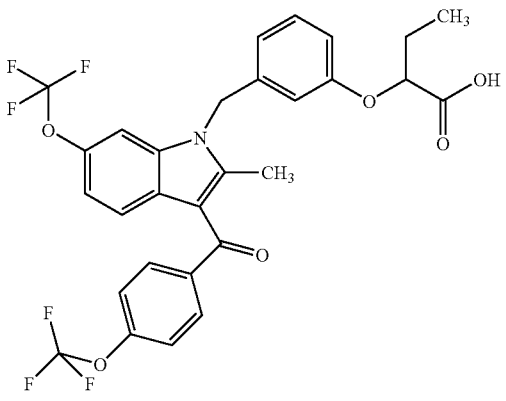 | 595.5 | M + H | 4.24 |
| 161 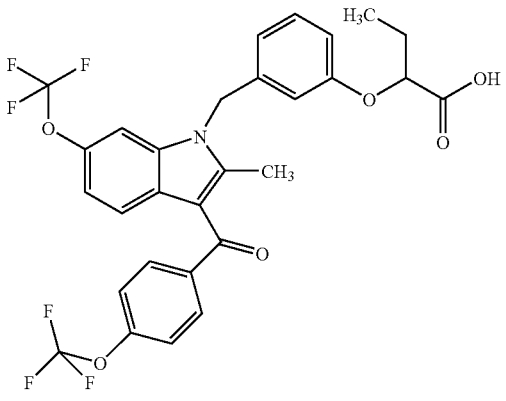 | 595.5 | M + H | 4.24 |

TABLE 3-continued
Compounds Where R³ is Benzoyl
| MOLSTRUCTURE | PARENT WEIGHT | Mass Spec | Retention Time |
|---|---|---|---|
| 162 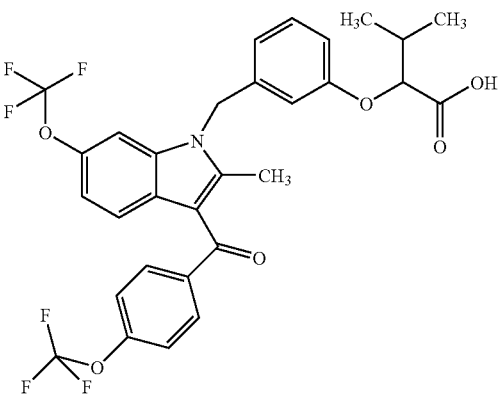 | 609.527 | | |
| 163 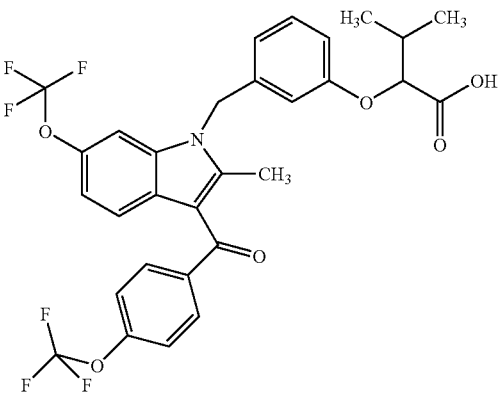 | 609.527 | | |
| 164 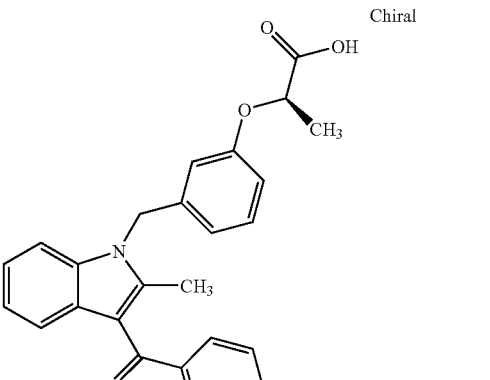 Chiral | 447.923 | 448 | 3.66 min |

TABLE 3-continued
Compounds Where R³ is Benzoyl
| MOLSTRUCTURE | | PARENT WEIGHT | Mass Spec | Retention Time |
|---|---|---|---|---|
| 165 | 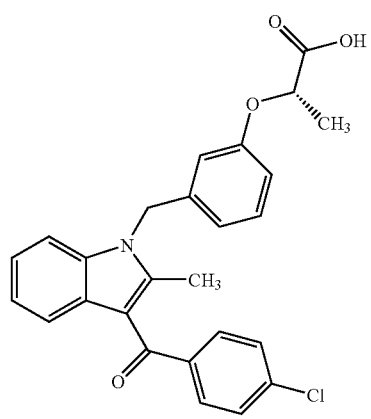 Chiral | 447.923 | 448.1 | 3.63 min |
| 166 | 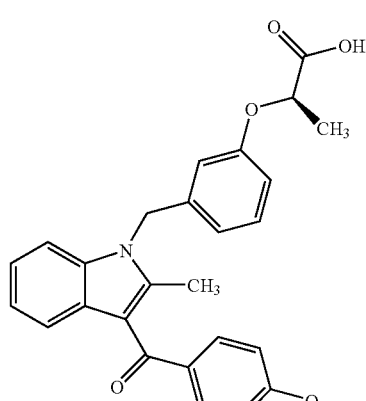 Chiral | 443.504 | 444.1 | 3.32 min |
| 167 | 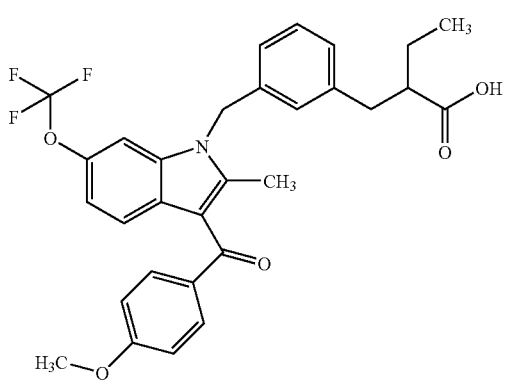 | 539.557 | M + H | 4.05 |

TABLE 3-continued
Compounds Where R³ is Benzoyl
| MOLSTRUCTURE | | PARENT WEIGHT | Mass Spec | Retention Time |
|---|---|---|---|---|
| 168 | 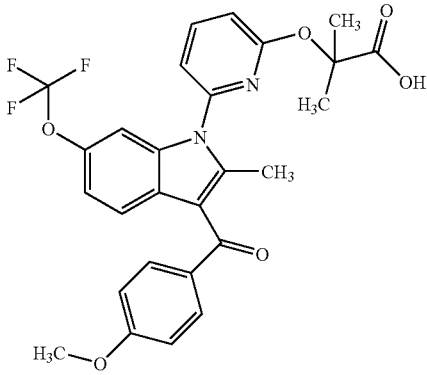 | 528.489 | 529.2 (M + 1) | 3.94 min |
| 169 | 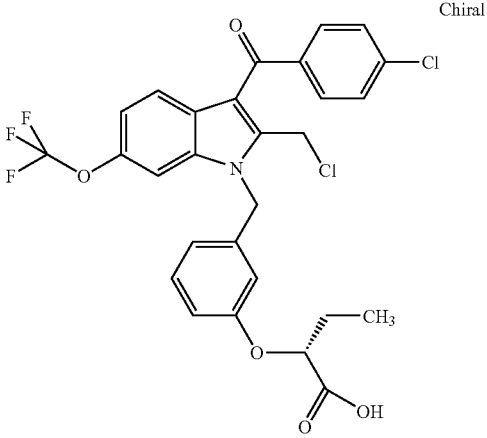 Chiral | 580.392 | M + 1 = 580 | 4.43 |
| 170 | 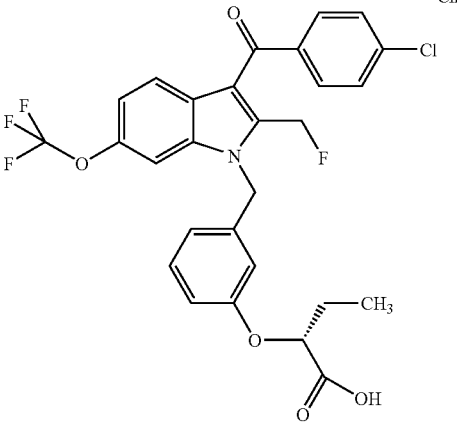 Chiral | 563.938 | M + 1 = 564 | 4.27 |

TABLE 3-continued

Compounds Where R³ is Benzoyl

| MOLSTRUCTURE | PARENT WEIGHT | Mass Spec | Retention Time |
|---|---|---|---|
| 171 | 573.593 | 574.1 | 3.43 min |
| 172 | 589.592 | 590.3 | 3.61 min |
| 173 | 557.593 | 558 | 4.24 min |
| 174 | 543.566 | 543.9 | 3.87 min |

TABLE 3-continued

Compounds Where R³ is Benzoyl

| MOLSTRUCTURE | PARENT WEIGHT | Mass Spec | Retention Time |
|---|---|---|---|
| 175 | 543.566 | 544.1 | 3.61 min |
| 176 (Chiral) | 527.502 | 528.4 (M + 1) | 3.73 min |
| 177 (Chiral) | 531.92 | 532.4 (M + 1) | 3.99 min |

TABLE 3-continued
Compounds Where R³ is Benzoyl
| MOLSTRUCTURE | | PARENT WEIGHT | Mass Spec | Retention Time |
|---|---|---|---|---|
| 178 | 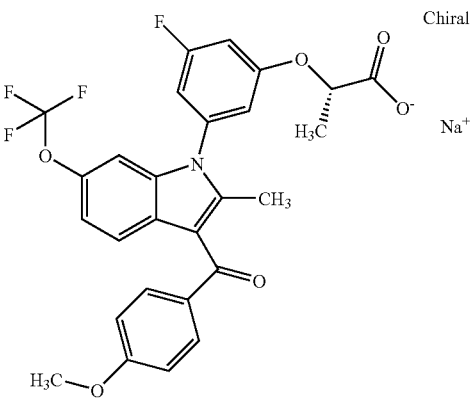 Chiral | 531.465 | 532.3 (M + 1) | 3.63 min |
| 179 | 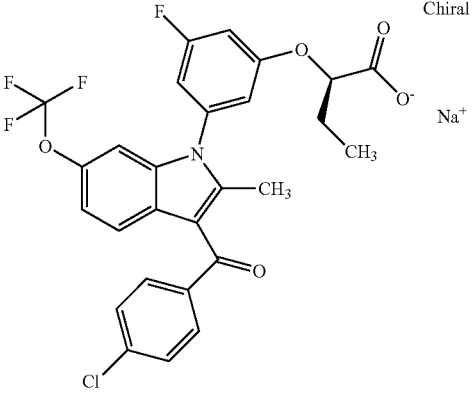 Chiral | 549.911 | 550.3 (M + 1) | 4.03 min |
| 180 | 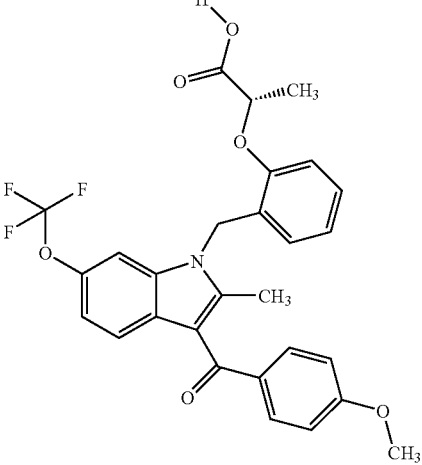 | | | |

TABLE 3-continued

Compounds Where R³ is Benzoyl

| MOLSTRUCTURE | PARENT WEIGHT | Mass Spec | Retention Time |
|---|---|---|---|
| 181 | | | |
| 182 | | | |
| 183 | | | |

TABLE 3-continued

Compounds Where R³ is Benzoyl

| MOLSTRUCTURE | PARENT WEIGHT | Mass Spec | Retention Time |
| --- | --- | --- | --- |
| 184 | | | |
| 185 | | | |
| 186 | | | |
| 187 | | | |

TABLE 3-continued

Compounds Where R³ is Benzoyl

| MOLSTRUCTURE | PARENT WEIGHT | Mass Spec | Retention Time |
|---|---|---|---|

188 [structure]

189 [structure]

TABLE 3A

Compounds Where R³ is Benzoyl 1. (2S)-2-(3-{[3-(4-methoxybenzoyl)-2-methyl-1H-indol-1-yl]methyl}phenoxy)propanoic acid
2. (2S)-2-(3-{[3-(4-methoxybenzoyl)-2-methyl-6-(trifluoromethoxy)-1H-indol-1-yl]methyl}phenoxy)propanoic acid
3. (2S)-2-(3-{[3-(4-chlorobenzoyl)-2-methyl-6-(trifluoromethoxy)-1H-indol-1-yl]methyl}phenoxy)propanoic acid
4. (2S)-2-(3-{[3-(4-methoxybenzoyl)-2-methyl-5-(trifluoromethoxy)-1H-indol-1-yl]methyl}phenoxy)propanoic acid
5. (2R)-2-(3-{[3-(4-methoxybenzoyl)-2-methyl-6-(trifluoromethoxy)-1H-indol-1-yl]methyl}phenoxy)propanoic acid
6. (2S)-2-{3-[3-(4-methoxybenzoyl)-2-methyl-6-(trifluoromethoxy)-1H-indol-1-yl]phenoxy}propanoic acid
7. 2-(3-{[3-(4-methoxybenzoyl)-2-methyl-6-(trifluoromethoxy)-1H-indol-1-yl]methyl}phenoxy)-2-methylpropanoic acid
8. 2-{3-[3-(4-methoxybenzoyl)-2-methyl-6-(trifluoromethoxy)-1H-indol-1-yl]phenoxy}-2-methylpropanoic acid
9. 3-(3-{[3-(4-methoxybenzoyl)-2-methyl-6-(trifluoromethoxy)-1H-indol-1-yl]methyl}phenyl)propanoic acid
10. 2-ethoxy-3-(3-{[3-(4-methoxybenzoyl)-2-methyl-6-(trifluoromethoxy)-1H-indol-1-yl]methyl}phenyl)propanoic acid
11. 3-(3-{[3-(4-methoxybenzoyl)-2-methyl-6-(trifluoromethoxy)-1H-indol-1-yl]methyl}phenyl)-2-(2,2,2-trifluoroethoxy)propanoic acid
12. 2-{3-[3-(4-chlorobenzoyl)-2-methyl-6-(trifluoromethoxy)-1H-indol-1-yl]phenoxy}-2-methylpropanoic acid
13. 2-{3-[3-[(6-chloropyridin-3-yl)carbonyl]-2-methyl-6-(trifluoromethoxy)-1H-indol-1-yl]phenoxy}-2-methylpropanoic acid
14. 2-{3-[3-[(6-ethoxypyridin-3-yl)carbonyl]-2-methyl-6-(trifluoromethoxy)-1H-indol-1-yl]phenoxy}-2-methylpropanoic acid
15. 3-{3-[3-(4-methoxybenzoyl)-2-methyl-6-(trifluoromethoxy)-1H-indol-1-yl]phenyl}propanoic acid
16. 3-{3-[3-(4-methoxybenzoyl)-2-methyl-6-(trifluoromethoxy)-1H-indol-1-yl]phenyl}-2-(2,2,2-trifluoroethoxy)propanoic acid
17. 2-{3-[3-[(2-chloropyridin-3-yl)carbonyl]-2-methyl-6-(trifluoromethoxy)-1H-indol-1-yl]phenoxy}-2-methylpropanoic acid
18. 2-methyl-2-{3-[2-methyl-3-[(6-methylpyridin-2-yl)carbonyl]-6-(trifluoromethoxy)-1H-indol-1-yl]phenoxy}propanoic acid TABLE 3A-continued

| Compounds Where R³ is Benzoyl |

| | |
|---|---|
| 19 | 2-methyl-2-{3-[2-methyl-3-(quinolin-2-ylcarbonyl)-6-(trifluoromethoxy)-1H-indol-1-yl]phenoxy}propanoic acid |
| 20 | 3-{3-[3-(4-chlorobenzoyl)-2-methyl-6-(trifluoromethoxy)-1H-indol-1-yl]phenyl}-2-(2,2,2-trifluoroethoxy)propanoic acid |
| 21 | 2-{3-[3-(2-chloro-6-methylisonicotinoyl)-2-methyl-6-(trifluoromethoxy)-1H-indol-1-yl]phenoxy}-2-methylpropanoic acid |
| 22 | 2-{3-[3-(isoquinolin-1-ylcarbonyl)-2-methyl-6-(trifluoromethoxy)-1H-indol-1-yl]phenoxy}-2-methylpropanoic acid |
| 23 | (2S)-2-(2-chloro-5-{[3-(4-methoxybenzoyl)-2-methyl-6-(trifluoromethoxy)-1H-indol-1-yl]methyl}phenoxy)propanoic acid |
| 24 | (2S)-2-(3-{[3-(4-chlorobenzoyl)-2-methyl-6-(trifluoromethoxy)-1H-indol-1-yl]methyl}-4-propylphenoxy)propanoic acid |
| 25 | (2R)-2-(3-{[3-(4-chlorobenzoyl)-2-methyl-6-(trifluoromethoxy)-1H-indol-1-yl]methyl}-4-propylphenoxy)propanoic acid |
| 26 | (2S)-2-(2-chloro-5-{[3-(4-chlorobenzoyl)-2-methyl-6-(trifluoromethoxy)-1H-indol-1-yl]methyl}phenoxy)propanoic acid |
| 27 | (2S)-2-{2-chloro-5-[3-(4-methoxybenzoyl)-2-methyl-6-(trifluoromethoxy)-1H-indol-1-yl]phenoxy}propanoic acid |
| 28 | (2R)-2-(2-chloro-5-{[3-(4-methoxybenzoyl)-2-methyl-6-(trifluoromethoxy)-1H-indol-1-yl]methyl}phenoxy)propanoic acid |
| 29 | (2R)-2-(2-chloro-5-{[3-(4-chlorobenzoyl)-2-methyl-6-(trifluoromethoxy)-1H-indol-1-yl]methyl}phenoxy)propanoic acid |
| 30 | (2S)-2-(4-chloro-3-{[3-(4-methoxybenzoyl)-2-methyl-6-(trifluoromethoxy)-1H-indol-1-yl]methyl}phenoxy)propanoic acid |
| 31 | (2S)-2-(4-chloro-3-{[3-(4-chlorobenzoyl)-2-methyl-6-(trifluoromethoxy)-1H-indol-1-yl]methyl}phenoxy)propanoic acid |
| 32 | (2R)-2-{2-chloro-5-[3-(4-chlorobenzoyl)-2-methyl-6-(trifluoromethoxy)-1H-indol-1-yl]phenoxy}propanoic acid |
| 33 | (2S)-2-{2-chloro-5-[3-(4-chlorobenzoyl)-2-methyl-6-(trifluoromethoxy)-1H-indol-1-yl]phenoxy}propanoic acid |
| 34 | (2R)-2-(4-chloro-3-{[3-(4-methoxybenzoyl)-2-methyl-6-(trifluoromethoxy)-1H-indol-1-yl]methyl}phenoxy)propanoic acid |
| 35 | (2R)-2-(4-chloro-3-{[3-(4-chlorobenzoyl)-2-methyl-6-(trifluoromethoxy)-1H-indol-1-yl]methyl}phenoxy)propanoic acid |
| 36 | (2S)-2-(3-{1-[3-(4-chlorobenzoyl)-2-methyl-6-(trifluoromethoxy)-1H-indol-1-yl]ethyl}phenoxy)propanoic acid |
| 37 | (2S)-2-(3-{[3-(2,4-dichlorobenzoyl)-2-methyl-6-(trifluoromethoxy)-1H-indol-1-yl]methyl}phenoxy)propanoic acid |
| 38 | (2R)-2-(3-{[3-(2,4-dichlorobenzoyl)-2-methyl-6-(trifluoromethoxy)-1H-indol-1-yl]methyl}phenoxy)propanoic acid |
| 39 | 2-ethyl-5-{[3-(4-methoxybenzoyl)-2-methyl-6-(trifluoromethoxy)-1H-indol-1-yl]methyl}-2,3-dihydro-1-benzofuran-2-carboxylic acid |
| 40 | 5-{[3-(4-chlorobenzoyl)-2-methyl-6-(trifluoromethoxy)-1H-indol-1-yl]methyl}-2-ethyl-2,3-dihydro-1-benzofuran-2-carboxylic acid |
| 41 | 6-{[3-(4-methoxybenzoyl)-2-methyl-6-(trifluoromethoxy)-1H-indol-1-yl]methyl}-2-methylchromane-2-carboxylic acid |
| 42 | (2S)-2-{3-[3-(4-chlorobenzoyl)-2-methyl-6-(trifluoromethoxy)-1H-indol-1-yl]phenoxy}propanoic acid |
| 43 | (2R)-2-{3-[3-(4-chlorobenzoyl)-2-methyl-6-(trifluoromethoxy)-1H-indol-1-yl]phenoxy}propanoic acid |
| 44 | 6-{[3-(4-chlorobenzoyl)-2-methyl-6-(trifluoromethoxy)-1H-indol-1-yl]methyl}-2-methylchromane-2-carboxylic acid |
| 45 | (2S)-2-(3-{[3-(4-chloro-2-methoxybenzoyl)-2-methyl-6-(trifluoromethoxy)-1H-indol-1-yl]methyl}phenoxy)propanoic acid |
| 46 | (2R)-2-(3-{[3-(4-chloro-2-methoxybenzoyl)-2-methyl-6-(trifluoromethoxy)-1H-indol-1-yl]methyl}phenoxy)propanoic acid |
| 47 | (2S)-2-(3-{[3-(4-chloro-2-methylbenzoyl)-2-methyl-6-(trifluoromethoxy)-1H-indol-1-yl]methyl}phenoxy)propanoic acid |
| 48 | (2R)-2-(3-{[3-(4-chloro-2-methylbenzoyl)-2-methyl-6-(trifluoromethoxy)-1H-indol-1-yl]methyl}phenoxy)propanoic acid |
| 49 | (3-{[3-(4-chlorobenzoyl)-2-methyl-6-(trifluoromethoxy)-1H-indol-1-yl]methyl}phenoxy)(cyclohexyl)acetic acid |
| 50 | 2-(3-{[3-(4-chlorobenzoyl)-2-methyl-6-(trifluoromethoxy)-1H-indol-1-yl]methyl}phenoxy)butanoic acid |
| 51 | 2-(3-{[3-(4-chlorobenzoyl)-2-methyl-6-(trifluoromethoxy)-1H-indol-1-yl]methyl}phenoxy)-4-methylpentanoic acid |
| 52 | 2-(3-{[3-(4-chlorobenzoyl)-2-methyl-6-(trifluoromethoxy)-1H-indol-1-yl]methyl}phenoxy)pentanoic acid |
| 53 | (3-{[3-(4-chlorobenzoyl)-2-methyl-6-(trifluoromethoxy)-1H-indol-1-yl]methyl}phenoxy)(phenyl)acetic acid |
| 54 | 1-(3-{[3-(4-chlorobenzoyl)-2-methyl-6-(trifluoromethoxy)-1H-indol-1-yl]methyl}phenoxy)cyclobutanecarboxylic acid |
| 55 | (2R)-2-(3-{[3-(4-chlorobenzoyl)-2-methyl-6-(trifluoromethoxy)-1H-indol-1-yl]methyl}phenoxy)propanoic acid |
| 56 | 2-(3-{[3-(4-chlorobenzoyl)-2-methyl-6-(trifluoromethoxy)-1H-indol-1-yl]methyl}phenoxy)-3-methylbutanoic acid |

TABLE 3A-continued

Compounds Where R³ is Benzoyl

| | |
|---|---|
| 57 | (2S)-2-(3-{[3-(4-methoxy-2-methylbenzoyl)-2-methyl-6-(trifluoromethoxy)-1H-indol-1-yl]methyl}phenoxy)propanoic acid |
| 58 | (2R)-2-(3-{[3-(4-methoxy-2-methylbenzoyl)-2-methyl-6-(trifluoromethoxy)-1H-indol-1-yl]methyl}phenoxy)propanoic acid |
| 59 | (2S)-2-(3-{[3-(4-chlorobenzoyl)-2-methyl-6-(trifluoromethoxy)-1H-indol-1-yl]methyl}phenoxy)butanoic acid |
| 60 | (2R)-2-(3-{[3-(4-chlorobenzoyl)-2-methyl-6-(trifluoromethoxy)-1H-indol-1-yl]methyl}phenoxy)butanoic acid |
| 61 | 2-(3-{[3-(4-chlorobenzoyl)-2-methyl-6-(trifluoromethoxy)-1H-indol-1-yl]methyl}phenoxy)pentanoic acid |
| 62 | 2-(3-{[3-(4-chlorobenzoyl)-2-methyl-6-(trifluoromethoxy)-1H-indol-1-yl]methyl}phenoxy)pentanoic acid |
| 63 | (2R)-2-ethyl-7-{[3-(4-methoxybenzoyl)-2-methyl-6-(trifluoromethoxy)-1H-indol-1-yl]methyl}chromane-2-carboxylic acid |
| 64 | (2R)-7-{[3-(4-chlorobenzoyl)-2-methyl-6-(trifluoromethoxy)-1H-indol-1-yl]methyl}-2-ethylchromane-2-carboxylic acid |
| 65 | (2R)-7-{[3-(2,4-dichlorobenzoyl)-2-methyl-6-(trifluoromethoxy)-1H-indol-1-yl]methyl}-2-ethylchromane-2-carboxylic acid |
| 66 | (2S)-2-ethyl-7-{[3-(4-methoxybenzoyl)-2-methyl-6-(trifluoromethoxy)-1H-indol-1-yl]methyl}chromane-2-carboxylic acid |
| 67 | (2S)-7-{[3-(4-chlorobenzoyl)-2-methyl-6-(trifluoromethoxy)-1H-indol-1-yl]methyl}-2-ethylchromane-2-carboxylic acid |
| 68 | (2S)-2-(3-{[2-methyl-3-(2,4,6-trichlorobenzoyl)-6-(trifluoromethoxy)-1H-indol-1-yl]methyl}phenoxy)propanoic acid |
| 69 | (2R)-2-(3-{[2-methyl-3-(2,4,6-trichlorobenzoyl)-6-(trifluoromethoxy)-1H-indol-1-yl]methyl}phenoxy)propanoic acid |
| 70 | (2S)-2-{3-[2-methyl-3-(quinolin-2-ylcarbonyl)-6-(trifluoromethoxy)-1H-indol-1-yl]phenoxy}propanoic acid |
| 71 | (2R)-2-{3-[2-methyl-3-(quinolin-2-ylcarbonyl)-6-(trifluoromethoxy)-1H-indol-1-yl]phenoxy}propanoic acid |
| 72 | 2-{3-[3-(4-chlorobenzoyl)-2-methyl-6-(trifluoromethoxy)-1H-indol-1-yl]phenoxy}butanoic acid |
| 73 | 2-(3-{[3-(2,4-dichlorobenzoyl)-2-methyl-6-(trifluoromethoxy)-1H-indol-1-yl]methyl}phenoxy)butanoic acid |
| 74 | 2-(3-{[3-(2,4-dichlorobenzoyl)-2-methyl-6-(trifluoromethoxy)-1H-indol-1-yl]methyl}phenoxy)butanoic acid |
| 75 | 2-(3-{[3-(2,4-dichlorobenzoyl)-2-methyl-6-(trifluoromethoxy)-1H-indol-1-yl]methyl}phenoxy)pentanoic acid |
| 76 | 2-(3-{[3-(2,4-dichlorobenzoyl)-2-methyl-6-(trifluoromethoxy)-1H-indol-1-yl]methyl}phenoxy)pentanoic acid |
| 77 | 2-{3-[3-(4-chlorobenzoyl)-2-methyl-6-(trifluoromethoxy)-1H-indol-1-yl]phenoxy}pentanoic acid |
| 78 | 2-(3-{[3-(4-chlorobenzoyl)-2-methyl-6-(trifluoromethoxy)-1H-indol-1-yl]methyl}phenoxy)-3-methylbutanoic acid |
| 79 | 2-(3-{[3-(4-chlorobenzoyl)-2-methyl-6-(trifluoromethoxy)-1H-indol-1-yl]methyl}phenoxy)-3-methylbutanoic acid |
| 80 | 2-(4-chloro-3-{[3-(4-chlorobenzoyl)-2-methyl-6-(trifluoromethoxy)-1H-indol-1-yl]methyl}phenoxy)butanoic acid |
| 81 | 2-(2-chloro-5-{[3-(4-methoxybenzoyl)-2-methyl-6-(trifluoromethoxy)-1H-indol-1-yl]methyl}phenoxy)butanoic acid |
| 82 | 2-(2-chloro-5-{[3-(4-chlorobenzoyl)-2-methyl-6-(trifluoromethoxy)-1H-indol-1-yl]methyl}phenoxy)butanoic acid |
| 83 | 2-(4-chloro-3-{[3-(4-chlorobenzoyl)-2-methyl-6-(trifluoromethoxy)-1H-indol-1-yl]methyl}phenoxy)pentanoic acid |
| 84 | 2-(2-chloro-5-{[3-(4-chlorobenzoyl)-2-methyl-6-(trifluoromethoxy)-1H-indol-1-yl]methyl}phenoxy)pentanoic acid |
| 85 | 2-(4-chloro-3-{[3-(4-methoxybenzoyl)-2-methyl-6-(trifluoromethoxy)-1H-indol-1-yl]methyl}phenoxy)butanoic acid |
| 86 | 2-(4-chloro-3-{[3-(4-methoxybenzoyl)-2-methyl-6-(trifluoromethoxy)-1H-indol-1-yl]methyl}phenoxy)pentanoic acid |
| 87 | 2-(4-chloro-3-{[3-(2,4-dichlorobenzoyl)-2-methyl-6-(trifluoromethoxy)-1H-indol-1-yl]methyl}phenoxy)butanoic acid |
| 88 | 2-(4-chloro-3-{[3-(2,4-dichlorobenzoyl)-2-methyl-6-(trifluoromethoxy)-1H-indol-1-yl]methyl}phenoxy)pentanoic acid |
| 89 | (2R)-2-(3-{[3-(2-chloro-4-methoxybenzoyl)-2-methyl-6-(trifluoromethoxy)-1H-indol-1-yl]methyl}phenoxy)propanoic acid |
| 90 | (2S)-2-(3-{[3-(2-chloro-4-methoxybenzoyl)-2-methyl-6-(trifluoromethoxy)-1H-indol-1-yl]methyl}phenoxy)propanoic acid |
| 91 | 2-(3-{[3-(4-chlorobenzoyl)-2-methyl-6-(trifluoromethoxy)-1H-indol-1-yl]methyl}phenoxy)-2-methylbutanoic acid |
| 92 | 2-(3-{[3-(4-chlorobenzoyl)-2-ethyl-6-(trifluoromethoxy)-1H-indol-1-yl]methyl}phenoxy)-2-methylbutanoic acid |
| 93 | 2-(3-{[3-(4-chlorobenzoyl)-2-methyl-6-(trifluoromethoxy)-1H-indol-1-yl]methyl}phenoxy)-2-methylpentanoic acid |
| 94 | 2-(2-chloro-5-{[3-(4-methoxybenzoyl)-2-methyl-6-(trifluoromethoxy)-1H-indol-1-yl]methyl}phenoxy)-2-methylbutanoic acid |

TABLE 3A-continued

Compounds Where R³ is Benzoyl

| | |
|---|---|
| 95 | 2-(2-chloro-5-{[3-(4-chlorobenzoyl)-2-methyl-6-(trifluoromethoxy)-1H-indol-1-yl]methyl}phenoxy)-2-methylbutanoic acid |
| 96 | 2-(2-chloro-5-{[3-(4-methoxybenzoyl)-2-methyl-6-(trifluoromethoxy)-1H-indol-1-yl]methyl}phenoxy)-2-methylpentanoic acid |
| 97 | 2-(2-chloro-5-{[3-(4-chlorobenzoyl)-2-methyl-6-(trifluoromethoxy)-1H-indol-1-yl]methyl}phenoxy)-2-methylpentanoic acid |
| 98 | 2-(2-chloro-5-{[3-(4-methoxybenzoyl)-2-methyl-6-(trifluoromethoxy)-1H-indol-1-yl]methyl}phenoxy)-2-ethylbutanoic acid |
| 99 | 2-(2-chloro-5-{[3-(4-methoxybenzoyl)-2-methyl-6-(trifluoromethoxy)-1H-indol-1-yl]methyl}phenoxy)-2-ethylpentanoic acid |
| 100 | 2-(2-chloro-5-{[3-(4-chlorobenzoyl)-2-methyl-6-(trifluoromethoxy)-1H-indol-1-yl]methyl}phenoxy)-2-ethylbutanoic acid |
| 101 | 2-(2-chloro-5-{[3-(4-chlorobenzoyl)-2-methyl-6-(trifluoromethoxy)-1H-indol-1-yl]methyl}phenoxy)-2-ethylpentanoic acid |
| 102 | 2-(3-{[3-(2,4-dichlorobenzoyl)-2-methyl-6-(trifluoromethoxy)-1H-indol-1-yl]methyl}phenoxy)-3,3,3-trifluoropropanoic acid |
| 103 | 2-(3-{[3-(2-chloro-4-methoxybenzoyl)-2-methyl-6-(trifluoromethoxy)-1H-indol-1-yl]methyl}phenoxy)butanoic acid |
| 104 | 2-(3-{[3-(4-chlorobenzoyl)-2-methyl-6-(trifluoromethoxy)-1H-indol-1-yl]methyl}phenoxy)-2-methylbutanoic acid |
| 105 | 2-(3-{[3-(4-chlorobenzoyl)-2-methyl-6-(trifluoromethoxy)-1H-indol-1-yl]methyl}phenoxy)-2-methylbutanoic acid |
| 106 | 2-(2-chloro-5-{[3-(4-methoxybenzoyl)-2-methyl-6-(trifluoromethoxy)-1H-indol-1-yl]methyl}phenoxy)butanoic acid |
| 107 | 2-(2-cbloro-5-{[3-(4-methoxybenzoyl)-2-methyl-6-(trifluoromethoxy)-1H-indol-1-yl]methyl}phenoxy)butanoic acid |
| 108 | 2-(2-fluoro-5-{[3-(4-methoxybenzoyl)-2-methyl-6-(trifluoromethoxy)-1H-indol-1-yl]methyl}phenoxy)pentanoic acid |
| 109 | 2-(2-tluoro-5-{[3-(4-methoxybenzoyl)-2-methyl-6-(trifluoromethoxy)-1H-indol-1-yl]methyl}phenoxy)pentanoic acid |
| 110 | 2-(2-fluoro-5-{[3-(4-methoxybenzoyl)-2-methyl-6-(trifluoromethoxy)-1H-indol-1-yl]methyl}phenoxy)pentanoic acid |
| 111 | (4-chlorophenyl)[2-methyl-1-{3-[(1S)-1-(2H-tetrazol-5-yl)ethoxy]benzyl}-6-(trifluoromethoxy)-1H-indol-3-yl]methanone |
| 112 | 2-(3-{[3-(4-methoxybenzoyl)-2-methyl-6-(trifluoromethoxy)-1H-indol-1-yl]methyl}benzyl)butanoic acid |
| 113 | 2-(3-{[3-(4-chlorobenzoyl)-2-methyl-6-(trifluoromethoxy)-1H-indol-1-yl]methyl}benzyl)butanoic acid |
| 114 | (3-{[3-(4-methoxybenzoyl)-2-methyl-6-(trifluoromethoxy)-1H-indol-1-yl]methyl}benzyl)(methyl)malonic acid |
| 115 | 3-(3-{[3-(4-methoxybenzoyl)-2-methyl-6-(trifluoromethoxy)-1H-indol-1-yl]methyl}phenyl)-2-phenylpropanoic acid |
| 116 | 3-(3-{[3-(4-chlorobenzoyl)-2-methyl-6-(trifluoromethoxy)-1H-indol-1-yl]methyl}phenyl)-2-phenylpropanoic acid |
| 117 | 2-(2-fluoro-5-{[3-(4-methoxybenzoyl)-2-methyl-6-(trifluoromethoxy)-1H-indol-1-yl]methyl}phenoxy)-3-methylbutanoic acid |
| 118 | 2-(5-{[3-(4-chlorobenzoyl)-2-methyl-6-(trifluoromethoxy)-1H-indol-1-yl]methyl}-2-fluorophenoxy)-3-methylbutanoic acid |
| 119 | 2-(2-chloro-5-{[3-(4-methoxybenzoyl)-2-methyl-6-(trifluoromethoxy)-1H-indol-1-yl]methyl}phenoxy)-3-methylbutanoic acid |
| 120 | 2-(2-chloro-5-{[3-(4-chlorobenzoyl)-2-methyl-6-(trifluoromethoxy)-1H-indol-1-yl]methyl}phenoxy)-3-methylbutanoic acid |
| 121 | 3-(3-{[3-(4-methoxybenzoyl)-2-methyl-6-(trifluoromethoxy)-1H-indol-1-yl]methyl}phenyl)-2-methylpropanoic acid |
| 122 | 3-(3-{[3-(4-chlorobenzoyl)-2-methyl-6-(trifluoromethoxy)-1H-indol-1-yl]methyl}phenyl)-2-methylpropanoic acid |
| 123 | 2-(5-{[3-(4-chlorobenzoyl)-2-methyl-6-(trifluoromethoxy)-1H-indol-1-yl]methyl}-2-fluorophenoxy)pentanoic acid |
| 124 | (2S)-2-{5-[3-[4-(ethylthio)benzoyl]-2-methyl-6-(trifluoromethoxy)-1H-indol-1-yl]-2-fluorophenoxy}propanoic acid |
| 125 | (2R)-2-(3-{[3-(4-fluorobenzoyl)-2-methyl-6-(trifluoromethoxy)-1H-indol-1-yl]methyl}phenoxy)propanoic acid |
| 126 | (2R)-2-[3-({2-methyl-6-(trifluoromethoxy)-3-[4-(trifluoromethoxy)benzoyl]-1H-indol-1-yl}methyl)phenoxy]propanoic acid |
| 127 | (2E)-3-(3-{[3-(4-chlorobenzoyl)-2-methyl-6-(trifluoromethoxy)-1H-indol-1-yl]methyl}phenyl)acrylic acid |
| 128 | (2S,3R)-3-(3-{[3-(4-chlorobenzoyl)-2-methyl-6-(trifluoromethoxy)-1H-indol-1-yl]methyl}phenyl)-2,3-dihydroxypropanoic acid |
| 129 | (4-chlorophenyl)[2-methyl-1-{3-[1-(2H-tetrazol-5-yl)propoxy]benzyl}-6-(trifluoromethoxy)-1H-indol-3-yl]methanone |
| 130 | (2R)-2-(3-{[3-(4-methoxybenzoyl)-2-methyl-6-(trifluoromethoxy)-1H-indol-1-yl]methyl}phenoxy)butanoic acid |
| 131 | 2-(2-fluoro-5-{[3-(4-methoxybenzoyl)-2-methyl-6-(trifluoromethoxy)-1H-indol-1-yl]methyl}phenoxy)butanoic acid |
| 132 | 2-(2-fluoro-5-{[3-(4-methoxybenzoyl)-2-methyl-6-(trifluoromethoxy)-1H-indol-1-yl]methyl}phenoxy)butanoic acid |

TABLE 3A-continued

Compounds Where R³ is Benzoyl

| | |
|---|---|
| 133 | 2-(5-{[3-(4-chlorobenzoyl)-2-methyl-6-(trifluoromethoxy)-1H-indol-1-yl]methyl}-2-fluorophenoxy)butanoic acid |
| 134 | 2-(5-{[3-(4-chlorobenzoyl)-2-methyl-6-(trifluoromethoxy)-1H-indol-1-yl]methyl}-2-fluorophenoxy)butanoic acid |
| 135 | 2-(3-{[3-(4-chlorobenzoyl)-2-methyl-6-(trifluoromethoxy)-1H-indol-1-yl]methyl}phenoxy)-4,4,4-trifluorobutanoic acid |
| 136 | (2R)-2-(3-{[3-(4-chlorobenzoyl)-2-ethyl-6-(trifluoromethoxy)-1H-indol-1-yl]methyl}phenoxy)butanoic acid |
| 137 | (2S)-2-(3-{[3-(4-chlorobenzoyl)-2-ethyl-6-(trifluoromethoxy)-1H-indol-1-yl]methyl}phenoxy)butanoic acid |
| 138 | 2-{5-[3-(4-chlorobenzoyl)-2-methyl-6-(trifluoromethoxy)-1H-indol-1-yl]-2-fluorophenoxy}-2-methylpropanoic acid |
| 139 | (2S)-2-{5-[3-(4-chlorobenzoyl)-2-methyl-6-(trifluoromethoxy)-1H-indol-1-yl]-2-fluorophenoxy}propanoic acid |
| 140 | (2R)-2-{5-[3-(4-chlorobenzoyl)-2-methyl-6-(trifluoromethoxy)-1H-indol-1-yl]-2-fluorophenoxy}propanoic acid |
| 141 | 2-(3-{[3-(4-methoxybenzoyl)-2-methyl-6-(trifluoromethoxy)-1H-indol-1-yl]methyl}phenoxy)-2-methylbutanoic acid |
| 142 | 2-(3-{[3-(4-methoxybenzoyl)-2-methyl-6-(trifluoromethoxy)-1H-indol-1-yl]methyl}phenoxy)-2-methylpentanoic acid |
| 143 | 2-(3-{[3-(4-chlorobenzoyl)-2-ethyl-6-(trifluoromethoxy)-1H-indol-1-yl]methyl}phenoxy)-3-methylbutanoic acid |
| 144 | 2-(3-{[3-(4-chlorobenzoyl)-2-isopropyl-6-(trifluoromethoxy)-1H-indol-1-yl]methyl}phenoxy)butanoic acid |
| 145 | 2-(3-{[3-(4-chlorobenzoyl)-2-propyl-6-(trifluoromethoxy)-1H-indol-1-yl]methyl}phenoxy)butanoic acid |
| 146 | 2-(3-{[3-(4-chlorobenzoyl)-2-propyl-6-(trifluoromethoxy)-1H-indol-1-yl]methyl}phenoxy)butanoic acid |
| 147 | 2-(3-{[3-(4-chlorobenzoyl)-2-propyl-6-(trifluoromethoxy)-1H-indol-1-yl]methyl}phenoxy)-3-methylbutanoic acid |
| 148 | 2-(3-{[3-(4-chlorobenzoyl)-2-propyl-6-(trifluoromethoxy)-1H-indol-1-yl]methyl}phenoxy)-3-methylbutanoic acid |
| 149 | 2-(3-{[3-(4-chlorobenzoyl)-2-ethyl-6-(trifluoromethoxy)-1H-indol-1-yl]methyl}phenoxy)-3-methylbutanoic acid |
| 150 | 2-(3-{[3-(4-chlorobenzoyl)-2-ethyl-6-(trifluoromethoxy)-1H-indol-1-yl]methyl}phenoxy)-3-methylbutanoic acid |
| 151 | 2-(3-{[3-(4-chlorobenzoyl)-2-methyl-6-(trifluoromethoxy)-1H-indol-1-yl]methyl}-4-fluorophenoxy)-4,4,4-trifluorobutanoic acid |
| 152 | 2-{3-[3-(4-chlorobenzoyl)-2-methyl-6-(trifluoromethoxy)-1H-indol-1-yl]-5-fluorophenoxy}-2-methylpropanoic acid |
| 153 | (2S)-2-{3-[3-(4-chlorobenzoyl)-2-methyl-6-(trifluoromethoxy)-1H-indol-1-yl]-5-fluorophenoxy}propanoic acid |
| 154 | (2R)-2-{3-[3-(4-chlorobenzoyl)-2-methyl-6-(trifluoromethoxy)-1H-indol-1-yl]-5-fluorophenoxy}propanoic acid |
| 155 | 2-({6-[3-(4-chlorobenzoyl)-2-methyl-6-(trifluoromethoxy)-1H-indol-1-yl]pyridin-2-yl}oxy)-2-methylpropanoic acid |
| 156 | 2-(3-{[3-(4-chlorobenzoyl)-2-(methoxymethyl)-6-(trifluoromethoxy)-1H-indol-1-yl]methyl}phenoxy)butanoic acid |
| 157 | 2-(3-{[3-(4-chlorobenzoyl)-2-(chloromethyl)-6-(trifluoromethoxy)-1H-indol-1-yl]methyl}phenoxy)butanoic acid |
| 158 | 2-(3-{[3-(4-chlorobenzoyl)-2-(hydroxymethyl)-6-(trifluoromethoxy)-1H-indol-1-yl]methyl}phenoxy)butanoic acid |
| 159 | 2-(3-{[2-(bromomethyl)-3-(4-chlorobenzoyl)-6-(trifluoromethoxy)-1H-indol-1-yl]methyl}phenoxy)butanoic acid |
| 160 | 2-[3-({2-methyl-6-(trifluoromethoxy)-3-[4-(trifluoromethoxy)benzoyl]-1H-indol-1-yl}methyl)phenoxy]butanoic acid |
| 161 | 2-[3-({2-methyl-6-(trifluoromethoxy)-3-[4-(trifluoromethoxy)benzoyl]-1H-indol-1-yl}methyl)phenoxy]butanoic acid |
| 162 | 3-methyl-2-[3-({2-methyl-6-(trifluoromethoxy)-3-[4-(trifluoromethoxy)benzoyl]-1H-indol-1-yl}methyl)phenoxy]butanoic acid |
| 163 | 3-methyl-2-[3-({2-methyl-6-(trifluoromethoxy)-3-[4-(trifluoromethoxy)benzoyl]-1H-indol-1-yl}methyl)phenoxy]butanoic acid |
| 164 | (2R)-2-(3-{[3-(4-chlorobenzoyl)-2-methyl-1H-indol-1-yl]methyl}phenoxy)propanoic acid |
| 165 | (2S)-2-(3-{[3-(4-chlorobenzoyl)-2-methyl-1H-indol-1-yl]methyl}phenoxy)propanoic acid |
| 166 | (2R)-2-(3-{[3-(4-methoxybenzoyl)-2-methyl-1H-indol-1-yl]methyl}phenoxy)propanoic acid |
| 167 | 2-(3-{[3-(4-methoxybenzoyl)-2-methyl-6-(trifluoromethoxy)-1H-indol-1-yl]methyl}benzyl)butanoic acid |
| 168 | 2-({6-[3-(4-methoxybenzoyl)-2-methyl-6-(trifluoromethoxy)-1H-indol-1-yl]pyridin-2-yl}oxy)-2-methylpropanoic acid |
| 169 | (2R)-2-(3-{[3-(4-chlorobenzoyl)-2-(chloromethyl)-6-(trifluoromethoxy)-1H-indol-1-yl]methyl}phenoxy)butanoic acid |
| 170 | (2R)-2-(3-{[3-(4-chlorobenzoyl)-2-(fluoromethyl)-6-(trifluoromethoxy)-1H-indol-1-yl]methyl}phenoxy)butanoic acid |

TABLE 3A-continued

Compounds Where R³ is Benzoyl

| | |
|---|---|
| 171 | 2-[(3-{[3-(4-methoxybenzoyl)-2-methyl-6-(trifluoromethoxy)-1H-indol-1-yl]methyl}phenyl)sulfinyl]-2-methylpropanoic acid |
| 172 | 2-[(3-{[3-(4-methoxybenzoyl)-2-methyl-6-(trifluoromethoxy)-1H-indol-1-yl]methyl}phenyl)sulfonyl]-2-methylpropanoic acid |
| 173 | 2-[(3-{[3-(4-methoxybenzoyl)-2-methyl-6-(trifluoromethoxy)-1H-indol-1-yl]methyl}phenyl)thio]-2-methylpropanoic acid |
| 174 | 2-[(3-{[3-(4-methoxybenzoyl)-2-methyl-6-(trifluoromethoxy)-1H-indol-1-yl]methyl}phenyl)thio]propanoic acid |
| 175 | 2-[(3-{[3-(4-methoxybenzoyl)-2-methyl-6-(trifluoromethoxy)-1H-indol-1-yl]methyl}phenyl)thio]propanoic acid |
| 176 | (2R)-2-{3-[3-(4-methoxybenzoyl)-2-methyl-6-(trifluoromethoxy)-1H-indol-1-yl]phenoxy}butanoic acid |
| 177 | (2R)-2-{3-[3-(4-chlorobenzoyl)-2-methyl-6-(trifluoromethoxy)-1H-indol-1-yl]phenoxy}butanoic acid |
| 178 | (2R)-2-{3-fluoro-5-[3-(4-methoxybenzoyl)-2-methyl-6-(trifluoromethoxy)-1H-indol-1-yl]phenoxy}propanoic acid |
| 179 | (2R)-2-{3-[3-(4-chlorobenzoyl)-2-methyl-6-(trifluoromethoxy)-1H-indol-1-yl]-5-fluorophenoxy}butanoic acid |
| 180 | (2S)-2-(2-{[3-(4-methoxybenzoyl)-2-methyl-6-(trifluoromethoxy)-1H-indol-1-yl]methyl}phenoxy)propanoic acid |
| 181 | (2R)-2-(2-{[3-(4-methoxybenzoyl)-2-methyl-6-(trifluoromethoxy)-1H-indol-1-yl]methyl}phenoxy)propanoic acid |
| 182 | 2-(2-{[3-(4-methoxybenzoyl)-2-methyl-6-(trifluoromethoxy)-1H-indol-1-yl]methyl}phenoxy)-2-methylpropanoic acid |
| 183 | (2R)-2-(2-{[3-(4-methoxybenzoyl)-2-methyl-6-(trifluoromethoxy)-1H-indol-1-yl]methyl}phenoxy)butanoic acid |
| 184 | (2S)-2-(2-{[3-(4-methoxybenzoyl)-2-methyl-6-(trifluoromethoxy)-1H-indol-1-yl]methyl}phenoxy)butanoic acid |
| 185 | (2S)-2-(4-{[3-(4-methoxybenzoyl)-2-methyl-6-(trifluoromethoxy)-1H-indol-1-yl]methyl}phenoxy)propanoic acid |
| 186 | (2R)-2-(4-{[3-(4-methoxybenzoyl)-2-methyl-6-(trifluoromethoxy)-1H-indol-1-yl]methyl}phenoxy)propanoic acid |
| 187 | 2-(4-{[3-(4-methoxybenzoyl)-2-methyl-6-(trifluoromethoxy)-1H-indol-1-yl]methyl}phenoxy)-2-methylpropanoic acid |
| 188 | (2R)-2-(4-{[3-(4-methoxybenzoyl)-2-methyl-6-(trifluoromethoxy)-1H-indol-1-yl]methyl}phenoxy)butanoic acid |
| 189 | 2-(4-{[3-(4-methoxybenzoyl)-2-methyl-6-(trifluoromethoxy)-1H-indol-1-yl]methyl}phenoxy)-2-methylpropanoic acid |

TABLE 4

Compound Where R³ is Phenyl

| | MOLSTRUCTURE | PARENT WEIGHT | Mass Spec | Retention Time |
|---|---|---|---|---|
| 1 | Chiral | 499.491 | 500(M + 1) | 4.22 |

TABLE 4-continued
Compound Where R³ is Phenyl
| | MOLSTRUCTURE | | PARENT WEIGHT | Mass Spec | Retention Time |
|---|---|---|---|---|---|
| 2 | 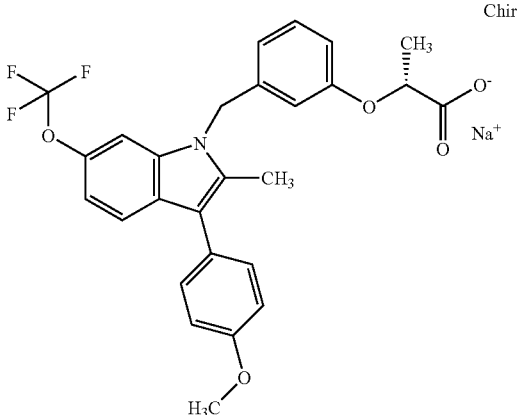 | Chiral | 499.491 | 500(M + 1) | 4.22 |
| 3 | 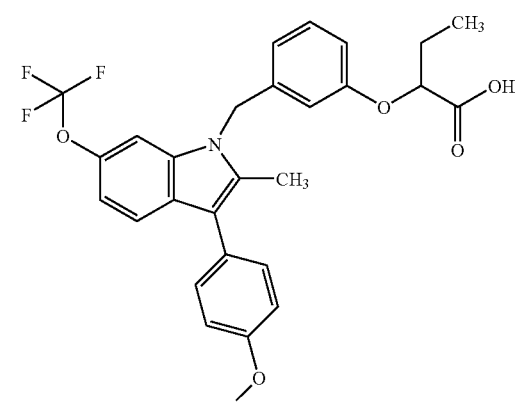 | | 513.518 | 514(M + 1) | 4.28 |
| 4 | 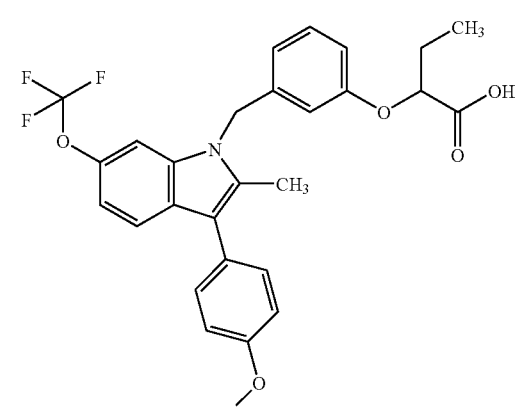 | | 513.518 | 514(M + 1) | 4.29 |

TABLE 4-continued
Compound Where R³ is Phenyl
| | MOLSTRUCTURE | PARENT WEIGHT | Mass Spec | Retention Time |
|---|---|---|---|---|
| 5 | 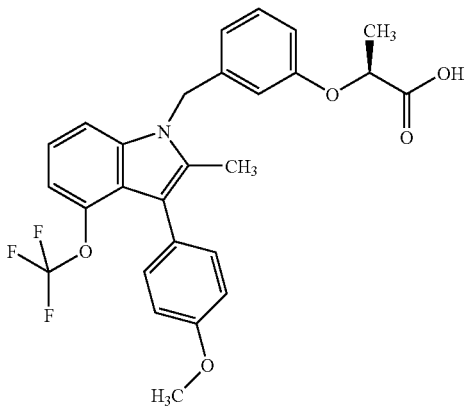 | 499.491 | 500(M + 1) | 4.14 |
| 6 | 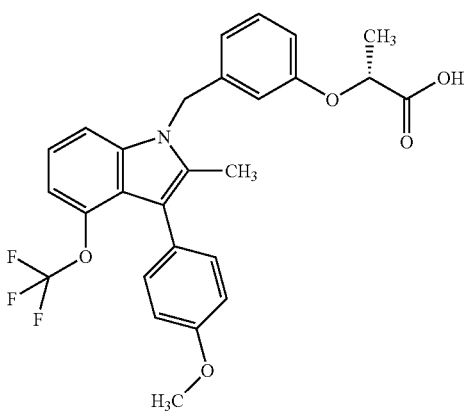 | 499.491 | 500(M + 1) | 4.14 |
| 7 | 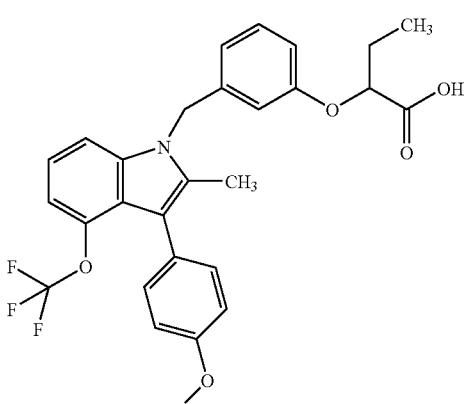 | 513.518 | 514(M + 1) | 4.19 |

TABLE 4-continued
Compound Where R³ is Phenyl
| | MOLSTRUCTURE | PARENT WEIGHT | Mass Spec | Retention Time |
|---|---|---|---|---|
| 8 | 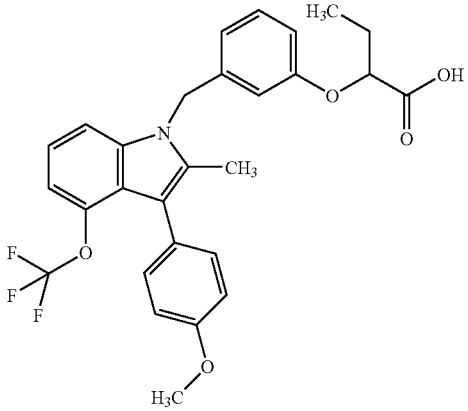 | 513.518 | 514(M + 1) | 4.19 |
| 9 | 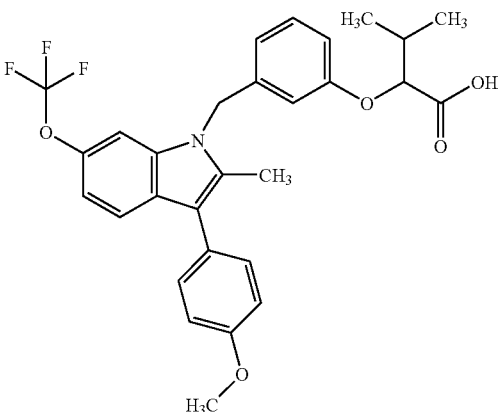 | 527.545 | 528(M + 1) | 4.35 |
| 10 | 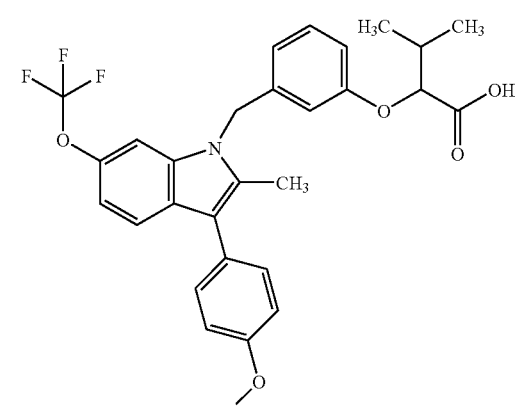 | 527.545 | 528(M + 1) | 4.36 |

TABLE 4-continued

Compound Where R³ is Phenyl

| | MOLSTRUCTURE | PARENT WEIGHT | Mass Spec | Retention Time |
|---|---|---|---|---|
| 11 | | 567.49 | 568(M + 1) | 4.07 |
| 12 | | 567.49 | 568(M + 1) | 4.07 |
| 13 | | 601.935 | 602(M + 1) | 4.21 |

TABLE 4-continued
Compound Where R³ is Phenyl
| MOLSTRUCTURE | PARENT WEIGHT | Mass Spec | Retention Time |
|---|---|---|---|
| 14 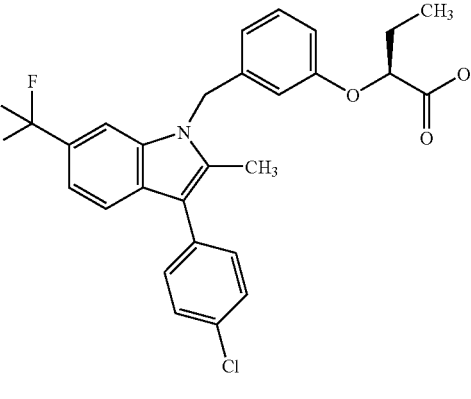 | 501.937 | 502(M + 1) | 4.15 |
| 15 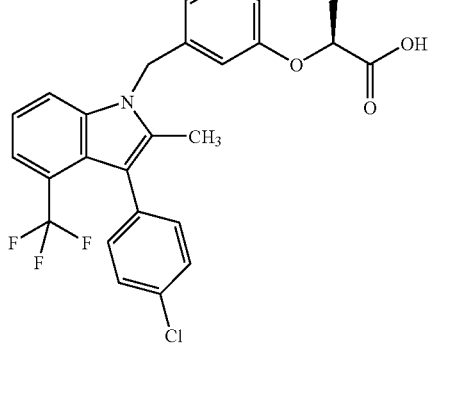 | 501.937 | 502(M + 1) | 4 |
| 16 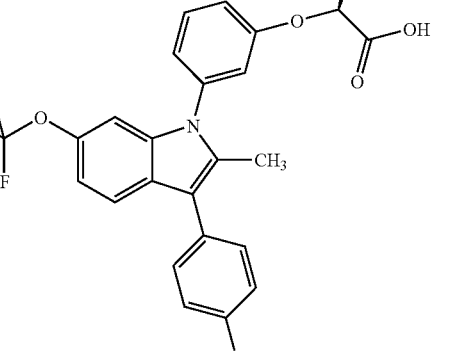 Chiral | 489.883 | M + H | 4.26 |

TABLE 4-continued
| | Compound Where R³ is Phenyl | | | |
|---|---|---|---|---|
| | MOLSTRUCTURE | PARENT WEIGHT | Mass Spec | Retention Time |
| 17 | 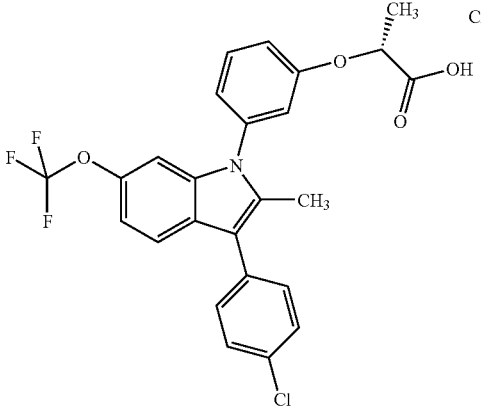 Chiral | 489.883 | M + H | 4.26 |
| 18 | 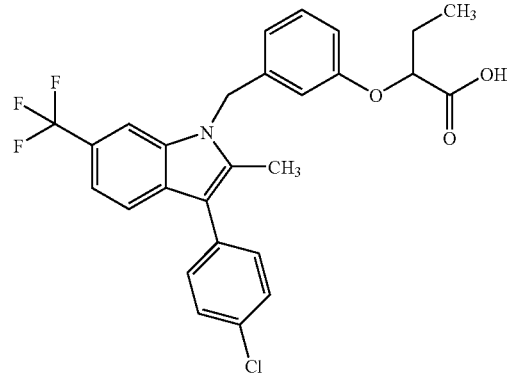 | 501.937 | 502(M + 1) | 4.15 |
| 19 | 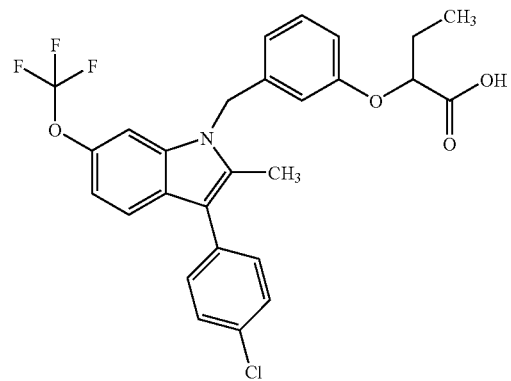 | 517.937 | 518(M + 1) | 4.2 |

TABLE 4-continued

Compound Where R³ is Phenyl

| | MOLSTRUCTURE | PARENT WEIGHT | Mass Spec | Retention Time |
|---|---|---|---|---|
| 20 | | 517.937 | 518(M + 1) | 4.2 |
| 21 | | 501.937 | 502(M + 1) | 4.18 |
| 22 | | 517.937 | 502(M + 1) | 4.21 |
| 23 | | 503.91 | M + H | 4.45 |

TABLE 4-continued

Compound Where R³ is Phenyl

| | MOLSTRUCTURE | PARENT WEIGHT | Mass Spec | Retention Time |
|---|---|---|---|---|
| 24 | | 503.91 | M + H | 4.43 |

TABLE 4A

Compound Where R³ is Phenyl 1. (2S)-2-(3-{[3-(4-methoxyphenyl)-2-methyl-6-(trifluoromethoxy)-1H-indol-1-yl]methyl}phenoxy)propanoic acid
2. (2R)-2-(3-{[3-(4-methoxyphenyl)-2-methyl-6-(trifluoromethoxy)-1H-indol-1-yl]methyl}phenoxy)propanoic acid
3. 2-(3-{[3-(4-methoxyphenyl)-2-methyl-6-(trifluoromethoxy)-1H-indol-1-yl]methyl}phenoxy)butanoic acid
4. 2-(3-{[3-(4-methoxyphenyl)-2-methyl-6-(trifluoromethoxy)-1H-indol-1-yl]methyl}phenoxy)butanoic acid
5. (2S)-2-(3-{[3-(4-methoxyphenyl)-2-methyl-4-(trifluoromethoxy)-1H-indol-1-yl]methyl}phenoxy)propanoic acid
6. (2R)-2-(3-{[3-(4-methoxyphenyl)-2-methyl-4-(trifluoromethoxy)-1H-indol-1-yl]methyl}phenoxy)propanoic acid
7. 2-(3-{[3-(4-methoxyphenyl)-2-methyl-4-(trifluoromethoxy)-1H-indol-1-yl]methyl}phenoxy)butanoic acid
8. 2-(3-{[3-(4-methoxyphenyl)-2-methyl-4-(trifluoromethoxy)-1H-indol-1-yl]methyl}phenoxy)butanoic acid
9. 2-(3-{[3-(4-methoxyphenyl)-2-methyl-6-(trifluoromethoxy)-1H-indol-1-yl]methyl}phenoxy)-3-methylbutanoic acid
10. 2-(3-{[3-(4-methoxyphenyl)-2-methyl-6-(trifluoromethoxy)-1H-indol-1-yl]methyl}phenoxy)-3-methylbutanoic acid
11. 2-(3-{[3-(4-methoxyphenyl)-6-(trifluoromethoxy)-2-(trifluoromethyl)-1H-indol-1-yl]methyl}phenoxy)butanoic acid
12. 2-(3-{[3-(4-methoxyphenyl)-6-(trifluoromethoxy)-2-(trifluoromethyl)-1H-indol-1-yl]methyl}phenoxy)butanoic acid
13. 2-(2-chloro-5-{[3-(4-methoxyphenyl)-6-(trifluoromethoxy)-2-(trifluoromethyl)-1H-indol-1-yl]methyl}phenoxy)butanoic acid
14. (2S)-2-(3-{[3-(4-chlorophenyl)-2-methyl-6-(trifluoromethyl)-1H-indol-1-yl]methyl}phenoxy)butanoic acid
15. (2S)-2-(3-{[3-(4-chlorophenyl)-2-methyl-4-(trifluoromethyl)-1H-indol-1-yl]methyl}phenoxy)butanoic acid
16. (2S)-2-{3-[3-(4-chlorophenyl)-2-methyl-6-(trifluoromethoxy)-1H-indol-1-yl]phenoxy}propanoic acid
17. (2R)-2-{3-[3-(4-chlorophenyl)-2-methyl-6-(trifluoromethoxy)-1H-indol-1-yl]phenoxy}propanoic acid
18. 2-(3-{[3-(4-chlorophenyl)-2-methyl-6-(trifluoromethyl)-1H-indol-1-yl]methyl}phenoxy)butanoic acid
19. 2-(3-{[3-(4-chlorophenyl)-2-methyl-6-(trifluoromethyl)-1H-indol-1-yl]methyl}phenoxy)butanoic acid
20. 2-(3-{[3-(4-chlorophenyl)-2-methyl-6-(trifluoromethoxy)-1H-indol-1-yl]methyl}phenoxy)butanoic acid
21. 2-(3-{[3-(4-chlorophenyl)-2-methyl-6-(trifluoromethyl)-1H-indol-1-yl]methyl}phenoxy)-2-methylpropanoic acid
22. 2-(3-{[3-(4-chlorophenyl)-2-methyl-6-(trifluoromethoxy)-1H-indol-1-yl]methyl}phenoxy)-2-methylpropanoic acid
23. 2-{3-[3-(4-chlorophenyl)-2-methyl-6-(trifluoromethoxy)-1H-indol-1-yl]phenoxy}butanoic acid
24. 2-{3-[3-(4-chlorophenyl)-2-methyl-6-(trifluoromethoxy)-1H-indol-1-yl]phenoxy}butanoic acid

What is claimed is:

1. A method of treating a disease, condition or disorder selected from the group consisting of (1) non-insulin dependent Type 2 diabetes mellitus (NIDDM), (2) hyperglycemia, (3) low glucose tolerance, (4) insulin resistance, (6) a lipid disorder, (7) dyslipidemia, (8) hyperlipidemia, (9) hypertriglyceridemia, (10) hypercholesterolemia, (11) low HDL levels, (12) high LDL levels, (13) atherosclerosis, comprising administering an effective amount of a compound selected from the group consisting of:

(Ex 3)
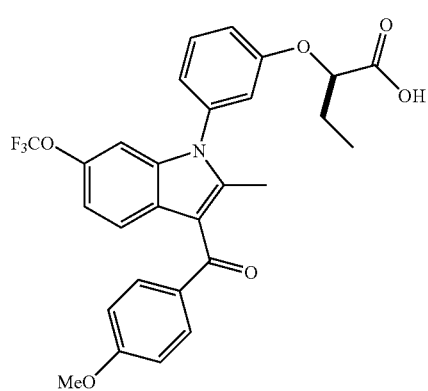

(Ex 4)
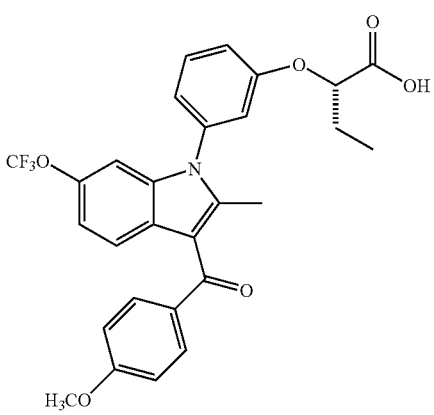

(Ex 5)
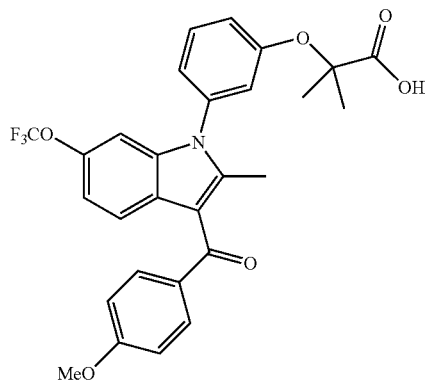

(Ex 8)
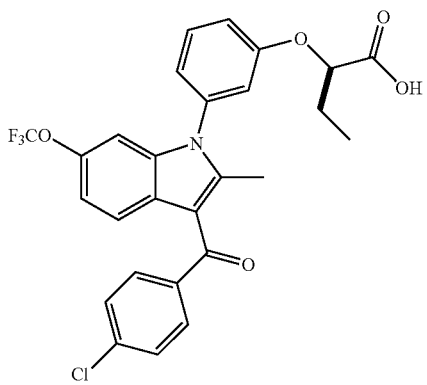

(Ex 10)
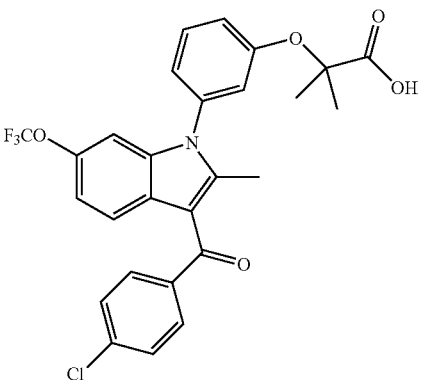

(Ex 11)
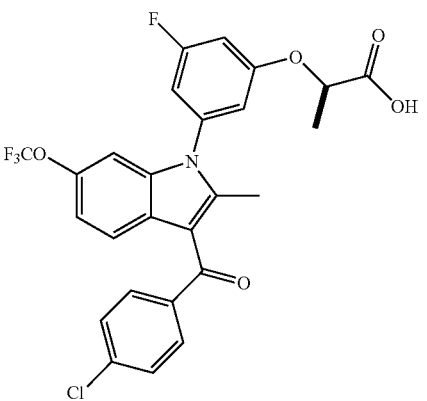

(Ex 16)
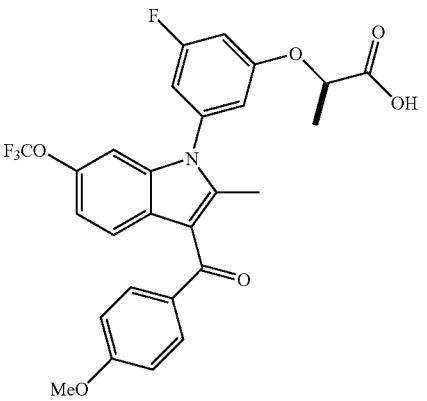

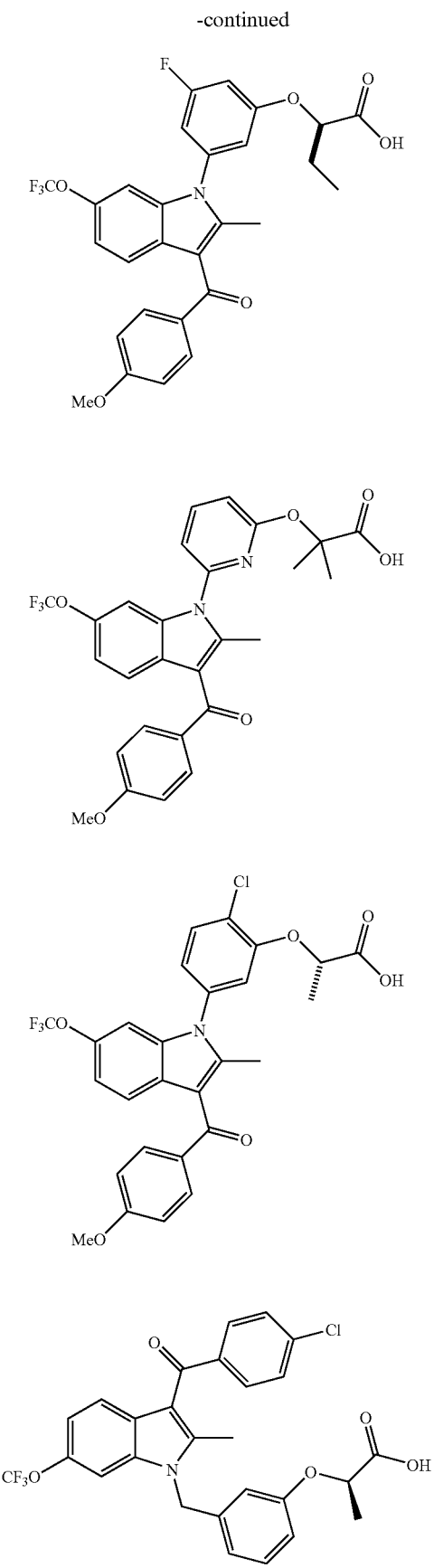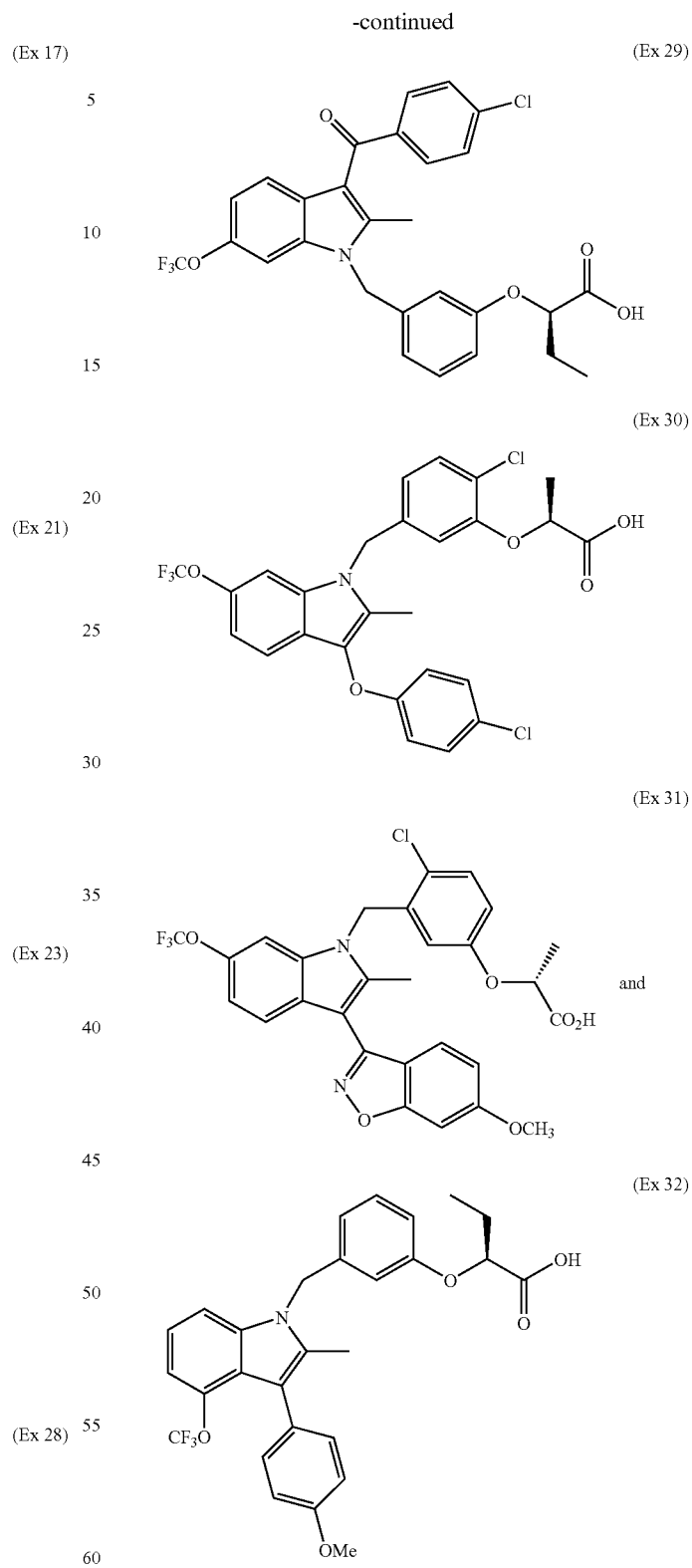
or a pharmaceutically acceptable salt or solvate thereof.
2. A method in accordance with claim 1 further comprising administering to a patient in need of such treatment a therapeutically effective amount of an HMG-CoA reductase inhibitor.

3. The method of claim 2, wherein the HMG-CoA reductase inhibitor is a statin selected from the group consisting of lovastatin, simvastatin, pravastatin, fluvastatin, atorvastatin, itavastatin, ZD-4522, rivastatin, and rosuvastatin.

4. A method in accordance with claim 1 wherein the compound is of the formula:

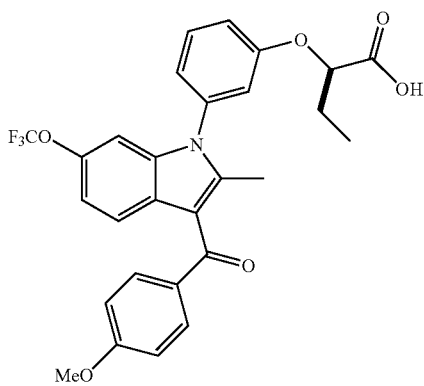

or a pharmaceutically acceptable salt thereof.

5. A method in accordance with claim 1 wherein the compound is of the formula:

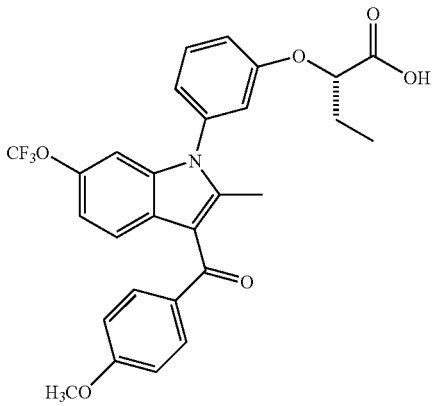

or a pharmaceutically acceptable salt thereof.

6. A method in accordance with claim 1 wherein the compound is of the formula:

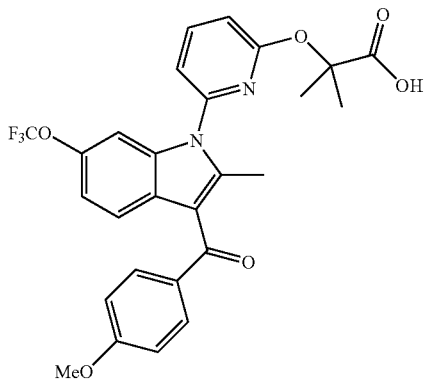

or a pharmaceutically acceptable salt thereof.

7. A method in accordance with claim 1 wherein the compound is of the formula:

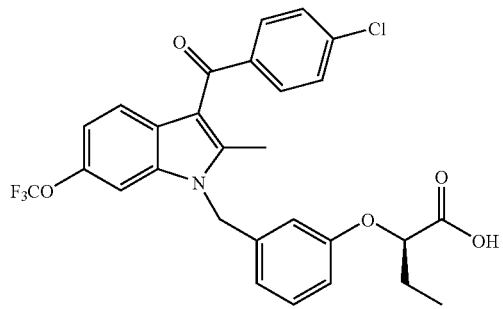

or a pharmaceutically acceptable salt thereof.

8. A method in accordance with claim 1 wherein the compound is of the formula:

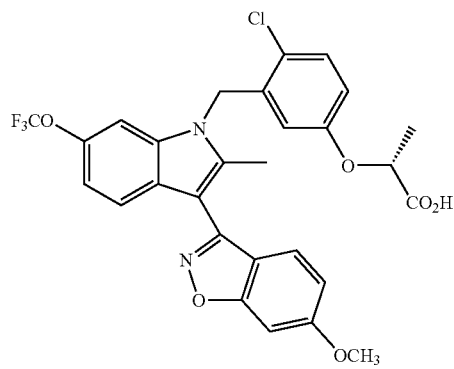

or a pharmaceutically acceptable salt thereof.

9. A pharmaceutical composition comprising a compound selected from the group consisting of:

(Ex 3)

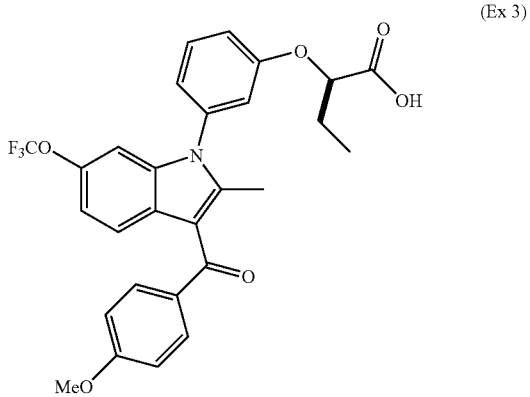

297
-continued
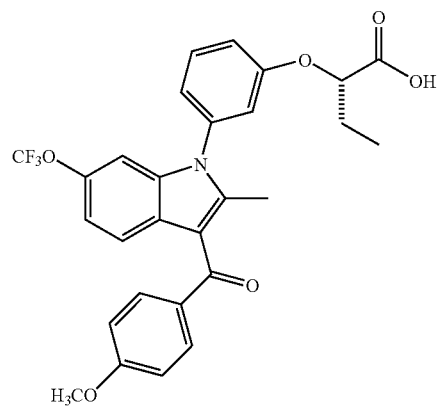
(Ex 4)
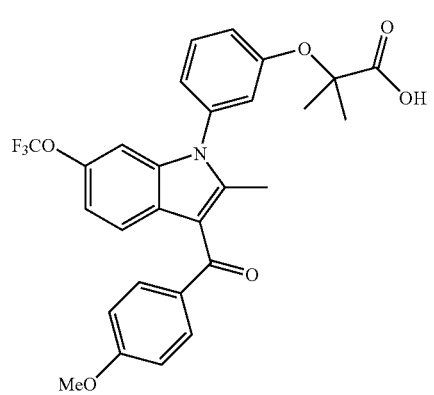
(Ex 5)
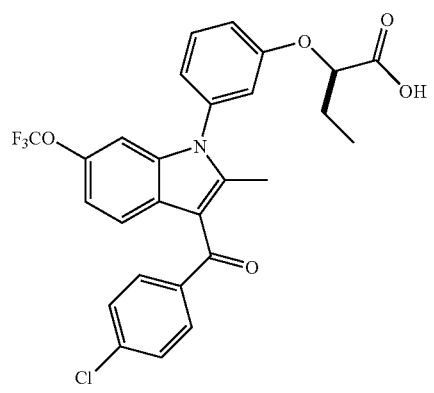
(Ex 8)
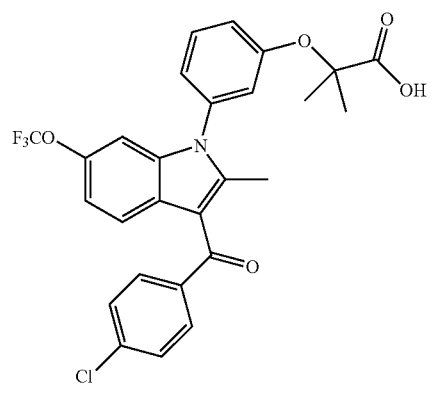
(Ex 10)
298
-continued
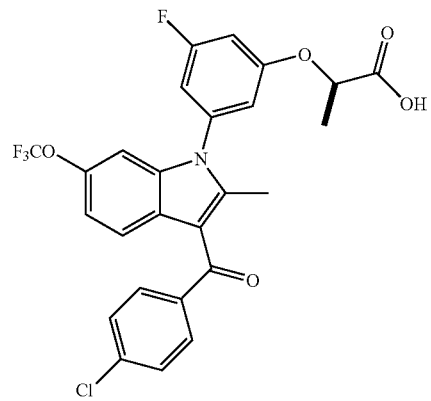
(Ex 11)
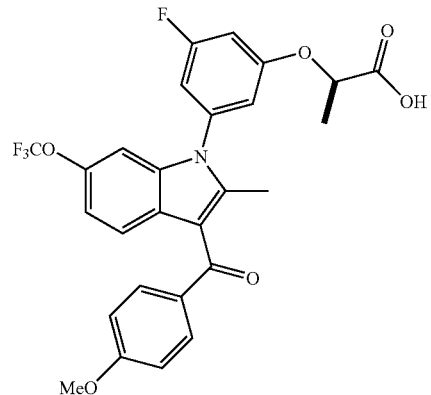
(Ex 16)
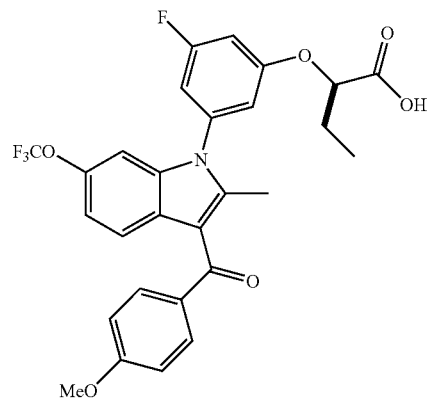
(Ex 17)
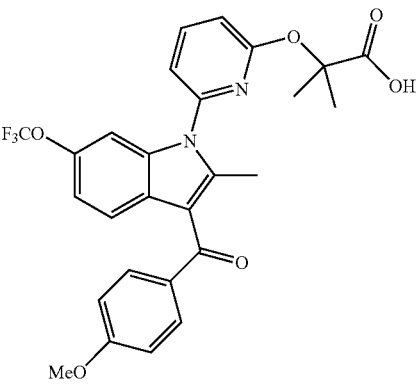
(Ex 21)

-continued
(Ex 23)
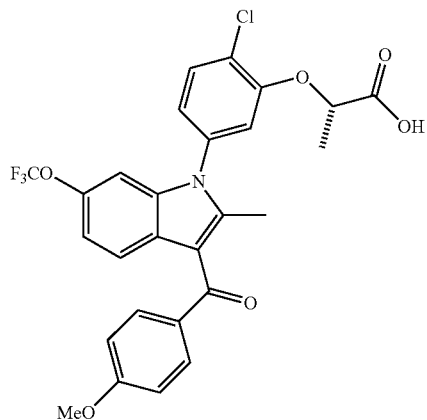
(Ex 28)
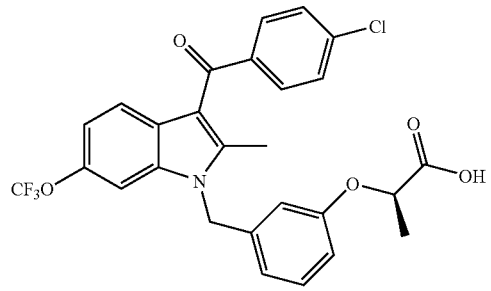
(Ex 29)
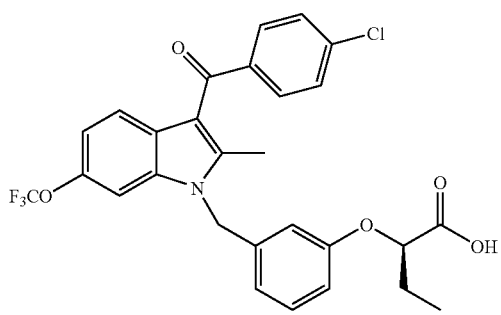
(Ex 30)
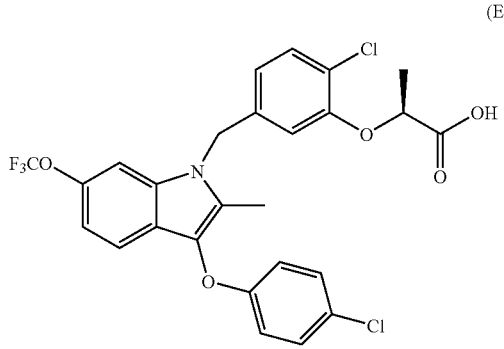
-continued
(Ex 31)
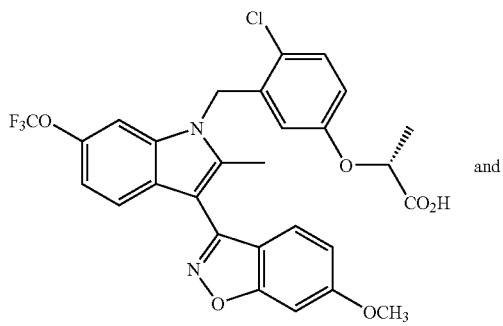
and
(Ex 32)
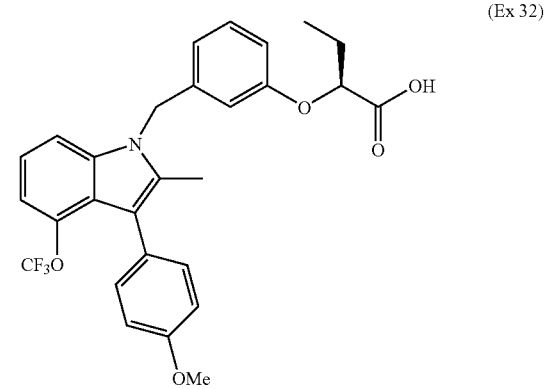
or a pharmaceutically acceptable salt thereof in combination with a pharmaceutically acceptable carrier.
10. A pharmaceutical composition in accordance with claim 9 wherein the compound is of the formula:
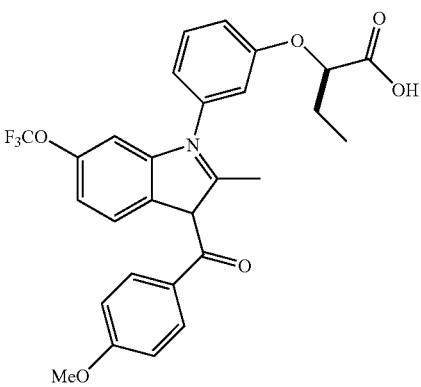
or a pharmaceutically acceptable salt thereof.

11. A pharmaceutical composition in accordance with claim 9, wherein the compound is of the formula:

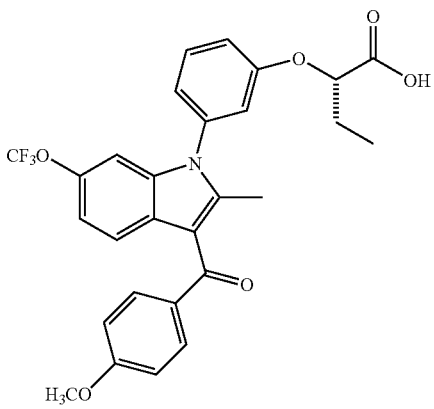

or a pharmaceutically acceptable salt thereof.

12. A pharmaceutical composition in accordance with claim 9 wherein the compound is of the formula;

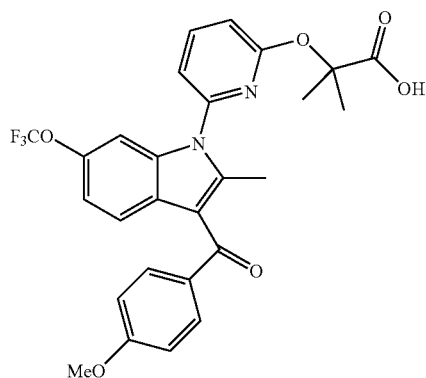

or a pharmaceutically acceptable salt thereof.

13. A pharmaceutical composition in accordance with claim 9 wherein the compound is of the formula:

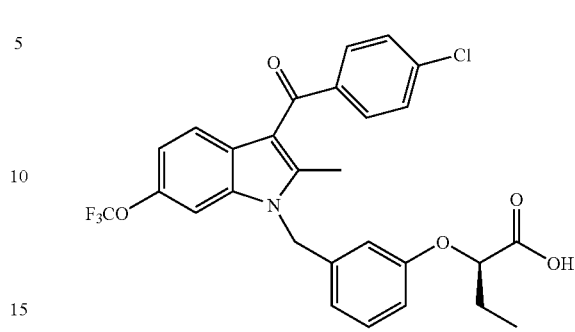

or a pharmaceutically acceptable salt thereof.

14. A pharmaceutical composition in accordance with claim 9 wherein the compound is of the formula

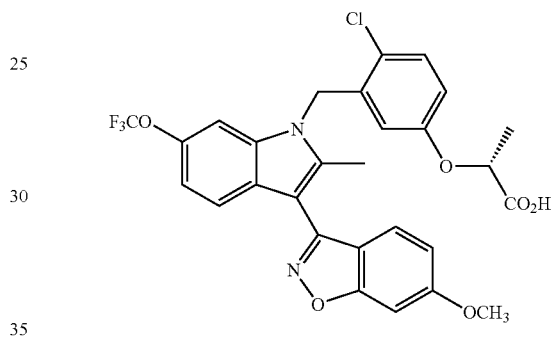

or a pharmaceutically acceptable salt thereof.

* * * * *